(12) United States Patent
Foster et al.

(10) Patent No.: US 8,067,200 B2
(45) Date of Patent: *Nov. 29, 2011

(54) FUSION PROTEINS

(75) Inventors: Keith Foster, Salisbury (GB); John Chaddock, Salisbury (GB); Philip Marks, Abingdon (GB); Patrick Stancombe, Salisbury (GB); Kei Roger Aoki, Irvine, CA (US); Joseph Francis, Irvine, CA (US); Lance Steward, Irvine, CA (US)

(73) Assignees: Syntaxin Ltd., Abingdon (GB); Allergan Inc., Irvine, CA (US)

( * ) Notice: Subject to any disclaimer, the term of this patent is extended or adjusted under 35 U.S.C. 154(b) by 636 days.

This patent is subject to a terminal disclaimer.

(21) Appl. No.: 11/792,210

(22) PCT Filed: Dec. 1, 2005

(86) PCT No.: PCT/GB2005/004585
§ 371 (c)(1),
(2), (4) Date: Apr. 9, 2008

(87) PCT Pub. No.: WO2006/059093
PCT Pub. Date: Jun. 8, 2006

(65) Prior Publication Data
US 2010/0247509 A1    Sep. 30, 2010

(30) Foreign Application Priority Data

Dec. 1, 2004  (GB) .................................. 0426394.3
Mar. 10, 2005  (GB) .................................. 0504964.8

(51) Int. Cl.
*C12P 21/06* (2006.01)
*C17H 17/00* (2006.01)
*C07K 14/00* (2006.01)

(52) U.S. Cl. .................. 435/69.1; 435/320.1; 536/23.1; 514/350

(58) Field of Classification Search .................. 530/350; 514/2; 536/23.1; 435/69.1, 320.1
See application file for complete search history.

(56) References Cited

U.S. PATENT DOCUMENTS

| | | | |
|---|---|---|---|
| 5,668,255 A | 9/1997 | Murphy | |
| 5,989,545 A | 11/1999 | Foster et al. | |
| 5,998,375 A * | 12/1999 | Thorgersen et al. | 514/13 |
| 6,136,564 A | 10/2000 | Kopetzki | |
| 6,395,513 B1 | 5/2002 | Foster | |
| 6,461,617 B1 | 10/2002 | Shone | |
| 6,632,440 B1 | 10/2003 | Quinn | |
| 6,776,990 B2 | 8/2004 | Sachs | |
| 6,843,998 B1 | 1/2005 | Steward | |
| 6,962,703 B2 | 11/2005 | Foster | |
| 7,052,702 B1 | 5/2006 | Duggan | |
| 7,056,729 B2 | 6/2006 | Donovan | |
| 7,132,259 B1 | 11/2006 | Dolly | |
| 7,192,596 B2 | 3/2007 | Shone | |
| 7,208,466 B1 | 4/2007 | Foster | |
| 7,244,436 B2 | 7/2007 | Donovan | |
| 7,244,437 B2 | 7/2007 | Donovan | |
| 7,262,291 B2 | 8/2007 | Donovan | |
| 7,276,473 B2 | 10/2007 | Sachs | |
| 7,413,742 B2 | 8/2008 | Donovan | |
| 7,419,676 B2 | 9/2008 | Dolly | |
| 7,422,877 B2 | 9/2008 | Dolly | |
| 7,452,543 B2 | 11/2008 | Chaddock | |
| 7,494,661 B2 | 2/2009 | Sanders | |
| 7,514,088 B2 | 4/2009 | Steward | |
| 7,658,933 B2 * | 2/2010 | Foster et al. | 424/239.1 |
| 7,659,092 B2 * | 2/2010 | Foster et al. | 435/69.1 |
| 7,709,228 B2 | 5/2010 | Dolly | |
| 7,736,659 B2 | 6/2010 | Donovan | |
| 7,740,868 B2 | 6/2010 | Steward | |
| 7,749,514 B2 | 7/2010 | Steward | |
| 7,780,968 B2 | 8/2010 | Donovan | |
| 7,785,606 B2 | 8/2010 | Ichtchenko | |
| 7,811,584 B2 | 10/2010 | Steward | |
| 7,833,535 B2 | 11/2010 | Donovan | |

(Continued)

FOREIGN PATENT DOCUMENTS

EP    1 422 240 A2    5/2004

(Continued)

OTHER PUBLICATIONS

Sagane et al. 1999; Dichain structure of botulinum neurotoxin: Idnetification of cleavage sites in Types C, D, and F neurotoxin molecules. J. Protein Chemistry 18(8): 995-892.* U.S. Appl. No. 11/798,610, Quinn.
U.S. Appl. No. 08/513,878, filed Dec. 1, 1995, North.
U.S. Appl. No. 09/572,431, filed May 17, 2000, North.
U.S. Appl. No. 11/819,648, filed Jun. 28, 2007, Foster.
Chaddock, et al., "Retargeted Clostridial Endopeptidases: Inhibition of Nociceptive Neurotransmitter Release In vitro, and Antinociceptive Activity in In vivo Models of Pain," Movement Disorders, 19:S42-S47 (2004).

(Continued)

*Primary Examiner* — Karen Carlson
(74) *Attorney, Agent, or Firm* — Roylance, Abrams, Berdo & Goodman LLP

(57) ABSTRACT

A single chain, polypeptide fusion protein, comprising: a non-cytotoxic protease, or a fragment thereof, which protease or protease fragment is capable of cleaving a protein of the exocytic fusion apparatus of a nociceptive sensory afferent; a Targeting Moiety that is capable of binding to a Binding Site on the nociceptive sensory afferent, which Binding Site is capable of undergoing endocytosis to be incorporated into an endosome within the nociceptive sensory afferent; a protease cleavage site at which site the fusion protein is cleavable by a protease, wherein the protease cleavage site is located between the non-cytotoxic protease or fragment thereof and the Targeting Moiety; and a translocation domain that is capable of translocating the protease or protease fragment from within an endosome, across the endosomal membrane and into the cytosol of the nociceptive sensory afferent. Nucleic acid sequences encoding the polypeptide fusion proteins, methods of preparing same and uses thereof are also described.

35 Claims, 29 Drawing Sheets

U.S. PATENT DOCUMENTS

Figure 1:
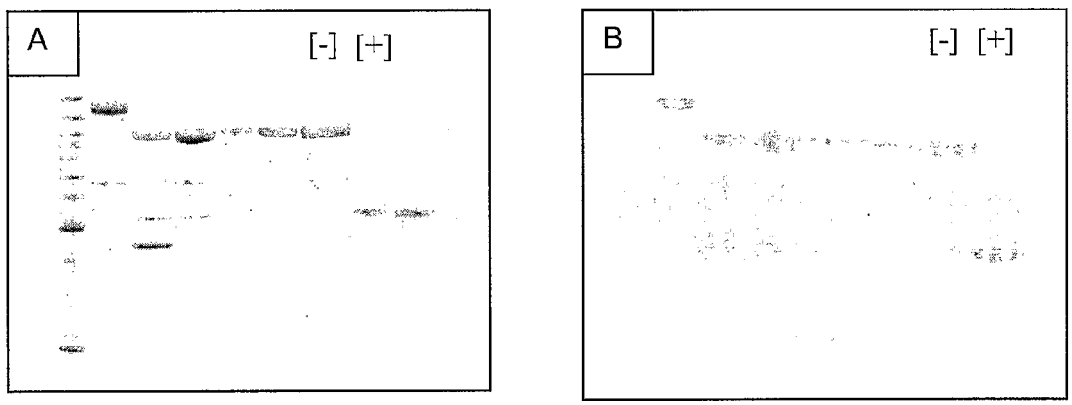

| | | | |
|---|---|---|---|
| 7,887,810 B2 | 2/2011 | Foster | |
| 7,892,560 B2 | 2/2011 | Foster | |
| 7,897,157 B2 | 3/2011 | Steward | |
| 2003/0049264 A1 | 3/2003 | Foster et al. | |
| 2003/0180289 A1 | 9/2003 | Foster | |
| 2004/0071736 A1 | 4/2004 | Quinn | |
| 2004/0115727 A1 | 6/2004 | Steward | |
| 2005/0095251 A1 | 5/2005 | Steward | |
| 2005/0244435 A1 | 11/2005 | Shone | |
| 2006/0051356 A1 | 3/2006 | Foster | |
| 2006/0110410 A1 | 5/2006 | Shone | |
| 2006/0216283 A1 | 9/2006 | Foster | |
| 2007/0010447 A1 | 1/2007 | Quinn | |
| 2007/0010475 A1 | 1/2007 | Richardson | |
| 2007/0066559 A1 | 3/2007 | Richardson | |
| 2007/0184048 A1 | 8/2007 | Foster | |
| 2007/0184070 A1 | 8/2007 | Shone | |
| 2007/0248626 A1 | 10/2007 | Shone | |
| 2008/0025994 A1 | 1/2008 | Steward | |
| 2008/0032928 A1 | 2/2008 | Quinn | |
| 2008/0032931 A1 | 2/2008 | Steward | |
| 2008/0038274 A1 | 2/2008 | Foster | |
| 2008/0070278 A1 | 3/2008 | North | |
| 2008/0182294 A1 | 7/2008 | Dolly | |
| 2008/0311622 A1 | 12/2008 | Dolly | |
| 2009/0004224 A1 | 1/2009 | Steward | |
| 2009/0005313 A1 | 1/2009 | Steward | |
| 2009/0018081 A1 | 1/2009 | Steward | |
| 2009/0030182 A1 | 1/2009 | Dolly | |
| 2009/0030188 A1 | 1/2009 | Dolly | |
| 2009/0042270 A1 | 2/2009 | Dolly | |
| 2009/0069238 A1 | 3/2009 | Steward | |
| 2009/0081730 A1 | 3/2009 | Dolly | |
| 2009/0087458 A1 | 4/2009 | Dolly | |
| 2009/0104234 A1 | 4/2009 | Francis | |
| 2009/0117157 A1 | 5/2009 | Brin | |
| 2009/0162341 A1 | 6/2009 | Foster | |
| 2010/0034802 A1 | 2/2010 | Foster | |
| 2010/0055761 A1 | 3/2010 | Seed | |
| 2010/0196421 A1 | 8/2010 | Ichtchenko | |
| 2010/0209955 A1 | 8/2010 | Oyler | |
| 2010/0303757 A1 | 12/2010 | Francis | |
| 2010/0303789 A1 | 12/2010 | Francis | |
| 2010/0303791 A1 | 12/2010 | Francis | |
| 2011/0091437 A1 | 4/2011 | Foster | |

FOREIGN PATENT DOCUMENTS

| | | | |
|---|---|---|---|
| WO | WO 96/33273 | | 10/1996 |
| WO | 97/07208 | * | 2/1997 |
| WO | 98/07864 A1 | | 2/1998 |
| WO | 99/17806 A1 | | 4/1999 |
| WO | WO 00/57897 | | 10/2000 |
| WO | 01/14570 A1 | | 3/2001 |
| WO | 02/07759 A3 | | 1/2002 |
| WO | 2004/024909 A2 | | 3/2004 |
| WO | 2005/023309 A2 | | 3/2005 |
| WO | 2006/026780 | | 3/2006 |
| WO | 2006/059093 | | 6/2006 |
| WO | 2006/059105 | | 6/2006 |
| WO | 2006/059113 | | 6/2006 |
| WO | WO 2006/059113 | | 6/2006 |
| WO | 2007/138339 | | 12/2007 |

OTHER PUBLICATIONS

Blanc, Jacky P. et al., Examination of the Requirement for an Amphiphilic Helical Structure in B-Endorphin through the Design, Synthesis, and Study of Model Peptides, The Journal of Biological Chemistry, vol. 258, No. 13, 1983, pp. 8277-8284.

Shone, Clifford C. et al., A 50-kDa fragment from the NH2-terminus of the heavy subunit of *Clostridium botulinum* type A neurotoxin forms channels in lipid vesicles, Eur. J. Biochem. 167, 175-180, 1987.

Wagner, Ernst et al., Influenza virus hemagglutinin HA-2 N-terminal fusogenic peptides augment gene transfer by transferrin-polylysine-DNA complexes: Toward a synthetic virus-like gene-transfer vehicle, Proc. Natl. Acad. Sci, USA, vol. 89, pp. 7934-7938, 1992.

Plank, Christian et al., The Influence of Endosome-disruptive Peptides on Gene Transfer Using Synthetic Virus-like Gene Transfer Systems, The Journal of Biological Chemistry, vol. 269, No. 17, 1994, pp. 12918-12924.

Dooley, Colette T., et al., Binding and In Vitro Activities of Peptides with High Affinity for the Nociceptin/Orphanin FQ Receptor, ORL1, The Journal of Pharmacology and Experimental Therapeutics, 1997, vol. 283, No. 2, pp. 735-741.

Vergnollie, N. et al., Proteinase-activated receptor-2 and hyperalgesia: A novel pain pathway, Nature Medicine, vol. 7, No. 7, 2001, pp. 821-826.

Rizzi, Daniela et al., [Arg14, LYS15]Nociceptin, a Highly Potent Agonist of the Nociceptin/Orphanin FQ Receptor: in Vitro and in Vivo Studies, The Journal of Pharmacology and Experimental Therapeutics, 2002, vol. 300, No. 1 pp. 57-63.

Turton, Kathryn et al., Botulinum and tetanus neurotoxins: structure, function and therapeutic utility, Trends in Biochemical Sciences, vol. 27, No. 11, 2002, pp. 552-558.

Maile, Rebecca et al., Effects of nociceptin and analogues of nociceptin upon spontaneous dorsal root activity recorded from an in vitro preparation of rat spinal cord, Neuroscience Letters 350 (2003) 190-192.

Chaddock, John A. et al., Manipulation of Signal Transduction by Botulinum Neurotoxins and their Derivatives, Current Signal Transduction Therapy, 2007, 2, 221-225.

Guerrini, Remo et al., Address and Message Sequences for the Nociceptin Receptor: A Structure-Activity Study of Nociceptin-(1-13)-peptide amide, J. Med. Chem., 1997, 40, 1789-1793.

Schiavo, Giampietro et al., Neurotoxins Affecting Neuroexocytosis, Physiological Reviews, vol. 80, No. 2, 2000, pp. 717-766.

Xu, X.J. et al., Galanin and spinal nociceptive mechanisms: recent advances and therapeutic implications, Neuropeptides, 2000, 34(3 &4), 137-147.

Okada, Kazushi et al., Highly Potent Nociceptin Analog Containing the Arg-Lys Triple Repeat, Biochemical and Biophysical Research Communications, 278, 493-498, 2000.

Mogil, Jeffrey S. et al., The Molecular and Behavioral Pharmacology of the Orphanin FQ/Nociceptin Peptide and Receptor Family, Pharmacological Reviews, 2001, vol. 53, No. 3, pp. 381-415.

Chaddock, J.A., et al., A Conjugate Composed of Nerve Growth Factor Coupled to a Non-Toxic Derivative of *Clostridium botulinum* Neurotoxin Type A Can Inhibit Neurotransmitter Release In Vitro, Growth Factors 18(2):147-155, 2000.

Chaddock, J.A., et al., Expression and Purification of Catalytically Active, Non-Toxic Endopeptidase Derivatives of *Clostridium botulinum* Toxin Type A, Protein Expression and Purification 25(2):219-228, 2002.

Chaddock, J.A., et al., Inhibition of Vesicular Secretion in Both Neuronal and Nonneuronal Cells by Retargeted Endopeptidase Derivative of *Clostridium botulinum* Neurotoxin Type A, Infection and Immunity 68(5):2587-2593, 2000.

Cui, M., et al., Retargeted Clostridial Endopeptidase: Antinociceptive Activity in Preclinical Models of Pain, Naunyn-Schmiedeberg's Archives of Pharmacology:R16, 2002.

Duggan, M.J., et al., Inhibition of Release of Neurotransmitters from Rat Dorsal Root Ganglia by a Novel Conjugate of a *Clostridium botulinum* Toxin A Endopeptidase Fragment and *Erythrina cristagalli* Lectin, Journal of Biological Chemistry 277(38):34846-34852, 2002.

Foster, K.A., et al., Re-Engineering the Target Specificity of Clostridial Neurotoxins: A Route to Novel Therapeutics, Neurotoxicity Research 9(2,3):101-107, 2006.

Inoue, M., et al., Nociceptin/Orphannin FQ-Induced Nociceptive Responses Through Substance P Release From Peripheral Nerve Endings in Mice, PNAS (Proceedings of the National Academy of Sciences USA), 95 (18):10949-10953, 1998.

Sutton, J.M., et al., Preparation of Specifically Activatable Endopeptidase Derivatives of *Clostridium botulinum* Toxins Type A, B, and C and Their Applications, Protein Expression and Purification 40(1):31-41, 2005.

* cited by examiner

Figure 5

Competition Assay : Nociceptin-LH$_N$/A Fusions
vs 1nM [$^3$H]-Nociceptin on eDRGs (4°C)

- Tocris Nociceptin
- Noci-LHA fusion
- L-noci-HN fusion
- Control

Duration of action following eDRG exposure for 1 Day

Figure 12

Figure 14

FUSION PROTEINS

This invention relates to non-cytotoxic fusion proteins, and to the therapeutic application thereof as analgesic molecules.

Toxins may be generally divided into two groups according to the type of effect that they have on a target cell. In more detail, the first group of toxins kill their natural target cells, and are therefore known as cytotoxic toxin molecules. This group of toxins is exemplified inter alia by plant toxins such as ricin, and abrin, and by bacterial toxins such as diphtheria toxin, and *Pseudomonas* exotoxin A. Cytotoxic toxins have attracted much interest in the design of "magic bullets" (e.g. immunoconjugates, which comprise a cytotoxic toxin component and an antibody that binds to a specific marker on a target cell) for the treatment of cellular disorders and conditions such as cancer. Cytotoxic toxins typically kill their target cells by inhibiting the cellular process of protein synthesis.

The second group of toxins, which are known as non-cytotoxic toxins, do not (as their name confirms) kill their natural target cells. Non-cytotoxic toxins have attracted much less commercial interest than have their cytotoxic counterparts, and exert their effects on a target cell by inhibiting cellular processes other than protein synthesis. Non-cytotoxic toxins are produced by a variety of plants, and by a variety of microorganisms such as *Clostridium* sp. and *Neisseria* sp.

Clostridial neurotoxins are proteins that typically have a molecular mass of the order of 150 kDa. They are produced by various species of bacteria, especially of the genus *Clostridium*, most importantly *C. tetani* and several strains of *C. botulinum, C. butyricum* and *C. argentinense*. There are at present eight different classes of the clostridial neurotoxin, namely: tetanus toxin, and botulinum neurotoxin in its serotypes A, B, C1, D, E, F and G, and they all share similar structures and modes of action.

Clostridial neurotoxins represent a major group of non-cytotoxic toxin molecules, and are synthesised by the host bacterium as single polypeptides that are modified post-translationally by a proteolytic cleavage event to form two polypeptide chains joined together by a disulphide bond. The two chains are termed the heavy chain (H-chain or "HC"), which has a molecular mass of approximately 100 kDa, and the light chain (L-chain or "LC"), which has a molecular mass of approximately 50 kDa.

L-chains possess a protease function (zinc-dependent endopeptidase activity) and exhibit a high substrate specificity for vesicle and/or plasma membrane associated proteins involved in the exocytic process. L-chains from different clostridial species or serotypes may hydrolyse different but specific peptide bonds in one of three substrate proteins, namely synaptobrevin, syntaxin or SNAP-25. These substrates are important components of the neurosecretory machinery.

*Neisseria* sp., most importantly from the species *N. gonorrhoeae*, produce functionally similar non-cytotoxic proteases. An example of such a protease is IgA protease (see WO99/58571).

It has been well documented in the art that toxin molecules may be re-targeted to a cell that is not the toxin's natural target cell. When so re-targeted, the modified toxin is capable of binding to a desired target cell and, following subsequent translocation into the cytosol, is capable of exerting its effect on the target cell. Said re-targeting is achieved by replacing the natural Targeting Moiety (TM) of the toxin with a different TM. In this regard, the TM is selected so that it will bind to a desired target cell, and allow subsequent passage of the modified toxin into an endosome within the target cell. The modified toxin also comprises a translocation domain to enable entry of the non-cytotoxic protease into the cell cytosol. The translocation domain can be the natural translocation domain of the toxin or it can be a different translocation domain obtained from a microbial protein with translocation activity.

For example, WO94/21300 describes modified clostridial neurotoxin molecules that are capable of regulating Integral Membrane Protein (IMP) density present at the cell surface of the target cell. The modified neurotoxin molecules are thus capable of controlling cell activity (e.g. glucose uptake) of the target cell. WO96/33273 and WO99/17806 describe modified clostridial neurotoxin molecules that target peripheral sensory afferents. The modified neurotoxin molecules are thus capable of demonstrating an analgesic effect. WO00/10598 describes the preparation of modified clostridial neurotoxin molecules that target mucus hypersecreting cells (or neuronal cells controlling said mucus hypersecreting cells), which modified neurotoxins are capable of inhibiting hypersecretion from said cells. WO01/21213 describes modified clostridial neurotoxin molecules that target a wide range of different types of non-neuronal target cells. The modified molecules are thus capable of preventing secretion from the target cells. Additional publications in the technical field of re-targeted toxin molecules include: WO00/62814; WO00/04926; U.S. Pat. No. 5,773,586; WO93/15766; WO00/61192; and WO99/58571.

The above-mentioned TM replacement may be effected by conventional chemical conjugation techniques, which are well known to a skilled person. In this regard, reference is made to Hermanson, G. T. (1996), Bioconjugate techniques, Academic Press, and to Wong, S. S. (1991), Chemistry of protein conjugation and cross-linking, CRC Press.

Chemical conjugation is, however, often imprecise. For example, following conjugation, a TM may become joined to the remainder of the conjugate at more than one attachment site.

Chemical conjugation is also difficult to control. For example, a TM may become joined to the remainder of the modified toxin at an attachment site on the protease component and/or on the translocation component. This is problematic when attachment to only one of said components (preferably at a single site) is desired for therapeutic efficacy.

Thus, chemical conjugation results in a mixed population of modified toxin molecules, which is undesirable.

As an alternative to chemical conjugation, TM replacement may be effected by recombinant preparation of a single polypeptide fusion protein (see WO98/07864). This technique is based on the in vivo bacterial mechanism by which native clostridial neurotoxin (i.e. holotoxin) is prepared, and results in a fusion protein having the following structural arrangement:

$NH_2$-[protease component]-[translocation component]-[TM]-COOH

According to WO98/07864, the TM is placed towards the C-terminal end of the fusion protein. The fusion protein is then activated by treatment with a protease, which cleaves at a site between the protease component and the translocation component. A di-chain protein is thus produced, comprising the protease component as a single polypeptide chain covalently attached (via a disulphide bridge) to another single polypeptide chain containing the translocation component plus TM. Whilst the WO98/07864 methodology follows (in terms of structural arrangement of the fusion protein) the natural expression system of clostridial holotoxin, the present inventors have found that this system may result in the production of certain fusion proteins that have a substantially-reduced binding ability for the intended target cell.

There is therefore a need for an alternative or improved system for constructing a non-cytotoxic fusion protein.

The present invention addresses one or more of the above-mentioned problems by providing a single chain, polypeptide fusion protein, comprising:
  a. a non-cytotoxic protease, or a fragment thereof, which protease or protease fragment is capable of cleaving a protein of the exocytic fusion apparatus in a nociceptive sensory afferent;
  b. a Targeting Moiety that is capable of binding to a Binding Site on the nociceptive sensory afferent, which Binding Site is capable of undergoing endocytosis to be incorporated into an endosome within the nociceptive sensory afferent;
  c. a protease cleavage site at which site the fusion protein is cleavable by a protease, wherein the protease cleavage site is located between the non-cytotoxic protease or fragment thereof and the Targeting Moiety; and
  d. a translocation domain that is capable of translocating the protease or protease fragment from within an endosome, across the endosomal membrane and into the cytosol of the nociceptive sensory afferent.

The WO98/07864 system works well for the preparation of conjugates having a TM that requires a C-terminal domain for interaction with a Binding Site on a target cell. In this regard, WO98/07864 provides fusion proteins having a C-terminal domain that is "free" to interact with a Binding Site on a target cell. The present inventors have found that this structural arrangement is not suitable for all TMs. One such category of TM is a group of TMs that binds to nociceptive sensory afferents. In more detail, the present inventors have found that the WO 98/07864 fusion protein system is not optimal for TMs requiring a N-terminal domain for interaction with a binding site on a nociceptive sensory afferent. This problem is particularly acute with TMs that require a specific N-terminus amino acid residue or a specific sequence of amino acid residues including the N-terminus amino acid residue for interaction with a binding site on a nociceptive sensory afferent.

In contrast to WO98/07864, the present invention provides a system for preparing non-cytotoxic conjugates, wherein the TM component of the conjugate includes the relevant binding domain in an intra domain or an amino acid sequence located towards the middle (ie. of the linear peptide sequence) of the TM, or preferably located towards the N-terminus of the TM, or more preferably at or near to the N-terminus. The N-terminal domain is capable of binding to a Binding Site on a nociceptive sensory afferent, and the TM preferably has a requirement for a specific and defined sequence of amino acid residue(s) to be free at its N-terminus.

The non-cytotoxic protease component of the present invention is a non-cytotoxic protease, or a fragment thereof, which protease or protease fragment is capable of cleaving different but specific peptide bonds in one of three substrate proteins, namely synaptobrevin, syntaxin or SNAP-25, of the exocytic fusion apparatus in a nociceptive sensory afferent. These substrates are important components of the neuro-secretory machinery. The non-cytotoxic protease component of the present invention is preferably a neisserial IgA protease or a fragment thereof or a clostridial neurotoxin L-chain or a fragment thereof. A particularly preferred non-cytotoxic protease component is a botulinum neurotoxin (BoNT) L-chain or a fragment thereof.

The translocation component of the present invention enables translocation of the non-cytotoxic protease (or fragment thereof) into the target cell such that functional expression of protease activity occurs within the cytosol of the target cell. The translocation component is preferably capable of forming ion-permeable pores in lipid membranes under conditions of low pH. Preferably it has been found to use only those portions of the protein molecule capable of pore-formation within the endosomal membrane. The translocation component may be obtained from a microbial protein source, in particular from a bacterial or viral protein source. Hence, in one embodiment, the translocation component is a translocating domain of an enzyme, such as a bacterial toxin or viral protein. The translocation component of the present invention is preferably a clostridial neurotoxin H-chain or a fragment thereof. Most preferably it is the $H_N$ domain (or a functional component thereof), wherein $H_N$ means a portion or fragment of the H-chain of a clostridial neurotoxin approximately equivalent to the amino-terminal half of the H-chain, or the domain corresponding to that fragment in the intact H-chain.

The TM component of the present invention is responsible for binding the conjugate of the present invention to a Binding Site on a target cell. Thus, the TM component is simply a ligand through which a conjugate of the present invention binds to a selected target cell.

In the context of the present invention, the target cell is a nociceptive sensory afferent, preferably a primary nociceptive afferent (e.g. an A-fibre such as an Aδ-fibre or a C-fibre). Thus, the conjugates of the present invention are capable of inhibiting neurotransmitter or neuromodulator [e.g. glutamate, substance P, calcitonin-gene related peptide (CGRP), and/or neuropeptide Y] release from discrete populations of nociceptive sensory afferent neurons. In use, the conjugates reduce or prevent the transmission of sensory afferent signals (e.g. neurotransmitters or neuromodulators) from peripheral to central pain fibres, and therefore have application as therapeutic molecules for the treatment of pain, in particular chronic pain.

It is routine to confirm that a TM binds to a nociceptive sensory afferent. For example, a simple radioactive displacement experiment may be employed in which tissue or cells representative of the nociceptive sensory afferent (for example DRGs) are exposed to labelled (e.g. tritiated) ligand in the presence of an excess of unlabelled ligand. In such an experiment, the relative proportions of non-specific and specific binding may be assessed, thereby allowing confirmation that the ligand binds to the nociceptive sensory afferent target cell. Optionally, the assay may include one or more binding antagonists, and the assay may further comprise observing a loss of ligand binding. Examples of this type of experiment can be found in Hulme, E. C. (1990), Receptor-binding studies, a brief outline, pp. 303-311, In Receptor biochemistry, A Practical Approach, Ed. E. C. Hulme, Oxford University Press.

The fusion proteins of the present invention generally demonstrate a reduced binding affinity (in the region of up to 100-fold) for nociceptive sensory afferent target cells when compared with the corresponding 'free' TM. However, despite this observation, the fusion proteins of the present invention surprisingly demonstrate good efficacy. This can be attributed to two principal features. First, the non-cytotoxic protease component is catalytic—thus, the therapeutic effect of a few such molecules is rapidly amplified. Secondly, the receptors present on the nociceptive sensory afferents need only act as a gateway for entry of the therapeutic, and need not necessarily be stimulated to a level required in order to achieve a ligand-receptor mediated pharmacological response. Accordingly, the fusion proteins of the present invention may be administered at a dosage that is much lower that would be employed for other types of analgesic molecules such as NSAIDS, morphine, and gabapentin. The latter molecules are typically administered at high microgram to milligram (even up to hundreds of milligram) quantities, whereas the fusion proteins of the present invention may be administered at much lower dosages, typically at least 10-fold lower, and more typically at 100-fold lower.

The TM preferably comprises a maximum of 50 amino acid residues, more preferably a maximum of 40 amino acid residues, particularly preferably a maximum of 30 amino acid residues, and most preferably a maximum of 20 amino acid residues.

Opioids represent a preferred group of TMs of the present invention. Within this family of peptides is included enkephalins (met and leu), endomorphins 1 and 2, β-endorphin and dynorphin. Opioid peptides are frequently used in the clinic to modify the activity to nociceptors, and other cells involved in the pain response. As exemplified by the three-step World Health Organisation Analgesic Ladder, opioids have entry points into the pharmacological treatment of chronic cancer and non-cancer pain at all three stages, underlining their importance to the treatment of pain. Reference to opioids embraces fragments, variants and derivatives thereof, which retain the ability to bind to nociceptive sensory afferents.

The TM of the invention can also be a molecule that acts as an "agonist" at one or more of the receptors present on a nociceptive sensory afferent, more particularly on a primary nociceptive afferent. Conventionally, an agonist has been considered any molecule that can either increase or decrease activities within a cell, namely any molecule that simply causes an alteration of cell activity. For example, the conventional meaning of an agonist would include a chemical substance capable of combining with a receptor on a cell and initiating a reaction or activity, or a drug that induces an active response by activating receptors, whether the response is an increase or decrease in cellular activity.

However, for the purposes of this invention, an agonist is more specifically defined as a molecule that is capable of stimulating the process of exocytic fusion in a target cell, which process is susceptible to inhibition by a protease (or fragment thereof) capable of cleaving a protein of the exocytic fusion apparatus in said target cell.

Accordingly, the particular agonist definition of the present invention would exclude many molecules that would be conventionally considered as agonists. For example, nerve growth factor (NGF) is an agonist in respect of its ability to promote neuronal differentiation via binding to a TrkA receptor. However, NGF is not an agonist when assessed by the above criteria because it is not a principal inducer of exocytic fusion. In addition, the process that NGF stimulates (i.e. cell differentiation) is not susceptible to inhibition by the protease activity of a non-cytotoxic toxin molecule.

The agonist properties of a TM that binds to a receptor on a nociceptive afferent can be confirmed using the methods described in Example 10.

In a preferred embodiment of the invention, the target for the TM is the $ORL_1$ receptor. This receptor is a member of the G-protein-coupled class of receptors, and has a seven transmembrane domain structure. The properties of the $ORL_1$ receptor are discussed in detail in Mogil & Pasternak (2001), *Pharmacological Reviews*, Vol. 53, No. 3, pages 381-415.

In one embodiment, the TM is a molecule that binds (preferably that specifically binds) to the $ORL_1$ receptor. More preferably, the TM is an "agonist" of the $ORL_1$ receptor. The term "agonist" in this context is defined as above.

The agonist properties of a TM that binds to an $ORL_1$ receptor can be confirmed using the methods described in Example 10. These methods are based on previous experiments [see Inoue et al. 1998 [Proc. Natl. Acad. Sci., 95, 10949-10953]), which confirm that the natural agonist of the $ORL_1$ receptor, nociceptin, causes the induction of substance P release from nociceptive primary afferent neurons. This is supported by the fact that:

the nociceptin-induced responses are abolished by specific NK1 receptor (the substance P receptor) antagonists; and pre-treatment of the cells with capsaicin (which depletes substance P from small diameter primary afferent neurons) attenuates the nociceptin-induced responses.

Similarly, Inoue et al. confirm that an intraplantar injection of botulinum neurotoxin type A abolishes the nociceptin-induced responses. Since it is known that BoNT inhibits the release of substance P from primary afferent neurons (Welch et al., 2000, Toxicon, 38, 245-258), this confirms the link between nociceptin-$ORL_1$ interaction and subsequent release of substance P.

Thus, a TM can be said to have agonist activity at the $ORL_1$ receptor if the TM causes an induction in the release of substance P from a nociceptive sensory afferent neuron (see Example 10).

In a particularly preferred embodiment of the invention, the TM is nociceptin—the natural ligand for the $ORL_1$ receptor. Nociceptin targets the $ORL_1$ receptor with high affinity. Examples of other preferred TMs include:

| Code | Sequence | Ref. | SEQ ID NO. |
|---|---|---|---|
| Nociceptin 1-17 | FGGFTGARKSARKLANQ | [1] | 37, 38 |
| Nociceptin 1-11 | FGGFTGARKSA | [1] | 39, 40 |
| Nociceptin [Y10]1-11 | FGGFTGARKYA | [1] | 41, 42 |
| Nociceptin [Y11]1-11 | FGGFTGARKSY | [1] | 43, 44 |
| Nociceptin [Y14]1-17 | FGGFTGARKSARKYANQ | [1] | 45, 46 |
| Nociceptin 1-13 | FGGFTGARKSARK | [2] | 47, 48 |
| Nociceptin [R14K15] 1-17 (also known in this specification as "variant" nociceptin) | FGGFTGARKSARKRKNQ | [3, 4] | 49, 50 |

-continued

| Code | Sequence | Ref. | SEQ ID NO. |
|---|---|---|---|
| Peptide agonist | Peptide agonists from combinatorial library approach | [5] | — |

[1] Mogil & Pasternak, 2001, Pharmacol. Rev., 53, 381-415
[2] Maile et al., 2003, Neurosci. Lett., 350, 190-192
[3] Rizzi et al., 2002, J. Pharmacol. Exp. Therap., 300, 57-63
[4] Okada et al., 2000, Biochem. Biophys. Res. Commun., 278, 493-498
[5] Dooley et al:, 1997, J Pharmacol Exp Ther. 283(2), 735-41.

The above-identified "variant" TM demonstrates particularly good binding affinity (when compared with natural nociceptin) for nociceptive sensory afferents. This is surprising as the amino acid modifications occur at a position away from the N-terminus of the TM. Moreover, the modifications are almost at the C-terminus of the TM, which in turn is attached to a large polypeptide sequence (i.e. the translocation domain). Generally speaking, a TM-containing fusion protein will demonstrate an approximate 100-fold reduction in binding ability vis-à-vis the TM per se. The above-mentioned "variant" TM per se demonstrates an approximate 3- to 10-fold increase in binding ability for a nociceptive sensory afferent (e.g. via the ORL1 receptor) vis-à-vis natural nociceptin. Thus, a "variant" TM-containing fusion might be expected to demonstrate an approximate 10-fold reduction in binding ability for a nociceptive sensory afferent (e.g. via the ORL1 receptor) vis-à-vis 'free' nociceptin. However, the present inventors have demonstrated that such "variant" TM-containing fusion proteins demonstrate a binding ability that (most surprisingly) closely mirrors that of 'free' nociceptin— see FIG. 14.

In the context of the present invention, the term opioid or an agonist of the $ORL_1$ receptor (such as nociceptin, or any one of the peptides listed in the table above) embraces molecules having at least 70%, preferably at least 80%, more preferably at least 90%, and most preferably at least 95% homology with said opioid or agonist. The agonist homologues retain the agonist properties of nociceptin at the $ORL_1$ receptor, which may be tested using the methods provided in Example 10. Similarly, an opioid homologue substantially retains the binding function of the opioid with which it shows high homology.

The invention also encompasses fragments, variants, and derivatives of any one of the TMs described above. These fragments, variants, and derivatives substantially retain the properties that are ascribed to said TMs.

In addition to the above-mentioned opioid and non-opioid classes of TMs, a variety of other polypeptides are suitable for targeting the conjugates of the present invention to nociceptive sensory afferents (e.g. to nociceptors). In this regard, particular reference is made to galanin and derivatives of galanin. Galanin receptors are found pre- and post-synaptically in DRGs (Liu & Hokfelt, (2002), Trends Pharm. Sci., 23(10), 468-74), and are enhanced in expression during neuropathic pain states. Proteinase-activated receptors (PARs) are also a preferred group of TMs of the present invention, most particularly PAR-2. It is known that agonists of PAR-2 induce/elicit acute inflammation, in part via a neurogenic mechanism. PAR2 is expressed by primary spinal afferent neurons, and PAR2 agonists stimulate release of substance P (SP) and calcitonin gene-related peptide (CGRP) in peripheral tissues A particularly preferred set of TMs of the present invention includes:

| Ligand | Reference |
|---|---|
| Nociceptin | Guerrini, et al., (1997) J. Med. Chem., 40, pp. 1789-1793 |
| β-endorphin | Blanc, et al., (1983) J. Biol. Chem., 258(13), pp. 8277-8284 |
| Endomorphin-1; Endomorphin-2 | Zadina, et al., (1997). Nature, 386, pp. 499-502 |
| Dynorphin | Fields & Basbaum (2002) Chapter 11, In The Textbook of Pain, Wall & Melzack eds. |
| Met-enkephalin | Fields & Basbaum (2002) Chapter 11, In The Textbook of Pain, Wall & Melzack eds. |
| Leu-enkephalin | Fields & Basbaum (2002) Chapter 11, In The Textbook of Pain, Wall & Melzack eds. |
| Galanin | Xu et al., (2000) Neuropeptides, 34 (3&4), 137-147 |
| PAR-2 peptide | Vergnolle et al., (2001) Nat. Med., 7(7), 821-826 |

The protease cleavage site of the present invention allows cleavage (preferably controlled cleavage) of the fusion protein at a position between the non-cytotoxic protease component and the TM component. It is this cleavage reaction that converts the fusion protein from a single chain polypeptide into a disulphide-linked, di-chain polypeptide.

According to a preferred embodiment of the present invention, the TM binds via a domain or amino acid sequence that is located away from the C-terminus of the TM. For example, the relevant binding domain may include an intra domain or an amino acid sequence located towards the middle (i.e. of the linear peptide sequence) of the TM. Preferably, the relevant binding domain is located towards the N-terminus of the TM, more preferably at or near to the N-terminus.

In one embodiment, the single chain polypeptide fusion may include more than one proteolytic cleavage site. However, where two or more such sites exist, they are different, thereby substantially preventing the occurrence of multiple cleavage events in the presence of a single protease. In another embodiment, it is preferred that the single chain polypeptide fusion has a single protease cleavage site.

The protease cleavage sequence(s) may be introduced (and/or any inherent cleavage sequence removed) at the DNA level by conventional means, such as by site-directed mutagenesis. Screening to confirm the presence of cleavage sequences may be performed manually or with the assistance of computer software (e.g. the MapDraw program by DNASTAR, Inc.).

Whilst any protease cleavage site may be employed, the following are preferred:

| | | |
|---|---|---|
| Enterokinase | (DDDDK↓) | (SEQ ID NO: 89) |
| Factor Xa | (IEGR↓/IDGR↓) | (SEQ ID NO: 90) |
| TEV (Tobacco Etch virus) | (ENLYFQ↓G) | (SEQ ID NO: 91) |
| Thrombin | (LVPR↓GS) | (SEQ ID NO: 92) |
| PreScission | (LEVLFQ↓GP). | (SEQ ID NO: 93) |

Also embraced by the term protease cleavage site is an intein, which is a self-cleaving sequence. The self-splicing reaction is controllable, for example by varying the concentration of reducing agent present.

In use, the protease cleavage site is cleaved and the N-terminal region (preferably the N-terminus) of the TM becomes exposed. The resulting polypeptide has a TM with an N-terminal domain or an intra domain that is substantially free from the remainder of the conjugate. This arrangement ensures that the N-terminal component (or intra domain) of the TM may interact directly with a Binding Site on a target cell.

In a preferred embodiment, the TM and the protease cleavage site are distanced apart in the fusion protein by at most 10 amino acid residues, more preferably by at most 5 amino acid residues, and most preferably by zero amino acid residues. Thus, following cleavage of the protease cleavage site, a conjugate is provided with a TM that has an N-terminal domain that is substantially free from the remainder of the conjugate. This arrangement ensures that the N-terminal component of the Targeting Moiety may interact directly with a Binding Site on a target cell.

One advantage associated with the above-mentioned activation step is that the TM only becomes susceptible to N-terminal degradation once proteolytic cleavage of the fusion protein has occurred. In addition, the selection of a specific protease cleavage site permits selective activation of the polypeptide fusion into a di-chain conformation.

Construction of the single-chain polypeptide fusion of the present invention places the protease cleavage site between the TM and the non-cytotoxic protease component.

It is preferred that, in the single-chain fusion, the TM is located between the protease cleavage site and the translocation component. This ensures that the TM is attached to the translocation domain (i.e. as occurs with native clostridial holotoxin), though in the case of the present invention the order of the two components is reversed vis-à-vis native holotoxin. A further advantage with this arrangement is that the TM is located in an exposed loop region of the fusion protein, which has minimal structural effects on the conformation of the fusion protein. In this regard, said loop is variously referred to as the linker, the activation loop, the inter-domain linker, or just the surface exposed loop (Schiavo et al 2000, Phys. Rev., 80, 717-766; Turton et al., 2002, Trends Biochem. Sci., 27, 552-558).

In one embodiment, in the single chain polypeptide, the non-cytotoxic protease component and the translocation component are linked together by a disulphide bond. Thus, following cleavage of the protease cleavage site, the polypeptide assumes a di-chain conformation, wherein the protease and translocation components remain linked together by the disulphide bond. To this end, it is preferred that the protease and translocation components are distanced apart from one another in the single chain fusion protein by a maximum of 100 amino acid residues, more preferably a maximum of 80 amino acid residues, particularly preferably by a maximum of 60 amino acid residues, and most preferably by a maximum of 50 amino acid residues.

In one embodiment, the non-cytotoxic protease component forms a disulphide bond with the translocation component of the fusion protein. For example, the amino acid residue of the protease component that forms the disulphide bond is located within the last 20, preferably within the last 10 C-terminal amino acid residues of the protease component. Similarly, the amino acid residue within the translocation component that forms the second part of the disulphide bond may be located within the first 20, preferably within the first 10 N-terminal amino acid residues of the translocation component.

Alternatively, in the single chain polypeptide, the non-cytotoxic protease component and the TM may be linked together by a disulphide bond. In this regard, the amino acid residue of the TM that forms the disulphide bond is preferably located away from the N-terminus of the TM, more preferably towards to C-terminus of the TM.

In one embodiment, the non-cytotoxic protease component forms a disulphide bond with the TM component of the fusion protein. In this regard, the amino acid residue of the protease component that forms the disulphide bond is preferably located within the last 20, more preferably within the last 10 C-terminal amino acid residues of the protease component. Similarly, the amino acid residue within the TM component that forms the second part of the disulphide bond is preferably located within the last 20, more preferably within the last 10 C-terminal amino acid residues of the TM.

The above disulphide bond arrangements have the advantage that the protease and translocation components are arranged in a manner similar to that for native clostridial neurotoxin. By way of comparison, referring to the primary amino acid sequence for native clostridial neurotoxin, the respective cysteine amino acid residues are distanced apart by between 8 and 27 amino acid residues—taken from Popoff, M R & Marvaud, J-C, 1999, Structural & genomic features of clostridial neurotoxins, Chapter 9, in The Comprehensive Sourcebook of Bacterial Protein Toxins. Ed. Alouf & Freer:

| Serotype[1] | Sequence | 'Native' length between C-C | SEQ ID NO: |
|---|---|---|---|
| BoNT/A1 | CVRGIITSKTKS----LDKGYNKALNDLC | 23 | 94 |
| BoNT/A2 | CVRGIIPFKTKS----LDEGYNKALNDLC | 23 | 95 |
| BoNT/B | CKSVKAPG------------------IC | 8 | 96 |
| BoNT/C | CHKAIDGRS----------LYNKTLDC | 15 | 97 |

-continued

| Serotype[1] | Sequence | 'Native' length between C-C | SEQ ID NO: |
|---|---|---|---|
| BoNT/D | CLRLTK--------------NSRDDSTC | 12 | 98 |
| BoNT/E | CKN-IVSVK----------GIRK---SIC | 13 | 99 |
| BoNT/F | CKS-VIPRK----------GTKAPP-RLC | 15 | 100 |
| BoNT/G | CKPVMYKNT----------GKSE----QC | 13 | 101 |
| TeNT | CKKIIPPTNIRENLYNRTASLTDLGGELC | 27 | 102 |

[1]Information from proteolytic strains only

The fusion protein may comprise one or more purification tags, which are located N-terminal to the protease component and/or C-terminal to the translocation component.

Whilst any purification tag may be employed, the following are preferred:
His-tag (e.g. 6×histidine), preferably as a C-terminal and/or N-terminal tag
MBP-tag (maltose binding protein), preferably as an N-terminal tag
GST-tag (glutathione-S-transferase), preferably as an N-terminal tag
His-MBP-tag, preferably as an N-terminal tag
GST-MBP-tag, preferably as an N-terminal tag
Thioredoxin-tag, preferably as an N-terminal tag
CBD-tag (Chitin Binding Domain), preferably as an N-terminal tag.

According to a further embodiment of the present invention, one or more peptide spacer molecules may be included in the fusion protein. For example, a peptide spacer may be employed between a purification tag and the rest of the fusion protein molecule (e.g. between an N-terminal purification tag and a protease component of the present invention; and/or between a C-terminal purification tag and a translocation component of the present invention). A peptide spacer may be also employed between the TM and translocation components of the present invention.

A variety of different spacer molecules may be employed in any of the fusion proteins of the present invention. Examples of such spacer molecules include those illustrated in FIGS. 28 and 29. Particular mention here is made to GS15, GS20, GS25, and Hx27—see FIGS. 28 and 29.

The present inventors have unexpectedly found that the fusion proteins (eg. CPNv/A) of the present invention may demonstrate an improved binding activity for nociceptive sensory afferents when the size of the spacer is selected so that (in use) the C-terminus of the TM and the N-terminus of the translocation component are separated from one another by 40-105 angstroms, preferably by 50-100 angstroms, and more preferably by 50-90 angstroms. In another embodiment, the preferred spacers have an amino acid sequence of 11-29 amino acid residues, preferably 15-27 amino acid residues, and more preferably 20-27 amino acid residues. Suitable spacers may be routinely identified and obtained according to Crasto, C. J. and Feng, J. A. (2000) May, 13(5), pp. 309-312— see also the website with the address: fccc./edu/research/labs/feng/limker.html.

In accordance with a second aspect of the present invention, there is provided a DNA sequence that encodes the above-mentioned single chain polypeptide. In a preferred aspect of the present invention, the DNA sequence is prepared as part of a DNA vector, wherein the vector comprises a promoter and terminator.

In a preferred embodiment, the vector has a promoter selected from:

| Promoter | Induction Agent | Typical Induction Condition |
|---|---|---|
| Tac (hybrid) | IPTG | 0.2 mM (0.05-2.0 mM) |
| AraBAD | L-arabinose | 0.2% (0.002-0.4%) |
| T7-lac operator | IPTG | 0.2 mM (0.05-2.0 mM) |

The DNA construct of the present invention is preferably designed in silico, and then synthesised by conventional DNA synthesis techniques.

The above-mentioned DNA sequence information is optionally modified for codon-biasing according to the ultimate host cell (e.g. *E. coli*) expression system that is to be employed.

The DNA backbone is preferably screened for any inherent nucleic acid sequence, which when transcribed and translated would produce an amino acid sequence corresponding to the protease cleave site encoded by the second peptide-coding sequence. This screening may be performed manually or with the assistance of computer software (e.g. the MapDraw program by DNASTAR, Inc.).

According to a further embodiment of the present invention, there is provided a method of preparing a non-cytotoxic agent, comprising:
 a. contacting a single-chain polypeptide fusion protein of the invention with a protease capable of cleaving the protease cleavage site;
 b. cleaving the protease cleavage site, and thereby forming a di-chain fusion protein.

This aspect provides a di-chain polypeptide, which generally mimics the structure of clostridial holotoxin. In more detail, the resulting di-chain polypeptide typically has a structure wherein:
 a. the first chain comprises the non-cytotoxic protease, or a fragment thereof, which protease or protease fragment is capable of cleaving a protein of the exocytic fusion apparatus of a nociceptive sensory afferent;
 b. the second chain comprises the TM and the translocation domain that is capable of translocating the protease or protease fragment from within an endosome, across the endosomal membrane and into the cytosol of the nociceptive sensory afferent; and
 the first and second chains are disulphide linked together.

According to a further aspect of the present invention, there is provided use of a single chain or di-chain polypeptide of the invention, for the manufacture of a medicament for treating, preventing or ameliorating pain.

According to a related aspect, there is provided a method of treating, preventing or ameliorating pain in a subject, comprising administering to said patient a therapeutically effective amount of a single chain or di-chain polypeptide of the invention.

The present invention addresses a wide range of pain conditions, in particular chronic pain conditions. Preferred conditions include cancerous and non-cancerous pain, inflammatory pain and neuropathic pain. The opioid-fusions of the present application are particularly suited to addressing inflammatory pain, though may be less suited to addressing neuropathic pain. The galanin-fusions are more suited to addressing neuropathic pain.

In use, the polypeptides of the present invention are typically employed in the form of a pharmaceutical composition in association with a pharmaceutical carrier, diluent and/or excipient, although the exact form of the composition may be tailored to the mode of administration. Administration is preferably to a mammal, more preferably to a human.

The polypeptides may, for example, be employed in the form of a sterile solution for intra-articular administration or intra-cranial administration. Spinal injection (e.g. epidural or intrathecal) is preferred.

The dosage ranges for administration of the polypeptides of the present invention are those to produce the desired therapeutic effect. It will be appreciated that the dosage range required depends on the precise nature of the components, the route of administration, the nature of the formulation, the age of the patient, the nature, extent or severity of the patient's condition, contraindications, if any, and the judgement of the attending physician.

Suitable daily dosages are in the range 0.0001-1 mg/kg, preferably 0.0001-0.5 mg/kg, more preferably 0.002-0.5 mg/kg, and particularly preferably 0.004-0.5 mg/kg. The unit dosage can vary from less that 1 microgram to 30 mg, but typically will be in the region of 0.01 to 1 mg per dose, which may be administered daily or preferably less frequently, such as weekly or six monthly.

A particularly preferred dosing regimen is based on 2.5 ng of fusion protein (e.g. CPNv/A) as the 1× dose. In this regard, preferred dosages are in the range 1×-100× (i.e. 2.5-250 ng). This dosage range is significantly lower (i.e. at least 10-fold, typically 100-fold lower) than would be employed with other types of analgesic molecules such as NSAIDS, morphine, and gabapentin. Moreover, the above-mentioned difference is considerably magnified when the same comparison is made on a molar basis—this is because the fusion proteins of the present invention have a considerably greater Mw than do conventional 'small' molecule therapeutics.

Wide variations in the required dosage, however, are to be expected depending on the precise nature of the components, and the differing efficiencies of various routes of administration.

Variations in these dosage levels can be adjusted using standard empirical routines for optimisation, as is well understood in the art.

Compositions suitable for injection may be in the form of solutions, suspensions or emulsions, or dry powders which are dissolved or suspended in a suitable vehicle prior to use.

Fluid unit dosage forms are typically prepared utilising a pyrogen-free sterile vehicle. The active ingredients, depending on the vehicle and concentration used, can be either dissolved or suspended in the vehicle.

In preparing administrable solutions, the polypeptides can be dissolved in a vehicle, the solution being made isotonic if necessary by addition of sodium chloride and sterilised by filtration through a sterile filter using aseptic techniques before filling into suitable sterile vials or ampoules and sealing. Alternatively, if solution stability is adequate, the solution in its sealed containers may be sterilised by autoclaving.

Advantageously additives such as buffering, solubilising, stabilising, preservative or bactericidal, suspending or emulsifying agents may be dissolved in the vehicle.

Dry powders which are dissolved or suspended in a suitable vehicle prior to use may be prepared by filling pre-sterilised drug substance and other ingredients into a sterile container using aseptic technique in a sterile area.

Alternatively the polypeptides and other ingredients may be dissolved in an aqueous vehicle, the solution is sterilized by filtration and distributed into suitable containers using aseptic technique in a sterile area. The product is then freeze dried and the containers are sealed aseptically.

Parenteral suspensions, suitable for intramuscular, subcutaneous or intradermal injection, are prepared in substantially the same manner, except that the sterile components are suspended in the sterile vehicle, instead of being dissolved and sterilisation cannot be accomplished by filtration. The components may be isolated in a sterile state or alternatively it may be sterilised after isolation, e.g. by gamma irradiation.

Advantageously, a suspending agent for example polyvinylpyrrolidone is included in the composition/s to facilitate uniform distribution of the components.

DEFINITIONS SECTION

Targeting Moiety (TM) means any chemical structure associated with an agent that functionally interacts with a Binding Site to cause a physical association between the agent and the surface of a target cell. In the context of the present invention, the target cell is a nociceptive sensory afferent. The term TM embraces any molecule (i.e. a naturally occurring molecule, or a chemically/physically modified variant thereof) that is capable of binding to a Binding Site on the target cell, which Binding Site is capable of internalisation (e.g. endosome formation)—also referred to as receptor-mediated endocytosis. The TM may possess an endosomal membrane translocation function, in which case separate TM and Translocation Domain components need not be present in an agent of the present invention.

The TM of the present invention binds (preferably specifically binds) to a nociceptive sensory afferent (e.g. a primary nociceptive afferent). In this regard, specifically binds means that the TM binds to a nociceptive sensory afferent (e.g. a primary nociceptive afferent) with a greater affinity than it binds to other neurons such as non-nociceptive afferents, and/or to motor neurons (i.e. the natural target for clostridial neurotoxin holotoxin). The term "specifically binding" can also mean that a given TM binds to a given receptor, for example the $ORL_1$ receptor, with a binding affinity (Ka) of $10^6$ $M^{-1}$ or greater, preferably $10^7$ $M^{-1}$ or greater, more preferably $10^8$ $M^{-1}$ or greater, and most preferably, $10^9$ $M^{-1}$ or greater.

For the purposes of this invention, an agonist is defined as a molecule that is capable of stimulating the process of exocytic fusion in a target cell, which process is susceptible to inhibition by a protease (or fragment thereof) capable of cleaving a protein of the exocytic fusion apparatus in said target cell.

Accordingly, the particular agonist definition of the present invention would exclude many molecules that would be conventionally considered as agonists.

For example, nerve growth factor (NGF) is an agonist in respect of its ability to promote neuronal differentiation via binding to a TrkA receptor. However, NGF is not an agonist when assessed by the above criteria because it is not a principal inducer of exocytic fusion. In addition, the process that NGF stimulates (i.e. cell differentiation) is not susceptible to inhibition by the protease activity of a non-cytotoxic toxin molecule.

The term "fragment", when used in relation to a protein, means a peptide having at least thirty-five, preferably at least twenty-five, more preferably at least twenty, and most preferably at least ten amino acid residues of the protein in question.

The term "variant", when used in relation to a protein, means a peptide or peptide fragment of the protein that contains one or more analogues of an amino acid (e.g. an unnatural amino acid), or a substituted linkage.

The term "derivative", when used in relation to a protein, means a protein that comprises the protein in question, and a further peptide sequence. The further peptide sequence should preferably not interfere with the basic folding and thus conformational structure of the original protein. Two or more peptides (or fragments, or variants) may be joined together to form a derivative. Alternatively, a peptide (or fragment, or variant) may be joined to an unrelated molecule (e.g. a second, unrelated peptide). Derivatives may be chemically synthesized, but will be typically prepared by recombinant nucleic acid methods. Additional components such as lipid, and/or polysaccharide, and/or polyketide components may be included.

Throughout this specification, reference to the "$ORL_1$ receptor" embraces all members of the $ORL_1$ receptor family. Members of the $ORL_1$ receptor family typically have a seven transmembrane domain structure and are coupled to G-proteins of the $G_i$ and $G_0$ families. A method for determining the G-protein-stimulating activity of ligands of the $ORL_1$ receptor is given in Example 12. A method for measuring reduction in cellular cAMP levels following $ORL_1$ activation is given in Example 11. A further characteristic of members of the $ORL_1$ receptor family is that they are typically able to bind nociceptin (the natural ligand of $ORL_1$). As an example, all alternative splice variants of the $ORL_1$ receptor, are members of the $ORL_1$ receptor family.

The term non-cytotoxic means that the protease molecule in question does not kill the target cell to which it has been re-targeted.

The protease of the present invention embraces all naturally-occurring non-cytotoxic proteases that are capable of cleaving one or more proteins of the exocytic fusion apparatus in eukaryotic cells.

The protease of the present invention is preferably a bacterial protease (or fragment thereof). More preferably the bacterial protease is selected from the genera *Clostridium* or *Neisseria* (e.g. a clostridial L-chain, or a neisserial IgA protease preferably from *N. gonorrhoeae*).

The present invention also embraces modified non-cytotoxic proteases, which include amino acid sequences that do not occur in nature and/or synthetic amino acid residues, so long as the modified proteases still demonstrate the above-mentioned protease activity.

The protease of the present invention preferably demonstrates a serine or metalloprotease activity (e.g. endopeptidase activity). The protease is preferably specific for a SNARE protein (e.g. SNAP-25, synaptobrevin/VAMP, or syntaxin).

Particular mention is made to the protease domains of neurotoxins, for example the protease domains of bacterial neurotoxins. Thus, the present invention embraces the use of neurotoxin domains, which occur in nature, as well as recombinantly prepared versions of said naturally-occurring neurotoxins.

Exemplary neurotoxins are produced by clostridia, and the term clostridial neurotoxin embraces neurotoxins produced by *C. tetani* (TeNT), and by *C. botulinum* (BoNT) serotypes A-G, as well as the closely related BoNT-like neurotoxins produced by *C. baratii* and *C. butyricum*. The above-mentioned abbreviations are used throughout the present specification. For example, the nomenclature BoNT/A denotes the source of neurotoxin as BoNT (serotype A). Corresponding nomenclature applies to other BoNT serotypes.

The term L-chain fragment means a component of the L-chain of a neurotoxin, which fragment demonstrates a metalloprotease activity and is capable of proteolytically cleaving a vesicle and/or plasma membrane associated protein involved in cellular exocytosis.

A Translocation Domain is a molecule that enables translocation of a protease (or fragment thereof) into a target cell such that a functional expression of protease activity occurs within the cytosol of the target cell. Whether any molecule (e.g. a protein or peptide) possesses the requisite translocation function of the present invention may be confirmed by any one of a number of conventional assays.

For example, Shone C. (1987) describes an in vitro assay employing liposomes, which are challenged with a test molecule. Presence of the requisite translocation function is confirmed by release from the liposomes of $K^+$ and/or labelled NAD, which may be readily monitored [see Shone C. (1987) Eur. J. Biochem; vol. 167(1): pp. 175-180].

A further example is provided by Blaustein R. (1987), which describes a simple in vitro assay employing planar phospholipid bilayer membranes. The membranes are challenged with a test molecule and the requisite translocation function is confirmed by an increase in conductance across said membranes [see Blaustein (1987) FEBS Letts; vol. 226, no. 1: pp. 115-120].

Additional methodology to enable assessment of membrane fusion and thus identification of Translocation Domains suitable for use in the present invention are provided by Methods in Enzymology Vol 220 and 221, Membrane Fusion Techniques, Parts A and B, Academic Press 1993.

The Translocation Domain is preferably capable of formation of ion-permeable pores in lipid membranes under conditions of low pH. Preferably it has been found to use only those portions of the protein molecule capable of pore-formation within the endosomal membrane.

The Translocation Domain may be obtained from a microbial protein source, in particular from a bacterial or viral protein source. Hence, in one embodiment, the Translocation Domain is a translocating domain of an enzyme, such as a bacterial toxin or viral protein.

It is well documented that certain domains of bacterial toxin molecules are capable of forming such pores. It is also known that certain translocation domains of virally expressed membrane fusion proteins are capable of forming such pores. Such domains may be employed in the present invention.

The Translocation Domain may be of a clostridial origin, namely the $H_N$ domain (or a functional component thereof). $H_N$ means a portion or fragment of the H-chain of a clostridial neurotoxin approximately equivalent to the amino-terminal half of the H-chain, or the domain corresponding to that fragment in the intact H-chain. It is preferred that the H-chain substantially lacks the natural binding function of the $H_C$ component of the H-chain. In this regard, the $H_C$ function may be removed by deletion of the $H_C$ amino acid sequence (either at the DNA synthesis level, or at the post-synthesis level by nuclease or protease treatment). Alternatively, the $H_C$ function may be inactivated by chemical or biological treatment. Thus, the H-chain is preferably incapable of binding to the Binding Site on a target cell to which native clostridial neurotoxin (i.e. holotoxin) binds.

In one embodiment, the translocation domain is a $H_N$ domain (or a fragment thereof) of a clostridial neurotoxin. Examples of suitable clostridial Translocation Domains include:

| Botulinum type A neurotoxin | amino acid residues (449-871) |
| Botulinum type B neurotoxin | amino acid residues (441-858) |
| Botulinum type C neurotoxin | amino acid residues (442-866) |
| Botulinum type D neurotoxin | amino acid residues (446-862) |
| Botulinum type E neurotoxin | amino acid residues (423-845) |
| Botulinum type F neurotoxin | amino acid residues (440-864) |
| Botulinum type G neurotoxin | amino acid residues (442-863) |
| Tetanus neurotoxin | amino acid residues (458-879) |

For further details on the genetic basis of toxin production in *Clostridium botulinum* and *C. tetani*, we refer to Henderson et al (1997) in *The Clostridia: Molecular Biology and Pathogenesis, Academic press.*

The term $H_N$ embraces naturally-occurring neurotoxin $H_N$ portions, and modified $H_N$ portions having amino acid sequences that do not occur in nature and/or synthetic amino acid residues, so long as the modified $H_N$ portions still demonstrate the above-mentioned translocation function.

Alternatively, the Translocation Domain may be of a non-clostridial origin (see Table 4). Examples of non-clostridial Translocation Domain origins include, but not be restricted to, the translocation domain of diphtheria toxin [O=Keefe et al., Proc. Natl. Acad. Sci. USA (1992) 89, 6202-6206; Silverman et al., J. Biol. Chem. (1993) 269, 22524-22532; and London, E. (1992) *Biochem. Biophys. Acta.,* 1112, pp. 25-51], the translocation domain of *Pseudomonas* exotoxin type A [Prior et al. Biochemistry (1992) 31, 3555-3559], the translocation domains of anthrax toxin [Blanke et al. Proc. Natl. Acad. Sci. USA (1996) 93, 8437-8442], a variety of fusogenic or hydrophobic peptides of translocating function [Plank et al. J. Biol. Chem. (1994) 269, 12918-12924; and Wagner et al (1992) *PNAS,* 89, pp. 7934-7938], and amphiphilic peptides [Murata et al (1992) *Biochem.,* 31, pp. 1986-1992]. The Translocation Domain may mirror the Translocation Domain present in a naturally-occurring protein, or may include amino acid variations so long as the variations do not destroy the translocating ability of the Translocation Domain.

Particular examples of viral Translocation Domains suitable for use in the present invention include certain translocating domains of virally expressed membrane fusion proteins. For example, Wagner et al. (1992) and Murata et al. (1992) describe the translocation (i.e. membrane fusion and vesiculation) function of a number of fusogenic and amphiphilic peptides derived from the N-terminal region of influenza virus haemagglutinin. Other virally expressed membrane fusion proteins known to have the desired translocating activity are a translocating domain of a fusogenic peptide of Semliki Forest Virus (SFV), a translocating domain of vesicular stomatitis virus (VSV) glycoprotein G, a translocating domain of SER virus F protein and a translocating domain of Foamy virus envelope glycoprotein. Virally encoded Aspike proteins have particular application in the context of the present invention, for example, the E1 protein of SFV and the G protein of the G protein of VSV.

Use of the Translocation Domains listed in Table (below) includes use of sequence variants thereof. A variant may comprise one or more conservative nucleic acid substitutions and/or nucleic acid deletions or insertions, with the proviso that the variant possesses the requisite translocating function. A variant may also comprise one or more amino acid substitutions and/or amino acid deletions or insertions, so long as the variant possesses the requisite translocating function.

| Translocation domain source | Amino acid residues | References |
|---|---|---|
| Diphtheria toxin | 194-380 | Silverman et al., 1994, J. Biol. Chem. 269, 22524-22532 London E., 1992, Biochem. Biophys. Acta., 1113, 25-51 |
| Domain II of pseudomonas exotoxin | 405-613 | Prior et al., 1992, Biochemistry 31, 3555-3559 Kihara & Pastan, 1994, Bioconj Chem. 5, 532-538 |
| Influenza virus haemagglutinin | GLFGAIAGFIENGWE GMIDGWYG, and Variants thereof | Plank et al., 1994, J. Biol. Chem. 269, 12918-12924 Wagner et al., 1992, PNAS, 89, 7934-7938 Murata et al., 1992, Biochemistry 31, 1986-1992 |
| Semliki Forest virus fusogenic protein | Translocation domain | Kielian et al., 1996, J Cell Biol. 134(4), 863-872 |
| Vesicular Stomatitis virus glycoprotein G | 118-139 | Yao et al., 2003, Virology 310(2), 319-332 |
| SER virus F protein | Translocation domain | Seth et al., 2003, J Virol 77(11) 6520-6527 |
| Foamy virus envelope glycoprotein | Translocation domain | Picard-Maureau et al., 2003, J Virol. 77(8), 4722-4730 |

Figures

Figure 2:
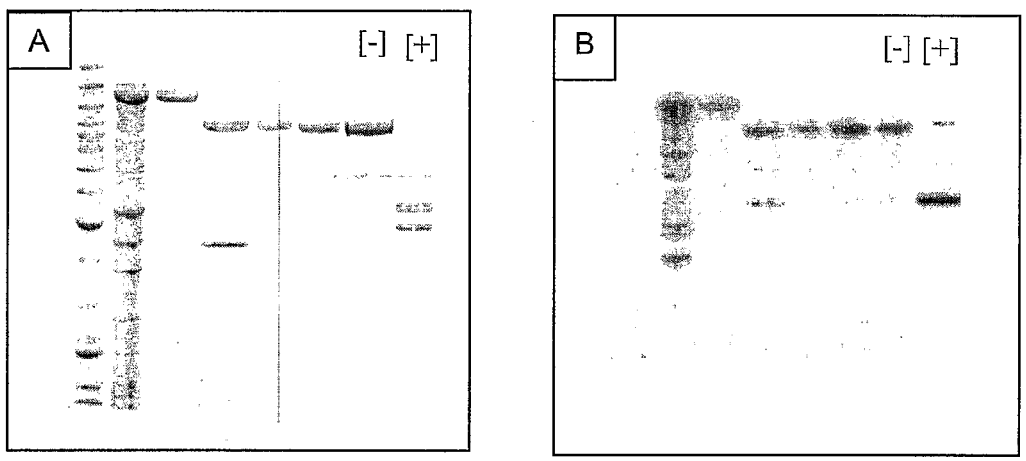
Figure 3:
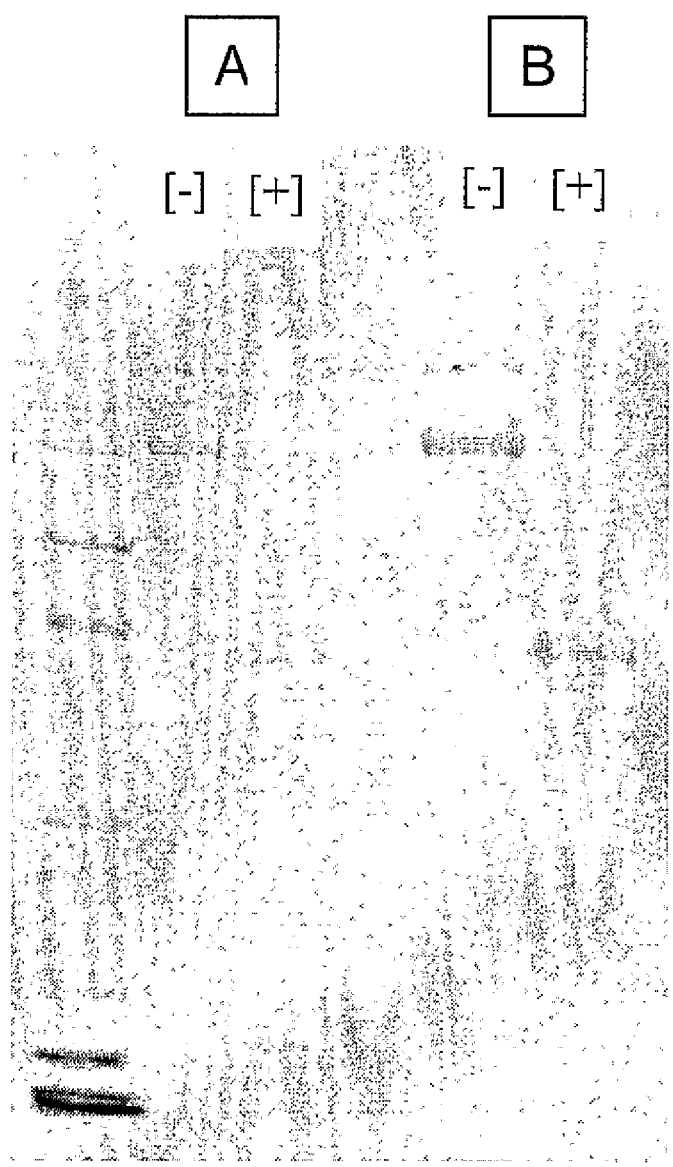

| Figure 1 | Purification of a LC/A-nociceptin-$H_N$/A fusion protein |
| Figure 2 | Purification of a nociceptin-LC/A-$H_N$/A fusion protein |
| Figure 3 | Purification of a LC/C-nociceptin-$H_N$/C fusion protein |

-continued

Figure 4:
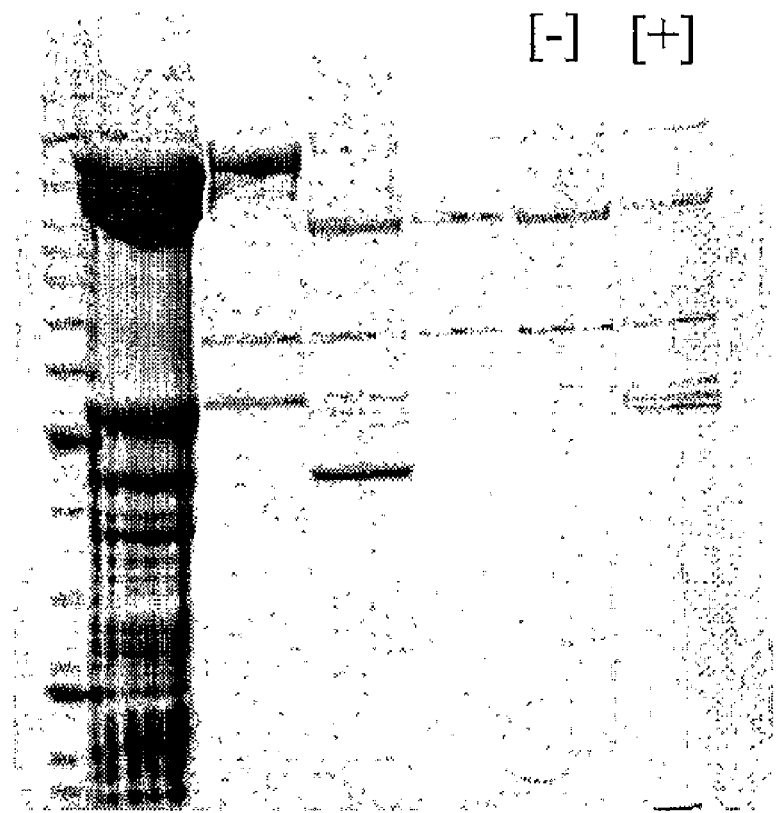
Figure 6:
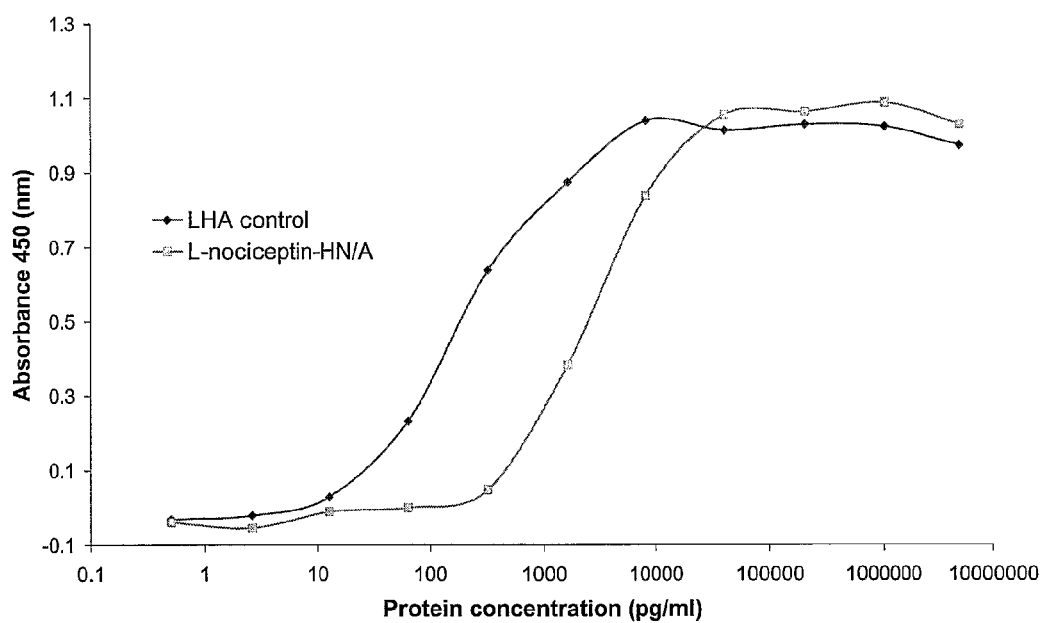
Figure 7:
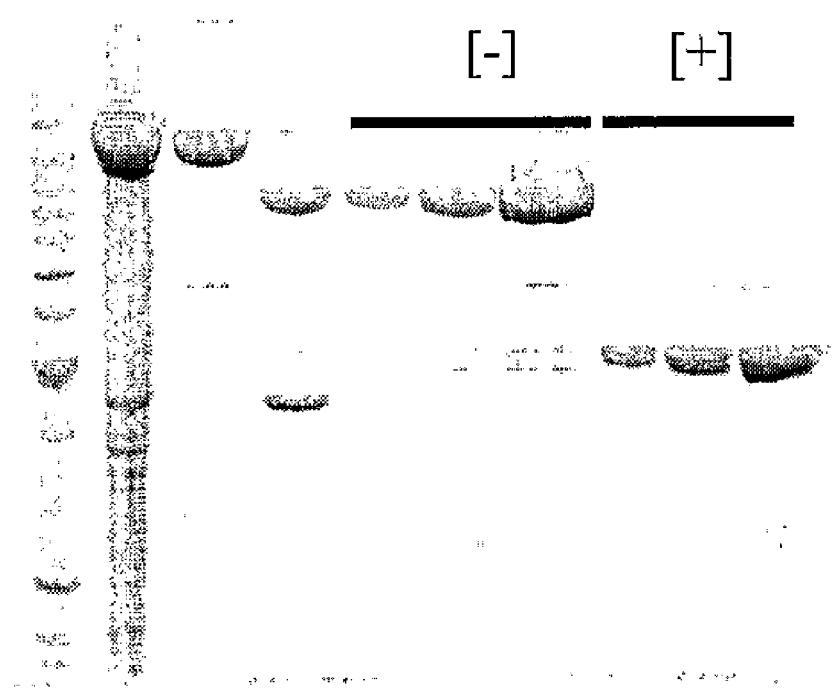
Figure 8:
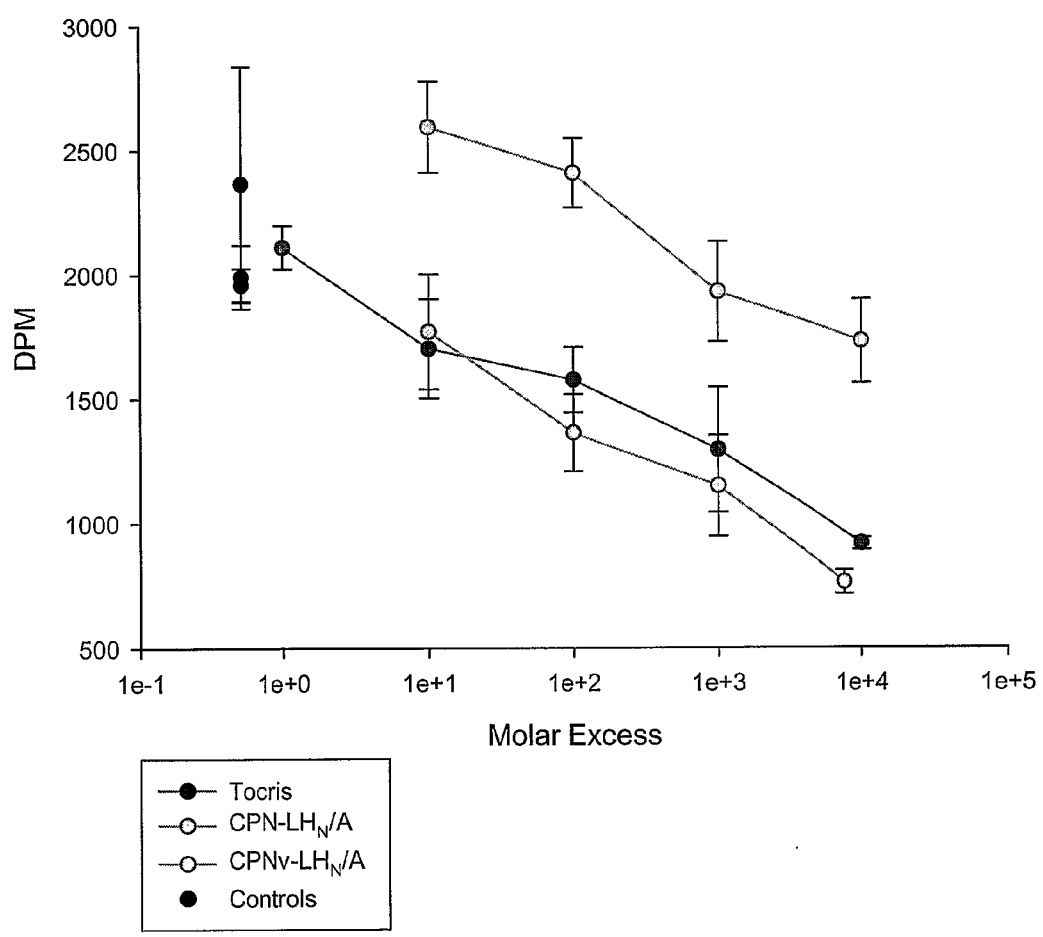
Figure 9:
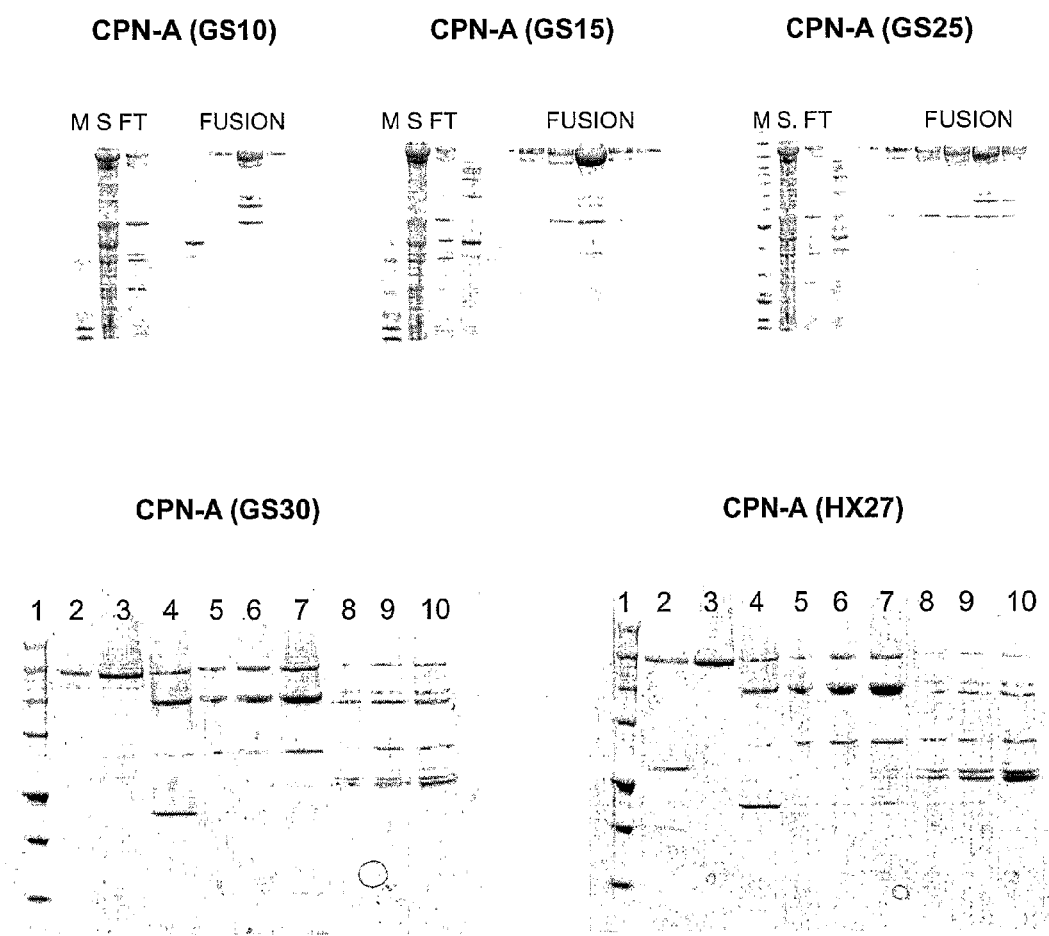
Figure 10:
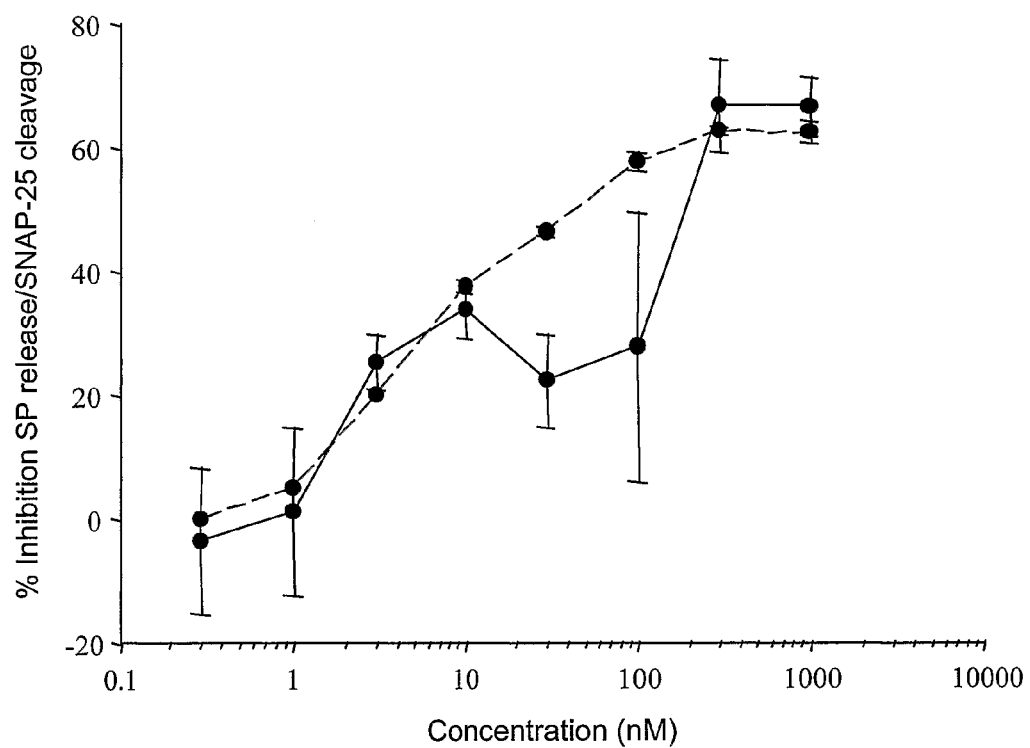
Figure 11:
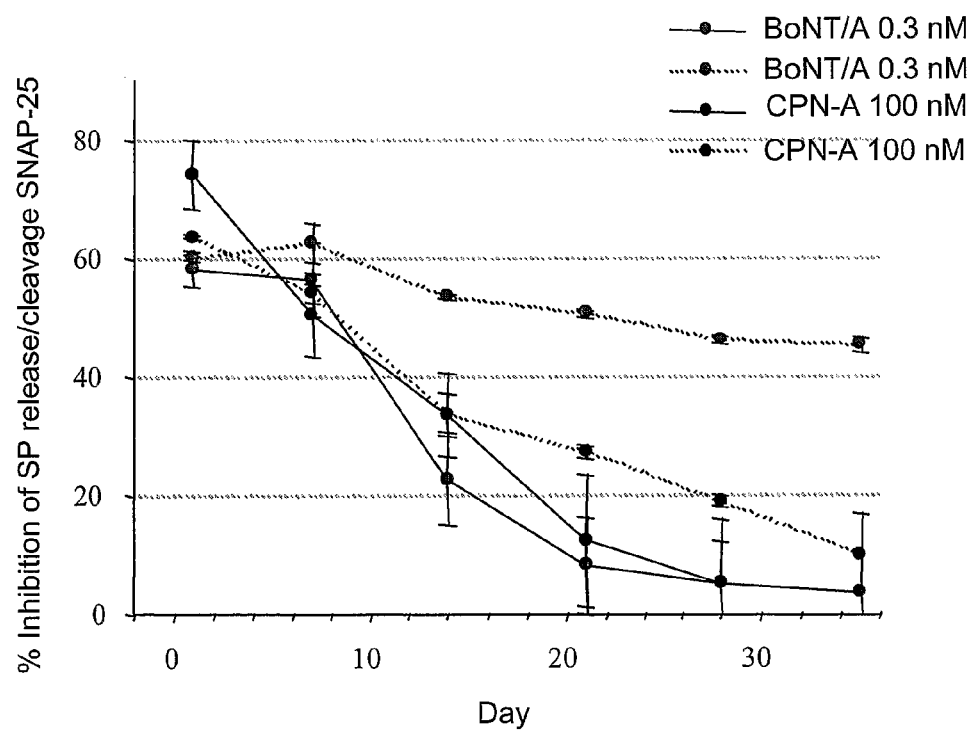
Figure 13:
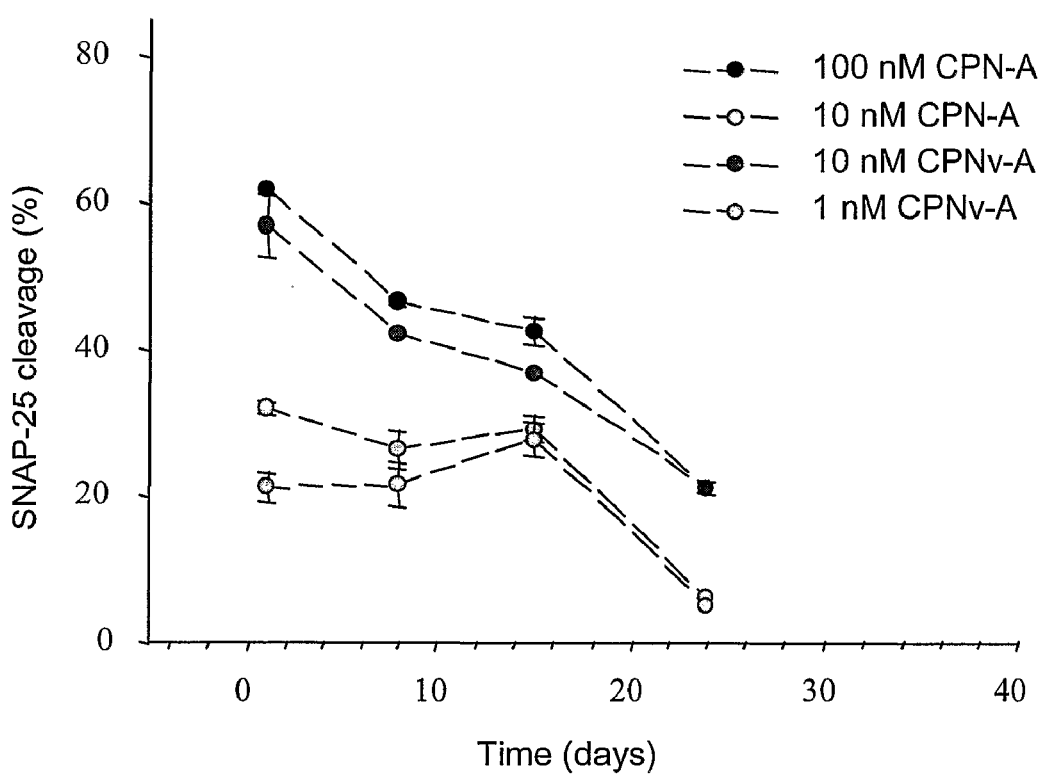
Figure 15:
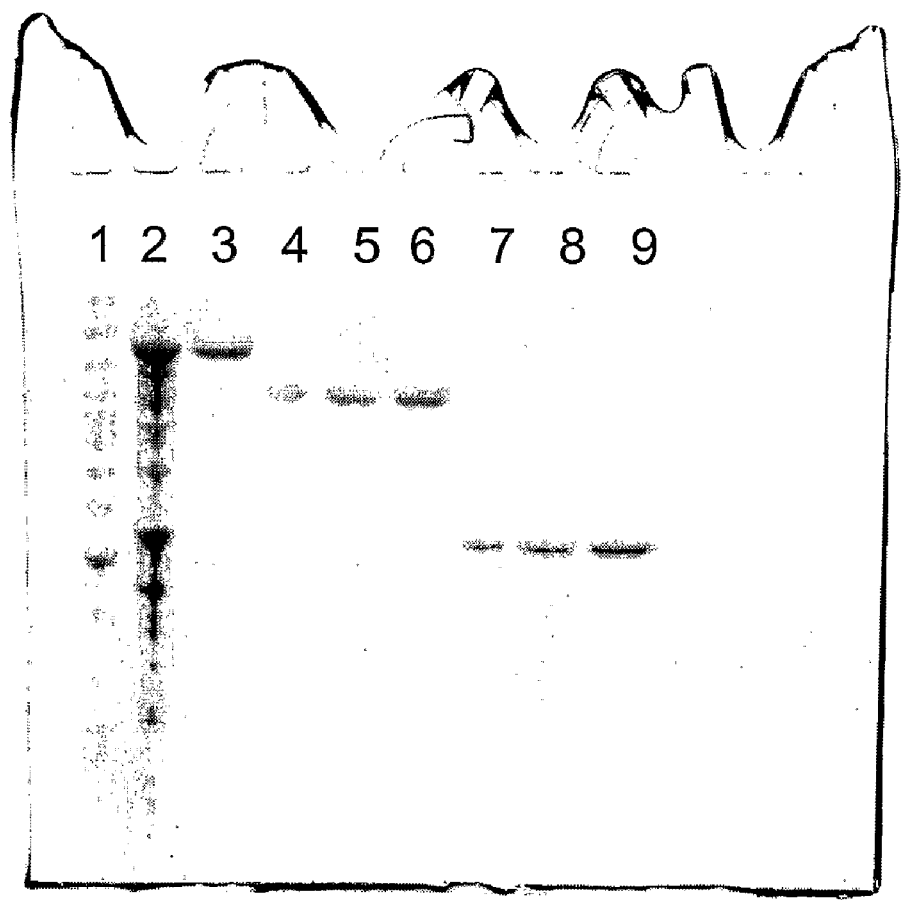
Figure 16:
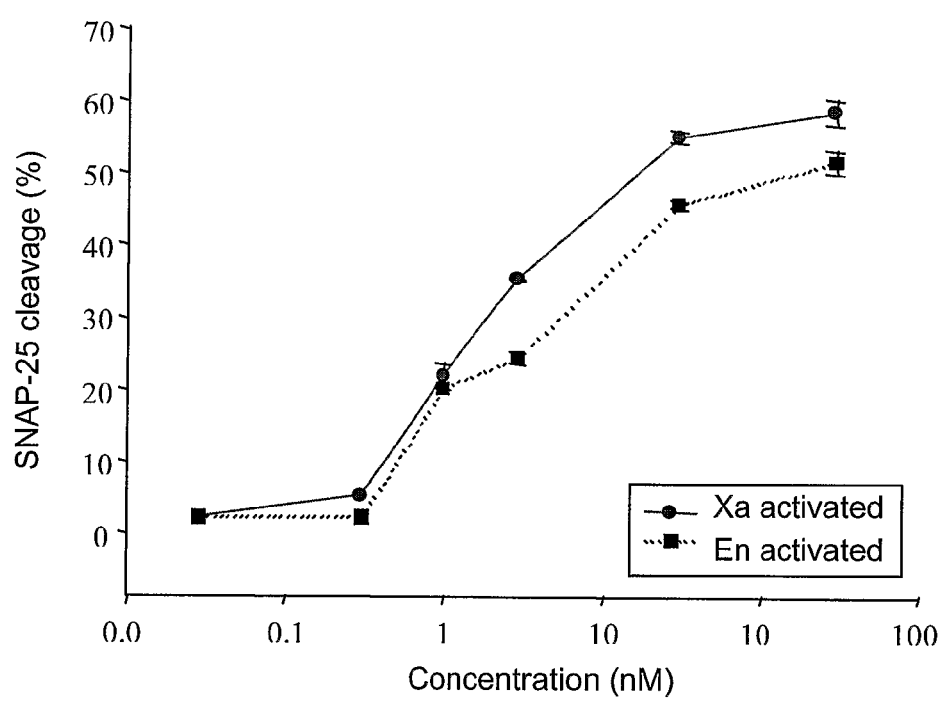
Figure 17:
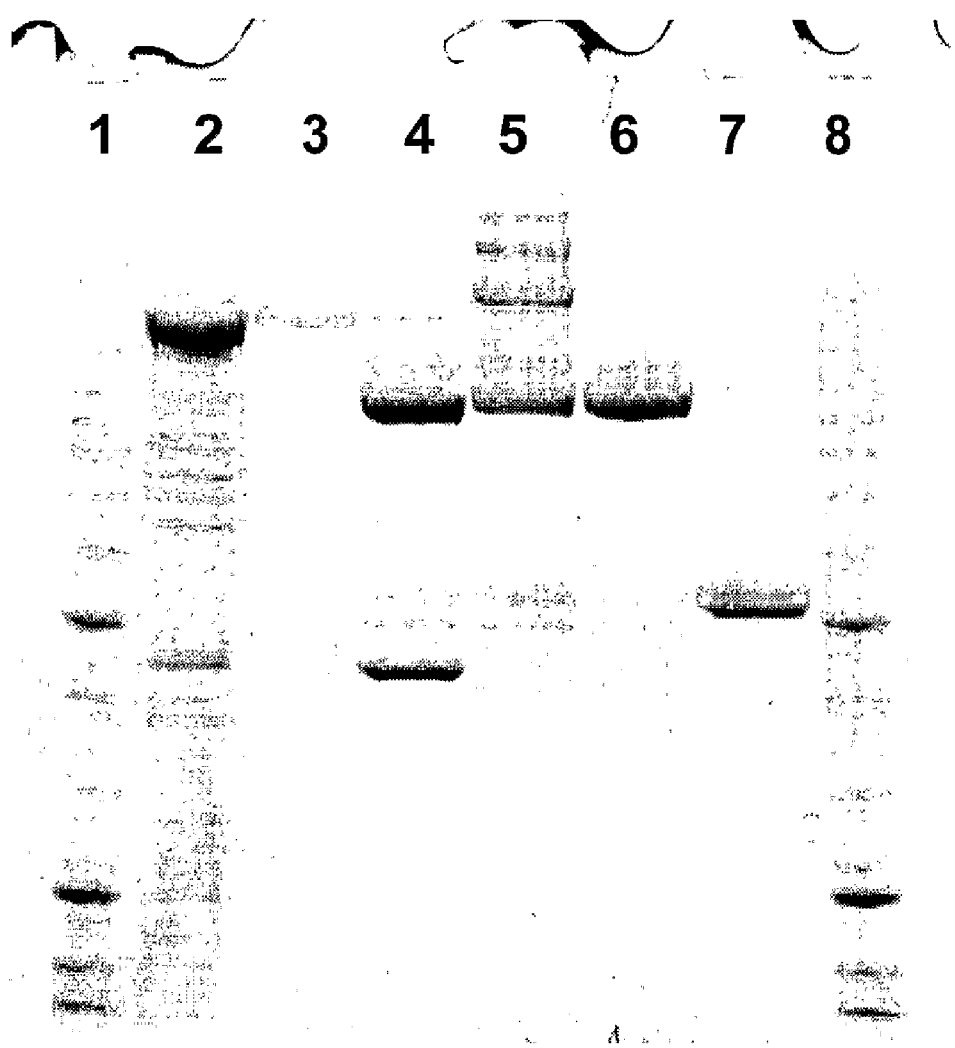
Figure 18:
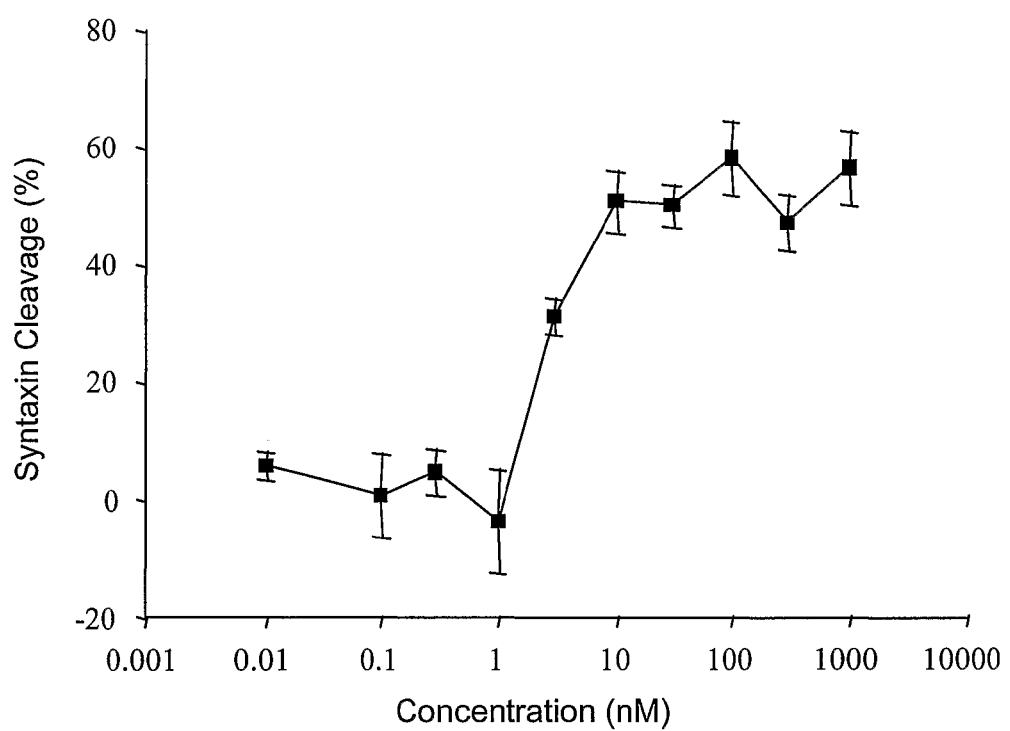
Figure 19:
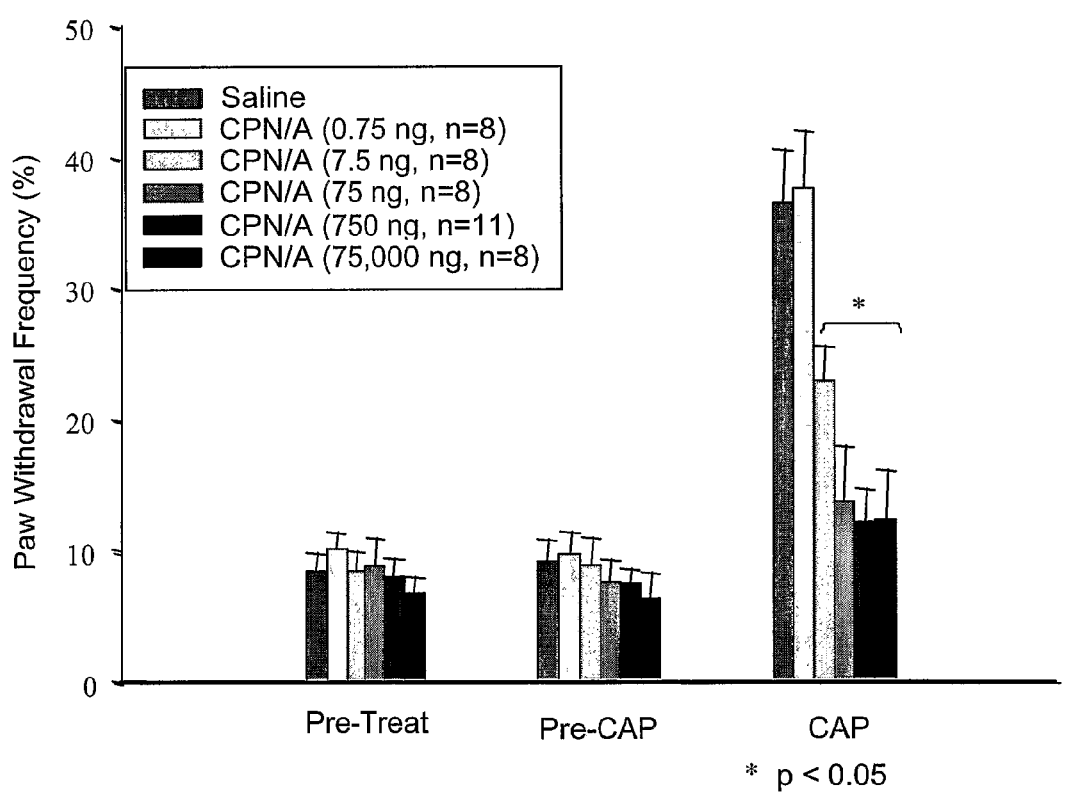
Figure 20:
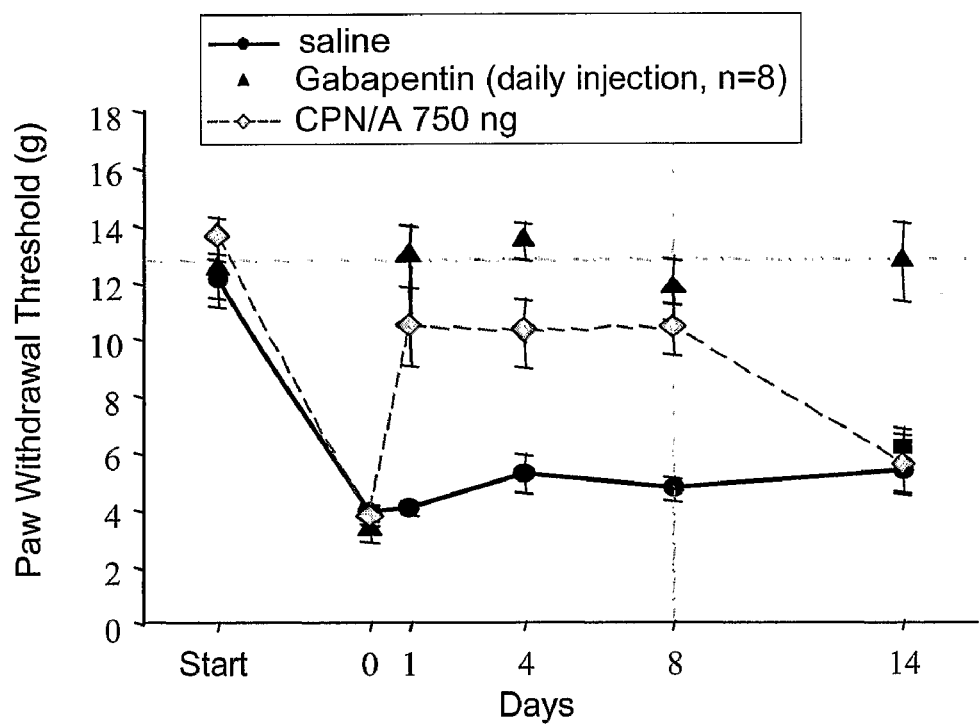
Figure 21:
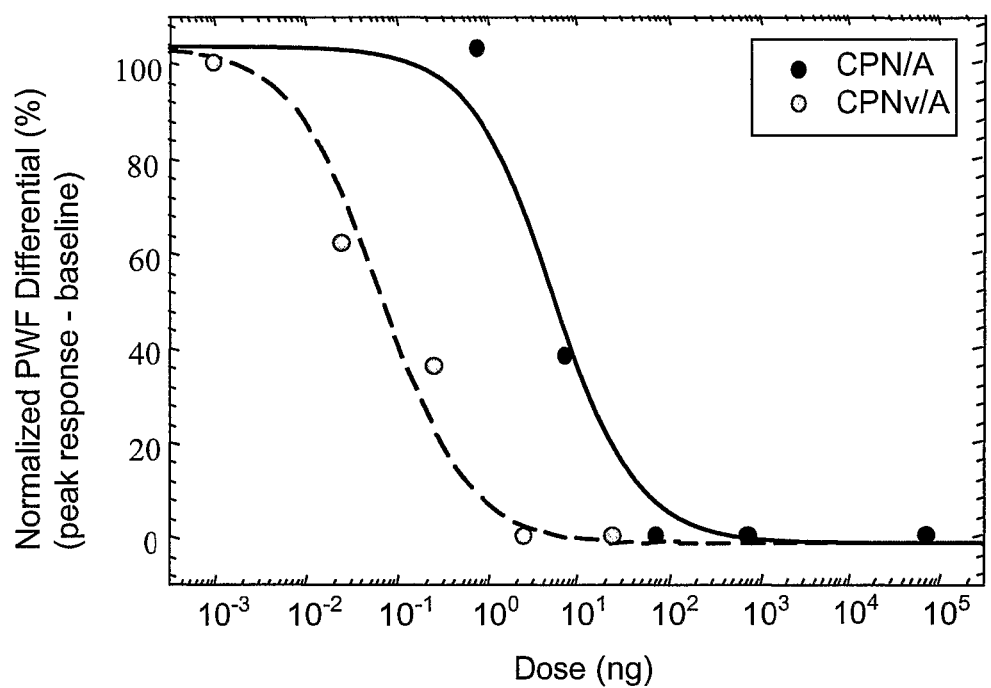
Figure 22:
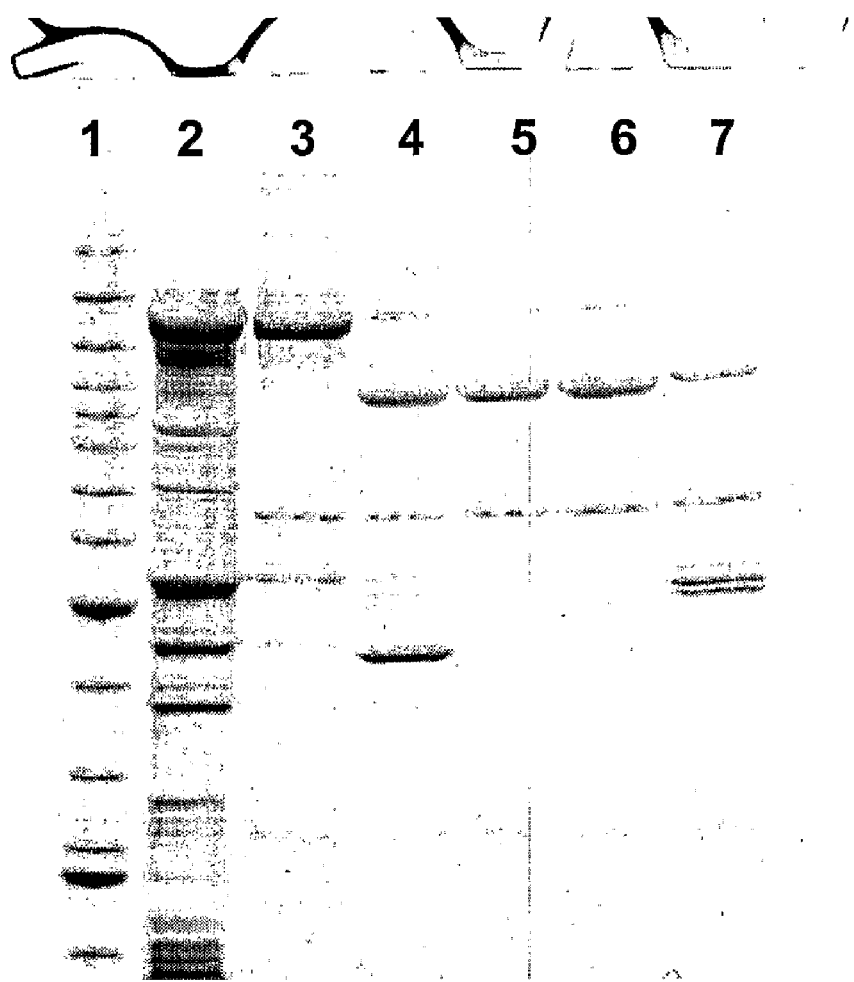
Figure 23:
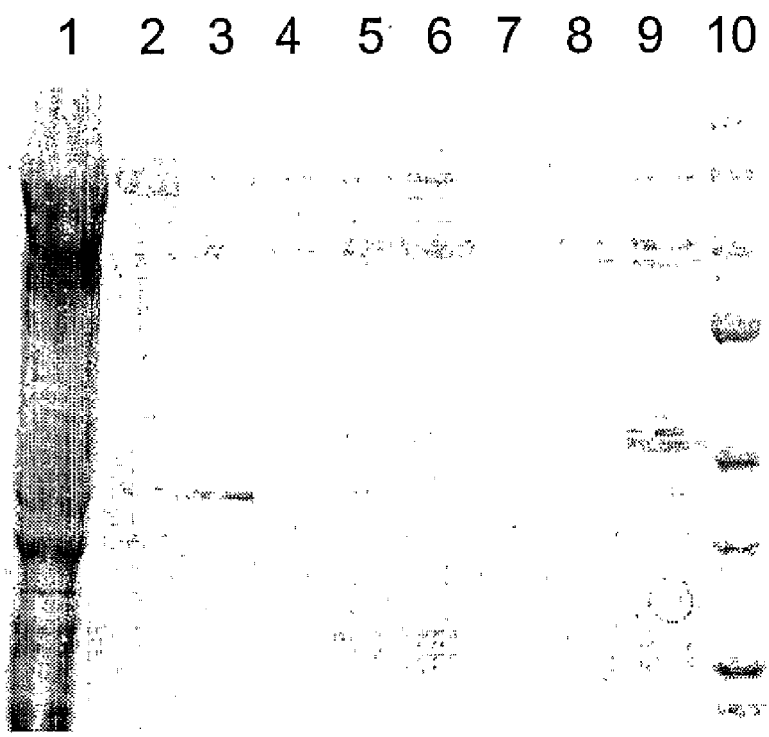
Figure 24:
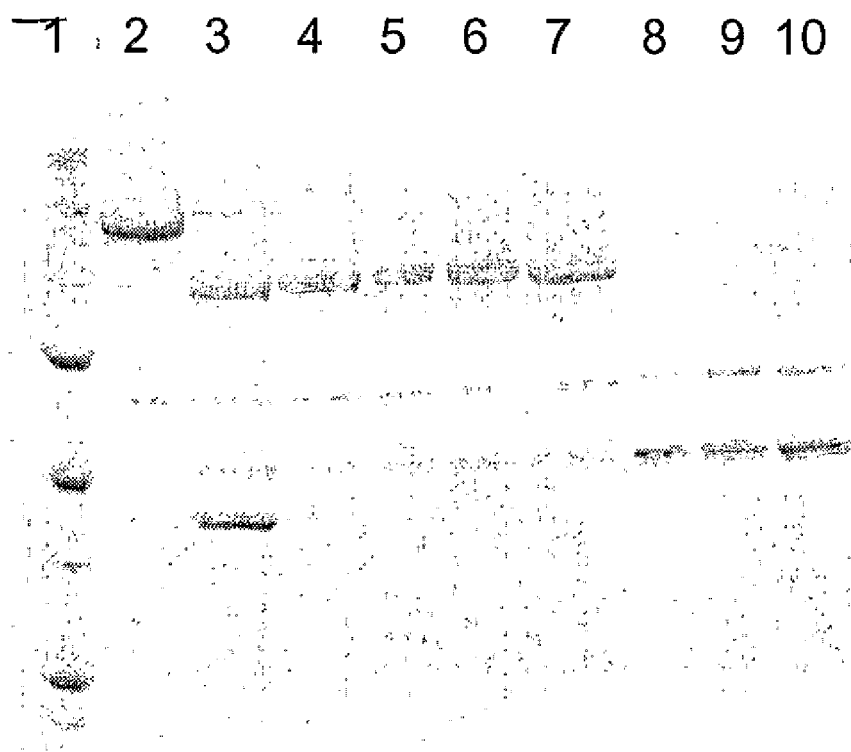
Figure 25:
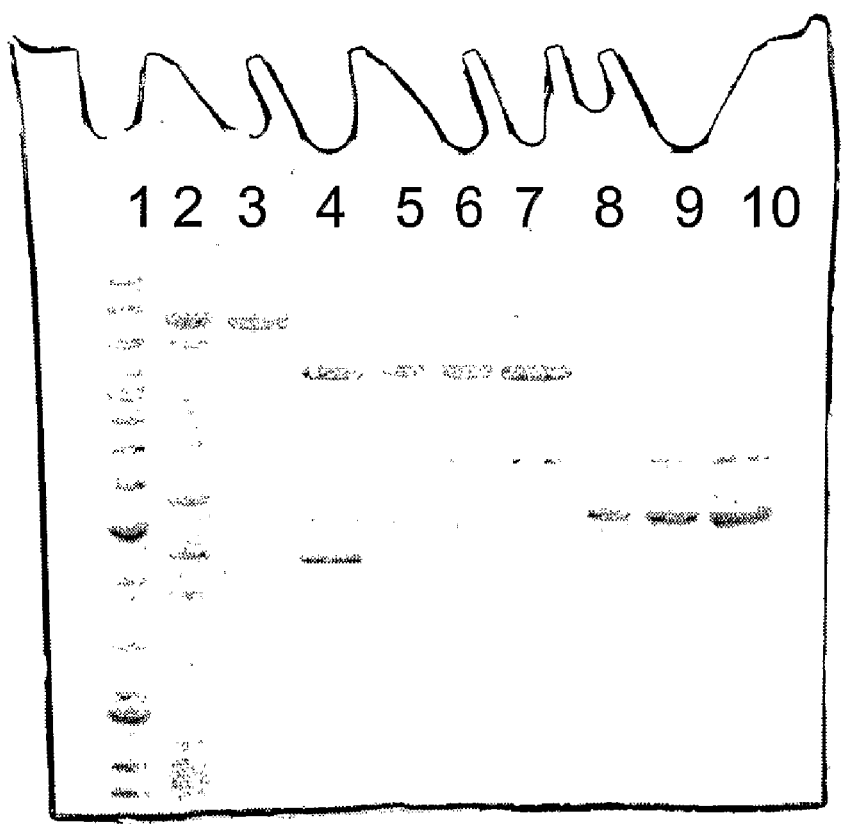
Figure 26:
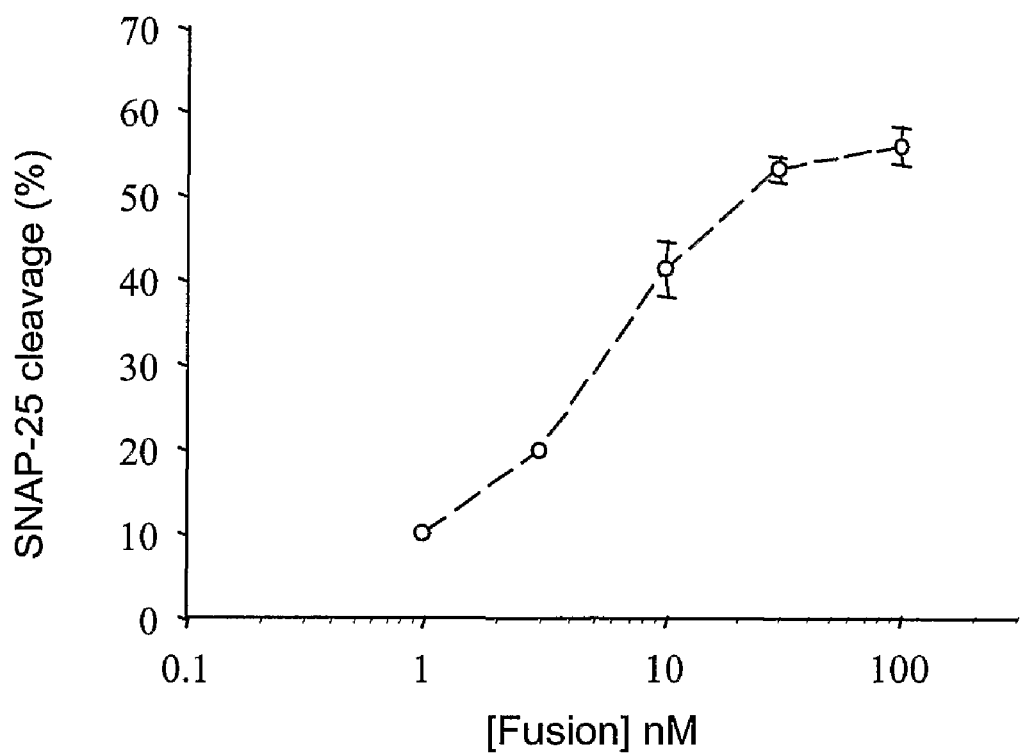
Figure 27:
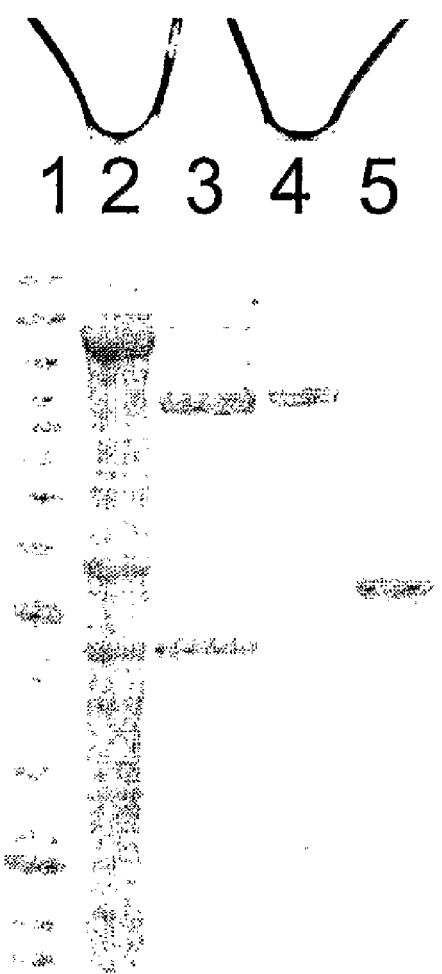
Figure 28:
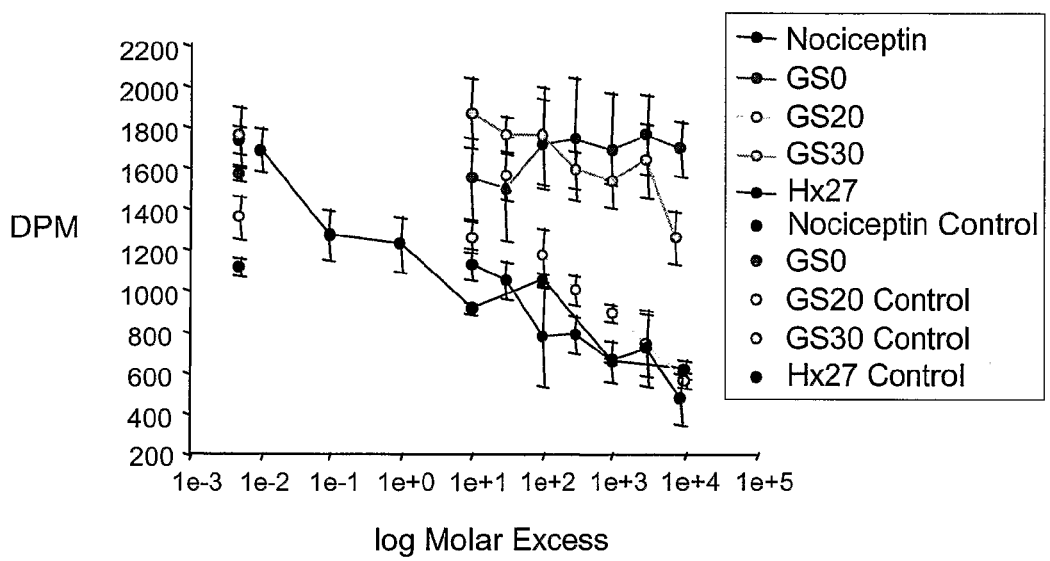
Figure 28:
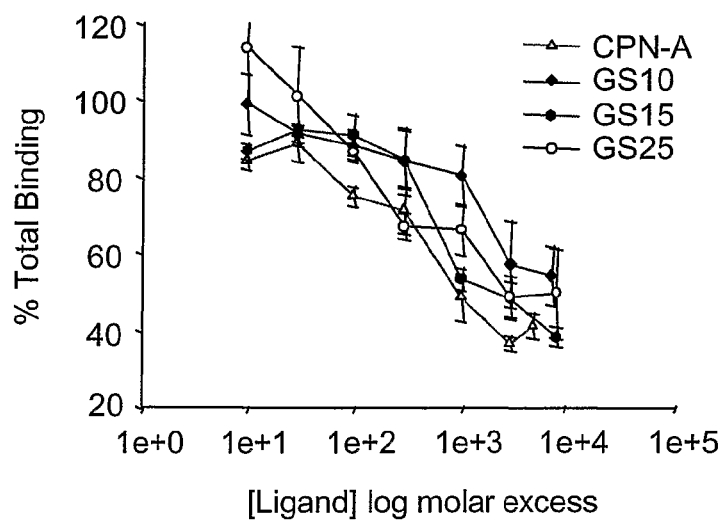
Figure 29:
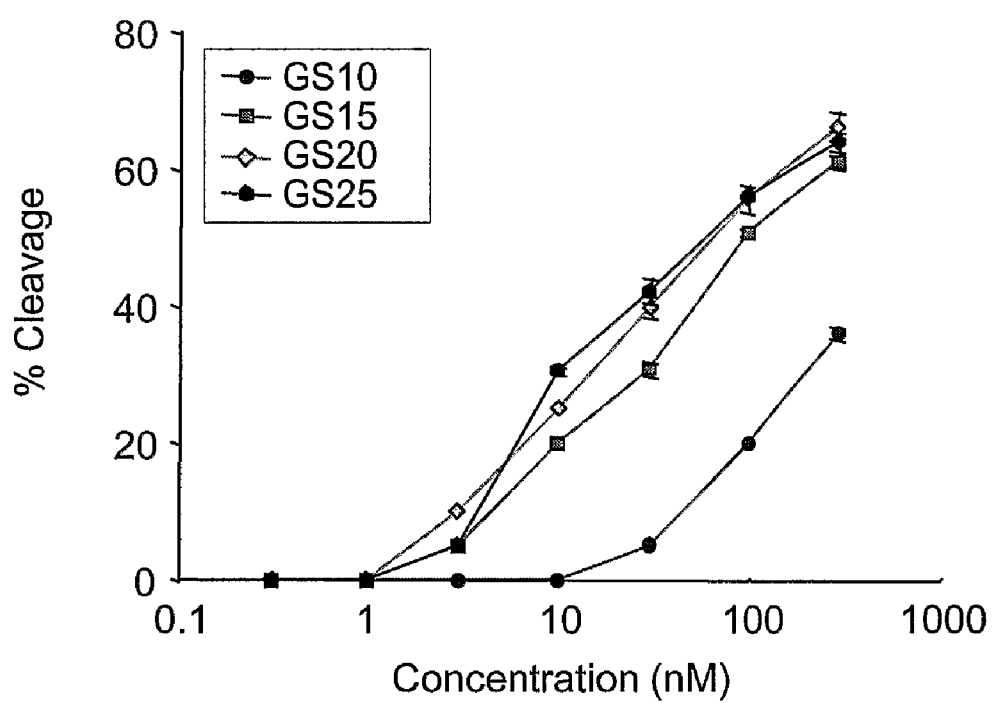

| Figures | |
|---|---|
| Figure 4 | Purification of a LC/A-met enkephalin-H$_N$/A fusion protein |
| Figure 5 | Comparison of binding efficacy of a LC/A-nociceptin-H$_N$/A fusion protein and a nociceptin-LC/A-H$_N$/A fusion protein |
| Figure 6 | In vitro catalytic activity of a LC/A-nociceptin-H$_N$/A fusion protein |
| Figure 7 | Purification of a LC/A-nociceptin variant-H$_N$/A fusion protein |
| Figure 8 | Comparison of binding efficacy of a LC/A-nociceptin-H$_N$/A fusion protein and a LC/A-nociceptin variant-H$_N$/A fusion protein |
| Figure 9 | Expressed/purified LC/A-nociceptin-H$_N$/A fusion protein family with variable spacer length product(s) |
| Figure 10 | Inhibition of SP release and cleavage of SNAP-25 by CPN-A |
| Figure 11 | Inhibition of SP release and cleavage of SNAP-25 over extended time periods after exposure of DRG to CPN-A |
| Figure 12 | Cleavage of SNAP-25 by CPNv-A |
| Figure 13 | Cleavage of SNAP-25 over extended time periods after exposure of DRG to CPNv-A |
| Figure 14 | CPNv-A fusion-mediated displacement of [3H]-nociceptin binding |
| Figure 15 | Expressed/purified CPNv(Ek)-A product |
| Figure 16 | Cleavage of SNAP-25 by CPNv(Ek)-A |
| Figure 17 | Expressed/purified CPNv-C product |
| Figure 18 | Cleavage of syntaxin by CPNv-C |
| Figure 19 | CPN-A efficacy in the Acute Capsaicin-Induced Mechanical Allodynia model |
| Figure 20 | CPN-A efficacy in the Streptozotocin (STZ)-Induced Peripheral Diabetic Neuropathy (Neuropathic Pain) model |
| Figure 21 | CPNv-A efficacy in the Acute Capsaicin-Induced Mechanical Allodynia model |
| Figure 22 | Expressed/purified LC/A-CPLE-H$_N$/A product |
| Figure 23 | Expressed/purified LC/A-CPBE-H$_N$/A product |
| Figure 24 | Expressed/purified CPOP-A product |
| Figure 25 | Expressed/purified CPOPv-A product |
| Figure 26 | In vitro SNAP-25 cleavage in a DRG cell model |
| Figure 27 | Expressed/purified CPNv-A-FXa-HT (removable his-tag) |
| Figure 28 | In vitro efficacy of LC/A-nociceptin-H$_N$/A fusion proteins with variable spacer length, as assessed by ligand competition assay |
| Figure 29 | In vitro efficacy of LC/A-nociceptin-H$_N$/A fusion proteins with variable spacer length, as assessed by in vitro SNAP-25 cleavage |

The Figures are now described in more detail.

FIG. 1—Purification of a LC/A-nociceptin-H$_N$/A fusion protein

Using the methodology outlined in Example 9, a LC/A-nociceptin-H$_N$/A fusion protein was purified from *E. coli* BL21 cells. Briefly, the soluble products obtained following cell disruption were applied to a nickel-charged affinity capture column. Bound proteins were eluted with 100 mM imidazole, treated with Factor Xa to activate the fusion protein and remove the maltose-binding protein (MBP) tag, then re-applied to a second nickel-charged affinity capture column. Samples from the purification procedure were assessed by SDS-PAGE (Panel A) and Western blotting (Panel B). Anti-nociceptin antisera (obtained from Abcam) were used as the primary antibody for Western blotting. The final purified material in the absence and presence of reducing agent is identified in the lanes marked [−] and [+] respectively.

FIG. 2—Purification of a nociceptin-LC/A-H$_N$/A fusion protein

Using the methodology outlined in Example 9, a nociceptin-LC/A-H$_N$/A fusion protein was purified from *E. coli* BL21 cells. Briefly, the soluble products obtained following cell disruption were applied to a nickel-charged affinity capture column. Bound proteins were eluted with 100 mM imidazole, treated with Factor Xa to activate the fusion protein and remove the maltose-binding protein (MBP) tag, then re-applied to a second nickel-charged affinity capture column. Samples from the purification procedure were assessed by SDS-PAGE (Panel A) and Western blotting (Panel B). Anti-nociceptin antisera (obtained from Abcam) were used as the primary antibody for Western blotting. The final purified material in the absence and presence of reducing agent is identified in the lanes marked [−] and [+] respectively.

FIG. 3—Purification of a LC/C-nociceptin-H$_N$/C fusion protein

Using the methodology outlined in Example 9, an LC/C-nociceptin-H$_N$/C fusion protein was purified from *E. coli* BL21 cells. Briefly, the soluble products obtained following cell disruption were applied to a nickel-charged affinity capture column. Bound proteins were eluted with 100 mM imidazole, treated with Factor Xa to activate the fusion protein and remove the maltose-binding protein (MBP) tag, then re-applied to a second nickel-charged affinity capture column. Samples from the purification procedure were assessed by SDS-PAGE (Panel A) and Western blotting (Panel B). Anti-nociceptin antisera (obtained from Abcam) were used as the primary antibody for Western blotting. The final purified material in the absence and presence of reducing agent is identified in the lanes marked [−] and [+] respectively.

FIG. 4—Purification of a LC/A-met enkephalin-H$_N$/A fusion protein

Using the methodology outlined in Example 9, an LC/A-met enkephalin-H$_N$/A fusion protein was purified from *E. coli* BL21 cells. Briefly, the soluble products obtained following cell disruption were applied to a nickel-charged affinity capture column. Bound proteins were eluted with 100 mM imidazole, treated with Factor Xa to activate the fusion protein and remove the maltose-binding protein (MBP) tag, then re-applied to a second nickel-charged affinity capture column. Samples from the purification procedure were assessed by SDS-PAGE. The final purified material in the absence and presence of reducing agent is identified in the lanes marked [−] and [+] respectively.

FIG. 5—Comparison of binding efficacy of a LC/A-nociceptin-H$_N$/A fusion protein and a nociceptin-LC/A-H$_N$/A fusion protein The ability of nociceptin fusions to bind to the ORL$_1$ receptor was assessed using a simple competition-based assay. Primary cultures of dorsal root ganglia (DRG) were exposed to varying concentrations of test material in the presence of 1 nM [3H]-nociceptin. The reduction in specific binding of the radiolabelled ligand was assessed by scintillation counting, and plotted in comparison to the efficacy of unlabelled ligand (Tocris nociceptin). It is clear that the LC/A-nociceptin-H$_N$/A fusion is far superior to the nociceptin-LC/A-H$_N$/A fusion at interacting with the ORL$_1$ receptor.

FIG. 6—In vitro catalytic activity of a LC/A-nociceptin-H$_N$/A fusion protein

The in vitro endopeptidase activity of the purified LC/A-nociceptin-H$_N$/A fusion protein was determined essentially as described in Chaddock et al 2002, Prot. Express Purif. 25, 219-228. Briefly, SNAP-25 peptide immobilised to an ELISA plate was exposed to varying concentrations of fusion protein for 1 hour at 37° C. Following a series of washes, the amount of cleaved SNAP-25 peptide was quantified by reactivity with a specific antisera.

FIG. 7—Purification of a LC/A-nociceptin variant-H$_N$/A fusion protein

Using the methodology outlined in Example 9, an LC/A-nociceptin variant-H$_N$/A fusion protein was purified from *E. coli* BL21 cells. Briefly, the soluble products obtained following cell disruption were applied to a nickel-charged affinity capture column. Bound proteins were eluted with 100 mM imidazole, treated with Factor Xa to activate the fusion protein and remove the maltose-binding protein (MBP) tag, then re-applied to a second nickel-charged affinity capture column. Samples from the purification procedure were assessed by SDS-PAGE. The final purified material in the absence and presence of reducing agent is identified in the lanes marked [−] and [+] respectively.

FIG. 8—Comparison of binding efficacy of a LC/A-nociceptin-$H_N$/A fusion protein and a LC/A-nociceptin variant-$H_N$/A fusion protein The ability of nociceptin fusions to bind to the $ORL_1$ receptor was assessed using a simple competition-based assay. Primary cultures of dorsal root ganglia (DRG) were exposed to varying concentrations of test material in the presence of 1 nM [3H]-nociceptin. The reduction in specific binding of the radiolabelled ligand was assessed by scintillation counting, and plotted in comparison to the efficacy of unlabelled ligand (Tocris nociceptin). It is clear that the LC/A-nociceptin variant-$H_N$/A fusion (CPNv-LHA) is superior to the LC/A-nociceptin-$H_N$/A fusion (CPN-LHA) at interacting with the $ORL_1$ receptor.

FIG. 9—Expressed/purified LC/A-nociceptin-$H_N$/A fusion protein family with variable spacer length product(s)

Using the methodology outlined in Example 9, variants of the LC/A-CPN-$H_N$/A fusion consisting of GS10, GS30 and HX27 are purified from *E. coli* cell paste. Samples from the purification of LC/A-CPN(GS10)-$H_N$/A, LC/A-CPN (GS15)-$H_N$/A, LC/A-CPN(GS25)-$H_N$/A, LC/A-CPN (GS30)-$H_N$/A and LC/A-CPN(HX27)-$H_N$/A were assessed by SDS-PAGE prior to staining with Coomassie Blue. The electrophoresis profile indicates purification of a disulphide-bonded di-chain species of the expected molecular mass of CPBE-A. Top panel: M=benchmark molecular mass markers; S=total *E. coli* protein soluble fraction; FT=proteins that did not bind to the $Ni^{2+}$-charged Sepharose column; FUSION=fusion protein eluted by the addition of imidazole. Bottom panel: Lane 1=benchmark molecular mass markers; Lane 2=total *E. coli* protein soluble fraction; Lane 3=purified material following initial capture on $Ni^{2+}$-charged Sepharose; Lane 4=Factor Xa treated material prior to final capture on $Ni^{2+}$-charged Sepharose; Lane 5=purified final material post activation with Factor Xa (5 µl); Lane 6=purified final material post activation with Factor Xa (10 µl); Lane 7=purified final material post activation with Factor Xa (20 µl); Lane 8=purified final material post activation with Factor Xa+DTT (5 µl); Lane 9=purified final material post activation with Factor Xa+DTT (10 µl); Lane 10=purified final material post activation with Factor Xa+DTT (20 µl).

FIG. 10—Inhibition of SP release and cleavage of SNAP-25 by CPN-A

Briefly, primary cultures of dorsal root ganglia (DRG) were exposed to varying concentrations of CPN-A for 24 hours. Cellular proteins were separated by SDS-PAGE, Western blotted, and probed with anti-SNAP-25 to facilitate an assessment of SNAP-25 cleavage. The percentage of cleaved SNAP-25 was calculated by densitometric analysis and plotted against fusion concentration (dashed line). Material was also recovered for an analysis of substance P content using a specific EIA kit. Inhibition of substance P release is illustrated by the solid line. The fusion concentration required to achieve 50% maximal SNAP-25 cleavage is estimated to be 6.30±2.48 nM.

FIG. 11—Inhibition of SP release and cleavage of SNAP-25 over extended time periods after exposure of DRG to CPN-A Primary cultures of dorsal root ganglia (DRG) were exposed to varying concentrations of CPN-A for 24 hours. Botulinum neurotoxin (BoNT/A) was used as a control. After this initial exposure, extracellular material was removed by washing, and the cells incubated at 37° C. for varying periods of time. At specific time points, cellular proteins were separated by SDS-PAGE, Western blotted, and probed with anti-SNAP-25 to facilitate an assessment of SNAP-25 cleavage. The percentage of cleaved SNAP-25 was calculated by densitometric analysis and illustrated by the dotted lines. Material was also recovered for an analysis of substance P content using a specific EIA kit. Inhibition of substance P release is illustrated by the solid lines.

FIG. 12—Cleavage of SNAP-25 by CPNv-A

Primary cultures of dorsal root ganglia (DRG) were exposed to varying concentrations of CPNv-A for 24 hours. Cellular proteins were separated by SDS-PAGE, Western blotted, and probed with anti-SNAP-25 to facilitate an assessment of SNAP-25 cleavage. The percentage of cleaved SNAP-25 was calculated by densitometric analysis. The fusion concentration required to achieve 50% maximal SNAP-25 cleavage is estimated to be 1.38±0.36 nM.

FIG. 13—Cleavage of SNAP-25 over extended time periods after exposure of DRG to CPNv-A Primary cultures of dorsal root ganglia (DRG) were exposed to varying concentrations of CPNv-A for 24 hours. CPN-A was used as a control. After this initial exposure, extracellular material was removed by washing, and the cells incubated at 37° C. for varying periods of time. At specific time points, cellular proteins were separated by SDS-PAGE, Western blotted, and probed with anti-SNAP-25 to facilitate an assessment of SNAP-25 cleavage. The percentage of cleaved SNAP-25 was calculated by densitometric analysis.

Figure 14:
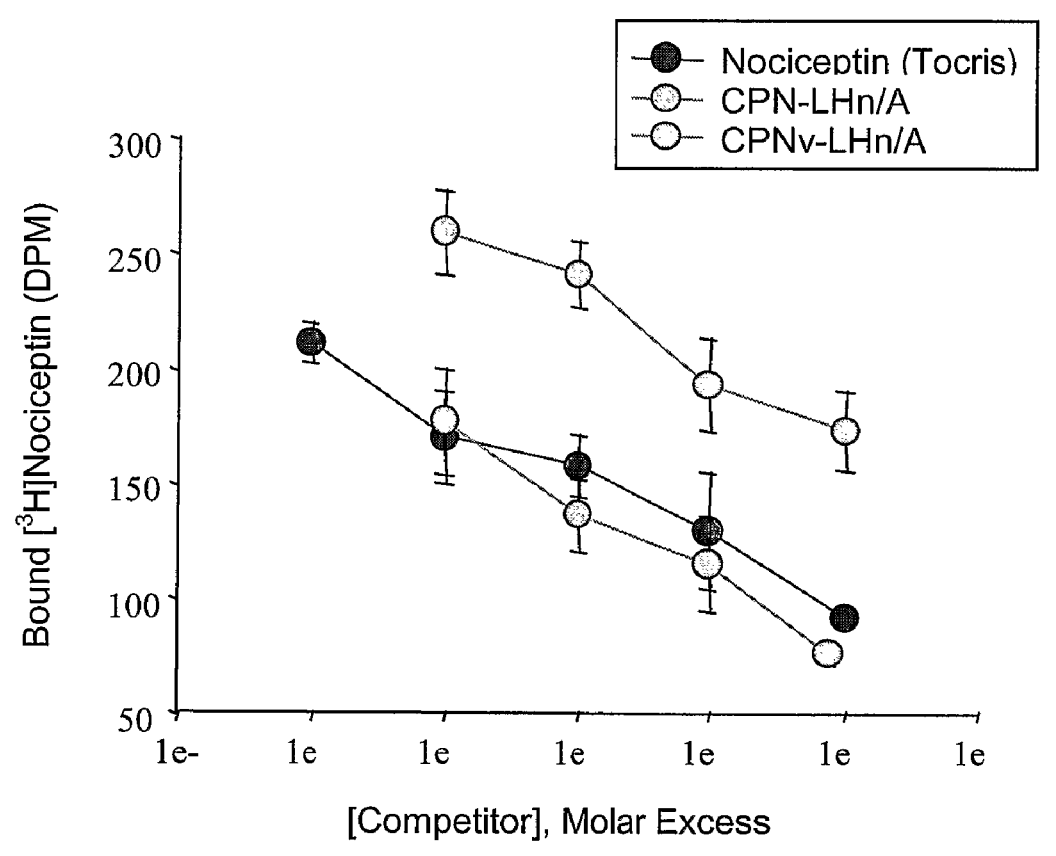

FIG. 14—CPNv-A fusion-mediated displacement of [3H]-nociceptin binding

The ability of nociceptin fusions to bind to the $ORL_1$ receptor was assessed using a simple competition-based assay. Primary cultures of dorsal root ganglia (DRG) were exposed to varying concentrations of test material in the presence of 1 nM [3H]-nociceptin. The reduction in specific binding of the radiolabelled ligand was assessed by scintillation counting, and plotted in comparison to the efficacy of unlabelled ligand (Tocris nociceptin). It is clear that the LC/A-nociceptin variant-$H_N$/A fusion (labelled as CPNv-LHnA) is superior to the LC/A-nociceptin-$H_N$/A fusion (labelled as CPN-LHnA) at interacting with the $ORL_1$ receptor.

FIG. 15—Expressed/purified CPNv(Ek)-A product

Proteins were subjected to SDS-PAGE prior to staining with Coomassie Blue. The electrophoresis profile indicates purification of a disulphide-bonded di-chain species of the expected molecular mass of CPNv(Ek)-A. Lane 1=benchmark molecular mass markers; Lane 2=total *E. coli* protein soluble fraction; Lane 3=purified material following initial capture on $Ni^{2+}$-charged Sepharose; Lane 4=purified final material post activation with enterokinase (5 µl); Lane 5=purified final material post activation with enterokinase (10 µl); Lane 6=purified final material post activation with enterokinase (20 µl); Lane 7=purified final material post activation with enterokinase+DTT (5 µl); Lane 8=purified final material post activation with enterokinase+DTT (10 µl); Lane 9=purified final material post activation with enterokinase+DTT (20 µl).

FIG. 16—Cleavage of SNAP-25 by CPNv(Ek)-A

Primary cultures of dorsal root ganglia (DRG) were exposed to varying concentrations of CPNv(Ek)-A for 24 hours. Cellular proteins were separated by SDS-PAGE, Western blotted, and probed with anti-SNAP-25 to facilitate an assessment of SNAP-25 cleavage. The percentage of cleaved SNAP-25 was calculated by densitometric analysis. CPNv-A as prepared in Example 9 was used for comparison purposes. The percentage cleavage of SNAP-25 by CPNv(Ek)-A (labelled as En activated) and CPNv-A (labelled as Xa activated) are illustrated.

FIG. 17—Expressed/purified CPNv-C product

Proteins were subjected to SDS-PAGE prior to staining with Coomassie Blue. The electrophoresis profile indicates purification of a disulphide-bonded di-chain species of the expected molecular mass of CPNv-C. Lane 1=benchmark molecular mass markers; Lane 2=total *E. coli* protein soluble fraction; Lane 3=purified material following initial capture on $Ni^{2+}$-charged Sepharose; Lane 4=Factor Xa treated material prior to final capture on $Ni^{2+}$-charged Sepharose; Lane 5=purified material following second capture on $Ni^{2+}$-charged Sepharose; Lane 6=final purified material; Lane 7=final purified material+DTT; Lane 8=benchmark molecular mass markers.

FIG. 18—Cleavage of syntaxin by CPNv-C

Primary cultures of dorsal root ganglia (DRG) were exposed to varying concentrations of CPNv-C for 24 hours. Cellular proteins were separated by SDS-PAGE, Western blotted, and probed with anti-syntaxin to facilitate an assessment of syntaxin cleavage. The percentage of cleaved syntaxin was calculated by densitometric analysis. The fusion concentration required to achieve 50% maximal syntaxin cleavage is estimated to be 3.13±1.96 nM.

FIG. 19—CPN-A efficacy in the Acute Capsaicin-Induced Mechanical Allodynia model The ability of an LC/A-nociceptin-$H_N$/A fusion (CPN/A) to inhibit capsaicin-induced mechanical allodynia was evaluated following subcutaneous intraplantar injection in the rat hind paw. Test animals were evaluated for paw withdrawal frequency (PWF %) in response to a 10 g Von Frey filament stimulus series (10 stimuli×3 trials) prior to recruitment into the study (Pre-Treat); after subcutaneous intraplantar treatment with CPN/A but before capsaicin (Pre-CAP); and following capsaicin challenge post-injection of CPN/A (average of responses at 15' and 30'; CAP). Capsaicin challenge was achieved by injection of 10 μL of a 0.3% solution. Sample dilutions were prepared in 0.5% BSA/saline.

FIG. 20—CPN-A efficacy in the Streptozotocin (STZ)-Induced Peripheral Diabetic Neuropathy (Neuropathic Pain) model Male Sprague-Dawley rats (250-300 g) are treated with 65 mg/kg STZ in citrate buffer (I.V.) and blood glucose and lipid are measured weekly to define the readiness of the model. Paw Withdrawal Threshold (PWT) is measured in response to a Von Frey filament stimulus series over a period of time. Allodynia is said to be established when the PWT on two consecutive test dates (separated by 1 week) measures below 6 g on the scale. At this point, rats are randomized to either a saline group (negative efficacy control), gabapentin group (positive efficacy control) or a test group (CPN/A). Test materials (20-25 μl) are injected subcutaneously as a single injection (except gabapentin) and the PWT is measured at 1 day post-treatment and periodically thereafter over a 2 week period. Gabapentin (30 mg/kg i.p. @ 3 ml/kg injection volume) is injected daily, 2 hours prior to the start of PWT testing.

FIG. 21—CPNv-A efficacy in the Acute Capsaicin-Induced Mechanical Allodynia model The ability of an LC/A-nociceptin variant-$H_N$/A fusion (CPNv/A) to inhibit capsaicin-induced mechanical allodynia was evaluated following subcutaneous intraplantar injection in the rat hind paw. Test animals were evaluated for paw withdrawal frequency (PWF %) in response to a 10 g Von Frey filament stimulus series (10 stimuli×3 trials) prior to recruitment into the study (Pre-Treat), after subcutaneous intraplantar treatment with CPNv/A but before capsaicin (Pre-CAP), and following capsaicin challenge post-injection of CPNv/A (average of responses at 15' and 30'; CAP). Capsaicin challenge was achieved by injection of 10 μL of a 0.3% solution. Sample dilutions were prepared in 0.5% BSA/saline. These data are expressed as a normalized paw withdrawal frequency differential, in which the difference between the peak response (post-capsaicin) and the baseline response (pre-capsaicin) is expressed as a percentage. With this analysis, it can be seen that CPNv/A is more potent than CPN/A since a lower dose of CPNv/A is required to achieve similar analgesic effect to that seen with CPN/A.

FIG. 22—Expressed/purified LC/A-CPLE-$H_N$/A product

Proteins were subjected to SDS-PAGE prior to staining with Coomassie Blue. The electrophoresis profile indicates purification of a disulphide-bonded di-chain species of the expected molecular mass of CPLE-A. Lane 1=benchmark molecular mass markers; Lane 2=total *E. coli* protein soluble fraction; Lane 3=purified material following initial capture on $Ni^{2+}$-charged Sepharose; Lane 4=Factor Xa treated material prior to final capture on $Ni^{2+}$-charged Sepharose; Lane 5=purified material following second capture on $Ni^{2+}$-charged Sepharose; Lane 6=final purified material; Lane 7=final purified material+DTT.

FIG. 23—Expressed/purified LC/A-CPBE-$H_N$/A product

Proteins were subjected to SDS-PAGE prior to staining with Coomassie Blue. The electrophoresis profile indicates purification of a disulphide-bonded di-chain species of the expected molecular mass of CPBE-A. Lane 1=total *E. coli* protein soluble fraction; Lane 2=purified material following initial capture on $Ni^{2+}$-charged Sepharose; Lane 3=Factor Xa treated material prior to final capture on $Ni^{2+}$-charged Sepharose; Lane 4=purified final material post activation with Factor Xa (5 μl); Lane 5=purified final material post activation with Factor Xa (10 μl); Lane 6=purified final material post activation with Factor Xa (20 μl); Lane 7=purified final material post activation with Factor Xa+DTT (5 μl); Lane 8=purified final material post activation with Factor Xa+DTT (10 μl); Lane 9=purified final material post activation with Factor Xa+DTT (20 μl); Lane 10=benchmark molecular mass markers.

FIG. 24—Expressed/purified CPOP-A product

Proteins were subjected to SDS-PAGE prior to staining with Coomassie Blue. The electrophoresis profile indicates purification of a disulphide-bonded di-chain species of the expected molecular mass of CPOP-A. Lane 1=benchmark molecular mass markers; Lane 2=purified material following initial capture on $Ni^{2+}$-charged Sepharose; Lane 3=Factor Xa treated material prior to final capture on $Ni^{2+}$-charged Sepharose; Lane 4=purified material following second capture on $Ni^{2+}$-charged Sepharose; Lane 5=purified final material post activation with Factor Xa (5 μl); Lane 6=purified final material post activation with Factor Xa (10 μl); Lane 7=purified final material post activation with Factor Xa (20 μl); Lane 8=purified final material post activation with Factor Xa+DTT (5 μl); Lane 9=purified final material post activation with Factor Xa+DTT (10 μl); Lane 10=purified final material post activation with Factor Xa+DTT (20 μl).

FIG. 25—Expressed/purified CPOPv-A product

Proteins were subjected to SDS-PAGE prior to staining with Coomassie Blue. The electrophoresis profile indicates purification of a disulphide-bonded di-chain species of the expected molecular mass of CPOPv-A. Lane 1=benchmark molecular mass markers; Lane 2=total *E. coli* protein soluble fraction; Lane 3=purified material following initial capture on $Ni^{2+}$-charged Sepharose; Lane 4=Factor Xa treated material prior to final capture on $Ni^{2+}$-charged Sepharose; Lane 5=purified final material post activation with Factor Xa (5 μl); Lane 6=purified final material post activation with Factor Xa (10 μl); Lane 7=purified final material post activation with Factor Xa (20 µl); Lane 8=purified final material post activation with Factor Xa+DTT (5 µl); Lane 9=purified final material post activation with Factor Xa+DTT (10 µl); Lane 10=purified final material post activation with Factor Xa+DTT (20 µl).

FIG. 26—In vitro SNAP-25 cleavage in a DRG cell model

Primary cultures of dorsal root ganglia (DRG) were exposed to varying concentrations of CPOPv-A for 24 hours. Cellular proteins were separated by SDS-PAGE, Western blotted, and probed with anti-SNAP-25 to facilitate an assessment of SNAP-25 cleavage. The percentage of cleaved SNAP-25 was calculated by densitometric analysis.

FIG. 27—Expressed/purified CPNv-A-FXa-HT (removable his-tag)

Proteins were subjected to SDS-PAGE prior to staining with Coomassie Blue. The electrophoresis profile indicates purification of a disulphide-bonded di-chain species of the expected molecular mass of CPNv-A-FXa-HT. Lane 1=benchmark molecular mass markers; Lane 2=total *E. coli* protein soluble fraction; Lane 3=Factor Xa treated material prior to final capture on $Ni^{2+}$-charged Sepharose; Lane 4=purified final material post activation with Factor Xa; Lane 5=purified final material post activation with Factor Xa+DTT.

FIG. 28—In vitro efficacy of LC/A-nociceptin-$H_N$/A fusion proteins with variable spacer length, as assessed by ligand competition assay The ability of LC/A-nociceptin-$H_N$/A fusions of variable spacer length to bind to the $ORL_1$ receptor was assessed using a simple competition-based assay. Primary cultures of dorsal root ganglia (DRG) were exposed to varying concentrations of test material in the presence of 1 nM [3H]-nociceptin. The reduction in specific binding of the radiolabelled ligand was assessed by scintillation counting, and plotted in comparison to the efficacy of unlabelled ligand (Tocris nociceptin). The upper panel illustrates the displacement characteristics of the GS0, GS20, GS30 and Hx27 spacers, whilst the lower panel illustrates the displacement achieved by the GS10, GS15 and GS25 spaced fusion proteins. It is concluded that the GS0 and GS30 spacers are ineffective, and the GS10 is poorly effective, at displacing nociceptin from the ORL1 receptor.

FIG. 29—In vitro efficacy of LC/A-nociceptin-$H_N$/A fusion proteins with variable spacer length, as assessed by in vitro SNAP-25 cleavage Primary cultures of dorsal root ganglia (DRG) were exposed to varying concentrations of CPN-A (of variable spacer length) for 24 hours. Cellular proteins were separated by SDS-PAGE, Western blotted, and probed with anti-SNAP-25 to facilitate an assessment of SNAP-25 cleavage. The percentage of cleaved SNAP-25 was calculated by densitometric analysis. The poorly effective binding characteristics of the GS10 spaced fusion protein (see FIG. 28) are reflected in the higher concentrations of fusion required to achieve cleavage of intracellular SNAP-25. GS0 and GS30 spaced fusion proteins were completely ineffective (date not shown). GS15, 20 and 25 spaced fusion proteins were similarly effective.

| SEQ ID NO: s | |
|---|---|
| SEQ ID NO: 1 | DNA sequence of the LC/A |
| SEQ ID NO: 2 | DNA sequence of the $H_N$/A |
| SEQ ID NO: 3 | DNA sequence of the LC/B |
| SEQ ID NO: 4 | DNA sequence of the $H_N$/B |
| SEQ ID NO: 5 | DNA sequence of the LC/C |
| SEQ ID NO: 6 | DNA sequence of the $H_N$/C |
| SEQ ID NO: 7 | DNA sequence of the CPN-A linker |
| SEQ ID NO: 8 | DNA sequence of the A linker |
| SEQ ID NO: 9 | DNA sequence of the N-terminal presentation nociceptin insert |
| SEQ ID NO: 10 | DNA sequence of the CPN-C linker |
| SEQ ID NO: 11 | DNA sequence of the CPBE-A linker |
| SEQ ID NO: 12 | DNA sequence of the CPNvar-A linker |
| SEQ ID NO: 13 | DNA sequence of the LC/A-CPN-$H_N$/A fusion |
| SEQ ID NO: 14 | Protein sequence of the LC/A-CPN-$H_N$/A fusion |
| SEQ ID NO: 15 | DNA sequence of the N-LC/A-$H_N$/A fusion |
| SEQ ID NO: 16 | Protein sequence of the N-LC/A-$H_N$/A fusion |
| SEQ ID NO: 17 | DNA sequence of the LC/C-CPN-$H_N$/C fusion |
| SEQ ID NO: 18 | Protein sequence of the LC/C-CPN-$H_N$/C fusion |
| SEQ ID NO: 19 | DNA sequence of the LC/C-CPN-$H_N$/C (A-linker) fusion |
| SEQ ID NO: 20 | Protein sequence of the LC/C-CPN-$H_N$/C (A-linker) fusion |
| SEQ ID NO: 21 | DNA sequence of the LC/A-CPME-$H_N$/A fusion |
| SEQ ID NO: 22 | Protein sequence of the LC/A-CPME-$H_N$/A fusion |
| SEQ ID NO: 23 | DNA sequence of the LC/A-CPBE-$H_N$/A fusion |
| SEQ ID NO: 24 | Protein sequence of the LC/A-CPBE-$H_N$/A fusion |
| SEQ ID NO: 25 | DNA sequence of the LC/A-CPNv-$H_N$/A fusion |
| SEQ ID NO: 26 | Protein sequence of the LC/A-CPNv-$H_N$/A fusion |
| SEQ ID NO: 27 | DNA sequence of the LC/A-CPN[1-11]-HN/A fusion |
| SEQ ID NO: 28 | Protein sequence of the LC/A-CPN[1-11]-HN/A fusion |
| SEQ ID NO: 29 | DNA sequence of the LC/A-CPN[[Y10]1-11]-HN/A fusion |
| SEQ ID NO: 30 | Protein sequence of the LC/A-CPN[[Y10]1-11]-HN/A fusion |
| SEQ ID NO: 31 | DNA sequence of the LC/A-CPN[[Y11]1-11]-HN/A fusion |
| SEQ ID NO: 32 | Protein sequence of the LC/A-CPN[[Y11]1-11]-HN/A fusion |
| SEQ ID NO: 33 | DNA sequence of the LC/A-CPN[[Y14]1-17]-HN/A fusion |
| SEQ ID NO: 34 | Protein sequence of the LC/A-CPN[[Y14]1-17]-HN/A fusion |
| SEQ ID NO: 35 | DNA sequence of the LC/A-CPN[1-13]-HN/A fusion |
| SEQ ID NO: 36 | Protein sequence of the LC/A-CPN[1-13]-HN/A fusion |
| SEQ ID NO: 37 | DNA sequence of CPN[1-17] |
| SEQ ID NO: 38 | Protein Sequence of CPN[1-17] |
| SEQ ID NO: 39 | DNA sequence of CPN[1-11] |
| SEQ ID NO: 40 | Protein sequence of CPN[1-11] |
| SEQ ID NO: 41 | DNA sequence of CPN[[Y10]1-11] |
| SEQ ID NO: 42 | Protein sequence of CPN[[Y10]1-11] |
| SEQ ID NO: 43 | DNA sequence of CPN[[Y11]1-11] |
| SEQ ID NO: 44 | Protein sequence of CPN[[Y11]1-11] |
| SEQ ID NO: 45 | DNA sequence of CPN[[Y14]1-17] |
| SEQ ID NO: 46 | Protein sequence of CPN[[Y14]1-17] |
| SEQ ID NO: 47 | DNA sequence of CPN[1-13] |
| SEQ ID NO: 48 | Protein sequence of CPN[1-13] |
| SEQ ID NO: 49 | DNA sequence of CPNv (also known as N[[R14K15]1-17]) |
| SEQ ID NO: 50 | Protein sequence of CPNv (also known as N[[R14K15]1-17]) |
| SEQ ID NO: 51 | DNA sequence of the nociceptin-spacer-LC/A-$H_N$/A fusion |
| SEQ ID NO: 52 | Protein sequence of the nociceptin-spacer-LC/A-$H_N$/A fusion |
| SEQ ID NO: 53 | DNA sequence of the CPN-A GS10 linker |
| SEQ ID NO: 54 | DNA sequence of the CPN-A GS15 linker |
| SEQ ID NO: 55 | DNA sequence of the CPN-A GS25 linker |
| SEQ ID NO: 56 | DNA sequence of the CPN-A GS30 linker |
| SEQ ID NO: 57 | DNA sequence of the CPN-A HX27 linker |
| SEQ ID NO: 58 | DNA sequence of the LC/A-CPN(GS15)-$H_N$/A fusion |
| SEQ ID NO: 59 | Protein sequence of the LC/A-CPN(GS15)-$H_N$/A fusion |
| SEQ ID NO: 60 | DNA sequence of the LC/A-CPN(GS25)-$H_N$/A fusion |
| SEQ ID NO: 61 | Protein sequence of the LC/A-CPN(GS25)-$H_N$/A fusion |
| SEQ ID NO: 62 | DNA sequence of the CPNvar-A Enterokinase activatable linker |
| SEQ ID NO: 63 | DNA sequence of the LC/A-CPNv(Ek)-$H_N$/A fusion |
| SEQ ID NO: 64 | Protein sequence of the LC/A-CPNv(Ek)-$H_N$/A fusion |
| SEQ ID NO: 65 | DNA sequence of the CPNvar-A linker |
| SEQ ID NO: 66 | DNA sequence of the LC/C-CPNv-$H_N$/C fusion (act. A) |
| SEQ ID NO: 67 | Protein sequence of the LC/C-CPNv-$H_N$/C fusion (act. A) |
| SEQ ID NO: 68 | DNA sequence of the LC/A-CPLE-$H_N$/A fusion |
| SEQ ID NO: 69 | Protein sequence of the LC/A-CPLE-$H_N$/A fusion |
| SEQ ID NO: 70 | DNA sequence of the LC/A-CPOP-$H_N$/A fusion |
| SEQ ID NO: 71 | Protein sequence of the LC/A-CPOP-$H_N$/A fusion |
| SEQ ID NO: 72 | DNA sequence of the LC/A-CPOPv-$H_N$/A fusion |
| SEQ ID NO: 73 | Protein sequence of the LC/A-CPOPv-$H_N$/A fusion |
| SEQ ID NO: 74 | DNA sequence of the IgA protease |
| SEQ ID NO: 75 | DNA sequence of the IgA-CPNv-$H_N$/A fusion |
| SEQ ID NO: 76 | Protein sequence of the IgA-CPNv-$H_N$/A fusion |
| SEQ ID NO: 77 | DNA sequence of the FXa-HT |
| SEQ ID NO: 78 | DNA sequence of the CPNv-A-FXa-HT |

-continued

| SEQ ID NO: s | |
|---|---|
| SEQ ID NO: 79 | Protein sequence of the CPNv-A-FXa-HT fusion |
| SEQ ID NO: 80 | DNA sequence of the DT translocation domain |
| SEQ ID NO: 81 | DNA sequence of the CPLE-DT-A |
| SEQ ID NO: 82 | Protein sequence of the CPLE-DT-A fusion |
| SEQ ID NO: 83 | DNA sequence of the TeNT LC |
| SEQ ID NO: 84 | DNA sequence of the CPNv-TENT LC |
| SEQ ID NO: 85 | Protein sequence of the CPNV-TeNT LC fusion |
| SEQ ID NO: 86 | DNA sequence of the CPNvar-C linker |
| SEQ ID NO: 87 | DNA sequence of the LC/C-CPNv-$H_N$/C fusion (act. C) |
| SEQ ID NO: 88 | Protein sequence of the LC/C-CPNv-$H_N$/C fusion (act. C) |

EXAMPLES

Example 1

Preparation of a LC/A and $H_N$/A Backbone Clones

The following procedure creates the LC and $H_N$ fragments for use as the component backbone for multidomain fusion expression. This example is based on preparation of a serotype A based clone (SEQ ID NO:1 and SEQ ID NO:2), though the procedures and methods are equally applicable to the other serotypes [illustrated by the sequence listing for serotype B (SEQ ID NO:3 and SEQ ID NO:4) and serotype C (SEQ ID NO:5 and SEQ ID NO:6)].

Preparation of Cloning and Expression Vectors pCR 4 (Invitrogen) is the chosen standard cloning vector, selected due to the lack of restriction sequences within the vector and adjacent sequencing primer sites for easy construct confirmation. The expression vector is based on the pMAL (NEB) expression vector, which has the desired restriction sequences within the multiple cloning site in the correct orientation for construct insertion (BamHI-SalI-PstI-HindIII). A fragment of the expression vector has been removed to create a non-mobilisable plasmid and a variety of different fusion tags have been inserted to increase purification options.

Preparation of Protease (e.g. LC/A) Insert

The LC/A (SEQ ID NO:1) is created by one of two ways: The DNA sequence is designed by back translation of the LC/A amino acid sequence [obtained from freely available database sources such as GenBank (accession number P10845) or Swissprot (accession locus BXA1_CLOBO) using one of a variety of reverse translation software tools (for example EditSeq best E. coli reverse translation (DNASTAR Inc.), or Backtranslation tool v2.0 (Entelechon)]. BamHI/SalI recognition sequences are incorporated at the 5' and 3' ends respectively of the sequence, maintaining the correct reading frame. The DNA sequence is screened (using software such as MapDraw, DNASTAR Inc.) for restriction enzyme cleavage sequences incorporated during the back translation. Any cleavage sequences that are found to be common to those required by the cloning system are removed manually from the proposed coding sequence ensuring common E. coli codon usage is maintained. E. coli codon usage is assessed by reference to software programs such as Graphical Codon Usage Analyser (Geneart), and the % GC content and codon usage ratio assessed by reference to published codon usage tables (for example GenBank Release 143, 13 Sep. 2004). This optimised DNA sequence containing the LC/A open reading frame (ORF) is then commercially synthesized (for example by Entelechon, Geneart or Sigma-Genosys) and is provided in the pCR 4 vector.

The alternative method is to use PCR amplification from an existing DNA sequence with BamHI and SalI restriction enzyme sequences incorporated into the 5' and 3' PCR primers respectively. Complementary oligonucleotide primers are chemically synthesised by a supplier (for example MWG or Sigma-Genosys), so that each pair has the ability to hybridize to the opposite strands (3' ends pointing "towards" each other) flanking the stretch of Clostridium target DNA, one oligonucleotide for each of the two DNA strands. To generate a PCR product the pair of short oligonucleotide primers specific for the Clostridium DNA sequence are mixed with the Clostridium DNA template and other reaction components and placed in a machine (the 'PCR machine') that can change the incubation temperature of the reaction tube automatically, cycling between approximately 94° C. (for denaturation), 55° C. (for oligonucleotide annealing), and 72° C. (for synthesis). Other reagents required for amplification of a PCR product include a DNA polymerase (such as Taq or Pfu polymerase), each of the four nucleotide dNTP building blocks of DNA in equimolar amounts (50-200 μM) and a buffer appropriate for the enzyme optimised for $Mg^{2+}$ concentration (0.5-5 mM).

The amplification product is cloned into pCR 4 using either, TOPO TA cloning for Taq PCR products or Zero Blunt TOPO cloning for Pfu PCR products (both kits commercially available from Invitrogen). The resultant clone is checked by sequencing. Any additional restriction sequences which are not compatible with the cloning system are then removed using site directed mutagenesis [for example, using Quickchange (Stratagene Inc.)].

Preparation of Translocation (e.g. $H_N$) Insert

The $H_N$/A (SEQ ID NO:2) is created by one of two ways: The DNA sequence is designed by back translation of the $H_N$/A amino acid sequence [obtained from freely available database sources such as GenBank (accession number P10845) or Swissprot (accession locus BXA1_CLOBO)] using one of a variety of reverse translation software tools [for example EditSeq best E. coli reverse translation (DNASTAR Inc.), or Backtranslation tool v2.0 (Entelechon)]. A PstI restriction sequence added to the N-terminus and XbaI-stop codon-HindIII to the C-terminus ensuring the correct reading frame is maintained. The DNA sequence is screened (using software such as MapDraw, DNASTAR Inc.) for restriction enzyme cleavage sequences incorporated during the back translation. Any sequences that are found to be common to those required by the cloning system are removed manually from the proposed coding sequence ensuring common E. coli codon usage is maintained. E. coli codon usage is assessed by reference to software programs such as Graphical Codon Usage Analyser (Geneart), and the % GC content and codon usage ratio assessed by reference to published codon usage tables (for example GenBank Release 143, 13 Sep. 2004). This optimised DNA sequence is then commercially synthesized (for example by Entelechon, Geneart or Sigma-Genosys) and is provided in the pCR 4 vector.

The alternative method is to use PCR amplification from an existing DNA sequence with PstI and XbaI-stop codon-HindIII restriction enzyme sequences incorporated into the 5' and 3' PCR primers respectively. The PCR amplification is performed as described above. The PCR product is inserted into pCR 4 vector and checked by sequencing. Any additional restriction sequences which are not compatible with the cloning system are then removed using site directed mutagenesis [for example using Quickchange (Stratagene Inc.)].

Example 2

Preparation of a LC/A-Nociceptin-H$_N$/A Fusion Protein (Nociceptin is N-Terminal of the H$_N$-Chain)

Preparation of Linker-Nociceptin-Spacer Insert

The LC-H$_N$ linker can be designed from first principle, using the existing sequence information for the linker as the template. For example, the serotype A linker (in this case defined as the inter-domain polypeptide region that exists between the cysteines of the disulphide bridge between LC and H$_N$) is 23 amino acids long and has the sequence VRGI-ITSKTKSLDKGYNKALNDL (SEQ ID NO:104). Within this sequence, it is understood that proteolytic activation in nature leads to an H$_N$ domain that has an N-terminus of the sequence ALNDL. This sequence information is freely available from available database sources such as GenBank (accession number P10845) or Swissprot (accession locus BXA1_CLOBO). Into this linker a Factor Xa site, nociceptin and spacer are incorporated; and using one of a variety of reverse translation software tools [for example EditSeq best *E. coli* reverse translation (DNASTAR Inc.), or Backtranslation tool v2.0 (Entelechon)], the DNA sequence encoding the linker-ligand-spacer region is determined. Restriction sites are then incorporated into the DNA sequence and can be arranged as BamHI-SalI-linker-protease site-nociceptin-NheI-spacer-SpeI-PstI-XbaI-stop codon-HindIII (SEQ ID NO:7). It is important to ensure the correct reading frame is maintained for the spacer, nociceptin and restriction sequences and that the XbaI sequence is not preceded by the bases, TC, which would result on DAM methylation. The DNA sequence is screened for restriction sequence incorporation, and any additional sequences are removed manually from the remaining sequence ensuring common *E. coli* codon usage is maintained. *E. coli* codon usage is assessed by reference to software programs such as Graphical Codon Usage Analyser (Geneart), and the % GC content and codon usage ratio assessed by reference to published codon usage tables (for example, GenBank Release 143, 13 Sep. 2004). This optimised DNA sequence is then commercially synthesized (for example by Entelechon, Geneart or Sigma-Genosys) and is provided in the pCR 4 vector.

Preparation of the LC/A-nociceptin-H$_N$/A Fusion

In order to create the LC-linker-nociceptin-spacer-H$_N$ construct (SEQ ID NO:13), the pCR 4 vector encoding the linker (SEQ ID NO:7) is cleaved with BamHI+SalI restriction enzymes. This cleaved vector then serves as the recipient vector for insertion and ligation of the LC/A DNA (SEQ ID NO:1) cleaved with BamHI+SalI. The resulting plasmid DNA is then cleaved with PstI+XbaI restriction enzymes and serves as the recipient vector for the insertion and ligation of the H$_N$/A DNA (SEQ ID NO:2) cleaved with PstI+XbaI. The final construct contains the LC-linker-nociceptin-spacer-H$_N$ ORF (SEQ ID NO:13) for transfer into expression vectors for expression to result in a fusion protein of the sequence illustrated in SEQ ID NO:14.

Example 3

Preparation of a Nociceptin-LC/A-H$_N$/A Fusion Protein (Nociceptin is N-terminal of the LC-Chain)

The LC/A-H$_N$/A backbone is constructed as described in Example 2 using the synthesised A serotype linker with the addition of a Factor Xa site for activation, arranged as BamHI-SalI-linker-protease site-linker-PstI-XbaI-stop codon-HindIII (SEQ ID NO:8). The LC/A-H$_N$/A backbone and the synthesised N-terminal presentation nociceptin insert (SEQ ID NO:9) are cleaved with BamHI+HindIII restriction enzymes, gel purified and ligated together to create a nociceptin-spacer-LC-linker-H$_N$. The ORF (SEQ ID NO:15) is then cut out using restriction enzymes AvaI+XbaI for transfer into expression vectors for expression to result in a fusion protein of the sequence illustrated in SEQ ID NO:16.

Example 4

Preparation of a LC/C-Nociceptin-H$_N$/C Fusion Protein

Following the methods used in Examples 1 and 2, the LC/C (SEQ ID NO:5) and H$_N$/C (SEQ ID NO:6) are created and inserted into the C serotype linker arranged as BamHI-SalI-linker-protease site-nociceptin-NheI-spacer-SpeI-PstI-XbaI-stop codon-HindIII (SEQ ID NO:10). The final construct contains the LC-linker-nociceptin-spacer-H$_N$ ORF (SEQ ID NO:17) for expression as a protein of the sequence illustrated in SEQ ID NO:18.

Example 5

Preparation of a LC/C-Nociceptin-H$_N$/C Fusion Protein with a Serotype A Activation Sequence Following the methods used in Examples 1 and 2, the LC/C (SEQ ID NO:5) and H$_N$/C (SEQ ID NO:6) are created and inserted into the A serotype linker arranged as BamHI-SalI-linker-protease site-nociceptin-NheI-spacer-SpeI-PstI-XbaI-stop codon-HindIII (SEQ ID NO:7). The final construct contains the LC-linker-nociceptin-spacer-H$_N$ ORF (SEQ ID NO:19) for expression as a protein of the sequence illustrated in SEQ ID NO:20.

Example 6

Preparation of a LC/A-Met Enkephalin-H$_N$/A Fusion Protein

Due to the small, five-amino acid, size of the met-enkephalin ligand the LC/A-met enkephalin-H$_N$/A fusion is created by site directed mutagenesis [for example using Quickchange (Stratagene Inc.)] using the LC/A-nociceptin-H$_N$/A fusion (SEQ ID NO:13) as a template. Oligonucleotides are designed encoding the YGGFM (SEQ ID NO:105) met-enkephalin peptide, ensuring standard *E. coli* codon usage is maintained and no additional restriction sites are incorporated, flanked by sequences complimentary to the linker region of the LC/A-nociceptin-H$_N$/A fusion (SEQ ID NO:13) either side on the nociceptin section. The SDM product is checked by sequencing and the final construct containing the LC-linker-met enkephalin-spacer-H$_N$ ORF (SEQ ID NO:21) for expression as a protein of the sequence illustrated in SEQ ID NO:22.

Example 7

Preparation of a LC/A-β Endorphin-H$_N$/A Fusion Protein

Following the methods used in Examples 1 and 2, the LC/A (SEQ ID NO:1) and H$_N$/A (SEQ ID NO:2) are created and inserted into the A serotype β endorphin linker arranged as BamHI-SalI-linker-protease site-β endorphin-NheI-spacer-SpeI-PstI-XbaI-stop codon-HindIII (SEQ ID NO:11). The final construct contains the LC-linker-β endorphin-spacer-H$_N$ ORF (SEQ ID NO:23) for expression as a protein of the sequence illustrated in SEQ ID NO:24.

Example 8

Preparation of a LC/A-Nociceptin Variant-H$_N$/A Fusion Protein

Following the methods used in Examples 1 and 2, the LC/A (SEQ ID NO:1) and H$_N$/A (SEQ ID NO:2) are created and inserted into the A serotype nociceptin variant linker arranged as BamHI-SalI-linker-protease site-nociceptin variant-NheI-spacer-SpeI-PstI-XbaI-stop codon-HindIII (SEQ ID NO:12). The final construct contains the LC-linker-nociceptin variant-spacer-H$_N$ ORF (SEQ ID NO:25) for expression as a protein of the sequence illustrated in SEQ ID NO:26.

Example 9

Purification Method for LC/A-Nociceptin-H$_N$/A Fusion Protein

Defrost falcon tube containing 25 ml 50 mM HEPES pH 7.2, 200 mM NaCl and approximately 10 g of *E. coli* BL21 cell paste. Make the thawed cell paste up to 80 ml with 50 mM HEPES pH 7.2, 200 mM NaCl and sonicate on ice 30 seconds on, 30 seconds off for 10 cycles at a power of 22 microns ensuring the sample remains cool. Spin the lysed cells at 18 000 rpm, 4° C. for 30 minutes. Load the supernatant onto a 0.1 M NiSO$_4$ charged Chelating column (20-30 ml column is sufficient) equilibrated with 50 mM HEPES pH 7.2, 200 mM NaCl. Using a step gradient of 10 and 40 mM imidazol, wash away the non-specific bound protein and elute the fusion protein with 100 mM imidazol. Dialyse the eluted fusion protein against 5 L of 50 mM HEPES pH 7.2, 200 mM NaCl at 4° C. overnight and measure the OD of the dialysed fusion protein. Add 1 unit of factor Xa per 100 µg fusion protein and Incubate at 25° C. static overnight. Load onto a 0.1 M NiSO$_4$ charged Chelating column (20-30 ml column is sufficient) equilibrated with 50 mM HEPES pH 7.2, 200 mM NaCl. Wash column to baseline with 50 mM HEPES pH 7.2, 200 mM NaCl. Using a step gradient of 10 and 40 mM imidazol, wash away the non-specific bound protein and elute the fusion protein with 100 mM imidazol. Dialyse the eluted fusion protein against 5 L of 50 mM HEPES pH 7.2, 200 mM NaCl at 4° C. overnight and concentrate the fusion to about 2 mg/ml, aliquot sample and freeze at −20° C. Test purified protein using OD, BCA, purity analysis and SNAP-25 assessments.

Example 10

Confirmation of TM Agonist Activity by Measuring Release of Substance P from Neuronal Cell Cultures Materials
Substance P EIA is obtained from R&D Systems, UK.
Methods
Primary neuronal cultures of eDRG are established as described previously (Duggan et al., 2002). Substance P release from the cultures is assessed by EIA, essentially as described previously (Duggan et al., 2002). The TM of interest is added to the neuronal cultures (established for at least 2 weeks prior to treatment); control cultures are performed in parallel by addition of vehicle in place of TM. Stimulated (100 mM KCl) and basal release, together with total cell lysate content, of substance P are obtained for both control and TM treated cultures. Substance P immunoreactivity is measured using Substance P Enzyme Immunoassay Kits (Cayman Chemical Company, USA or R&D Systems, UK) according to manufacturers' instructions.

The amount of Substance P released by the neuronal cells in the presence of the TM of interest is compared to the release obtained in the presence and absence of 100 mM KCl. Stimulation of Substance P release by the TM of interest above the basal release, establishes that the TM of interest is an "agonist ligand" as defined in this specification. If desired the stimulation of Substance P release by the TM of interest can be compared to a standard Substance P release-curve produced using the natural ORL-1 receptor ligand, nociceptin (Tocris).

Example 11

Confirmation of ORL$_1$ Receptor Activation by Measuring Forskolin-Stimulated cAMP Production Confirmation that a given TM is acting via the ORL$_1$ receptor is provided by the following test, in which the TMs ability to inhibit forskolin-stimulated cAMP production is assessed.
Materials
[$^3$H]adenine and [$^{14}$C]cAMP are obtained from GE Healthcare
Methods
The test is conducted essentially as described previously by Meunier et al. [Isolation and structure of the endogenous agonist of opioid receptor-like ORL$_1$ receptor. Nature 377: 532-535, 1995] in intact transfected-CHO cells plated on 24-well plastic plates.

To the cells is added [3H]adenine (1.0 µCi) in 0.4 ml of culture medium. The cells remain at 37° C. for 2 h to allow the adenine to incorporate into the intracellular ATP pool. After 2 h, the cells are washed once with incubation buffer containing: 130 mM NaCl, 4.8 mM KCl, 1.2 mM KH$_2$PO$_4$, 1.3 mM CaCl$_2$, 1.2 mM MgSO$_4$, 10 mM glucose, 1 mg/ml bovine serum albumin and 25 mM HEPES pH 7.4, and replaced with buffer containing forskolin (10 µM) and isobutylmethylxanthine (50 µM) with or without the TM of interest. After 10 min, the medium is aspirated and replaced with 0.5 ml, 0.2 M HCl. Approximately 1000 cpm of [$^{14}$C]cAMP is added to each well and used as an internal standard. The contents of the wells are then transferred to columns of 0.65 g dry alumina powder. The columns are eluted with 4 ml of 5 mM HCl, 0.5 ml of 0.1 M ammonium acetate, then two additional milliliters of ammonium acetate. The final eluate is collected into scintillation vials and counted for $^{14}$C and tritium. Amounts collected are corrected for recovery of [$^{14}$C]cAMP. TMs that are agonists at the ORL$_1$ receptor cause a reduction in the level of cAMP produced in response to forskolin.

Example 12

Confirmation of ORL$_1$ Receptor Activation Using a GTPγS Binding Functional Assay Confirmation that a given TM is acting via the ORL$_1$ receptor is also provided by the following test, a GTPγS binding functional assay.
Materials
[$^{35}$S]GTPγS is obtained from GE Healthcare
Wheatgerm agglutinin-coated (SPA) beads are obtained from GE Healthcare Methods This assay is carried out essentially as described by Traynor and Nahorski [Modulation by μ-opioid agonists of guanosine-5 —O-(3-[$^{35}$S]thio)triphosphate binding to membranes from human neuroblastoma SH-SY5Y cells. Mol. Pharmacol. 47: 848-854, 1995].

Cells are scraped from tissue culture dishes into 20 mM HEPES, 1 mM ethylenediaminetetraacetic acid, then centrifuged at 500×g for 10 min. Cells are resuspended in this buffer and homogenized with a Polytron Homogenizer.

The homogenate is centrifuged at 27,000×g for 15 min, and the pellet resuspended in buffer A, containing: 20 mM HEPES, 10 mM MgCl$_2$, 100 mM NaCl, pH 7.4. The suspension is recentrifuged at 20,000×g and suspended once more in buffer A. For the binding assay, membranes (8-15 μg protein) are incubated with [$^{35}$S]GTP S (50 pM), GDP (10 μM), with and without the TM of interest, in a total volume of 1.0 ml, for 60 min at 25° C. Samples are filtered over glass fibre filters and counted as described for the binding assays.

Example 13

Preparation of a LC/A-Nociceptin-H$_N$/A Fusion Protein (Nociceptin is N-Terminal of the H$_N$-Chain)

The linker-nociceptin-spacer insert is prepared as described in Example 2.
Preparation of the LC/A-Nociceptin-H$_N$/A Fusion In order to create the LC-linker-nociceptin-spacer-H$_N$ construct (SEQ ID NO:13), the pCR 4 vector encoding the linker (SEQ ID NO:7) is cleaved with BamHI+SalI restriction enzymes. This cleaved vector then serves as the recipient for insertion and ligation of the LC/A DNA (SEQ ID NO:1) also cleaved with BamHI+SalI. The resulting plasmid DNA is then cleaved with BamHI+HindIII restriction enzymes and the LC/A-linker fragment inserted into a similarly cleaved vector containing a unique multiple cloning site for BamHI, SalI, PstI, and HindIII such as the pMAL vector (NEB). The H$_N$/A DNA (SEQ ID NO:2) is then cleaved with PstI+HindIII restriction enzymes and inserted into the similarly cleaved pMAL-LC/A-linker construct. The final construct contains the LC-linker-nociceptin-spacer-H$_N$ ORF (SEQ ID NO:13) for expression as a protein of the sequence illustrated in SEQ ID NO:14.

Example 14

Preparation of a Nociceptin-LC/A-H$_N$/A Fusion Protein (Nociceptin is N-Terminal of the LC-Chain)

In order to create the nociceptin-spacer-LC/A-H$_N$/A construct, an A serotype linker with the addition of a Factor Xa site for activation, arranged as BamHI-SalI-linker-protease site-linker-PstI-XbaI-stop codon-HindIII (SEQ ID NO:8) is synthesised as described in Example 13. The pCR 4 vector encoding the linker is cleaved with BamHI+SalI restriction enzymes. This cleaved vector then serves as the recipient for insertion and ligation of the LC/A DNA (SEQ ID NO:1) also cleaved with BamHI+SalI. The resulting plasmid DNA is then cleaved with BamHI+HindIII restriction enzymes and the LC/A-linker fragment inserted into a similarly cleaved vector containing the synthesised N-terminal presentation nociceptin insert (SEQ ID NO:9). This construct is then cleaved with AvaI+HindIII and inserted into an expression vector such as the pMAL plasmid (NEB). The H$_N$/A DNA (SEQ ID NO:2) is then cleaved with PstI+HindIII restriction enzymes and inserted into the similarly cleaved pMAL-nociceptin-LC/A-linker construct. The final construct contains the nociceptin-spacer-LC/A-H$_N$/A ORF (SEQ ID NO:51) for expression as a protein of the sequence illustrated in SEQ ID NO:52.

Example 15

Preparation and Purification of an LC/A-Nociceptin-H$_N$/A Fusion Protein Family with Variable Spacer Length Using the same strategy as employed in Example 2, a range of DNA linkers were prepared that encoded nociceptin and variable spacer content. Using one of a variety of reverse translation software tools [for example EditSeq best E. coli reverse translation (DNASTAR Inc.), or Backtranslation tool v2.0 (Entelechon)], the DNA sequence encoding the linker-ligand-spacer region is determined. Restriction sites are then incorporated into the DNA sequence and can be arranged as BamHI-SalI-linker-protease site-nociceptin-NheI-spacer-SpeI-PstI-XbaI-stop codon-HindIII (SEQ ID NO:53 to SEQ ID NO:57). It is important to ensure the correct reading frame is maintained for the spacer, nociceptin and restriction sequences and that the XbaI sequence is not preceded by the bases, TC which would result on DAM methylation. The DNA sequence is screened for restriction sequence incorporation and any additional sequences are removed manually from the remaining sequence ensuring common E. coli codon usage is maintained. E. coli codon usage is assessed by reference to software programs such as Graphical Codon Usage Analyser (Geneart), and the % GC content and codon usage ratio assessed by reference to published codon usage tables (for example GenBank Release 143, 13 Sep. 2004). This optimised DNA sequence is then commercially synthesized (for example by Entelechon, Geneart or Sigma-Genosys) and is provided in the pCR 4 vector.

The spacers that were created included:

TABLE 1

| Code | Protein sequence of the linker | SEQ ID of the linker DNA |
|---|---|---|
| GS10 | ALAGGGGSALVLQ (SEQ ID NO: 106) | 53 |
| GS15 | ALAGGGGSGGGGSALVLQ (SEQ ID NO: 107) | 54 |
| GS25 | ALAGGGGSGGGGSGGGGSGGGGSALVLQ (SEQ ID NO: 108) | 55 |
| GS30 | ALAGGGGSGGGGSGGGGSGGGGSGGGGSALVLQ (SEQ ID NO: 109) | 56 |
| HX27 | ALAAEAAAKEAAAKEAAAKAGGGGSALVLQ (SEQ ID NO: 110) | 57 |

By way of example, in order to create the LC/A-CPN (GS15)-H$_N$/A fusion construct (SEQ ID NO:58), the pCR 4 vector encoding the linker (SEQ ID NO:54) is cleaved with BamHI+SalI restriction enzymes. This cleaved vector then serves as the recipient vector for insertion and ligation of the LC/A DNA (SEQ ID NO:1) also cleaved with BamHI+SalI. The resulting plasmid DNA is then cleaved with BamHI+HindIII restriction enzymes and the LC/A-linker fragment inserted into a similarly cleaved vector containing a unique multiple cloning site for BamHI, SalI, PstI, and HindIII such as the pMAL vector (NEB). The H$_N$/A DNA (SEQ ID NO:2) is then cleaved with PstI+HindIII restriction enzymes and inserted into the similarly cleaved pMAL-LC/A-linker construct. The final construct contains the LC/A-CPN(GS15)-$H_N$/A ORF (SEQ ID NO:58) for expression as a protein of the sequence illustrated in SEQ ID NO:59.

As a further example, to create the LC/A-CPN(GS25)-$H_N$/A fusion construct (SEQ ID NO:60), the pCR 4 vector encoding the linker (SEQ ID NO:55) is cleaved with BamHI+SalI restriction enzymes. This cleaved vector then serves as the recipient vector for insertion and ligation of the LC/A DNA (SEQ ID NO:1) cleaved with BamHI+SalI. The resulting plasmid DNA is then cleaved with BamHI+HindIII restriction enzymes and the LC/A-linker fragment inserted into a similarly cleaved vector containing a unique multiple cloning site for BamHI, SalI, PstI, and HindIII such as the pMAL vector (NEB). The $H_N$/A DNA (SEQ ID NO:2) is then cleaved with PstI+HindIII restriction enzymes and inserted into the similarly cleaved pMAL-LC/A-linker construct. The final construct contains the LC/A-CPN(GS25)-$H_N$/A ORF (SEQ ID NO:60) for expression as a protein of the sequence illustrated in SEQ ID NO:61.

Variants of the LC/A-CPN-$H_N$/A fusion consisting of GS10, GS30 and HX27 are similarly created. Using the purification methodology described in Example 9, fusion protein is purified from *E. coli* cell paste. FIG. 9 illustrates the purified product obtained in the case of LC/A-CPN(GS10)-$H_N$/A, LC/A-CPN(GS15)-$H_N$/A, LC/A-CPN(GS25)-$H_N$/A, LC/A-CPN(GS30)-$H_N$/A and LC/A-CPN(HX27)-$H_N$/A.

Example 16

Assessment of In Vitro Efficacy of an LC/A-Nociceptin-$H_N$/A Fusion

Fusion protein prepared according to Examples 2 and 9 was assessed in the eDRG neuronal cell model.

Assays for the inhibition of substance P release and cleavage of SNAP-25 have been previously reported (Duggan et al., 2002, *J. Biol. Chem.*, 277, 34846-34852). Briefly, dorsal root ganglia neurons are harvested from 15-day-old fetal Sprague-Dawley rats and dissociated cells plated onto 24-well plates coated with Matrigel at a density of $1 \times 10^6$ cells/well. One day post-plating the cells are treated with 10 µM cytosine β-D-arabinofuranoside for 48 h. Cells are maintained in Dulbecco's minimal essential medium supplemented with 5% heat-inactivated fetal bovine serum, 5 mM L-glutamine, 0.6% D-glucose, 2% B27 supplement, and 100 ng/ml 2.5 S mouse nerve growth factor. Cultures are maintained for 2 weeks at 37° C. in 95% air/5% $CO_2$ before addition of test materials.

Release of substance P from eDRG is assessed by enzyme-linked immunosorbent assay. Briefly, eDRG cells are washed twice with low potassium-balanced salt solution (BSS: 5 mM KCl, 137 mM NaCl, 1.2 mM $MgCl_2$, 5 mM glucose, 0.44 mM $KH_2PO_4$, 20 mM HEPES, pH 7.4, 2 mM $CaCl_2$). Basal samples are obtained by incubating each well for 5 min. with 1 ml of low potassium BSS. After removal of this buffer, the cells are stimulated to release by incubation with 1 ml of high potassium buffer (BSS as above with modification to include 100 mM KCl isotonically balanced with NaCl) for 5 min. All samples are removed to tubes on ice prior to assay of substance P. Total cell lysates are prepared by addition of 250 µl of 2 M acetic acid/0.1% trifluoroacetic acid to lyse the cells, centrifugal evaporation, and resuspension in 500 µl of assay buffer. Diluted samples are assessed for substance P content. Substance P immunoreactivity is measured using Substance P Enzyme Immunoassay Kits (Cayman Chemical Company or R&D Systems) according to manufacturers' instructions. Substance P is expressed in pg/ml relative to a standard substance P curve run in parallel.

SDS-PAGE and Western blot analysis were performed using standard protocols (Novex). SNAP-25 proteins were resolved on a 12% Tris/glycine polyacrylamide gel (Novex) and subsequently transferred to nitrocellulose membrane. The membranes were probed with a monoclonal antibody (SMI-81) that recognises cleaved and intact SNAP-25. Specific binding was visualised using peroxidase-conjugated secondary antibodies and a chemiluminescent detection system. Cleavage of SNAP-25 was quantified by scanning densitometry (Molecular Dynamics Personal SI, ImageQuant data analysis software). Percent SNAP-25 cleavage was calculated according to the formula: (Cleaved SNAP-25/(Cleaved+Intact SNAP-25))×100.

Following exposure of eDRG neurons to an LC/A-nociceptin-$H_N$/A fusion (termed CPN-A), both inhibition of substance P release and cleavage of SNAP-25 are observed (FIG. 10). After 24 h exposure to the fusion, 50% of maximal SNAP-25 cleavage is achieved by a fusion concentration of 6.3±2.5 nM.

The effect of the fusion is also assessed at defined time points following a 16 h exposure of eDRG to CPN-A. FIG. 11 illustrates the prolonged duration of action of the CPN-A fusion protein, with measurable activity still being observed at 28 days post exposure.

Example 17

Assessment of In Vitro Efficacy of an LC/A-Nociceptin Variant-$H_N$/A Fusion

Fusion protein prepared according to Examples 8 and 9 was assessed in the eDRG neuronal cell mode using the method described in Example 16.

Following exposure of eDRG neurons to an LC/A-nociceptin variant-$H_N$/A fusion (termed CPNv-A), both inhibition of substance P release and cleavage of SNAP-25 are observed. After 24 h exposure to the fusion, 50% of maximal SNAP-25 cleavage is achieved by a fusion concentration of 1.4±0.4 nM (FIG. 12).

The effect of the fusion is also assessed at defined time points following a 16 h exposure of eDRG to CPN-A. FIG. 13 illustrates the prolonged duration of action of the CPN-A fusion protein, with measurable activity still being observed at 24 days post exposure.

The binding capability of the CPNv-A fusion protein is also assessed in comparison to the CPN-A fusion. FIG. 14 illustrates the results of a competition experiment to determine binding efficacy at the ORL-1 receptor. CPNv-A is demonstrated to displace [3H]-nociceptin, thereby confirming that access to the receptor is possible with the ligand in the central presentation format.

Example 18

Preparation of an LC/A-Nociceptin Variant-$H_N$/A Fusion Protein that is Activated by Treatment with Enterokinase Following the methods used in Examples 1 and 2, the LC/A (SEQ ID NO:1) and $H_N$/A (SEQ ID NO:2) are created and inserted into the A serotype nociceptin variant linker arranged as BamHI-SalI-linker-enterokinase protease site-nociceptin variant-NheI-spacer-SpeI-PstI-XbaI-stop codon-HindIII (SEQ ID NO:62). The final construct contains the LC-linkernociceptin variant-spacer-$H_N$ ORF sequences (SEQ ID NO:63) for expression as a protein of the sequence illustrated in SEQ ID NO:64. The fusion protein is termed CPNv(Ek)-A. FIG. 15 illustrates the purification of CPNv(Ek)-A from *E. coli* following the methods used in Example 9 but using Enterokinase for activation at 0.00064 µg per 100 µg of fusion protein.

Example 19

Assessment of In Vitro Efficacy of a LC/A-Nociceptin Variant-$H_N$/A Fusion that has been Activated by Treatment with Enterokinase The CPNv(Ek)-A prepared in Example 18 is obtained in a purified form and applied to the eDRG cell model to assess cleavage of SNAP-25 (using methodology from Example 16). FIG. 16 illustrates the cleavage of SNAP-25 following 24 h exposure of eDRG to CPNv(Ek)-A. The efficiency of cleavage is observed to be similar to that achieved with the Factor Xa-cleaved material, as recorded in Example 17.

Example 20

Preparation of an LC/C-Nociceptin Variant-$H_N$/C Fusion Protein with a Factor Xa Activation Linker Derived from Serotype A Following the methods used in Example 4, the LC/C (SEQ ID NO:5) and $H_N$/C (SEQ ID NO:6) are created and inserted into the A serotype nociceptin variant linker arranged as BamHI-SalI-linker-nociceptin variant-NheI-spacer-SpeI-PstI-XbaI-stop codon-HindIII (SEQ ID NO:65). The final construct contains the LC-linker-nociceptin variant-spacer-$H_N$ ORF sequences (SEQ ID NO:66) for expression as a protein of the sequence illustrated in SEQ ID NO:67. The fusion protein is termed CPNv-C (act. A). FIG. 17 illustrates the purification of CPNv-C (act. A) from *E. coli* following the methods used in Example 9.

Example 21

Assessment of In Vitro Efficacy of an LC/C-Nociceptin Variant-$H_N$/C Fusion Protein Following the methods used in Example 9, the CPNv-C (act. A) prepared in Example 20 is obtained in a purified form and applied to the eDRG cell model to assess cleavage of SNAP-25 (using methodology from Example 16). After 24 h exposure to the fusion, 50% of maximal syntaxin cleavage is achieved by a fusion concentration of 3.1±2.0 nM. FIG. 18 illustrates the cleavage of syntaxin following 24 h exposure of eDRG to CPNv-C (act. A).

Example 22

Assessment of In Vivo Efficacy of an LC/A-Nociceptin-HN/A Fusion

The ability of an LC/A-nociceptin-$H_N$/A fusion (CPN/A) to inhibit acute capsaicin-induced mechanical allodynia is evaluated following subcutaneous intraplantar injection in the rat hind paw. Test animals are evaluated for paw withdrawal frequency (PWF %) in response to a 10 g Von Frey filament stimulus series (10 stimuli×3 trials) prior to recruitment into the study, after subcutaneous treatment with CPN/A but before capsaicin, and following capsaicin challenge post-injection of CPN/A (average of responses at 15' and 30'). Capsaicin challenge is achieved by injection of 10 µL of a 0.3% solution. Sample dilutions are prepared in 0.5% BSA/saline. FIG. 19 illustrates the reversal of mechanical allodynia that is achieved by pre-treatment of the animals with a range of concentrations of LC/A-nociceptin-HN/A fusion.

The ability of an LC/A-nociceptin-HN/A fusion (CPN/A) to inhibit streptozotocin (STZ)-induced mechanical (tactile) allodynia in rats is evaluated. STZ-induced mechanical allodynia in rats is achieved by injection of streptozotocin (i.p. or i.v.) which yields destruction of pancreatic β-cells leading to loss of insulin production, with concomitant metabolic stress (hyperglycemia and hyperlipidemia). As such, STZ induces Type I diabetes. In addition, STZ treatment leads to progressive development of neuropathy, which serves as a model of chronic pain with hyperalgesia and allodynia that may reflect signs observed in diabetic humans (peripheral diabetic neuropathy).

Male Sprague-Dawley rats (250-300 g) are treated with 65 mg/kg STZ in citrate buffer (I.V.) and blood glucose and lipid are measured weekly to define the readiness of the model. Paw Withdrawal Threshold (PWT) is measured in response to a Von Frey filament stimulus series over a period of time. Allodynia is said to be established when the PWT on two consecutive test dates (separated by 1 week) measures below 6 g on the scale. At this point, rats are randomized to either a saline group (negative efficacy control), gabapentin group (positive efficacy control) or a test group (CPN/A). Test materials (20-25 µl) are injected subcutaneously as a single injection (except gabapentin) and the PWT is measured at 1 day post-treatment and periodically thereafter over a 2-week period. Gabapentin (30 mg/kg i.p. @ 3 ml/kg injection volume) is injected daily, 2 hours prior to the start of PWT testing. FIG. 20 illustrates the reversal of allodynia achieved by pre-treatment of the animals with 750 ng of CPN/A. Data were obtained over a 2-week period after a single injection of CPN/A Example 23

Assessment of In Vivo Efficacy of an LC/A-Nociceptin Variant-$H_N$/A Fusion

The ability of an LC/A-nociceptin variant-$H_N$/A fusion (CPNv/A) to inhibit capsaicin-induced mechanical allodynia is evaluated following subcutaneous intraplantar injection in the rat hind paw. Test animals are evaluated for paw withdrawal frequency (PWF %) in response to a 10 g Von Frey filament stimulus series (10 stimuli×3 trials) prior to recruitment into the study (Pre-Treat); after subcutaneous intraplantar treatment with CPNv/A but before capsaicin (Pre-CAP); and following capsaicin challenge post-injection of CPNv/A (average of responses at 15' and 30'; CAP). Capsaicin challenge is achieved by injection of 10 µL of a 0.3% solution. Sample dilutions are prepared in 0.5% BSA/saline.

FIG. 21 illustrates the reversal of allodynia that is achieved by pre-treatment of the animals with a range of concentrations of LC/A-nociceptin variant-$H_N$/A fusion in comparison to the reversal achieved with the addition of LC/A-nociceptin-$H_N$/A fusion. These data are expressed as a normalized paw withdrawal frequency differential, in which the difference between the peak response (post-capsaicin) and the baseline response (pre-capsaicin) is expressed as a percentage. With this analysis, it can be seen that CPNv/A is more

Example 24

Preparation of an LC/A-Leu Enkephalin-H$_N$/A Fusion Protein

Due to the small, five-amino acid, size of the leu-enkephalin ligand the LC/A-leu enkephalin-H$_N$/A fusion is created by site directed mutagenesis [for example using Quickchange (Stratagene Inc.)] using the LC/A-nociceptin-H$_N$/A fusion (SEQ ID NO:13) as a template. Oligonucleotides are designed encoding the YGGFL leu-enkephalin peptide, ensuring standard *E. coli* codon usage is maintained and no additional restriction sites are incorporated, flanked by sequences complimentary to the linker region of the LC/A-nociceptin-H$_N$/A fusion (SEQ ID NO:13) either side on the nociceptin section. The SDM product is checked by sequencing and the final construct containing the LC-linker-leu enkephalin-spacer-H$_N$ ORF (SEQ ID NO:68) for expression as a protein of the sequence illustrated in SEQ ID NO:69. The fusion protein is termed CPLE-A. FIG. 22 illustrates the purification of CPLE-A from *E. coli* following the methods used in Example 9.

Example 25

Expression and Purification of an LC/A-Beta-Endorphin-H$_N$/A Fusion Protein Following the methods used in Example 9, and with the LC/A-beta-endorphin-H$_N$/A fusion protein (termed CPBE-A) created in Example 7, the CPBE-A is purified from *E. coli*. FIG. 23 illustrates the purified protein as analysed by SDS-PAGE.

Example 26

Preparation of an LC/A-Nociceptin Mutant-H$_N$/A Fusion Protein

Due to the single amino acid modification necessary to mutate the nociceptin sequence at position 1 from a Phe to a Tyr, the LC/A-nociceptin mutant-H$_N$/A fusion is created by site directed mutagenesis [for example using Quickchange (Stratagene Inc.)] using the LC/A-nociceptin-H$_N$/A fusion (SEQ ID NO:13) as a template. Oligonucleotides are designed encoding tyrosine at position 1 of the nociceptin sequence, ensuring standard *E. coli* codon usage is maintained and no additional restriction sites are incorporated, flanked by sequences complimentary to the linker region of the LC/A-nociceptin-H$_N$/A fusion (SEQ ID NO:13) either side on the nociceptin section. The SDM product is checked by sequencing and the final construct containing the LC/A-nociceptin mutant-spacer-H$_N$/A fusion ORF (SEQ ID NO:70) for expression as a protein of the sequence illustrated in SEQ ID NO:71. The fusion protein is termed CPOP-A. FIG. 24 illustrates the purification of CPOP-A from *E. coli* following the methods used in Example 9.

Example 27

Preparation and Assessment of an LC/A-Nociceptin Variant Mutant-H$_N$/A Fusion Protein Due to the single amino acid modification necessary to mutate the nociceptin sequence at position 1 from a Phe to a Tyr, the LC/A-nociceptin variant mutant-H$_N$/A fusion is created by site directed mutagenesis [for example using Quickchange (Stratagene Inc.)] using the LC/A-nociceptin variant-H$_N$/A fusion (SEQ ID NO:25) as a template. Oligonucleotides are designed encoding tyrosine at position 1 of the nociceptin sequence, ensuring standard *E. coli* codon usage is maintained and no additional restriction sites are incorporated, flanked by sequences complimentary to the linker region of the LC/A-nociceptin variant-H$_N$/A fusion (SEQ ID NO:25) either side on the nociceptin section. The SDM product is checked by sequencing and the final construct containing the LC/A-nociceptin mutant-spacer-H$_N$/A fusion ORF (SEQ ID NO:72) for expression as a protein of the sequence illustrated in SEQ ID NO:73. The fusion protein is termed CPOPv-A. FIG. 25 illustrates the purification of CPOPv-A from *E. coli* following the methods used in Example 9.

Using methodology described in Example 16, CPOPv-A is assessed for its ability to cleave SNAP-25 in the eDRG cell model. FIG. 26 illustrates that CPOPv-A is able to cleave SNAP-25 in the eDRG model, achieving cleavage of 50% of the maximal SNAP-25 after exposure of the cells to approximately 5.9 nM fusion for 24 h.

Example 28

Preparation of an IgA Protease-Nociceptin Variant-H$_N$/A Fusion Protein

The IgA protease amino acid sequence was obtained from freely available database sources such as GenBank (accession number P09790). Information regarding the structure of the *N. Gonorrhoeae* IgA protease gene is available in the literature (Pohlner et al., Gene structure and extracellular secretion of *Neisseria gonorrhoeae* IgA protease, Nature, 1987, 325 (6103), 458-62). Using Backtranslation tool v2.0 (Entelechon), the DNA sequence encoding the IgA protease modified for *E. coli* expression was determined. A BamHI recognition sequence was incorporated at the 5' end and a codon encoding a cysteine amino acid and SalI recognition sequence were incorporated at the 3' end of the IgA DNA. The DNA sequence was screened using MapDraw, (DNASTAR Inc.) for restriction enzyme cleavage sequences incorporated during the back translation. Any cleavage sequences that are found to be common to those required for cloning were removed manually from the proposed coding sequence ensuring common *E. coli* codon usage is maintained. *E. coli* codon usage was assessed Graphical Codon Usage Analyser (Geneart), and the % GC content and codon usage ratio assessed by reference to published codon usage tables. This optimised DNA sequence (SEQ ID NO:74) containing the IgA open reading frame (ORF) is then commercially synthesized.

The IgA (SEQ ID NO:74) is inserted into the LC-linker-nociceptin variant-spacer-H$_N$ ORF (SEQ ID NO:25) using BamHI and SalI restriction enzymes to replace the LC with the IgA protease DNA. The final construct contains the IgA-linker-nociceptin variant-spacer-H$_N$ ORF (SEQ ID NO:75) for expression as a protein of the sequence illustrated in SEQ ID NO:76.

Example 29

Preparation and Assessment of a Nociceptin Targeted Endopeptidase Fusion Protein with a Removable Histidine Purification Tag DNA was prepared that encoded a Factor Xa removable his-tag (his6), although it is clear that alternative proteases site such as Enterokinase and alternative purification tags such as longer histidine tags are also possible. Using one of a variety of reverse translation software tools [for example EditSeq best *E. coli* reverse translation (DNASTAR Inc.), or Backtranslation tool v2.0 (Entelechon)], the DNA sequence encoding the Factor Xa removable his-tag region is determined. Restriction sites are then incorporated into the DNA sequence and can be arranged as NheI-linker-SpeI-PstI-$H_N$/A-XbaI-LEIEGRSGHHHHHHStop codon-HindIII (SEQ ID NO:77). The DNA sequence is screened for restriction sequence incorporated and any additional sequences are removed manually from the remaining sequence ensuring common *E. coli* codon usage is maintained. *E. coli* codon usage is assessed by reference to software programs such as Graphical Codon Usage Analyser (Geneart), and the % GC content and codon usage ratio assessed by reference to published codon usage tables (for example GenBank Release 143, 13 Sep. 2004). This optimised DNA sequence is then commercially synthesized (for example by Entelechon, Geneart or Sigma-Genosys) and is provided in the pCR 4 vector. In order to create CPNv-A-FXa-HT (SEQ ID NO:78, removable his-tag construct) the pCR 4 vector encoding the removable his-tag is cleaved with NheI and HindIII. The NheI-HindIII fragment is then inserted into the LC/A-CPNv-$H_N$/A vector (SEQ ID NO:25) that has also been cleaved by NheI and HindIII. The final construct contains the LC/A-linker-nociceptin variant-spacer-$H_N$-FXa-Histag-HindIII ORF sequences (SEQ ID NO:78) for expression as a protein of the sequence illustrated in SEQ ID NO:79. FIG. 27 illustrates the purification of CPNv-A-FXa-HT from *E. coli* following the methods used in Example 9.

Example 30

Preparation of a Leu-Enkephalin Targeted Endopeptidase Fusion Protein Containing a Translocation Domain Derived from Diphtheria Toxin The DNA sequence is designed by back translation of the amino acid sequence of the translocation domain of the diphtheria toxin (obtained from freely available database sources such as GenBank (accession number 1xDTT) using one of a variety of reverse translation software tools [for example EditSeq best *E. coli* reverse translation (DNASTAR Inc.), or Backtranslation tool v2.0 (Entelechon)]. Restriction sites are then incorporated into the DNA sequence and can be arranged as NheI-Linker-SpeI-PstI-diphtheria translocation domain-XbaI-stop codon-HindIII (SEQ ID NO:80). PstI/XbaI recognition sequences are incorporated at the 5' and 3' ends of the translocation domain respectively of the sequence maintaining the correct reading frame. The DNA sequence is screened (using software such as MapDraw, DNASTAR Inc.) for restriction enzyme cleavage sequences incorporated during the back translation. Any cleavage sequences that are found to be common to those required by the cloning system are removed manually from the proposed coding sequence ensuring common *E. coli* codon usage is maintained. *E. coli* codon usage is assessed by reference to software programs such as Graphical Codon Usage Analyser (Geneart), and the % GC content and codon usage ratio assessed by reference to published codon usage tables (for example GenBank Release 143, 13 Sep. 2004). This optimised DNA sequence containing the diphtheria translocation domain is then commercially synthesized as NheI-Linker-SpeI-PstI-diphtheria translocation domain-XbaI-stop codon-HindIII (for example by Entelechon, Geneart or Sigma-Genosys) and is provided in the pCR 4 vector (Invitrogen). The pCR 4 vector encoding the diphtheria translocation domain is cleaved with NheI and XbaI. The NheI-XbaI fragment is then inserted into the LC/A-CPLE-$H_N$/A vector (SEQ ID NO:68) that has also been cleaved by NheI and XbaI. The final construct contains the LC/A-leu-enkephalin-spacer-diphtheria translocation domain ORF sequences (SEQ ID NO:81) for expression as a protein of the sequence illustrated in SEQ ID NO:82.

Example 31

Preparation of a Nociceptin Variant Targeted Endopeptidase Fusion Protein Containing a LC Domain Derived from Tetanus Toxin The DNA sequence is designed by back translation of the tetanus toxin LC amino acid sequence (obtained from freely available database sources such as GenBank (accession number X04436) using one of a variety of reverse translation software tools [for example EditSeq best *E. coli* reverse translation (DNASTAR Inc.), or Backtranslation tool v2.0 (Entelechon)]. BamHI/SalI recognition sequences are incorporated at the 5' and 3' ends respectively of the sequence maintaining the correct reading frame (SEQ ID NO:83). The DNA sequence is screened (using software such as MapDraw, DNASTAR Inc.) for restriction enzyme cleavage sequences incorporated during the back translation. Any cleavage sequences that are found to be common to those required by the cloning system are removed manually from the proposed coding sequence ensuring common *E. coli* codon usage is maintained. *E. coli* codon usage is assessed by reference to software programs such as Graphical Codon Usage Analyser (Geneart), and the % GC content and codon usage ratio assessed by reference to published codon usage tables (for example GenBank Release 143, 13 Sep. 2004). This optimised DNA sequence containing the tetanus toxin LC open reading frame (ORF) is then commercially synthesized (for example by Entelechon, Geneart or Sigma-Genosys) and is provided in the pCR 4 vector (invitrogen). The pCR 4 vector encoding the TeNT LC is cleaved with BamHI and SalI. The BamHI-SalI fragment is then inserted into the LC/A-CPNv-$H_N$/A vector (SEQ ID NO:25) that has also been cleaved by BamHI and SalI. The final construct contains the TeNT LC-linker-nociceptin variant-spacer-$H_N$ ORF sequences (SEQ ID NO:84) for expression as a protein of the sequence illustrated in SEQ ID NO:85.

Example 32

Preparation of an LC/C-Nociceptin Variant-$H_N$/C Fusion Protein with a Native Serotype C Linker that is Susceptible to Factor Xa Cleavage Following the methods used in Example 4, the LC/C (SEQ ID NO:5) and $H_N$/C (SEQ ID NO:6) are created and inserted into the C serotype nociceptin variant linker arranged as BamHI-SalI-linker-nociceptin variant-NheI-spacer-SpeI-PstI-XbaI-stop codon-HindIII (SEQ ID NO:86). The final construct contains the LC-linker-nociceptin variant-spacer-$H_N$ ORF sequences (SEQ ID NO:87) for expression as a protein of the sequence illustrated in SEQ ID NO:88. The fusion protein is termed CPNv-C (act. C).

The invention claimed is:

1. A single chain, polypeptide fusion protein, comprising:
   a. a non-cytotoxic protease, or a fragment thereof, which protease or protease fragment cleaves a protein of the exocytic fusion apparatus of a nociceptive sensory afferent;
   b. a Targeting Moiety that binds to a Binding Site on the nociceptive sensory afferent, which Binding Site undergoes endocytosis to be incorporated into an endosome within the nociceptive sensory afferent;
   c. a protease cleavage site at which site the fusion protein is cleavable by a protease, wherein the protease cleavage site is located between the non-cytotoxic protease or fragment thereof and the Targeting Moiety; and
   d. a translocation domain that translocates the protease or protease fragment from within an endosome, across the endosomal membrane and into the cytosol of the nociceptive sensory afferent, wherein the Targeting Moiety is located between the protease cleavage site and the translocation domain.

2. The fusion protein according to claim 1, wherein the Targeting Moiety and the protease cleavage site are separated by at most 10 amino acid residues, preferably by at most 5 amino acid residues, and more preferably by at most zero amino acid residues.

3. The fusion protein according to claim 1, wherein the non-cytotoxic protease is a clostridial neurotoxin L-chain or an IgA protease.

4. The fusion protein according to claim 1, wherein the translocation domain is the $H_N$ domain of a clostridial neurotoxin.

5. The fusion protein according to claim 1, wherein the Targeting Moiety comprises at most 50 amino acid residues, preferably at most 40 amino acid residues, more preferably at least 30 amino acid residues, and most preferably at most 20 amino acid residues.

6. The fusion protein according to claim 1, wherein the Targeting Moiety is an opioid.

7. The fusion protein according to claim 1, wherein the Targeting Moiety is an agonist of a receptor present on a nociceptive sensory afferent.

8. The fusion protein according to claim 7, wherein the Targeting Moiety is an agonist of a receptor present on a primary nociceptive sensory afferent.

9. The fusion protein according to claim 1, wherein the Targeting Moiety binds to the $ORL_1$ receptor.

10. The fusion protein according to claim 9, wherein the Targeting Moiety binds specifically to the $ORL_1$ receptor.

11. The fusion protein according to claim 9 or 10, wherein the Targeting Moiety is an agonist of the $ORL_1$ receptor.

12. The fusion protein according to claim 9, wherein the Targeting Moiety has at least 70% identity to SEQ ID NO: 38.

13. The fusion protein according to claim 12, wherein the Targeting Moiety has at least 80% identity to SEQ ID NO:38.

14. The fusion protein according to claim 13, wherein the Targeting Moiety has at least 90% identity to SEQ ID NO:38.

15. The fusion protein according to claim 14, wherein the Targeting Moiety has at least 95% identity to SEQ ID NO:38.

16. The fusion protein according to claim 9, wherein the Targeting Moiety is SEQ ID NO:38 or a fragment thereof.

17. The fusion protein according to claim 9, wherein the Targeting Moiety is one of SEQ ID NOs: 40, 42, 44, 46, 48 or 50.

18. The fusion protein according to claim 9, wherein the Targeting Moiety is nociceptin.

19. The fusion protein according to claim 1, wherein the Targeting Moiety is selected from the group consisting of nociceptin, β-endorphin, endomorphine-1, endomorphine-2, dynorphin, met-enkephalin, leu-enkephalin, galanin, and PAR-2 peptide.

20. The fusion protein according to claim 1, wherein the fusion protein comprises a purification tag.

21. The fusion protein according to claim 20, wherein the fusion protein comprises a purification tag, which is present at the N-terminal and/or C-terminal end of the fusion protein.

22. The fusion protein according to claim 20, wherein the purification tag is joined to the fusion protein by a peptide spacer molecule.

23. The fusion protein according to claim 1, wherein the translocation domain is separated from the Targeting Moiety by a peptide spacer molecule.

24. A polypeptide fusion protein comprising any one of SEQ ID NOs: 14, 18, 20, 22, 24, 26, 28, 30, 32, 34, 36, 59, 61, 67, 69, 71, 73, 76, 79, 82, 85, or 88.

25. A nucleic acid molecule encoding the polypeptide fusion protein according to claim 1.

26. The nucleic acid molecule according to claim 25, wherein the nucleic acid molecule comprises any one of SEQ ID NOs: 1-13, 15, 17, 19, 21, 23, 25, 27, 29, 31, 33, 35, 37, 39, 41, 43, 45, 47, 49, 51, 58, 60, 66, 68, 70, 72, 75, 78, 81, 84, or 87.

27. A DNA vector, which comprises a promoter, a nucleic acid molecule according to claim 25 or claim 26, and a terminator, wherein said nucleic acid molecule is located downstream of the promoter, and said terminator is located downstream of the nucleic acid molecule.

28. A nucleic acid molecule that is complementary to a nucleic acid molecule according to claim 25 or claim 26.

29. A method for preparing a single-chain polypeptide fusion protein comprising expressing a nucleic acid molecule according to claim 25 or claim 26 in a host cell.

30. A method of preparing a non-cytotoxic agent, comprising:

acting a single-chain polypeptide fusion protein according to claim 1 with a protease under conditions in which the protease cleavage site is cleaved, thereby forming a di-chain fusion protein, which is the non-cytotoxic agent.

31. A non-cytotoxic di-chain fusion protein obtained by a method comprising: contacting a single chain, polypeptide fusion protein according to claim 1 with a protease under conditions in which the protease cleavage site is cleaved, wherein:

a. the first chain of the di-chain fusion protein comprises the non-cytotoxic protease, or a fragment thereof, which protease or protease fragment cleaves a protein of the exocytic fusion apparatus of a nociceptive sensory afferent;

b. the second chain of the di-chain fusion protein comprises the Targeting Moiety and the translocation domain that translocates the protease or protease fragment from within an endosome, across the endosomal membrane and into the cytosol of the nociceptive sensory afferent; and the first and second chains are disulphide linked together.

32. A pharmaceutical composition comprising the polypeptide of claim 1 or claim 31.

33. A method of treating, preventing or ameliorating pain in a subject, comprising administering to said subject a therapeutically effective amount of a fusion protein according to claim 1 or an agent according to claim 31.

34. A method according to claim 33, wherein the pain is chronic pain.

35. A method for preparing a single-chain polypeptide fusion protein comprising expressing the DNA vector according to claim 27 in a host cell.

* * * * *

SEQUENCE LISTING

<160> NUMBER OF SEQ ID NOS: 110

<210> SEQ ID NO 1
<211> LENGTH: 1302
<212> TYPE: DNA
<213> ORGANISM: Artificial Sequence
<220> FEATURE:
<223> OTHER INFORMATION: chemically synthesized polynucleotide encoding
      clostridial neurotoxin serotype A light chain

<400> SEQUENCE: 1

| | | | | | |
|---|---|---|---|---|---|
| ggatccatgg | agttcgttaa | caaacagttc | aactataaag | acccagttaa | cggtgttgac | 60 |
| attgcttaca | tcaaaatccc | gaacgctggc | cagatgcagc | cggtaaaggc | attcaaaatc | 120 |
| cacaacaaaa | tctgggttat | cccggaacgt | gatacctta | ctaacccgga | agaaggtgac | 180 |
| ctgaacccgc | caccggaagc | gaaacaggtg | ccggtatctt | actatgactc | cacctacctg | 240 |
| tctaccgata | acgaaaagga | caactacctg | aaaggtgtta | ctaaactgtt | cgagcgtatt | 300 |
| tactccaccg | acctgggccg | tatgctgctg | actagcatcg | ttcgcggtat | cccgttctgg | 360 |
| ggcggttcta | ccatcgatac | cgaactgaaa | gtaatcgaca | ctaactgcat | caacgttatt | 420 |
| cagccggacg | gttcctatcg | ttccgaagaa | ctgaacctgg | tgatcatcgg | cccgtctgct | 480 |
| gatatcatcc | agttcgagtg | taagagcttt | ggtcacgaag | ttctgaacct | cacccgtaac | 540 |
| ggctacggtt | ccactcagta | catccgtttc | tctccggact | tcaccttcgg | ttttgaagaa | 600 |
| tccctggaag | tagacacgaa | cccactgctg | ggcgctggta | aattcgcaac | tgatcctgcg | 660 |
| gttaccctgg | ctcacgaact | gattcatgca | ggccaccgcc | tgtacggtat | cgccatcaat | 720 |
| ccgaaccgtg | tcttcaaagt | taacaccaac | gcgtattacg | agatgtccgg | tctggaagtt | 780 |
| agcttcgaag | aactgcgtac | ttttggcggt | cacgacgcta | aattcatcga | ctctctgcaa | 840 |
| gaaaacgagt | tccgtctgta | ctactataac | aagttcaaag | atatcgcatc | cacccctgaac | 900 |
| aaagcgaaat | ccatcgtggg | taccactgct | tctctccagt | acatgaagaa | cgtttttaaa | 960 |
| gaaaatacc | tgctcagcga | agacacctcc | ggcaaattct | ctgtagacaa | gttgaaattc | 1020 |
| gataaacttt | acaaaatgct | gactgaaatt | tacaccgaag | acaacttcgt | taagttctt | 1080 |
| aaagttctga | accgcaaaac | ctatctgaac | ttcgacaagg | cagtattcaa | aatcaacatc | 1140 |
| gtgccgaaag | ttaactacac | tatctacgat | ggtttcaacc | tgcgtaacac | caacctggct | 1200 |
| gctaatttta | acggccagaa | cacgaaaatc | aacaacatga | acttcacaaa | actgaaaaac | 1260 |
| ttcactggtc | tgttcgagtt | ttacaagctg | ctgtgcgtcg | ac | | 1302 |

<210> SEQ ID NO 2
<211> LENGTH: 1257
<212> TYPE: DNA
<213> ORGANISM: Artificial Sequence
<220> FEATURE:
<223> OTHER INFORMATION: chemically synthesized polynucleotide encoding
      clostridial neurotoxin serotype A heavy chain

<400> SEQUENCE: 2

| | | | | | |
|---|---|---|---|---|---|
| ctgcagtgta | tcaaggttaa | caactgggat | ttattcttca | gcccgagtga | agacaacttc | 60 |
| accaacgacc | tgaacaaagg | tgaagaaatc | acctcagata | ctaacatcga | agcagccgaa | 120 |
| gaaaacatct | cgctggacct | gatccagcag | tactacctga | cctttaattt | cgacaacgag | 180 |
| ccggaaaaca | tttctatcga | aaacctgagc | tctgatatca | tcggccagct | ggaactgatg | 240 |
| ccgaacatcg | aacgtttccc | aaacggtaaa | aagtacgagc | tggacaaata | taccatgttc | 300 |

```
cactacctgc gcgcgcagga atttgaacac ggcaaatccc gtatcgcact gactaactcc    360
gttaacgaag ctctgctcaa cccgtcccgt gtatacacct tcttctctag cgactacgtg    420
aaaaaggtca acaaagcgac tgaagctgca atgttcttgg gttgggttga acagcttgtt    480
tatgatttta ccgacgagac gtccgaagta tctactaccg acaaaattgc ggatatcact    540
atcatcatcc cgtacatcgg tccggctctg aacattggca acatgctgta caaagacgac    600
ttcgttggcg cactgatctt ctccggtgcg gtgatcctgc tggagttcat cccggaaatc    660
gccatcccgg tactgggcac ctttgctctg gtttcttaca ttgcaaacaa ggttctgact    720
gtacaaacca tcgacaacgc gctgagcaaa cgtaacgaaa atgggatga agtttacaaa    780 tatatcgtga ccaactggct ggctaaggtt aatactcaga tcgacctcat ccgcaaaaaa    840
atgaaagaag cactggaaaa ccaggcgaaa gctaccaagg caatcattaa ctaccagtac    900
aaccagtaca ccgaggaaga aaaaaacaac atcaacttca acatcgacga tctgtcctct    960
aaactgaacg aatccatcaa caaagctatg atcaacatca caagttcct gaaccagtgc   1020 tctgtaagct atctgatgaa ctccatgatc ccgtacggtg ttaaacgtct ggaggacttc   1080
gatgcgtctc tgaaagacgc cctgctgaaa tacatttacg acaaccgtgg cactctgatc   1140
ggtcaggttg atcgtctgaa ggacaaagtg aacaatacct tatcgaccga catccctttt   1200
cagctcagta aatatgtcga taaccaacgc cttttgtcca ctctagacta gaagctt      1257

<210> SEQ ID NO 3
<211> LENGTH: 1323
<212> TYPE: DNA
<213> ORGANISM: Artificial Sequence
<220> FEATURE:
<223> OTHER INFORMATION: chemically synthesized polynucleotide encoding
      clostridial neurotoxin serotype B light chain

<400> SEQUENCE: 3
ggatccatgc cggttaccat caacaacttc aactacaacg accgatcga caacaacaac     60 atcattatga tggaaccgcc gttcgcacgt ggtaccggac gttactacaa ggcttttaag   120
atcaccgacc gtatctggat catcccggaa cgttacacct tcggttacaa acctgaggac   180
ttcaacaaga gtagcgggat tttcaatcgt gacgtctgcg agtactatga tccagattat   240
ctgaatacca acgataagaa gaacatattc ctttcagacta tgattaaact cttcaaccgt   300
atcaaaagca aaccgctcgg tgaaaaactc ctcgaaatga ttatcaacgg tatcccgtac   360
ctcggtgacc gtcgtgtccc gcttgaagag ttcaacacca catcgcaag cgtcaccgtc   420 aacaaactca tcagcaaccc aggtgaagtc gaacgtaaaa aaggtatctt cgcaaacctc   480
atcatcttcg gtccgggtcc ggtcctcaac gaaaacgaaa ccatcgacat cggtatccag   540
aaccacttcg caagccgtga aggtttcggt ggtatcatgc agatgaaatt ctgcccggaa   600
tacgtcagtg tcttcaacaa cgtccaggaa aacaaaggtg caagcatctt caaccgtcgt   660
ggttacttca gcgacccggc actcatcctc atgcatgaac tcatccacgt cctccacggt   720
ctctacggta tcaaagttga cgacctcccg atcgtcccga cgagaagaa attcttcatg   780 cagagcaccg acgcaatcca ggctgaggaa ctctacacct tcggtggcca agacccaagt   840
atcataaccc cgtccaccga caaaagcatc tacgacaaag tcctccagaa cttcaggggt   900
atcgtggaca gactcaacaa agtcctcgtc tgcatcagcg acccgaacat caatatcaac   960
atatacaaga acaagttcaa agacaagtac aaattcgtcg aggacagcga aggcaaatac  1020
agcatcgacg tagaaagttt cgacaagctc tacaaagcc tcatgttcgg tttcaccgaa  1080
accaacatcg ccgagaacta caagatcaag acaagggcaa gttacttcag cgacagcctc  1140
```

```
ccgcctgtca aaatcaagaa cctcttagac aacgagattt acacaattga agagggcttc    1200
aacatcagtg acaaagacat ggagaaggaa tacagaggtc agaacaaggc tatcaacaaa    1260
caggcatacg aggagatcag caaagaacac ctcgcagtct acaagatcca gatgtgcgtc    1320
gac                                                                 1323
```

<210> SEQ ID NO 4
<211> LENGTH: 1260
<212> TYPE: DNA
<213> ORGANISM: Artificial Sequence
<220> FEATURE:
<223> OTHER INFORMATION: chemically synthesized polynucleotide encoding
      clostridial neurotoxin serotype B heavy chain

<400> SEQUENCE: 4

```
ctgcagtgca tcgacgttga caacgaagac ctgttcttca tcgctgacaa aaacagcttc     60
agtgacgacc tgagcaaaaa cgaacgtatc gaatacaaca cccagagcaa ctacatcgaa    120
aacgacttcc cgatcaacga actgatcctg acaccgacc tgataagtaa aatcgaactg    180
ccgagcgaaa acaccgaaag tctgaccgac ttcaacgttg acgttccggt ttacgaaaaa    240
cagccggcta tcaagaaaat cttcaccgac gaaaacacca tcttccagta cctgtacagc    300
cagaccttcc cgctggacat ccgtgacatc agtctgacca gcagtttcga cgacgctctg    360
ctgttcagca acaaagttta cagtttcttc agcatggact acatcaaaac cgctaacaaa    420
gttgttgaag cagggctgtt cgctggttgg gttaaacaga tcgttaacga cttcgttatc    480
gaagctaaca aaagcaacac tatggacaaa atcgctgaca tcagtctgat cgttccgtac    540
atcggtctgg ctctgaacgt tggtaacgaa accgctaaag gtaactttga aaacgctttc    600
gagatcgctg gtgcaagcat cctgctggag ttcatcccgg aactgctgat cccggttgtt    660
ggtgctttcc tgctggaaag ttacatcgac aacaaaaaca agatcatcaa aaccatcgac    720
aacgctctga ccaaacgtaa cgaaaaatgg agtgatatgt acggtctgat cgttgctcag    780
tggctgagca ccgtcaacac ccagttctac accatcaaag aaggtatgta caaagctctg    840
aactaccagg ctcaggctct ggaagagatc atcaaatacc gttacaacat ctacagtgag    900
aaggaaaaga gtaacatcaa catcgacttc aacgacatca cagcaaaact gaacgaaggt    960
atcaaccagg ctatcgacaa catcaacaac ttcatcaacg gttgcagtgt tagctacctg    1020
atgaagaaga tgatcccgct ggctgttgaa aaactgctgg acttcgacaa caccctgaaa    1080
aagaacctgc tgaactacat cgacgaaaac aagctgtacc tgatcggtag tgctgaatac    1140
gaaaaaagta agtgaacaa atacctgaag accatcatgc cgttcgacct gagtatctac    1200
accaacgaca ccatcctgat cgaaatgttc aacaaataca ctctctctaga ctagaagctt    1260
```

<210> SEQ ID NO 5
<211> LENGTH: 1329
<212> TYPE: DNA
<213> ORGANISM: Artificial Sequence
<220> FEATURE:
<223> OTHER INFORMATION: chemically synthesized polynucleotide encoding
      clostridial neurotoxin serotype C light chain

<400> SEQUENCE: 5

```
ggatccgaat tcatgccgat caccatcaac aacttcaact acagcgatcc ggtggataac     60
aaaaacatcc tgtacctgga tacccatctg aatacctgg cgaacgaacc ggaaaaagcg    120
tttcgtatca ccggcaacat ttgggttatt ccggatcgtt ttagccgtaa cagcaacccg    180
aatctgaata aaccgccgcg tgttaccagc ccgaaaagcg gttattacga tccgaactat    240
```

```
ctgagcaccg atagcgataa agataccttc ctgaaagaaa tcatcaaact gttcaaacgc      300
atcaacagcc gtgaaattgg cgaagaactg atctatcgcc tgagcaccga tattccgttt      360 ccggcaaca acaacacccc gatcaacacc tttgatttcg atgtggattt caacagcgtt      420
gatgttaaaa cccgccaggg taacaattgg gtgaaaaccg gcagcattaa cccgagcgtg      480
attattaccg gtccgcgcga aaacattatt gatccggaaa ccagcacctt taaactgacc      540
aacaacacct ttgcggcgca ggaaggtttt ggcgcgctga gcattattag cattagcccg      600
cgctttatgc tgacctatag caacgcgacc aacgatgttg gtgaaggccg tttcagcaaa      660
agcgaatttt gcatggaccc gatcctgatc ctgatgcatg aactgaacca tgcgatgcat      720
aacctgtatg gcatcgcgat tccgaacgat cagaccatta gcagcgtgac cagcaacatc      780
ttttacagcc agtacaacgt gaaactggaa tatgcggaaa tctatgcgtt tggcggtccg      840
accattgatc tgattccgaa aagcgcgcgc aaatacttcg aagaaaaagc gctggattac      900
tatcgcagca ttgcgaaacg tctgaacagc attaccaccg cgaatccgag cagcttcaac      960
aaatatatcg gcgaatataa acagaaactg atccgcaaat atcgctttgt ggtggaaagc     1020
agcggcgaag ttaccgttaa ccgcaataaa ttcgtggaac tgtacaacga actgacccag     1080
atcttcaccg aatttaacta tgcgaaaatc tataacgtgc agaaccgtaa aatctacctg     1140
agcaacgtgt atacccccggt gaccgcgaat attctggatg ataacgtgta cgatatccag     1200
aacggcttta acatcccgaa aagcaacctg aacgttctgt ttatgggcca gaacctgagc     1260
cgtaatccgg cgctgcgtaa agtgaacccg gaaaacatgc tgtacctgtt caccaaattt     1320
tgcgtcgac                                                             1329
```

<210> SEQ ID NO 6
<211> LENGTH: 1263
<212> TYPE: DNA
<213> ORGANISM: Artificial Sequence
<220> FEATURE:
<223> OTHER INFORMATION: chemically synthesized polynucleotide encoding clostridial neurotoxin serotype C heavy chain

<400> SEQUENCE: 6

```
ctgcagtgtc gtgaactgct ggtgaaaaac accgatctgc gtttattgg cgatatcagc       60 gatgtgaaaa ccgatatctt cctgcgcaaa gatatcaacg aagaaaccga agtgatctac      120
tacccggata acgtgagcgt tgatcaggtg atcctgagca aaaacaccag cgaacatggt      180
cagctggatc tgctgtatcc gagcattgat agcgaaagcg aaattctgcc gggcgaaaac      240
caggtgtttt acgataaccg tacccagaac gtggattacc tgaacagcta ttactacctg      300
gaaagccaga aactgagcga taacgtgaa gattttaccct ttacccgcag cattgaagaa      360 cgcgctggata cagcgcgaa agtttacacc tattttccga ccctggcgaa caaagttaat      420
gcgggtgttc agggcggtct gtttctgatg tgggcgaacg atgtggtgga agatttcacc      480
accaacatcc tgcgtaaaga taccctggat aaaatcagcg atgttagcgc gattattccg      540
tatattggtc cggcgctgaa cattagcaat agcgtgcgtc gtggcaattt taccgaagcg      600
tttgcggtta ccggtgtgac cattctgctg gaagcgtttc cggaatttac cattccggcg      660
ctgggtgcgt ttgtgatcta tagcaaagtg caggaacgca cgaaatcat caaaaccatc      720 gataactgcc tggaacagcg tattaaacgc tggaaagata gctatgaatg gatgatgggc      780
acctggctga gccgtattat cacccagttc aacaacatca gctaccagat gtacgatagc      840
ctgaactatc aggcgggtgc gattaaagcg aaaatcgatc tggaatacaa aaaatacagc      900
```

```
ggcagcgata aagaaaacat caaaagccag gttgaaaacc tgaaaaacag cctggatgtg      960
aaaattagcg aagcgatgaa taacatcaac aaattcatcc gcgaatgcag cgtgacctac     1020
ctgttcaaaa acatgctgcc gaaagtgatc gatgaactga acgaatttga tcgcaacacc     1080
aaagcgaaac tgatcaacct gatcgatagc cacaacatta ttctggtggg cgaagtggat     1140
aaactgaaag cgaaagttaa caacagcttc cagaacacca tcccgtttaa catcttcagc     1200
tataccaaca acagcctgct gaaagatatc atcaacgaat acttcaatct agactagaag     1260
ctt                                                                  1263
```

<210> SEQ ID NO 7
<211> LENGTH: 207
<212> TYPE: DNA
<213> ORGANISM: Artificial Sequence
<220> FEATURE:
<223> OTHER INFORMATION: chemically synthesized polynucleotide encoding
      a linker

<400> SEQUENCE: 7

```
ggatccacgc acgtcgacgg catcattacc tccaaaacta aatctctgat cgaaggtcgt      60
tttggcggtt tcacgggcgc acgcaaatca gcgcgtaaat tagctaacca ggcgctagcg     120
ggcggtggcg gtagcggcgg tggcggtagc ggcggtggcg gtagcgcact agtgctgcag     180
acgcacggtc tagaatgata aaagctt                                        207
```

<210> SEQ ID NO 8
<211> LENGTH: 108
<212> TYPE: DNA
<213> ORGANISM: Artificial Sequence
<220> FEATURE:
<223> OTHER INFORMATION: chemically synthesized polynucleotide encoding
      a linker

<400> SEQUENCE: 8

```
ggatccacgc acgtcgacgg catcattacc tccaaaacta aatctctgat agaaggtaga      60
aacaaagcgc tgaacctgca gacgcacggt ctagaatgat aaaagctt                 108
```

<210> SEQ ID NO 9
<211> LENGTH: 186
<212> TYPE: DNA
<213> ORGANISM: Artificial Sequence
<220> FEATURE:
<223> OTHER INFORMATION: chemically synthesized polynucleotide encoding
      nociceptin insert

<400> SEQUENCE: 9

```
catatgaata acctcgggat tgagggtcgt tttggcggtt tcacgggcgc acgcaaatca      60
gcgcgtaaat tagctaacca gactagtggc ggtggggta gtggcggtgg cggttcgggc     120
gggggtggga gccctagggg atccgtcgac ctgcagggtc tagaagcgct agcgtgataa     180
aagctt                                                              186
```

<210> SEQ ID NO 10
<211> LENGTH: 180
<212> TYPE: DNA
<213> ORGANISM: Artificial Sequence
<220> FEATURE:
<223> OTHER INFORMATION: chemically synthesized polynucleotide encoding
      a linker

<400> SEQUENCE: 10

```
ggatccacgc acgtcgacgc gattgatggt cgttttggcg gtttcacggg cgcacgcaaa      60
```

```
tcagcgcgta aattagctaa ccaggcgcta gcgggcggtg gcggtagcgg cggtggcgt     120 agcggcggtg gcggtagcgc actagtgctg cagacgcacg gtctagaatg ataaaagctt    180
```

<210> SEQ ID NO 11
<211> LENGTH: 249
<212> TYPE: DNA
<213> ORGANISM: Artificial Sequence
<220> FEATURE:
<223> OTHER INFORMATION: chemically synthesized polynucleotide encoding
      a linker

<400> SEQUENCE: 11

```
ggatccacgc acgtcgacgg catcattacc tccaaaacta atctctgat cgaaggtcgt     60 tacggtggtt tcatgacctc tgaaaaatct cagaccccgc tggttaccct gttcaaaaac   120
gctatcatca aaacgctta caaaaaggt gaagcgctag cgggtggtgg tggttctggt     180
ggtggtggtt ctggtggtgg tggttctgca ctagtgctgc agacgcacgg tctagaatga   240
taaaagctt                                                          249
```

<210> SEQ ID NO 12
<211> LENGTH: 207
<212> TYPE: DNA
<213> ORGANISM: Artificial Sequence
<220> FEATURE:
<223> OTHER INFORMATION: chemically synthesized polynucleotide encoding
      a linker

<400> SEQUENCE: 12

```
ggatccacgc acgtcgacgg catcattacc tccaaaacta atctctgat cgaaggtcgt     60 tttggcggtt tcacgggcgc acgcaaatca gcgcgtaaac gtaagaacca ggcgctagcg   120
ggcggtggcg gtagcggcgg tggcggtagc ggcggtggcg gtagcgcact agtgctgcag   180
acgcacggtc tagaatgata aaagctt                                       207
```

<210> SEQ ID NO 13
<211> LENGTH: 2709
<212> TYPE: DNA
<213> ORGANISM: Artificial Sequence
<220> FEATURE:
<223> OTHER INFORMATION: chemically synthesized polynucleotide encoding
      fusion protein

<400> SEQUENCE: 13

```
ggatccatgg agttcgttaa caaacagttc aactataaag acccagttaa cggtgttgac     60
attgcttaca tcaaaatccc gaacgctggc cagatgcagc cggtaaaggc attcaaaatc    120
cacaacaaaa tctgggttat cccggaacgt gatacccttta ctaacccgga agaaggtgac   180
ctgaacccgc caccggaagc gaaacaggtg ccggtatctt actatgactc cacctacctg   240
tctaccgata cgaaaagga caactacctg aaaggtgtta ctaaactgtt cgagcgtatt    300
tactccaccg acctgggccg tatgctgctg actagcatcg ttcgcggtat cccgttctgg   360
ggcggttcta ccatcgatac cgaactgaaa gtaatcgaca ctaactgcat caacgttatt   420
cagccggacg gttcctatcg ttccgaagaa ctgaacctgg tgatcatcgg cccgtctgct   480
gatatcatcc agttcgagtg taagagcttt ggtcacgaag ttctgaacct cacccgtaac   540
ggctacggtt ccactcagta catccgtttc tctccggact caccttcgg ttttgaagaa   600 tccctggaag tagacacgaa cccactgctg ggcgctggta attcgcaac tgatcctgcg    660 gttaccctgg ctcacgaact gattcatgca ggccaccgcc tgtacggtat cgccatcaat   720
ccgaaccgtg tcttcaaagt taacaccaac gcgtattacg agatgtccgg tctggaagtt    780
```

```
agcttcgaag aactgcgtac ttttggcggt cacgacgcta aattcatcga ctctctgcaa    840
gaaaacgagt tccgtctgta ctactataac aagttcaaag atatcgcatc caccctgaac    900
aaagcgaaat ccatcgtggg taccactgct tctctccagt acatgaagaa cgttttttaaa  960
gaaaaatacc tgctcagcga agacacctcc ggcaaattct ctgtagacaa gttgaaattc   1020
gataaacttt acaaaatgct gactgaaatt tacaccgaag acaacttcgt taagttcttt   1080
aaagttctga accgcaaaac ctatctgaac ttcgacaagg cagtattcaa aatcaacatc   1140
gtgccgaaag ttaactacac tatctacgat ggtttcaacc tgcgtaacac caacctggct   1200
gctaattttta acggccagaa cacggaaatc aacaacatga acttcacaaa actgaaaaac  1260
ttcactggtc tgttcgagtt ttacaagctg ctgtgcgtcg acggcatcat acctccaaa    1320
actaaatctc tgatagaagg tagatttggc ggtttcacgg gcgcacgcaa atcagcgcgt   1380
aaattagcta accaggcgct agcgggcggt ggcggtagcg cggtggcgg tagcggcgt     1440
ggcggtagcg cactagtgct gcagtgtatc aaggttaaca actgggattt attcttcagc   1500
ccgagtgaag acaacttcac caacgacctg aacaaaggtg aagaaatcac ctcagatact   1560
aacatcgaag cagccgaaga aaacatctcg ctggacctga tccagcagta ctacctgacc   1620
tttaatttcg acaacgagcc ggaaaacatt tctatcgaaa acctgagctc tgatatcatc   1680
ggccagctgg aactgatgcc gaacatcgaa cgtttcccaa acgtaaaaa gtacgagctg    1740
gacaaatata ccatgttcca ctacctgcgc gcgcaggaat ttgaacacgg caaatcccgt   1800
atcgcactga ctaactccgt taacgaagct ctgctcaacc cgtcccgtgt atacaccttc   1860
ttctctagcg actacgtgaa aaaggtcaac aaagcgactg aagctgcaat gttcttgggt   1920
tgggttgaac agcttgttta tgattttacc gacgagacgt ccgaagtatc tactaccgac   1980
aaaattgcgg atatcactat catcatcccg tacatcggtc cggctctgaa cattggcaac   2040
atgctgtaca agacgactt cgttggcgca ctgatcttct ccggtgcggt gatcctgctg    2100
gagttcatcc cggaaatcgc catcccggta ctgggcacct ttgctctggt tcttacatt    2160
gcaaacaagg ttctgactgt acaaaccatc gacaacgcgc tgagcaaacg taacgaaaaa   2220
tgggatgaag tttacaaata tatcgtgacc aactggctgg ctaaggttaa tactcagatc   2280
gacctcatcc gcaaaaaat gaagaagca ctggaaaaacc aggcggaagc taccaaggca    2340
atcattaact accagtacaa ccagtacacc gaggaagaaa aaacaacat caacttcaac    2400
atcgacgatc tgtcctctaa actgaacgaa tccatcaaca agctatgat caacatcaac    2460
aagttcctga accagtgctc tgtaagctat ctgatgaact ccatgatccc gtacggtgtt   2520
aaacgtctgg aggacttcga tgcgtctctg aaagacgccc tgctgaaata catttacgac   2580
aaccgtggca ctctgatcgg tcaggttgat cgtctgaagg acaaagtgaa caatacctta   2640
tcgaccgaca tccctttca gctcagtaaa tatgtcgata ccaacgcct ttgtccact      2700
ctagactag                                                           2709
```

<210> SEQ ID NO 14
<211> LENGTH: 902
<212> TYPE: PRT
<213> ORGANISM: Artificial Sequence
<220> FEATURE:
<223> OTHER INFORMATION: chemically synthesized fusion protein

<400> SEQUENCE: 14

Gly Ser Met Glu Phe Val Asn Lys Gln Phe Asn Tyr Lys Asp Pro Val
1               5                   10                  15

```
Asn Gly Val Asp Ile Ala Tyr Ile Lys Ile Pro Asn Ala Gly Gln Met
         20                  25                  30

Gln Pro Val Lys Ala Phe Lys Ile His Asn Lys Ile Trp Val Ile Pro
             35                  40                  45

Glu Arg Asp Thr Phe Thr Asn Pro Glu Glu Gly Asp Leu Asn Pro Pro
 50                  55                  60

Pro Glu Ala Lys Gln Val Pro Val Ser Tyr Tyr Asp Ser Thr Tyr Leu
 65                  70                  75                  80

Ser Thr Asp Asn Glu Lys Asp Asn Tyr Leu Lys Gly Val Thr Lys Leu
                 85                  90                  95

Phe Glu Arg Ile Tyr Ser Thr Asp Leu Gly Arg Met Leu Leu Thr Ser
                100                 105                 110

Ile Val Arg Gly Ile Pro Phe Trp Gly Gly Ser Thr Ile Asp Thr Glu
            115                 120                 125

Leu Lys Val Ile Asp Thr Asn Cys Ile Asn Val Ile Gln Pro Asp Gly
        130                 135                 140

Ser Tyr Arg Ser Glu Glu Leu Asn Leu Val Ile Ile Gly Pro Ser Ala
145                 150                 155                 160

Asp Ile Ile Gln Phe Glu Cys Lys Ser Phe Gly His Glu Val Leu Asn
                165                 170                 175

Leu Thr Arg Asn Gly Tyr Gly Ser Thr Gln Tyr Ile Arg Phe Ser Pro
            180                 185                 190

Asp Phe Thr Phe Gly Phe Glu Glu Ser Leu Glu Val Asp Thr Asn Pro
        195                 200                 205

Leu Leu Gly Ala Gly Lys Phe Ala Thr Asp Pro Ala Val Thr Leu Ala
    210                 215                 220

His Glu Leu Ile His Ala Gly His Arg Leu Tyr Gly Ile Ala Ile Asn
225                 230                 235                 240

Pro Asn Arg Val Phe Lys Val Asn Thr Asn Ala Tyr Tyr Glu Met Ser
                245                 250                 255

Gly Leu Glu Val Ser Phe Glu Glu Leu Arg Thr Phe Gly Gly His Asp
            260                 265                 270

Ala Lys Phe Ile Asp Ser Leu Gln Glu Asn Glu Phe Arg Leu Tyr Tyr
        275                 280                 285

Tyr Asn Lys Phe Lys Asp Ile Ala Ser Thr Leu Asn Lys Ala Lys Ser
    290                 295                 300

Ile Val Gly Thr Thr Ala Ser Leu Gln Tyr Met Lys Asn Val Phe Lys
305                 310                 315                 320

Glu Lys Tyr Leu Leu Ser Glu Asp Thr Ser Gly Lys Phe Ser Val Asp
                325                 330                 335

Lys Leu Lys Phe Asp Lys Leu Tyr Lys Met Leu Thr Glu Ile Tyr Thr
            340                 345                 350

Glu Asp Asn Phe Val Lys Phe Phe Lys Val Leu Asn Arg Lys Thr Tyr
        355                 360                 365

Leu Asn Phe Asp Lys Ala Val Phe Lys Ile Asn Ile Val Pro Lys Val
    370                 375                 380

Asn Tyr Thr Ile Tyr Asp Gly Phe Asn Leu Arg Asn Thr Asn Leu Ala
385                 390                 395                 400

Ala Asn Phe Asn Gly Gln Asn Thr Glu Ile Asn Asn Met Asn Phe Thr
                405                 410                 415

Lys Leu Lys Asn Phe Thr Gly Leu Phe Glu Phe Tyr Lys Leu Leu Cys
            420                 425                 430

Val Asp Gly Ile Ile Thr Ser Lys Thr Lys Ser Leu Ile Glu Gly Arg
        435                 440                 445
```

```
Phe Gly Gly Phe Thr Gly Ala Arg Lys Ser Ala Arg Lys Leu Ala Asn
    450                 455                 460

Gln Ala Leu Ala Gly Gly Gly Ser Gly Gly Gly Ser Gly Gly
465                 470                 475                 480

Gly Gly Ser Ala Leu Val Leu Gln Cys Ile Lys Val Asn Asn Trp Asp
                485                 490                 495

Leu Phe Phe Ser Pro Ser Glu Asp Asn Phe Thr Asn Asp Leu Asn Lys
            500                 505                 510

Gly Glu Glu Ile Thr Ser Asp Thr Asn Ile Glu Ala Ala Glu Glu Asn
            515                 520                 525

Ile Ser Leu Asp Leu Ile Gln Gln Tyr Tyr Leu Thr Phe Asn Phe Asp
    530                 535                 540

Asn Glu Pro Glu Asn Ile Ser Ile Glu Asn Leu Ser Ser Asp Ile Ile
545                 550                 555                 560

Gly Gln Leu Glu Leu Met Pro Asn Ile Glu Arg Phe Pro Asn Gly Lys
                565                 570                 575

Lys Tyr Glu Leu Asp Lys Tyr Thr Met Phe His Tyr Leu Arg Ala Gln
            580                 585                 590

Glu Phe Glu His Gly Lys Ser Arg Ile Ala Leu Thr Asn Ser Val Asn
            595                 600                 605

Glu Ala Leu Leu Asn Pro Ser Arg Val Tyr Thr Phe Phe Ser Ser Asp
610                 615                 620

Tyr Val Lys Lys Val Asn Lys Ala Thr Glu Ala Ala Met Phe Leu Gly
625                 630                 635                 640

Trp Val Glu Gln Leu Val Tyr Asp Phe Thr Asp Glu Thr Ser Glu Val
                645                 650                 655

Ser Thr Thr Asp Lys Ile Ala Asp Ile Thr Ile Ile Pro Tyr Ile
            660                 665                 670

Gly Pro Ala Leu Asn Ile Gly Asn Met Leu Tyr Lys Asp Asp Phe Val
            675                 680                 685

Gly Ala Leu Ile Phe Ser Gly Ala Val Ile Leu Leu Glu Phe Ile Pro
690                 695                 700

Glu Ile Ala Ile Pro Val Leu Gly Thr Phe Ala Leu Val Ser Tyr Ile
705                 710                 715                 720

Ala Asn Lys Val Leu Thr Val Gln Thr Ile Asp Asn Ala Leu Ser Lys
                725                 730                 735

Arg Asn Glu Lys Trp Asp Glu Val Tyr Lys Tyr Ile Val Thr Asn Trp
            740                 745                 750

Leu Ala Lys Val Asn Thr Gln Ile Asp Leu Ile Arg Lys Lys Met Lys
            755                 760                 765

Glu Ala Leu Glu Asn Gln Ala Glu Ala Thr Lys Ala Ile Ile Asn Tyr
    770                 775                 780

Gln Tyr Asn Gln Tyr Thr Glu Glu Lys Asn Asn Ile Asn Phe Asn
785                 790                 795                 800

Ile Asp Asp Leu Ser Ser Lys Leu Asn Glu Ser Ile Asn Lys Ala Met
                805                 810                 815

Ile Asn Ile Asn Lys Phe Leu Asn Gln Cys Ser Val Ser Tyr Leu Met
            820                 825                 830

Asn Ser Met Ile Pro Tyr Gly Val Lys Arg Leu Glu Asp Phe Asp Ala
            835                 840                 845

Ser Leu Lys Asp Ala Leu Leu Lys Tyr Ile Tyr Asp Asn Arg Gly Thr
850                 855                 860

Leu Ile Gly Gln Val Asp Arg Leu Lys Asp Lys Val Asn Asn Thr Leu
```

```
              865                 870                 875                 880
Ser Thr Asp Ile Pro Phe Gln Leu Ser Lys Tyr Val Asp Asn Gln Arg
                      885                 890                 895

Leu Leu Ser Thr Leu Asp
            900
```

<210> SEQ ID NO 15
<211> LENGTH: 2736
<212> TYPE: DNA
<213> ORGANISM: Artificial Sequence
<220> FEATURE:
<223> OTHER INFORMATION: chemically synthesized polynucleotide encoding fusion protein

<400> SEQUENCE: 15

```
ctcgggattg agggtcgttt tggcggtttc acgggcgcac gcaaatcagc gcgtaaatta      60
gctaaccaga ctagtggcgg tggggtagt ggcggtggcg gttcgggcgg gggtgggagc     120
cctagggat ccatggagtt cgttaacaaa cagttcaact ataaagaccc agttaacggt     180
gttgacattg cttacatcaa atcccgaac gctggccaga tgcagccggt aaaggcattc     240
aaaatccaca caaaatctg ggttatcccg aacgtgata cctttactaa cccggaagaa     300
ggtgacctga cccgccacc ggaagcgaaa caggtgccgg tatcttacta tgactccacc     360
tacctgtcta ccgataacga aaggacaac tacctgaaag tgttactaa actgttcgag     420
cgtatttact ccaccgacct gggccgtatg ctgctgacta gcatcgttcg cggtatcccg     480
ttctggggcg gttctaccat cgataccgaa ctgaaagtaa tcgacactaa ctgcatcaac     540
gttattcagc cggacggttc ctatcgttcc gaagaactga acctggtgat catcggcccg     600
tctgctgata tcatccagtt cgagtgtaag agctttggtc acgaagttct gaaccctcacc     660
cgtaacggct acggttccac tcagtacatc cgtttctctc cggacttcac cttcggtttt     720
gaagaatccc tggaagtaga cacgaaccca ctgctgggcg ctggtaaatt cgcaactgat     780
cctgcggtta ccctggctca cgaactgatt catgcaggcc accgcctgta cggtatcgcc     840
atcaatccga accgtgtctt caaagttaac accaacgcgt attacgagat gtccggtctg     900
gaagttagct cgaagaact gcgtactttt ggcggtcacg acgctaaatt catcgactct     960
ctgcaagaaa acgagttccg tctgtactac tataacaagt tcaaagatat cgcatccacc    1020
ctgaacaaag cgaaatccat cgtgggtacc actgcttctc tccagtacat gaagaacgtt    1080
tttaaagaaa ataccctgct cagcgaagac acctccggca aattctctgt agacaagttg    1140
aaattcgata aactttacaa aatgctgact gaaatttaca ccgaagacaa cttcgttaag    1200
ttctttaaag ttctgaaccg caaaaccctat ctgaacttcg acaaggcagt attcaaaatc    1260
aacatcgtgc cgaaagttaa ctacactatc tacgatggtt tcaacctgcg taacaccaac    1320
ctggctgcta attttaacgg ccagaacacg gaaatcaaca acatgaactt cacaaaactg    1380
aaaaacttca ctggtctgtt cgagttttac aagctgctgt gcgtcgacgg catcattacc    1440
tccaaaacta aatctctgat agaaggtaga aacaaagcgc tgaacgacct ctgtatcaag    1500
gttaacaact gggatttatt cttcagcccg agtgaagaca cttcaccaa cgacctgaac    1560
aaaggtgaag aaatcaccctc agatactaac atcgaagcag ccgaagaaaa catctcgctg    1620
gacctgatcc agcagtacta cctgaccttt aatttcgaca cgagccggga aaacatttct    1680
atcgaaaacc tgagctctga tatcatcggc cagctggaac tgatgccgaa catcgaacgt    1740
ttcccaaacg gtaaaaagta cgagctggac aaatatacca tgttccacta cctgcgcgcg    1800
caggaatttg aacacggcaa atcccgtatc gcactgacta actccgttaa cgaagctctg    1860
```

```
ctcaacccgt cccgtgtata caccttcttc tctagcgact acgtgaaaaa ggtcaacaaa    1920
gcgactgaag ctgcaatgtt cttgggttgg gttgaacagc ttgtttatga ttttaccgac    1980
gagacgtccg aagtatctac taccgacaaa attgcggata tcactatcat catcccgtac    2040
atcggtccgg ctctgaacat tggcaacatg ctgtacaaag acgacttcgt tggcgcactg    2100
atcttctccg gtgcggtgat cctgctggag ttcatcccgg aaatcgccat cccggtactg    2160
ggcacctttg ctctggtttc ttacattgca acaaggttc tgactgtaca aaccatcgac    2220
aacgcgctga gcaaacgtaa cgaaaaatgg gatgaagttt acaaatatat cgtgaccaac    2280
tggctggcta aggttaatac tcagatcgac ctcatccgca aaaaatgaa agaagcactg    2340 gaaaaccagg cggaagctac caaggcaatc attaactacc agtacaacca gtacaccgag    2400
gaagaaaaaa acaacatcaa cttcaacatc gacgatctgt cctctaaact gaacgaatcc    2460
atcaacaaag ctatgatcaa catcaacaag ttcctgaacc agtgctctgt aagctatctg    2520
atgaactcca tgatcccgta cggtgttaaa cgtctggagg acttcgatgc gtctctgaaa    2580
gacgccctgc tgaaatacat ttacgacaac cgtggcactc tgatcggtca ggttgatcgt    2640
ctgaaggaca aagtgaacaa taccttatcg accgacatcc ttttcagct cagtaaatat    2700 gtcgataacc aacgcctttt gtccactcta gactag                              2736
```

<210> SEQ ID NO 16
<211> LENGTH: 911
<212> TYPE: PRT
<213> ORGANISM: Artificial Sequence
<220> FEATURE:
<223> OTHER INFORMATION: chemically synthesized fusion protein

<400> SEQUENCE: 16

```
Leu Gly Ile Glu Gly Arg Phe Gly Gly Phe Thr Gly Ala Arg Lys Ser
1               5                   10                  15

Ala Arg Lys Leu Ala Asn Gln Thr Ser Gly Gly Gly Ser Gly Gly Gly
            20                  25                  30

Gly Gly Ser Gly Gly Gly Gly Ser Pro Arg Gly Ser Met Glu Phe Val
        35                  40                  45

Asn Lys Gln Phe Asn Tyr Lys Asp Pro Val Asn Gly Val Asp Ile Ala
    50                  55                  60

Tyr Ile Lys Ile Pro Asn Ala Gly Gln Met Gln Pro Val Lys Ala Phe
65                  70                  75                  80

Lys Ile His Asn Lys Ile Trp Val Ile Pro Glu Arg Asp Thr Phe Thr
                85                  90                  95

Asn Pro Glu Glu Gly Asp Leu Asn Pro Pro Glu Ala Lys Gln Val
            100                 105                 110

Pro Val Ser Tyr Tyr Asp Ser Thr Tyr Leu Ser Thr Asp Asn Glu Lys
        115                 120                 125

Asp Asn Tyr Leu Lys Gly Val Thr Lys Leu Phe Glu Arg Ile Tyr Ser
    130                 135                 140

Thr Asp Leu Gly Arg Met Leu Leu Thr Ser Ile Val Arg Gly Ile Pro
145                 150                 155                 160

Phe Trp Gly Gly Ser Thr Ile Asp Thr Glu Leu Lys Val Ile Asp Thr
                165                 170                 175

Asn Cys Ile Asn Val Ile Gln Pro Asp Gly Ser Tyr Arg Ser Glu Glu
            180                 185                 190

Leu Asn Leu Val Ile Ile Gly Pro Ser Ala Asp Ile Ile Gln Phe Glu
        195                 200                 205
```

-continued

```
Cys Lys Ser Phe Gly His Glu Val Leu Asn Leu Thr Arg Asn Gly Tyr
            210                 215                 220

Gly Ser Thr Gln Tyr Ile Arg Phe Ser Pro Asp Phe Thr Phe Gly Phe
225                 230                 235                 240

Glu Glu Ser Leu Glu Val Asp Thr Asn Pro Leu Leu Gly Ala Gly Lys
                245                 250                 255

Phe Ala Thr Asp Pro Ala Val Thr Leu Ala His Glu Leu Ile His Ala
                260                 265                 270

Gly His Arg Leu Tyr Gly Ile Ala Ile Asn Pro Asn Arg Val Phe Lys
                275                 280                 285

Val Asn Thr Asn Ala Tyr Tyr Glu Met Ser Gly Leu Glu Val Ser Phe
            290                 295                 300

Glu Glu Leu Arg Thr Phe Gly Gly His Asp Ala Lys Phe Ile Asp Ser
305                 310                 315                 320

Leu Gln Glu Asn Glu Phe Arg Leu Tyr Tyr Tyr Asn Lys Phe Lys Asp
                325                 330                 335

Ile Ala Ser Thr Leu Asn Lys Ala Lys Ser Ile Val Gly Thr Thr Ala
            340                 345                 350

Ser Leu Gln Tyr Met Lys Asn Val Phe Lys Glu Lys Tyr Leu Leu Ser
            355                 360                 365

Glu Asp Thr Ser Gly Lys Phe Ser Val Asp Lys Leu Lys Phe Asp Lys
370                 375                 380

Leu Tyr Lys Met Leu Thr Glu Ile Tyr Thr Glu Asp Asn Phe Val Lys
385                 390                 395                 400

Phe Phe Lys Val Leu Asn Arg Lys Thr Tyr Leu Asn Phe Asp Lys Ala
                405                 410                 415

Val Phe Lys Ile Asn Ile Val Pro Lys Val Asn Tyr Thr Ile Tyr Asp
            420                 425                 430

Gly Phe Asn Leu Arg Asn Thr Asn Leu Ala Ala Asn Phe Asn Gly Gln
                435                 440                 445

Asn Thr Glu Ile Asn Asn Met Asn Phe Thr Lys Leu Lys Asn Phe Thr
450                 455                 460

Gly Leu Phe Glu Phe Tyr Lys Leu Leu Cys Val Asp Gly Ile Ile Thr
465                 470                 475                 480

Ser Lys Thr Lys Ser Leu Ile Glu Gly Arg Asn Lys Ala Leu Asn Asp
                485                 490                 495

Leu Cys Ile Lys Val Asn Asn Trp Asp Leu Phe Phe Ser Pro Ser Glu
            500                 505                 510

Asp Asn Phe Thr Asn Asp Leu Asn Lys Gly Glu Glu Ile Thr Ser Asp
                515                 520                 525

Thr Asn Ile Glu Ala Ala Glu Glu Asn Ile Ser Leu Asp Leu Ile Gln
530                 535                 540

Gln Tyr Tyr Leu Thr Phe Asn Phe Asp Asn Glu Pro Glu Asn Ile Ser
545                 550                 555                 560

Ile Glu Asn Leu Ser Ser Asp Ile Ile Gly Gln Leu Glu Leu Met Pro
                565                 570                 575

Asn Ile Glu Arg Phe Pro Asn Gly Lys Lys Tyr Glu Leu Asp Lys Tyr
                580                 585                 590

Thr Met Phe His Tyr Leu Arg Ala Gln Glu Phe Glu His Gly Lys Ser
                595                 600                 605

Arg Ile Ala Leu Thr Asn Ser Val Asn Glu Ala Leu Leu Asn Pro Ser
            610                 615                 620

Arg Val Tyr Thr Phe Phe Ser Ser Asp Tyr Val Lys Lys Val Asn Lys
625                 630                 635                 640
```

Ala Thr Glu Ala Ala Met Phe Leu Gly Trp Val Glu Gln Leu Val Tyr
            645                 650                 655

Asp Phe Thr Asp Glu Thr Ser Glu Val Ser Thr Thr Asp Lys Ile Ala
            660                 665                 670

Asp Ile Thr Ile Ile Ile Pro Tyr Ile Gly Pro Ala Leu Asn Ile Gly
            675                 680                 685

Asn Met Leu Tyr Lys Asp Asp Phe Val Gly Ala Leu Ile Phe Ser Gly
            690                 695                 700

Ala Val Ile Leu Leu Glu Phe Ile Pro Glu Ile Ala Ile Pro Val Leu
705                 710                 715                 720

Gly Thr Phe Ala Leu Val Ser Tyr Ile Ala Asn Lys Val Leu Thr Val
            725                 730                 735

Gln Thr Ile Asp Asn Ala Leu Ser Lys Arg Asn Glu Lys Trp Asp Glu
            740                 745                 750

Val Tyr Lys Tyr Ile Val Thr Asn Trp Leu Ala Lys Val Asn Thr Gln
            755                 760                 765

Ile Asp Leu Ile Arg Lys Lys Met Lys Glu Ala Leu Glu Asn Gln Ala
            770                 775                 780

Glu Ala Thr Lys Ala Ile Ile Asn Tyr Gln Tyr Asn Gln Tyr Thr Glu
785                 790                 795                 800

Glu Glu Lys Asn Asn Ile Asn Phe Asn Ile Asp Asp Leu Ser Ser Lys
            805                 810                 815

Leu Asn Glu Ser Ile Asn Lys Ala Met Ile Asn Ile Asn Lys Phe Leu
            820                 825                 830

Asn Gln Cys Ser Val Ser Tyr Leu Met Asn Ser Met Ile Pro Tyr Gly
            835                 840                 845

Val Lys Arg Leu Glu Asp Phe Asp Ala Ser Leu Lys Asp Ala Leu Leu
            850                 855                 860

Lys Tyr Ile Tyr Asp Asn Arg Gly Thr Leu Ile Gly Gln Val Asp Arg
865                 870                 875                 880

Leu Lys Asp Lys Val Asn Asn Thr Leu Ser Thr Asp Ile Pro Phe Gln
            885                 890                 895

Leu Ser Lys Tyr Val Asp Asn Gln Arg Leu Leu Ser Thr Leu Asp
            900                 905                 910

<210> SEQ ID NO 17
<211> LENGTH: 2715
<212> TYPE: DNA
<213> ORGANISM: Artificial Sequence
<220> FEATURE:
<223> OTHER INFORMATION: chemically synthesized polynucleotide encoding
      fusion protein

<400> SEQUENCE: 17
ggatccgaat tcatgccgat caccatcaac aacttcaact acagcgatcc ggtggataac      60
aaaaacatcc tgtacctgga tacccatctg aataccctgg cgaacgaacc ggaaaaagcg     120
tttcgtatca ccggcaacat tgggttatt ccggatcgtt ttagccgtaa cagcaacccg      180
aatctgaata aaccgccgcg tgttaccagc ccgaaaagcg gttattacga tccgaactat     240
ctgagcaccg atagcgataa agataccttc ctgaaagaaa tcatcaaact gttcaaacgc     300
atcaacagcc gtgaaattgg cgaagaactg atctatcgcc tgagcaccga tattccgttt     360
ccgggcaaca acaacacccc gatcaacacc tttgatttcg atgtggattt caacagcgtt     420
gatgttaaaa cccgccaggg taacaattgg gtgaaaccg gcagcattaa cccgagcgtg      480
attattaccg gtccgcgcga aaacattatt gatccggaaa ccagcaccct taaactgacc     540

```
aacaacacct tgcggcgca ggaaggtttt ggcgcgctga gcattattag cattagcccg    600
cgctttatgc tgacctatag caacgcgacc aacgatgttg gtgaaggccg tttcagcaaa    660
agcgaatttt gcatggaccc gatcctgatc ctgatgcatg aactgaacca tgcgatgcat    720
aacctgtatg gcatcgcgat ccgaacgat cagaccatta gcagcgtgac cagcaacatc    780
ttttacagcc agtacaacgt gaaactggaa tatgcgaaaa tctatgcgtt tggcggtccg    840
accattgatc tgattccgaa agcgcgcgc aaatacttcg aagaaaaagc gctggattac    900
tatcgcagca ttgcgaaacg tctgaacagc attaccaccg cgaatccgag cagcttcaac    960
aaatatatcg gcgaatataa acagaaactg atccgcaaat atcgctttgt ggtggaaagc    1020
agcggcgaag ttaccgttaa ccgcaataaa ttcgtggaac tgtacaacga actgacccag    1080
atcttcaccg aatttaacta tgcgaaaatc tataacgtgc agaaccgtaa aatctacctg    1140
agcaacgtgt ataccccggt gaccgcgaat attctggatg ataacgtgta cgatatccag    1200
aacggcttta acatcccgaa aagcaacctg aacgttctgt ttatgggcca gaacctgagc    1260
cgtaatccgg cgctgcgtaa agtgaacccg gaaaacatgc tgtacctgtt caccaaattt    1320
tgcgtcgacg cgatagatgg tagatttggc ggtttcacgg cgcacgcaa atcagcgcgt    1380 aaattagcta accaggcgct agcgggcggt ggcggtagcg gcggtggcgg tagcggcggt    1440
ggcggtagcg cactagtgct gcagtgtcgt gaactgctgg tgaaaaacac cgatctgccg    1500
tttattggcg atatcagcga tgtgaaaacc gatatcttcc tgcgcaaaga tatcaacgaa    1560
gaaaccgaag tgatctacta cccggataac gtgagcgttg atcaggtgat cctgagcaaa    1620
aacaccagcg aacatggtca gctggatctg ctgtatccga gcattgatag cgaaagcgaa    1680
attctgccgg gcgaaaacca ggtgttttac gataaccgta cccagaacgt ggattacctg    1740
aacagctatt actacctgga aagccagaaa ctgagcgata acgtggaaga ttttaccttt    1800
acccgcagca ttgaagaagc gctggataac agcgcgaaag tttacaccta ttttccgacc    1860
ctggcgaaca aagttaatgc gggtgttcag ggcggtctgt ttctgatgtg ggcgaacgat    1920
gtggtggaag atttcaccac caacatcctg cgtaaagata ccctggataa aatcagcgat    1980
gttagcgcga ttattccgta tattggtccg gcgctgaaca ttagcaatag cgtgcgtcgt    2040
ggcaatttta ccgaagcgtt tgcggttacc ggtgtgacca ttctgctgga agcgtttccg    2100
gaatttacca ttccggcgct gggtgcgttt gtgatctata gcaaagtgca ggaacgcaac    2160
gaaatcatca aaaccatcga taactgcctg gaacagcgta ttaaacgctg gaaagatagc    2220
tatgaatgga tgatgggcac ctggctgagc cgtattatca cccagttcaa caacatcagc    2280
taccagatgt acgatagcct gaactatcag gcgggtgcga ttaaagcgaa aatcgatctg    2340
gaatacaaaa aatacagcgg cagcgataaa gaaaacatca aaagccaggt tgaaaacctg    2400
aaaaacagcc tggatgtgaa aattagcgaa gcgatgaata acatcaacaa attcatccgc    2460
gaatgcagcg tgacctacct gttcaaaaac atgctgccga agtgatcga tgaactgaac    2520 gaatttgatc gcaacaccaa agcgaaactg atcaacctga tcgatagcca caacattatt    2580
ctggtgggcg aagtggataa actgaaagcg aaagttaaca cagcttcca gaacaccatc    2640 ccgtttaaca tcttcagcta taccaacaac agcctgctga agatatcat caacgaatac    2700 ttcaatctga actag                                                   2715
```

<210> SEQ ID NO 18
<211> LENGTH: 904
<212> TYPE: PRT
<213> ORGANISM: Artificial Sequence
<220> FEATURE:
<223> OTHER INFORMATION: chemically synthesized fusion protein

<400> SEQUENCE: 18

Gly Ser Glu Phe Met Pro Ile Thr Ile Asn Asn Phe Asn Tyr Ser Asp
1               5                   10                  15

Pro Val Asp Asn Lys Asn Ile Leu Tyr Leu Asp Thr His Leu Asn Thr
            20                  25                  30

Leu Ala Asn Glu Pro Glu Lys Ala Phe Arg Ile Thr Gly Asn Ile Trp
        35                  40                  45

Val Ile Pro Asp Arg Phe Ser Arg Asn Ser Pro Asn Leu Asn Lys
50                  55                  60

Pro Pro Arg Val Thr Ser Pro Lys Ser Gly Tyr Tyr Asp Pro Asn Tyr
65              70                  75                  80

Leu Ser Thr Asp Ser Asp Lys Asp Thr Phe Leu Lys Glu Ile Ile Lys
                85                  90                  95

Leu Phe Lys Arg Ile Asn Ser Arg Glu Ile Gly Glu Glu Leu Ile Tyr
            100                 105                 110

Arg Leu Ser Thr Asp Ile Pro Phe Pro Gly Asn Asn Asn Thr Pro Ile
        115                 120                 125

Asn Thr Phe Asp Phe Asp Val Asp Phe Asn Ser Val Asp Val Lys Thr
    130                 135                 140

Arg Gln Gly Asn Asn Trp Val Lys Thr Gly Ser Ile Asn Pro Ser Val
145                 150                 155                 160

Ile Ile Thr Gly Pro Arg Glu Asn Ile Ile Asp Pro Glu Thr Ser Thr
                165                 170                 175

Phe Lys Leu Thr Asn Asn Thr Phe Ala Ala Gln Glu Gly Phe Gly Ala
            180                 185                 190

Leu Ser Ile Ile Ser Ile Ser Pro Arg Phe Met Leu Thr Tyr Ser Asn
        195                 200                 205

Ala Thr Asn Asp Val Gly Glu Gly Arg Phe Ser Lys Ser Glu Phe Cys
    210                 215                 220

Met Asp Pro Ile Leu Ile Leu Met His Glu Leu Asn His Ala Met His
225                 230                 235                 240

Asn Leu Tyr Gly Ile Ala Ile Pro Asn Asp Gln Thr Ile Ser Ser Val
                245                 250                 255

Thr Ser Asn Ile Phe Tyr Ser Gln Tyr Asn Val Lys Leu Glu Tyr Ala
            260                 265                 270

Glu Ile Tyr Ala Phe Gly Gly Pro Thr Ile Asp Leu Ile Pro Lys Ser
        275                 280                 285

Ala Arg Lys Tyr Phe Glu Glu Lys Ala Leu Asp Tyr Tyr Arg Ser Ile
    290                 295                 300

Ala Lys Arg Leu Asn Ser Ile Thr Thr Ala Asn Pro Ser Ser Phe Asn
305                 310                 315                 320

Lys Tyr Ile Gly Glu Tyr Lys Gln Lys Leu Ile Arg Lys Tyr Arg Phe
                325                 330                 335

Val Val Glu Ser Ser Gly Glu Val Thr Val Asn Arg Asn Lys Phe Val
            340                 345                 350

Glu Leu Tyr Asn Glu Leu Thr Gln Ile Phe Thr Glu Phe Asn Tyr Ala
        355                 360                 365

Lys Ile Tyr Asn Val Gln Asn Arg Lys Ile Tyr Leu Ser Asn Val Tyr
    370                 375                 380

Thr Pro Val Thr Ala Asn Ile Leu Asp Asp Asn Val Tyr Asp Ile Gln
385                 390                 395                 400

-continued

```
Asn Gly Phe Asn Ile Pro Lys Ser Asn Leu Asn Val Leu Phe Met Gly
                405                 410                 415
Gln Asn Leu Ser Arg Asn Pro Ala Leu Arg Lys Val Asn Pro Glu Asn
            420                 425                 430
Met Leu Tyr Leu Phe Thr Lys Phe Cys Val Asp Ala Ile Asp Gly Arg
        435                 440                 445
Phe Gly Gly Phe Thr Gly Ala Arg Lys Ser Ala Arg Lys Leu Ala Asn
    450                 455                 460
Gln Ala Leu Ala Gly Gly Gly Ser Gly Gly Gly Ser Gly Gly
465                 470                 475                 480
Gly Gly Ser Ala Leu Val Leu Gln Cys Arg Glu Leu Leu Val Lys Asn
                485                 490                 495
Thr Asp Leu Pro Phe Ile Gly Asp Ile Ser Asp Val Lys Thr Asp Ile
            500                 505                 510
Phe Leu Arg Lys Asp Ile Asn Glu Glu Thr Glu Val Ile Tyr Tyr Pro
        515                 520                 525
Asp Asn Val Ser Val Asp Gln Val Ile Leu Ser Lys Asn Thr Ser Glu
    530                 535                 540
His Gly Gln Leu Asp Leu Leu Tyr Pro Ser Ile Asp Ser Glu Ser Glu
545                 550                 555                 560
Ile Leu Pro Gly Glu Asn Gln Val Phe Tyr Asp Asn Arg Thr Gln Asn
                565                 570                 575
Val Asp Tyr Leu Asn Ser Tyr Tyr Leu Glu Ser Gln Lys Leu Ser
            580                 585                 590
Asp Asn Val Glu Asp Phe Thr Phe Thr Arg Ser Ile Glu Glu Ala Leu
    595                 600                 605
Asp Asn Ser Ala Lys Val Tyr Thr Tyr Phe Pro Thr Leu Ala Asn Lys
610                 615                 620
Val Asn Ala Gly Val Gln Gly Gly Leu Phe Leu Met Trp Ala Asn Asp
625                 630                 635                 640
Val Val Glu Asp Phe Thr Thr Asn Ile Leu Arg Lys Asp Thr Leu Asp
                645                 650                 655
Lys Ile Ser Asp Val Ser Ala Ile Ile Pro Tyr Ile Gly Pro Ala Leu
            660                 665                 670
Asn Ile Ser Asn Ser Val Arg Arg Gly Asn Phe Thr Glu Ala Phe Ala
        675                 680                 685
Val Thr Gly Val Thr Ile Leu Leu Glu Ala Phe Pro Glu Phe Thr Ile
    690                 695                 700
Pro Ala Leu Gly Ala Phe Val Ile Tyr Ser Lys Val Gln Glu Arg Asn
705                 710                 715                 720
Glu Ile Ile Lys Thr Ile Asp Asn Cys Leu Glu Gln Arg Ile Lys Arg
                725                 730                 735
Trp Lys Asp Ser Tyr Glu Trp Met Met Gly Thr Trp Leu Ser Arg Ile
            740                 745                 750
Ile Thr Gln Phe Asn Asn Ile Ser Tyr Gln Met Tyr Asp Ser Leu Asn
        755                 760                 765
Tyr Gln Ala Gly Ala Ile Lys Ala Lys Ile Asp Leu Glu Tyr Lys Lys
    770                 775                 780
Tyr Ser Gly Ser Asp Lys Glu Asn Ile Lys Ser Gln Val Glu Asn Leu
785                 790                 795                 800
Lys Asn Ser Leu Asp Val Lys Ile Ser Glu Ala Met Asn Asn Ile Asn
                805                 810                 815
Lys Phe Ile Arg Glu Cys Ser Val Thr Tyr Leu Phe Lys Asn Met Leu
            820                 825                 830
```

```
Pro Lys Val Ile Asp Glu Leu Asn Glu Phe Asp Arg Asn Thr Lys Ala
        835                 840                 845

Lys Leu Ile Asn Leu Ile Asp Ser His Asn Ile Ile Leu Val Gly Glu
    850                 855                 860

Val Asp Lys Leu Lys Ala Lys Val Asn Asn Ser Phe Gln Asn Thr Ile
865                 870                 875                 880

Pro Phe Asn Ile Phe Ser Tyr Thr Asn Asn Ser Leu Leu Lys Asp Ile
                885                 890                 895

Ile Asn Glu Tyr Phe Asn Leu Asp
            900

<210> SEQ ID NO 19
<211> LENGTH: 2742
<212> TYPE: DNA
<213> ORGANISM: Artificial Sequence
<220> FEATURE:
<223> OTHER INFORMATION: chemically synthesized polynucleotide encoding
      fusion protein

<400> SEQUENCE: 19
ggatccgaat tcatgccgat caccatcaac aacttcaact acagcgatcc ggtggataac        60
aaaaacatcc tgtacctgga tacccatctg aataccctgg cgaacgaacc ggaaaaagcg       120
tttcgtatca ccggcaacat ttgggttatt ccgatcgtt ttagccgtaa cagcaacccg        180
aatctgaata accgccgcg tgttaccagc ccgaaaagcg gttattacga tccgaactat        240
ctgagcaccg atagcgataa agatacccttc ctgaaagaaa tcatcaaact gttcaaacgc      300
atcaacagcc gtgaaattgg cgaagaactg atctatcgcc tgagcaccga tattccgttt       360
ccgggcaaca caacaccccc gatcaacacc tttgatttcg atgtggattt caacagcgtt       420
gatgttaaaa cccgccaggg taacaattgg gtgaaaaccg gcagcattaa cccgagcgtg       480
attattaccg gtccgcgcga aaacattatt gatccggaaa ccagcacctt taaactgacc       540
aacaacacct ttgcggcgca ggaaggtttt ggcgcgctga gcattattag cattagcccg       600
cgctttatgc tgacctatag caacgcgacc aacgatgttg tgaaggccg tttcagcaaa        660 agcgaatttt gcatggaccc gatcctgatc ctgatgcatg aactgaacca tgcgatgcat       720
aacctgtatg gcatcgcgat tccgaacgat cagaccatta gcagcgtgac cagcaacatc       780 tttttacagcc agtacaacgt gaaactggaa tatgcggaaa tctatgcgtt ggcggtccg      840 accattgatc tgattccgaa aagcgcgcgc aaatacttcg aagaaaaagc gctggattac       900
tatcgcagca ttgcgaaacg tctgaacagc attaccaccg cgaatccgag cagcttcaac       960
aaatatatcg cgaatataa acagaaactg atccgcaaat atcgctttgt ggtggaaagc       1020
agcggcgaag ttaccgttaa ccgcaataaa ttcgtggaac tgtacaacga actgaccccag      1080 atcttcaccg aatttaacta tgcgaaaatc tataacgtgc agaaccgtaa aatctacctg      1140
agcaacgtgt atacccggt gaccgcgaat attctggatg ataacgtgta cgatatccag        1200
aacggcttta acatcccgaa aagcaacctg aacgttctgt ttatgggcca gaacctgagc       1260
cgtaatccgg cgctgcgtaa agtgaacccg gaaaacatgc tgtacctgtt caccaaattt      1320
tgcgtcgacg gcatcattac ctccaaaact aaatctctga tagaaggtag atttggcggt      1380
ttcacgggcg cacgcaaatc agcgcgtaaa ttagctaacc aggcgctagc gggcggtggc      1440
ggtagcggcg gtggcggtag cggcggtggc ggtagcgcac tagtgctgca gtgtcgtgaa      1500
ctgctggtga aaacaccgga tctgccgttt attggcgata tcagcgatgt gaaaaccgat      1560
atcttcctgc gcaaagatat caacgaagaa accgaagtga tctactaccc ggataacgtg      1620
```

```
agcgttgatc aggtgatcct gagcaaaaac accagcgaac atggtcagct ggatctgctg      1680
tatccgagca ttgatagcga aagcgaaatt ctgccgggcg aaaaccaggt gttttacgat      1740
aaccgtaccc agaacgtgga ttacctgaac agctattact acctggaaag ccagaaactg      1800
agcgataacg tggaagattt tacctttacc cgcagcattg aagaagcgct ggataacagc      1860
gcgaaagttt acacctattt tccgaccctg cgcaacaaag ttaatgcggg tgttcagggc      1920
ggtctgtttc tgatgtgggc gaacgatgtg gtggaagatt tcaccaccaa catcctgcgt      1980
aaagataccc tggataaaat cagcgatgtt agcgcgatta ttccgtatat tggtccggcg      2040
ctgaacatta gcaatagcgt gcgtcgtggc aattttaccg aagcgtttgc ggttaccggt      2100
gtgaccattc tgctggaagc gtttccggaa tttaccattc cggcgctggg tgcgtttgtg      2160
atctatagca aagtgcagga acgcaacgaa atcatcaaaa ccatcgataa ctgcctggaa      2220
cagcgtatta aacgctggaa agatagctat gaatggatga tgggcaccctg gctgagccgt      2280 attatcaccc agttcaacaa catcagctac cagatgtacg atagcctgaa ctatcaggcg      2340
ggtgcgatta agcgaaaat cgatctggaa tacaaaaaat acagcggcag cgataaagaa      2400
aacatcaaaa gccaggttga aaacctgaaa acagcctggaa tgtgaaaat tagcgaagcg      2460 atgaataaca tcaacaaatt catccgcgaa tgcagcgtga cctacctgtt caaaaacatg      2520
ctgccgaaag tgatcgatga actgaacgaa tttgatcgca acaccaaagc gaaactgatc      2580
aacctgatcg atagccacaa cattattctg gtgggcgaag tggataaact gaaagcgaaa      2640
gttaacaaca gcttccagaa caccatcccg tttaacatct tcagctatac caacaacagc      2700
ctgctgaaag atatcatcaa cgaatacttc aatctagact ag                        2742
```

<210> SEQ ID NO 20
<211> LENGTH: 913
<212> TYPE: PRT
<213> ORGANISM: Artificial Sequence
<220> FEATURE:
<223> OTHER INFORMATION: chemically synthesized fusion protein

<400> SEQUENCE: 20

```
Gly Ser Glu Phe Met Pro Ile Thr Ile Asn Asn Phe Asn Tyr Ser Asp
1               5                   10                  15

Pro Val Asp Asn Lys Asn Ile Leu Tyr Leu Asp Thr His Leu Asn Thr
            20                  25                  30

Leu Ala Asn Glu Pro Glu Lys Ala Phe Arg Ile Thr Gly Asn Ile Trp
        35                  40                  45

Val Ile Pro Asp Arg Phe Ser Arg Asn Ser Asn Pro Asn Leu Asn Lys
    50                  55                  60

Pro Pro Arg Val Thr Ser Pro Lys Ser Gly Tyr Tyr Asp Pro Asn Tyr
65                  70                  75                  80

Leu Ser Thr Asp Ser Asp Lys Asp Thr Phe Leu Lys Glu Ile Ile Lys
                85                  90                  95

Leu Phe Lys Arg Ile Asn Ser Arg Glu Ile Gly Glu Glu Leu Ile Tyr
            100                 105                 110

Arg Leu Ser Thr Asp Ile Pro Phe Pro Gly Asn Asn Asn Thr Pro Ile
        115                 120                 125

Asn Thr Phe Asp Phe Asp Val Asp Phe Asn Ser Val Asp Val Lys Thr
    130                 135                 140

Arg Gln Gly Asn Asn Trp Val Lys Thr Gly Ser Ile Asn Pro Ser Val
145                 150                 155                 160

Ile Ile Thr Gly Pro Arg Glu Asn Ile Ile Asp Pro Glu Thr Ser Thr
```

```
                     165                 170                 175
        Phe Lys Leu Thr Asn Asn Thr Phe Ala Ala Gln Glu Gly Phe Gly Ala
                         180                 185                 190

Leu Ser Ile Ile Ser Ile Ser Pro Arg Phe Met Leu Thr Tyr Ser Asn
                         195                 200                 205

Ala Thr Asn Asp Val Gly Glu Gly Arg Phe Ser Lys Ser Glu Phe Cys
                         210                 215                 220

Met Asp Pro Ile Leu Ile Leu Met His Glu Leu Asn His Ala Met His
        225                 230                 235                 240

Asn Leu Tyr Gly Ile Ala Ile Pro Asn Asp Gln Thr Ile Ser Ser Val
                         245                 250                 255

Thr Ser Asn Ile Phe Tyr Ser Gln Tyr Asn Val Lys Leu Glu Tyr Ala
                         260                 265                 270

Glu Ile Tyr Ala Phe Gly Gly Pro Thr Ile Asp Leu Ile Pro Lys Ser
                         275                 280                 285

Ala Arg Lys Tyr Phe Glu Glu Lys Ala Leu Asp Tyr Tyr Arg Ser Ile
                         290                 295                 300

Ala Lys Arg Leu Asn Ser Ile Thr Thr Ala Asn Pro Ser Ser Phe Asn
        305                 310                 315                 320

Lys Tyr Ile Gly Glu Tyr Lys Gln Lys Leu Ile Arg Lys Tyr Arg Phe
                         325                 330                 335

Val Val Glu Ser Ser Gly Glu Val Thr Val Asn Arg Asn Lys Phe Val
                         340                 345                 350

Glu Leu Tyr Asn Glu Leu Thr Gln Ile Phe Thr Glu Phe Asn Tyr Ala
                         355                 360                 365

Lys Ile Tyr Asn Val Gln Asn Arg Lys Ile Tyr Leu Ser Asn Val Tyr
                         370                 375                 380

Thr Pro Val Thr Ala Asn Ile Leu Asp Asp Asn Val Tyr Asp Ile Gln
        385                 390                 395                 400

Asn Gly Phe Asn Ile Pro Lys Ser Asn Leu Asn Val Leu Phe Met Gly
                         405                 410                 415

Gln Asn Leu Ser Arg Asn Pro Ala Leu Arg Lys Val Asn Pro Glu Asn
                         420                 425                 430

Met Leu Tyr Leu Phe Thr Lys Phe Cys Val Asp Gly Ile Ile Thr Ser
                         435                 440                 445

Lys Thr Lys Ser Leu Ile Glu Gly Arg Phe Gly Phe Thr Gly Ala
                         450                 455                 460

Arg Lys Ser Ala Arg Lys Leu Ala Asn Gln Ala Leu Ala Gly Gly Gly
        465                 470                 475                 480

Gly Ser Gly Gly Gly Gly Ser Gly Gly Gly Ser Ala Leu Val Leu
                         485                 490                 495

Gln Cys Arg Glu Leu Leu Val Lys Asn Thr Asp Leu Pro Phe Ile Gly
                         500                 505                 510

Asp Ile Ser Asp Val Lys Thr Asp Ile Phe Leu Arg Lys Asp Ile Asn
                         515                 520                 525

Glu Glu Thr Glu Val Ile Tyr Tyr Pro Asp Asn Val Ser Val Asp Gln
        530                 535                 540

Val Ile Leu Ser Lys Asn Thr Ser Glu His Gly Gln Leu Asp Leu Leu
        545                 550                 555                 560

Tyr Pro Ser Ile Asp Ser Glu Ser Glu Ile Leu Pro Gly Glu Asn Gln
                         565                 570                 575

Val Phe Tyr Asp Asn Arg Thr Gln Asn Val Asp Tyr Leu Asn Ser Tyr
                         580                 585                 590
```

```
Tyr Tyr Leu Glu Ser Gln Lys Leu Ser Asp Asn Val Glu Asp Phe Thr
            595                 600                 605

Phe Thr Arg Ser Ile Glu Glu Ala Leu Asp Asn Ser Ala Lys Val Tyr
    610                 615                 620

Thr Tyr Phe Pro Thr Leu Ala Asn Lys Val Asn Ala Gly Val Gln Gly
625                 630                 635                 640

Gly Leu Phe Leu Met Trp Ala Asn Asp Val Val Glu Asp Phe Thr Thr
                645                 650                 655

Asn Ile Leu Arg Lys Asp Thr Leu Asp Lys Ile Ser Asp Val Ser Ala
                660                 665                 670

Ile Ile Pro Tyr Ile Gly Pro Ala Leu Asn Ile Ser Asn Ser Val Arg
                675                 680                 685

Arg Gly Asn Phe Thr Glu Ala Phe Ala Val Thr Gly Val Thr Ile Leu
            690                 695                 700

Leu Glu Ala Phe Pro Glu Phe Thr Ile Pro Ala Leu Gly Ala Phe Val
705                 710                 715                 720

Ile Tyr Ser Lys Val Gln Glu Arg Asn Glu Ile Ile Lys Thr Ile Asp
                725                 730                 735

Asn Cys Leu Glu Gln Arg Ile Lys Arg Trp Lys Asp Ser Tyr Glu Trp
                740                 745                 750

Met Met Gly Thr Trp Leu Ser Arg Ile Ile Thr Gln Phe Asn Asn Ile
            755                 760                 765

Ser Tyr Gln Met Tyr Asp Ser Leu Asn Tyr Gln Ala Gly Ala Ile Lys
    770                 775                 780

Ala Lys Ile Asp Leu Glu Tyr Lys Lys Tyr Ser Gly Ser Asp Lys Glu
785                 790                 795                 800

Asn Ile Lys Ser Gln Val Glu Asn Leu Lys Asn Ser Leu Asp Val Lys
                805                 810                 815

Ile Ser Glu Ala Met Asn Asn Ile Asn Lys Phe Ile Arg Glu Cys Ser
                820                 825                 830

Val Thr Tyr Leu Phe Lys Asn Met Leu Pro Lys Val Ile Asp Glu Leu
            835                 840                 845

Asn Glu Phe Asp Arg Asn Thr Lys Ala Lys Leu Ile Asn Leu Ile Asp
850                 855                 860

Ser His Asn Ile Ile Leu Val Gly Glu Val Asp Lys Leu Lys Ala Lys
865                 870                 875                 880

Val Asn Asn Ser Phe Gln Asn Thr Ile Pro Phe Asn Ile Phe Ser Tyr
                885                 890                 895

Thr Asn Asn Ser Leu Leu Lys Asp Ile Ile Asn Glu Tyr Phe Asn Leu
            900                 905                 910

Asp
```

<210> SEQ ID NO 21
<211> LENGTH: 2673
<212> TYPE: DNA
<213> ORGANISM: Artificial Sequence
<220> FEATURE:
<223> OTHER INFORMATION: chemically synthesized polynucleotide encoding
      fusion protein

<400> SEQUENCE: 21

```
ggatccatgg agttcgttaa caaacagttc aactataaag acccagttaa cggtgttgac      60
attgcttaca tcaaaatccc gaacgctggc cagatgcagc cggtaaaggc attcaaaatc     120
cacaacaaaa tctgggttat cccggaacgt gataccttta ctaacccgga agaaggtgac     180
ctgaacccgc caccggaagc gaaacaggtg ccggtatctt actatgactc cacctacctg     240
```

```
tctaccgata acgaaaagga caactacctg aaaggtgtta ctaaactgtt cgagcgtatt      300
tactccaccg acctgggccg tatgctgctg actagcatcg ttcgcggtat cccgttctgg      360
ggcggttcta ccatcgatac cgaactgaaa gtaatcgaca ctaactgcat caacgttatt      420
cagccggacg gttcctatcg ttccgaagaa ctgaacctgg tgatcatcgg cccgtctgct      480
gatatcatcc agttcgagtg taagagcttt ggtcacgaag ttctgaacct cacccgtaac      540
ggctacggtt ccactcagta catccgtttc tctccggact tcaccttcgg ttttgaagaa      600
tccctggaag tagacacgaa cccactgctg ggcgctggta aattcgcaac tgatcctgcg      660
gttaccctgg ctcacgaact gattcatgca ggccaccgcc tgtacggtat cgccatcaat      720
ccgaaccgtg tcttcaaagt taacaccaac gcgtattacg agatgtccgg tctggaagtt      780
agcttcgaag aactgcgtac ttttggcggt cacgacgcta aattcatcga ctctctgcaa      840
gaaaacgagt tccgtctgta ctactataac aagttcaaag atatcgcatc caccctgaac      900
aaagcgaaat ccatcgtggg taccactgct ctctccagt acatgaagaa cgttttaaa       960 gaaaaatacc tgctcagcga agacacctcc ggcaaattct ctgtagacaa gttgaaattc     1020
gataaacttt acaaaatgct gactgaaatt tacaccgaag acaacttcgt taagttcttt     1080
aaagttctga ccgcaaaac ctatctgaac ttcgacaagg cagtattcaa aatcaacatc      1140
gtgccgaaag ttaactacac tatctacgat ggtttcaacc tgcgtaacac caacctggct     1200
gctaatttta acggccagaa cacggaaatc aacaacatga acttcacaaa actgaaaaac     1260
ttcactggtc tgttcgagtt ttacaagctg ctgtgcgtcg acggcatcat acctccaaa      1320 actaaatctc tgatagaagg tagatacggt ggtttcatgg cgctagcggg cggtggcggt     1380
agcggcggtg gcgtagcgg cggtggcggt agcgcactag tgctgcagtg tatcaaggtt     1440
aacaactggg atttattctt cagcccgagt gaagacaact tcaccaacga cctgaacaaa     1500
ggtgaagaaa tcacctcaga tactaacatc gaagcagccg aagaaaacat ctcgctggac     1560
ctgatccagc agtactacct gaccttaaat ttcgacaacg agccggaaaa catttctatc     1620
gaaaacctga gctctgatat catccggccag ctggaactga tgccgaacat cgaacgttc     1680 ccaaacggta aaaagtacga gctggacaaa tataccatgt tccactacct gcgcgcgcag     1740
gaatttgaac acggcaaatc ccgtatcgca ctgactaact ccgttaacga agctctgctc     1800
aacccgtccc gtgtatacac cttcttctct agcgactacg tgaaaaaggt caacaaagcg     1860
actgaagctg caatgttctt gggttgggtt aacagcttg tttatgattt taccgacgag      1920 acgtccaag tatctactac cgacaaaatt gcggatatca ctatcatcat cccgtacatc      1980
ggtccggctc tgaacattgg caacatgctg tacaaagacg acttcgttgg cgcactgatc     2040
ttctccggtg cggtgatcct gctggagttc atcccggaaa tcgccatccc ggtactgggc     2100
acctttgctc tggtttctta cattgcaaac aaggttctga ctgtacaaac catcgacaac     2160
gcgctgagca acgtaacga aaatgggat gaagtttaca atatatcgt gaccaactgg        2220 ctggctaagg ttaatactca gatcgacctc atccgcaaaa aaatgaaaga agcactggaa     2280
aaccaggcgg aagctaccaa ggcaatcatt aactaccagt acaaccagta caccgaggaa     2340
gaaaaaaaca acatcaactt caacatcgac gatctgtcct ctaaactgaa cgaatccatc     2400
aacaaagcta tgatcaacat caacaagttc ctgaaccagt gctctgtaag ctatctgatg     2460
aactccatga tcccgtacgg tgttaaacgt ctggaggact cgatgcgtc tctgaaagac      2520 gccctgctga aatacattta cgacaaccgt ggcactctga tcggtcaggt tgatcgtctg     2580
aaggacaaag tgaacaatac cttatcgacc gacatcccctt ttcagctcag taaatatgtc    2640
```
gataaccaac gcctttgtc cactctagac tag         2673

<210> SEQ ID NO 22
<211> LENGTH: 890
<212> TYPE: PRT
<213> ORGANISM: Artificial Sequence
<220> FEATURE:
<223> OTHER INFORMATION: chemically synthesized fusion protein

<400> SEQUENCE: 22

Gly Ser Met Glu Phe Val Asn Lys Gln Phe Asn Tyr Lys Asp Pro Val
1               5                   10                  15

Asn Gly Val Asp Ile Ala Tyr Ile Lys Ile Pro Asn Ala Gly Gln Met
            20                  25                  30

Gln Pro Val Lys Ala Phe Lys Ile His Asn Lys Ile Trp Val Ile Pro
        35                  40                  45

Glu Arg Asp Thr Phe Thr Asn Pro Glu Glu Gly Asp Leu Asn Pro Pro
50                  55                  60

Pro Glu Ala Lys Gln Val Pro Val Ser Tyr Tyr Asp Ser Thr Tyr Leu
65                  70                  75                  80

Ser Thr Asp Asn Glu Lys Asp Asn Tyr Leu Lys Gly Val Thr Lys Leu
                85                  90                  95

Phe Glu Arg Ile Tyr Ser Thr Asp Leu Gly Arg Met Leu Leu Thr Ser
            100                 105                 110

Ile Val Arg Gly Ile Pro Phe Trp Gly Gly Ser Thr Ile Asp Thr Glu
        115                 120                 125

Leu Lys Val Ile Asp Thr Asn Cys Ile Asn Val Ile Gln Pro Asp Gly
130                 135                 140

Ser Tyr Arg Ser Glu Glu Leu Asn Leu Val Ile Ile Gly Pro Ser Ala
145                 150                 155                 160

Asp Ile Ile Gln Phe Glu Cys Lys Ser Phe Gly His Glu Val Leu Asn
                165                 170                 175

Leu Thr Arg Asn Gly Tyr Gly Ser Thr Gln Tyr Ile Arg Phe Ser Pro
            180                 185                 190

Asp Phe Thr Phe Gly Phe Glu Glu Ser Leu Glu Val Asp Thr Asn Pro
        195                 200                 205

Leu Leu Gly Ala Gly Lys Phe Ala Thr Asp Pro Ala Val Thr Leu Ala
210                 215                 220

His Glu Leu Ile His Ala Gly His Arg Leu Tyr Gly Ile Ala Ile Asn
225                 230                 235                 240

Pro Asn Arg Val Phe Lys Val Asn Thr Asn Ala Tyr Tyr Glu Met Ser
                245                 250                 255

Gly Leu Glu Val Ser Phe Glu Glu Leu Arg Thr Phe Gly Gly His Asp
            260                 265                 270

Ala Lys Phe Ile Asp Ser Leu Gln Glu Asn Glu Phe Arg Leu Tyr Tyr
        275                 280                 285

Tyr Asn Lys Phe Lys Asp Ile Ala Ser Thr Leu Asn Lys Ala Lys Ser
290                 295                 300

Ile Val Gly Thr Thr Ala Ser Leu Gln Tyr Met Lys Asn Val Phe Lys
305                 310                 315                 320

Glu Lys Tyr Leu Leu Ser Glu Asp Thr Ser Gly Lys Phe Ser Val Asp
                325                 330                 335

Lys Leu Lys Phe Asp Lys Leu Tyr Lys Met Leu Thr Glu Ile Tyr Thr
            340                 345                 350

Glu Asp Asn Phe Val Lys Phe Phe Lys Val Leu Asn Arg Lys Thr Tyr

```
                 355                 360                 365
Leu Asn Phe Asp Lys Ala Val Phe Lys Ile Asn Ile Val Pro Lys Val
370                 375                 380
Asn Tyr Thr Ile Tyr Asp Gly Phe Asn Leu Arg Asn Thr Asn Leu Ala
385                 390                 395                 400
Ala Asn Phe Asn Gly Gln Asn Thr Glu Ile Asn Asn Met Asn Phe Thr
                405                 410                 415
Lys Leu Lys Asn Phe Thr Gly Leu Phe Glu Phe Tyr Lys Leu Leu Cys
                420                 425                 430
Val Asp Gly Ile Ile Thr Ser Lys Thr Lys Ser Leu Ile Glu Gly Arg
                435                 440                 445
Tyr Gly Gly Phe Met Ala Leu Ala Gly Gly Gly Ser Gly Gly Gly
                450                 455                 460
Gly Ser Gly Gly Gly Ser Ala Leu Val Leu Gln Cys Ile Lys Val
465                 470                 475                 480
Asn Asn Trp Asp Leu Phe Phe Ser Pro Ser Glu Asp Asn Phe Thr Asn
                485                 490                 495
Asp Leu Asn Lys Gly Glu Glu Ile Thr Ser Asp Thr Asn Ile Glu Ala
                500                 505                 510
Ala Glu Glu Asn Ile Ser Leu Asp Leu Ile Gln Gln Tyr Tyr Leu Thr
                515                 520                 525
Phe Asn Phe Asp Asn Glu Pro Glu Asn Ile Ser Ile Glu Asn Leu Ser
                530                 535                 540
Ser Asp Ile Ile Gly Gln Leu Glu Leu Met Pro Asn Ile Glu Arg Phe
545                 550                 555                 560
Pro Asn Gly Lys Lys Tyr Glu Leu Asp Lys Tyr Thr Met Phe His Tyr
                565                 570                 575
Leu Arg Ala Gln Glu Phe Glu His Gly Lys Ser Arg Ile Ala Leu Thr
                580                 585                 590
Asn Ser Val Asn Glu Ala Leu Leu Asn Pro Ser Arg Val Tyr Thr Phe
                595                 600                 605
Phe Ser Ser Asp Tyr Val Lys Lys Val Asn Lys Ala Thr Glu Ala Ala
                610                 615                 620
Met Phe Leu Gly Trp Val Glu Gln Leu Val Tyr Asp Phe Thr Asp Glu
625                 630                 635                 640
Thr Ser Glu Val Ser Thr Thr Asp Lys Ile Ala Asp Ile Thr Ile Ile
                645                 650                 655
Ile Pro Tyr Ile Gly Pro Ala Leu Asn Ile Gly Asn Met Leu Tyr Lys
                660                 665                 670
Asp Asp Phe Val Gly Ala Leu Ile Phe Ser Gly Ala Val Ile Leu Leu
                675                 680                 685
Glu Phe Ile Pro Glu Ile Ala Ile Pro Val Leu Gly Thr Phe Ala Leu
                690                 695                 700
Val Ser Tyr Ile Ala Asn Lys Val Leu Thr Val Gln Thr Ile Asp Asn
705                 710                 715                 720
Ala Leu Ser Lys Arg Asn Glu Lys Trp Asp Glu Val Tyr Lys Tyr Ile
                725                 730                 735
Val Thr Asn Trp Leu Ala Lys Val Asn Thr Gln Ile Asp Leu Ile Arg
                740                 745                 750
Lys Lys Met Lys Glu Ala Leu Glu Asn Gln Ala Glu Ala Thr Lys Ala
                755                 760                 765
Ile Ile Asn Tyr Gln Tyr Asn Gln Tyr Thr Glu Glu Lys Asn Asn
770                 775                 780
```

```
Ile Asn Phe Asn Ile Asp Asp Leu Ser Ser Lys Leu Asn Glu Ser Ile
785                 790                 795                 800

Asn Lys Ala Met Ile Asn Ile Asn Lys Phe Leu Asn Gln Cys Ser Val
            805                 810                 815

Ser Tyr Leu Met Asn Ser Met Ile Pro Tyr Gly Val Lys Arg Leu Glu
            820                 825                 830

Asp Phe Asp Ala Ser Leu Lys Asp Ala Leu Leu Lys Tyr Ile Tyr Asp
                835                 840                 845

Asn Arg Gly Thr Leu Ile Gly Gln Val Asp Arg Leu Lys Asp Lys Val
            850                 855                 860

Asn Asn Thr Leu Ser Thr Asp Ile Pro Phe Gln Leu Ser Lys Tyr Val
865                 870                 875                 880

Asp Asn Gln Arg Leu Leu Ser Thr Leu Asp
                885                 890

<210> SEQ ID NO 23
<211> LENGTH: 2751
<212> TYPE: DNA
<213> ORGANISM: Artificial Sequence
<220> FEATURE:
<223> OTHER INFORMATION: chemically synthesized polynucleotide encoding
      fusion protein

<400> SEQUENCE: 23
ggatccatgg agttcgttaa caaacagttc aactataaag acccagttaa cggtgttgac      60
attgcttaca tcaaaatccc gaacgctggc cagatgcagc cggtaaaggc attcaaaatc     120
cacaacaaaa tctgggttat cccggaacgt gatacctta ctaacccgga agaaggtgac      180
ctgaacccgc caccggaagc gaaacaggtg ccggtatctt actatgactc cacctacctg     240
tctaccgata cgaaaagga caactacctg aaaggtgtta ctaaactgtt cgagcgtatt      300
tactccaccg acctgggccg tatgctgctg actagcatcg ttcgcggtat cccgttctgg     360
ggcggttcta ccatcgatac cgaactgaaa gtaatcgaca ctaactgcat caacgttatt     420
cagccggacg ttcctatcg ttccgaagaa ctgaacctgg tgatcatcgg cccgtctgct      480
gatatcatcc agttcgagtg taagagcttt ggtcacgaag ttctgaacct cacccgtaac    540
ggctacggtt ccactcagta catccgtttc tctccggact tcaccttcgg ttttgaagaa    600
tccctggaag tagacacgaa cccactgctg ggcgctggta attcgcaac tgatcctgcg     660 gttaccctgg ctcacgaact gattcatgca ggccaccgcc tgtacggtat cgccatcaat    720
ccgaaccgtg tcttcaaagt taacaccaac gcgtattacg agatgccgg tctggaagtt     780 agcttcgaag aactgcgtac ttttggcggt cacgacgcta aattcatcga ctctctgcaa    840
gaaaacgagt ccgtctgta ctactataac aagttcaaag atatcgcatc cacccctgaac    900 aaagcgaaat ccatcgtggg taccactgct ctctccagt acatgaagaa cgttttaaa     960 gaaaaatacc tgctcagcga agacacctcc ggcaaattct ctgtagacaa gttgaaattc    1020
gataaacttt acaaaatgct gactgaaatt tacaccgaag acaacttcgt taagttcttt    1080
aaagttctga accgcaaaac ctatctgaac ttcgacaagg cagtattcaa atcaacatc     1140 gtgccgaaag ttaactacac tatctacgat ggtttcaacc tgcgtaacac caacctggct    1200
gctaatttta acggcagaa cacggaaatc aacaacatga acttcacaaa actgaaaaac    1260
ttcactggtc tgttcgagtt ttacaagctg ctgtgcgtcg acggcatcat acctccaaaa    1320
actaaatctc tgatcgaagg tcgttacggt ggtttcatga cctctgaaaa atctcagacc    1380
ccgctggtta ccctgttcaa aaacgctatc atcaaaaacg cttacaaaaa aggtgaagcg    1440
```

```
ctagcgggtg gtggtggttc tggtggtggt ggttctggtg gtggtggttc tgcactagtg   1500
ctgcagtgta tcaaggttaa caactgggat ttattcttca gcccgagtga agacaacttc   1560
accaacgacc tgaacaaagg tgaagaaatc acctcagata ctaacatcga agcagccgaa   1620
gaaaacatct cgctggacct gatccagcag tactacctga cctttaattt cgacaacgag   1680
ccggaaaaca tttctatcga aaacctgagc tctgatatca tcggccagct ggaactgatg   1740
ccgaacatcg aacgtttccc aaacggtaaa agtacgagc tggacaaata ccatgttc    1800 cactacctgc gcgcgcagga atttgaacac ggcaaatccc gtatcgcact gactaactcc   1860
gttaacgaag ctctgctcaa cccgtcccgt gtatacacct tcttctctag cgactacgtg   1920
aaaaaggtca caaagcgac tgaagctgca atgttcttgg gttgggttga acagcttgtt    1980
tatgatttta ccgacgagac gtccgaagta tctactaccg acaaaattgc ggatatcact   2040
atcatcatcc cgtacatcgg tccggctctg aacattggca acatgctgta caaagacgac   2100
ttcgttggcg cactgatctt ctccggtgcg gtgatcctgc tggagttcat cccggaaatc   2160
gccatcccgg tactgggcac ctttgctctg gtttcttaca ttgcaaacaa ggttctgact   2220
gtacaaacca tcgacaacgc gctgagcaaa cgtaacgaaa atgggatga agtttacaaa    2280 tatatcgtga ccaactggct ggctaaggtt aatactcaga tcgacctcat ccgcaaaaaa   2340
atgaaagaag cactggaaaa ccaggcgaaa gctaccaagg caatcattaa ctaccagtac   2400
aaccagtaca ccgaggaaga aaaaaacaac atcaacttca acatcgacga tctgtcctct   2460
aaactgaacg aatccatcaa caaagctatg atcaacatca caagttcct gaaccagtgc    2520 tctgtaagct atctgatgaa ctccatgatc ccgtacggtg ttaaacgtct ggaggacttc   2580
gatgcgtctc tgaaagacgc cctgctgaaa tacatttacg acaaccgtgg cactctgatc   2640
ggtcaggttg atcgtctgaa ggacaaagtg aacaatacct tatcgaccga catcccttt    2700 cagctcagta aatatgtcga taaccaacgc cttttgtcca ctctagacta g            2751
```

<210> SEQ ID NO 24
<211> LENGTH: 916
<212> TYPE: PRT
<213> ORGANISM: Artificial Sequence
<220> FEATURE:
<223> OTHER INFORMATION: chemically synthesized fusion protein

<400> SEQUENCE: 24

```
Gly Ser Met Glu Phe Val Asn Lys Gln Phe Asn Tyr Lys Asp Pro Val
1               5                  10                  15

Asn Gly Val Asp Ile Ala Tyr Ile Lys Ile Pro Asn Ala Gly Gln Met
            20                  25                  30

Gln Pro Val Lys Ala Phe Lys Ile His Asn Lys Ile Trp Val Ile Pro
        35                  40                  45

Glu Arg Asp Thr Phe Thr Asn Pro Glu Glu Gly Asp Leu Asn Pro Pro
    50                  55                  60

Pro Glu Ala Lys Gln Val Pro Val Ser Tyr Tyr Asp Ser Thr Tyr Leu
65                  70                  75                  80

Ser Thr Asp Asn Glu Lys Asp Asn Tyr Leu Lys Gly Val Thr Lys Leu
                85                  90                  95

Phe Glu Arg Ile Tyr Ser Thr Asp Leu Gly Arg Met Leu Leu Thr Ser
            100                 105                 110

Ile Val Arg Gly Ile Pro Phe Trp Gly Gly Ser Thr Ile Asp Thr Glu
        115                 120                 125

Leu Lys Val Ile Asp Thr Asn Cys Ile Asn Val Ile Gln Pro Asp Gly
    130                 135                 140
```

-continued

```
Ser Tyr Arg Ser Glu Glu Leu Asn Leu Val Ile Ile Gly Pro Ser Ala
145                 150                 155                 160

Asp Ile Ile Gln Phe Glu Cys Lys Ser Phe His Glu Val Leu Asn
            165                 170                 175

Leu Thr Arg Asn Gly Tyr Gly Ser Thr Gln Tyr Ile Arg Phe Ser Pro
            180                 185                 190

Asp Phe Thr Phe Gly Phe Glu Glu Ser Leu Glu Val Asp Thr Asn Pro
            195                 200                 205

Leu Leu Gly Ala Gly Lys Phe Ala Thr Asp Pro Ala Val Thr Leu Ala
            210                 215                 220

His Glu Leu Ile His Ala Gly His Arg Leu Tyr Gly Ile Ala Ile Asn
225                 230                 235                 240

Pro Asn Arg Val Phe Lys Val Asn Thr Asn Ala Tyr Tyr Glu Met Ser
            245                 250                 255

Gly Leu Glu Val Ser Phe Glu Glu Leu Arg Thr Phe Gly Gly His Asp
            260                 265                 270

Ala Lys Phe Ile Asp Ser Leu Gln Glu Asn Glu Phe Arg Leu Tyr Tyr
            275                 280                 285

Tyr Asn Lys Phe Lys Asp Ile Ala Ser Thr Leu Asn Lys Ala Lys Ser
290                 295                 300

Ile Val Gly Thr Thr Ala Ser Leu Gln Tyr Met Lys Asn Val Phe Lys
305                 310                 315                 320

Glu Lys Tyr Leu Leu Ser Glu Asp Thr Ser Gly Lys Phe Ser Val Asp
            325                 330                 335

Lys Leu Lys Phe Asp Lys Leu Tyr Lys Met Leu Thr Glu Ile Tyr Thr
            340                 345                 350

Glu Asp Asn Phe Val Lys Phe Lys Val Leu Asn Arg Lys Thr Tyr
            355                 360                 365

Leu Asn Phe Asp Lys Ala Val Phe Lys Ile Asn Ile Val Pro Lys Val
            370                 375                 380

Asn Tyr Thr Ile Tyr Asp Gly Phe Asn Leu Arg Asn Thr Asn Leu Ala
385                 390                 395                 400

Ala Asn Phe Asn Gly Gln Asn Thr Glu Ile Asn Asn Met Asn Phe Thr
            405                 410                 415

Lys Leu Lys Asn Phe Thr Gly Leu Phe Glu Phe Tyr Lys Leu Leu Cys
            420                 425                 430

Val Asp Gly Ile Ile Thr Ser Lys Thr Lys Ser Leu Ile Glu Gly Arg
            435                 440                 445

Tyr Gly Gly Phe Met Thr Ser Glu Lys Ser Gln Thr Pro Leu Val Thr
            450                 455                 460

Leu Phe Lys Asn Ala Ile Ile Lys Asn Ala Tyr Lys Lys Gly Glu Ala
465                 470                 475                 480

Leu Ala Gly Gly Gly Ser Gly Gly Gly Ser Gly Gly Gly
            485                 490                 495

Ser Ala Leu Val Leu Gln Cys Ile Lys Val Asn Asn Trp Asp Leu Phe
            500                 505                 510

Phe Ser Pro Ser Glu Asp Asn Phe Thr Asn Asp Leu Asn Lys Gly Glu
            515                 520                 525

Glu Ile Thr Ser Asp Thr Asn Ile Glu Ala Ala Glu Glu Asn Ile Ser
            530                 535                 540

Leu Asp Leu Ile Gln Gln Tyr Tyr Leu Thr Phe Asn Phe Asp Asn Glu
545                 550                 555                 560

Pro Glu Asn Ile Ser Ile Glu Asn Leu Ser Ser Asp Ile Ile Gly Gln
```

```
                565                 570                 575
Leu Glu Leu Met Pro Asn Ile Glu Arg Phe Pro Asn Gly Lys Lys Tyr
            580                 585                 590
Glu Leu Asp Lys Tyr Thr Met Phe His Tyr Leu Arg Ala Gln Glu Phe
        595                 600                 605
Glu His Gly Lys Ser Arg Ile Ala Leu Thr Asn Ser Val Asn Glu Ala
    610                 615                 620
Leu Leu Asn Pro Ser Arg Val Tyr Thr Phe Phe Ser Ser Asp Tyr Val
625                 630                 635                 640
Lys Lys Val Asn Lys Ala Thr Glu Ala Ala Met Phe Leu Gly Trp Val
                645                 650                 655
Glu Gln Leu Val Tyr Asp Phe Thr Asp Glu Thr Ser Glu Val Ser Thr
            660                 665                 670
Thr Asp Lys Ile Ala Asp Ile Thr Ile Ile Pro Tyr Ile Gly Pro
        675                 680                 685
Ala Leu Asn Ile Gly Asn Met Leu Tyr Lys Asp Asp Phe Val Gly Ala
    690                 695                 700
Leu Ile Phe Ser Gly Ala Val Ile Leu Leu Glu Phe Ile Pro Glu Ile
705                 710                 715                 720
Ala Ile Pro Val Leu Gly Thr Phe Ala Leu Val Ser Tyr Ile Ala Asn
                725                 730                 735
Lys Val Leu Thr Val Gln Thr Ile Asp Asn Ala Leu Ser Lys Arg Asn
            740                 745                 750
Glu Lys Trp Asp Glu Val Tyr Lys Tyr Ile Val Thr Asn Trp Leu Ala
        755                 760                 765
Lys Val Asn Thr Gln Ile Asp Leu Ile Arg Lys Lys Met Lys Glu Ala
    770                 775                 780
Leu Glu Asn Gln Ala Glu Ala Thr Lys Ala Ile Ile Asn Tyr Gln Tyr
785                 790                 795                 800
Asn Gln Tyr Thr Glu Glu Lys Asn Asn Ile Asn Phe Asn Ile Asp
                805                 810                 815
Asp Leu Ser Ser Lys Leu Asn Glu Ser Ile Asn Lys Ala Met Ile Asn
            820                 825                 830
Ile Asn Lys Phe Leu Asn Gln Cys Ser Val Ser Tyr Leu Met Asn Ser
        835                 840                 845
Met Ile Pro Tyr Gly Val Lys Arg Leu Glu Asp Phe Asp Ala Ser Leu
    850                 855                 860
Lys Asp Ala Leu Leu Lys Tyr Ile Tyr Asp Asn Arg Gly Thr Leu Ile
865                 870                 875                 880
Gly Gln Val Asp Arg Leu Lys Asp Lys Val Asn Asn Thr Leu Ser Thr
                885                 890                 895
Asp Ile Pro Phe Gln Leu Ser Lys Tyr Val Asp Asn Gln Arg Leu Leu
            900                 905                 910
Ser Thr Leu Asp
        915

<210> SEQ ID NO 25
<211> LENGTH: 2709
<212> TYPE: DNA
<213> ORGANISM: Artificial Sequence
<220> FEATURE:
<223> OTHER INFORMATION: chemically synthesized polynucleotide encoding
      fusion protein

<400> SEQUENCE: 25
ggatccatgg agttcgttaa caaacagttc aactataaag acccagttaa cggtgttgac     60
```

```
attgcttaca tcaaaatccc gaacgctggc cagatgcagc cggtaaaggc attcaaaatc    120
cacaacaaaa tctgggttat cccggaacgt gatacctttta ctaacccgga agaaggtgac    180
ctgaacccgc caccggaagc gaaacaggtg ccggtatctt actatgactc cacctacctg    240
tctaccgata acgaaaagga caactacctg aaaggtgtta ctaaactgtt cgagcgtatt    300
tactccaccg acctgggccg tatgctgctg actagcatcg ttcgcggtat cccgttctgg    360
ggcggttcta ccatcgatac cgaactgaaa gtaatcgaca ctaactgcat caacgttatt    420
cagccggacg gttcctatcg ttccgaagaa ctgaacctgg tgatcatcgg cccgtctgct    480
gatatcatcc agttcgagtg taagagcttt ggtcacgaag ttctgaacct cacccgtaac    540
ggctacggtt ccactcagta catccgtttc tctccggact tcaccttcgg ttttgaagaa    600
tccctggaag tagacacgaa cccactgctg ggcgctggta aattcgcaac tgatcctgcg    660
gttaccctgg ctcacgaact gattcatgca ggccaccgcc tgtacggtat cgccatcaat    720
ccgaaccgtg tcttcaaagt taacaccaac gcgtattacg agatgtccgg tctggaagtt    780
agcttcgaag aactgcgtac ttttggcggt cacgacgcta aattcatcga ctctctgcaa    840
gaaaacgagt tccgtctgta ctactataac aagttcaaag atatcgcatc caccctgaac    900
aaagcgaaat ccatcgtggg taccactgct tctctccagt acatgaagaa cgttttaaa     960 gaaaaatacc tgctcagcga agacacctcc ggcaaattct ctgtagacaa gttgaaattc   1020
gataaacttt acaaaatgct gactgaaatt tacaccgaag acaacttcgt taagttcttt   1080
aaagttctga accgcaaaac ctatctgaac ttcgacaagg cagtattcaa aatcaacatc   1140
gtgccgaaag ttaactacac tatctacgat ggtttcaacc tgcgtaacac caacctggct   1200
gctaatttta acgccagaa cacggaaatc aacaacatga acttcacaaa actgaaaaac   1260
ttcactggtc tgttcgagtt ttacaagctg ctgtgcgtcg acggcatcat acctccaaa    1320 actaaatctc tgatagaagg tagatttggc ggtttcacgg gcgcacgcaa atcagcgcgt   1380
aaacgtaaga accaggcgct agcgggcggt ggcggtagcg gcggtggcgg tagcggcggt   1440
ggcggtagcg cactagtgct gcagtgtatc aaggttaaca actgggattt attcttcagc   1500
ccgagtgaag acaacttcac caacgacctg aacaaaggtg aagaaatcac ctcagatact   1560
aacatcgaag cagccgaaga aaacatctcg ctggacctga tccagcagta ctacctgacc   1620
tttaatttcg acaacgagcc ggaaaacatt tctatcgaaa acctgagctc tgatatcatc   1680
ggccagctgg aactgatgcc gaacatcgaa cgtttcccaa acggtaaaaa gtacgagctg   1740
gacaaatata ccatgttcca ctacctgcgc gcgcaggaat ttgaacacgg caaatcccgt   1800
atcgcactga ctaactccgt taacgaagct ctgctcaacc cgtcccgtgt atacaccttc   1860
ttctctagcg actacgtgaa aaaggtcaac aaagcgactg aagctgcaat gttcttgggt   1920
tgggttgaac agcttgttta tgattttacc gacgagacgt ccgaagtatc tactaccgac   1980
aaaattgcgg atatcactat catcatcccg tacatcggtc cggctctgaa cattggcaac   2040
atgctgtaca agacgactt cgttggcgca ctgatcttct ccggtgcggt gatcctgctg   2100
gagttcatcc cggaaatcgc catcccggta ctgggcacct ttgctctggt ttcttacatt   2160
gcaaacaagg ttctgactgt acaaaccatc gacaacgcgc tgagcaaacg taacgaaaaa   2220
tgggatgaag tttacaaata tatcgtgacc aactggctgg ctaaggttaa tactcagatc   2280
gacctcatcc gcaaaaaaat gaaagaagca ctggaaaacc aggcggaagc taccaaggca   2340
atcattaact accagtacaa ccagtacacc gaggaagaaa aaacaacat caacttcaac   2400 atcgacgatc tgtcctctaa actgaacgaa tccatcaaca aagctatgat caacatcaac   2460
```

```
aagttcctga accagtgctc tgtaagctat ctgatgaact ccatgatccc gtacggtgtt    2520
aaacgtctgg aggacttcga tgcgtctctg aaagacgccc tgctgaaata catttacgac    2580
aaccgtggca ctctgatcgg tcaggttgat cgtctgaagg acaaagtgaa caataccttaa   2640 tcgaccgaca tcccttttca gctcagtaaa tatgtcgata accaacgcct tttgtccact    2700
ctagactag                                                            2709
```

<210> SEQ ID NO 26
<211> LENGTH: 902
<212> TYPE: PRT
<213> ORGANISM: Artificial Sequence
<220> FEATURE:
<223> OTHER INFORMATION: chemically synthesized fusion protein

<400> SEQUENCE: 26

```
Gly Ser Met Glu Phe Val Asn Lys Gln Phe Asn Tyr Lys Asp Pro Val
1               5                   10                  15

Asn Gly Val Asp Ile Ala Tyr Ile Lys Ile Pro Asn Ala Gly Gln Met
            20                  25                  30

Gln Pro Val Lys Ala Phe Lys Ile His Asn Lys Ile Trp Val Ile Pro
        35                  40                  45

Glu Arg Asp Thr Phe Thr Asn Pro Glu Glu Gly Asp Leu Asn Pro Pro
    50                  55                  60

Pro Glu Ala Lys Gln Val Pro Val Ser Tyr Tyr Asp Ser Thr Tyr Leu
65                  70                  75                  80

Ser Thr Asp Asn Glu Lys Asp Asn Tyr Leu Lys Gly Val Thr Lys Leu
                85                  90                  95

Phe Glu Arg Ile Tyr Ser Thr Asp Leu Gly Arg Met Leu Leu Thr Ser
            100                 105                 110

Ile Val Arg Gly Ile Pro Phe Trp Gly Gly Ser Thr Ile Asp Thr Glu
        115                 120                 125

Leu Lys Val Ile Asp Thr Asn Cys Ile Asn Val Ile Gln Pro Asp Gly
    130                 135                 140

Ser Tyr Arg Ser Glu Glu Leu Asn Leu Val Ile Ile Gly Pro Ser Ala
145                 150                 155                 160

Asp Ile Ile Gln Phe Glu Cys Lys Ser Phe Gly His Glu Val Leu Asn
                165                 170                 175

Leu Thr Arg Asn Gly Tyr Gly Ser Thr Gln Tyr Ile Arg Phe Ser Pro
            180                 185                 190

Asp Phe Thr Phe Gly Phe Glu Glu Ser Leu Glu Val Asp Thr Asn Pro
        195                 200                 205

Leu Leu Gly Ala Gly Lys Phe Ala Thr Asp Pro Ala Val Thr Leu Ala
    210                 215                 220

His Glu Leu Ile His Ala Gly His Arg Leu Tyr Gly Ile Ala Ile Asn
225                 230                 235                 240

Pro Asn Arg Val Phe Lys Val Asn Thr Asn Ala Tyr Glu Met Ser
                245                 250                 255

Gly Leu Glu Val Ser Phe Glu Glu Leu Arg Thr Phe Gly Gly His Asp
            260                 265                 270

Ala Lys Phe Ile Asp Ser Leu Gln Glu Asn Glu Phe Arg Leu Tyr Tyr
        275                 280                 285

Tyr Asn Lys Phe Lys Asp Ile Ala Ser Thr Leu Asn Lys Ala Lys Ser
    290                 295                 300

Ile Val Gly Thr Thr Ala Ser Leu Gln Tyr Met Lys Asn Val Phe Lys
305                 310                 315                 320
```

```
Glu Lys Tyr Leu Leu Ser Glu Asp Thr Ser Gly Lys Phe Ser Val Asp
                325                 330                 335

Lys Leu Lys Phe Asp Lys Leu Tyr Lys Met Leu Thr Glu Ile Tyr Thr
            340                 345                 350

Glu Asp Asn Phe Val Lys Phe Lys Val Leu Asn Arg Lys Thr Tyr
        355                 360                 365

Leu Asn Phe Asp Lys Ala Val Phe Lys Ile Asn Ile Val Pro Lys Val
370                 375                 380

Asn Tyr Thr Ile Tyr Asp Gly Phe Asn Leu Arg Asn Thr Asn Leu Ala
385                 390                 395                 400

Ala Asn Phe Asn Gly Gln Asn Thr Glu Ile Asn Asn Met Asn Phe Thr
                405                 410                 415

Lys Leu Lys Asn Phe Thr Gly Leu Phe Glu Phe Tyr Lys Leu Leu Cys
            420                 425                 430

Val Asp Gly Ile Ile Thr Ser Lys Thr Lys Ser Leu Ile Glu Gly Arg
        435                 440                 445

Phe Gly Gly Phe Thr Gly Ala Arg Lys Ser Ala Arg Lys Arg Lys Asn
    450                 455                 460

Gln Ala Leu Ala Gly Gly Gly Ser Gly Gly Gly Ser Gly Gly
465                 470                 475                 480

Gly Gly Ser Ala Leu Val Leu Gln Cys Ile Lys Val Asn Asn Trp Asp
                485                 490                 495

Leu Phe Phe Ser Pro Ser Glu Asp Asn Phe Thr Asn Asp Leu Asn Lys
            500                 505                 510

Gly Glu Glu Ile Thr Ser Asp Thr Asn Ile Glu Ala Ala Glu Glu Asn
        515                 520                 525

Ile Ser Leu Asp Leu Ile Gln Gln Tyr Tyr Leu Thr Phe Asn Phe Asp
530                 535                 540

Asn Glu Pro Glu Asn Ile Ser Ile Glu Asn Leu Ser Ser Asp Ile Ile
545                 550                 555                 560

Gly Gln Leu Glu Leu Met Pro Asn Ile Glu Arg Phe Pro Asn Gly Lys
            565                 570                 575

Lys Tyr Glu Leu Asp Lys Tyr Thr Met Phe His Tyr Leu Arg Ala Gln
        580                 585                 590

Glu Phe Glu His Gly Lys Ser Arg Ile Ala Leu Thr Asn Ser Val Asn
    595                 600                 605

Glu Ala Leu Leu Asn Pro Ser Arg Val Tyr Thr Phe Phe Ser Ser Asp
610                 615                 620

Tyr Val Lys Lys Val Asn Lys Ala Thr Glu Ala Ala Met Phe Leu Gly
625                 630                 635                 640

Trp Val Glu Gln Leu Val Tyr Asp Phe Thr Asp Glu Thr Ser Glu Val
            645                 650                 655

Ser Thr Thr Asp Lys Ile Ala Asp Ile Thr Ile Ile Pro Tyr Ile
        660                 665                 670

Gly Pro Ala Leu Asn Ile Gly Asn Met Leu Tyr Lys Asp Asp Phe Val
    675                 680                 685

Gly Ala Leu Ile Phe Ser Gly Ala Val Ile Leu Leu Glu Phe Ile Pro
690                 695                 700

Glu Ile Ala Ile Pro Val Leu Gly Thr Phe Ala Leu Val Ser Tyr Ile
705                 710                 715                 720

Ala Asn Lys Val Leu Thr Val Gln Thr Ile Asp Asn Ala Leu Ser Lys
            725                 730                 735

Arg Asn Glu Lys Trp Asp Glu Val Tyr Lys Tyr Ile Val Thr Asn Trp
```

```
                740                  745                  750
Leu Ala Lys Val Asn Thr Gln Ile Asp Leu Ile Arg Lys Lys Met Lys
        755                  760                  765
Glu Ala Leu Glu Asn Gln Ala Glu Ala Thr Lys Ala Ile Ile Asn Tyr
        770                  775                  780
Gln Tyr Asn Gln Tyr Thr Glu Glu Lys Asn Asn Ile Asn Phe Asn
785                  790                  795                  800
Ile Asp Asp Leu Ser Ser Lys Leu Asn Glu Ser Ile Asn Lys Ala Met
                805                  810                  815
Ile Asn Ile Asn Lys Phe Leu Asn Gln Cys Ser Val Ser Tyr Leu Met
            820                  825                  830
Asn Ser Met Ile Pro Tyr Gly Val Lys Arg Leu Glu Asp Phe Asp Ala
            835                  840                  845
Ser Leu Lys Asp Ala Leu Leu Lys Tyr Ile Tyr Asp Asn Arg Gly Thr
        850                  855                  860
Leu Ile Gly Gln Val Asp Arg Leu Lys Asp Lys Val Asn Asn Thr Leu
865                  870                  875                  880
Ser Thr Asp Ile Pro Phe Gln Leu Ser Lys Tyr Val Asp Asn Gln Arg
                885                  890                  895
Leu Leu Ser Thr Leu Asp
            900

<210> SEQ ID NO 27
<211> LENGTH: 2691
<212> TYPE: DNA
<213> ORGANISM: Artificial Sequence
<220> FEATURE:
<223> OTHER INFORMATION: chemically synthesized polynucleotide encoding
      fusion protein

<400> SEQUENCE: 27
ggatccatgg agttcgttaa caaacagttc aactataaag acccagttaa cggtgttgac     60
attgcttaca tcaaaatccc gaacgctggc cagatgcagc cggtaaaggc attcaaaatc    120
cacaacaaaa tctgggttat cccggaacgt gataccttta ctaacccgga agaaggtgac    180
ctgaacccgc accggaagc gaaacaggtg ccggtatctt actatgactc cacctacctg    240
tctaccgata cgaaaaagga caactacctg aaaggtgtta ctaaactgtt cgagcgtatt    300
tactccaccg acctgggccg tatgctgctg actagcatcg ttcgcggtat cccgttctgg    360
ggcggttcta ccatcgatac cgaactgaaa gtaatcgaca ctaactgcat caacgttatt    420
cagccggacg gttcctatcg ttccgaagaa ctgaacctgg tgatcatcgg cccgtctgct    480
gatatcatcc agttcgagtg taagagcttt ggtcacgaag ttctgaacct cacccgtaac    540
ggctacggtt ccactcagta catccgtttc tctccggact tcaccttcgg ttttgaagaa    600
tccctggaag tagacacgaa cccactgctg ggcgctggta aattcgcaac tgatcctgcg    660
gttaccctgg ctcacgaact gattcatgca ggccaccgcc tgtacggtat cgccatcaat    720
ccgaaccgtg tcttcaaagt taacaccaac gcgtattacg agatgtccgg tctggaagtt    780
agcttcgaag aactgcgtac ttttggcggt cacgacgcta aattcatcga ctctctgcaa    840
gaaaacgagt ccgtctgta ctactataac aagttcaaag atatcgcatc caccctgaac    900
aaagcgaaat ccatcgtggg taccactgct tctctccagt acatgaagaa cgttttaaa    960 gaaaaatacc tgctcagcga agacacctcc ggcaaattct ctgtagacaa gttgaaattc   1020
gataaacttt acaaaatgct gactgaaatt tacaccgaag acaacttcgt taagttcttt   1080
aaagttctga accgcaaaac ctatctgaac ttcgacaagg cagtattcaa aatcaacatc   1140
```

```
gtgccgaaag ttaactacac tatctacgat ggtttcaacc tgcgtaacac caacctggct   1200
gctaatttta acggccagaa cacggaaatc aacaacatga acttcacaaa actgaaaaac   1260
ttcactggtc tgttcgagtt ttacaagctg ctgtgcgtcg acggcatcat tacctccaaa   1320
actaaatctc tgatagaagg tagatttggc ggtttcacgg gcgcacgcaa atcagcggcg   1380
ctagcgggcg gtggcggtag cggcggtggc ggtagcggcg gtggcggtag cgcactagtg   1440
ctgcagtgta tcaaggttaa caactgggat ttattcttca gcccgagtga agacaacttc   1500
accaacgacc tgaacaaagg tgaagaaatc acctcagata ctaacatcga agcagccgaa   1560
gaaaacatct cgctggacct gatccagcag tactacctga cctttaattt cgacaacgag   1620
ccggaaaaca tttctatcga aacctgagc tctgatatca tcggccagct ggaactgatg   1680
ccgaacatcg aacgtttccc aaacggtaaa aagtacgagc tggacaaata ccatgttc    1740 cactacctgc gcgcgcagga atttgaacac ggcaaatccc gtatcgcact gactaactcc   1800
gttaacgaag ctctgctcaa cccgtcccgt gtatacacct tcttctctag cgactacgtg   1860
aaaaaggtca caaagcgac tgaagctgca atgttcttgg gttgggttga acagcttgtt   1920
tatgatttta ccgacgagac gtccgaagta tctactaccg acaaaattgc ggatatcact   1980
atcatcatcc cgtacatcgg tccggctctg aacattggca acatgctgta caaagacgac   2040
ttcgttggcg cactgatctt ctccggtgcg gtgatcctgc tggagttcat cccggaaatc   2100
gccatcccgg tactgggcac ctttgctctg gtttcttaca ttgcaaacaa ggttctgact   2160
gtacaaacca tcgacaacgc gctgagcaaa cgtaacgaaa atgggatga agtttacaaa   2220 tatatcgtga ccaactggct ggctaaggtt aatactcaga tcgacctcat ccgcaaaaaa   2280
atgaaagaag cactggaaaa ccaggcggaa gctaccaagg caatcattaa ctaccagtac   2340
aaccagtaca ccgaggaaga aaaaaacaac atcaacttca acatcgacga tctgtcctct   2400
aaactgaacg aatccatcaa caaagctatg atcaacatca caagttcct gaaccagtgc   2460 tctgtaagct atctgatgaa ctccatgatc ccgtacggtg ttaaacgtct ggaggacttc   2520
gatgcgtctc tgaaagacgc cctgctgaaa tacatttacg acaaccgtgg cactctgatc   2580
ggtcaggttg atcgtctgaa ggacaaagtg aacaatacct tatcgaccga catcccttttt  2640 cagctcagta aatatgtcga taaccaacgc cttttgtcca ctctagacta g             2691
```

<210> SEQ ID NO 28
<211> LENGTH: 896
<212> TYPE: PRT
<213> ORGANISM: Artificial Sequence
<220> FEATURE:
<223> OTHER INFORMATION: chemically synthesized fusion protein

<400> SEQUENCE: 28

```
Gly Ser Met Glu Phe Val Asn Lys Gln Phe Asn Tyr Lys Asp Pro Val
1               5                  10                  15

Asn Gly Val Asp Ile Ala Tyr Ile Lys Ile Pro Asn Ala Gly Gln Met
            20                  25                  30

Gln Pro Val Lys Ala Phe Lys Ile His Asn Lys Ile Trp Val Ile Pro
        35                  40                  45

Glu Arg Asp Thr Phe Thr Asn Pro Glu Glu Gly Asp Leu Asn Pro Pro
    50                  55                  60

Pro Glu Ala Lys Gln Val Pro Val Ser Tyr Tyr Asp Ser Thr Tyr Leu
65                  70                  75                  80

Ser Thr Asp Asn Glu Lys Asp Asn Tyr Leu Lys Gly Val Thr Lys Leu
                85                  90                  95
```

```
Phe Glu Arg Ile Tyr Ser Thr Asp Leu Gly Arg Met Leu Leu Thr Ser
            100                 105                 110

Ile Val Arg Gly Ile Pro Phe Trp Gly Ser Thr Ile Asp Thr Glu
        115                 120                 125

Leu Lys Val Ile Asp Thr Asn Cys Ile Asn Val Ile Gln Pro Asp Gly
130                 135                 140

Ser Tyr Arg Ser Glu Glu Leu Asn Leu Val Ile Ile Gly Pro Ser Ala
145                 150                 155                 160

Asp Ile Ile Gln Phe Glu Cys Lys Ser Phe Gly His Glu Val Leu Asn
                165                 170                 175

Leu Thr Arg Asn Gly Tyr Gly Ser Thr Gln Tyr Ile Arg Phe Ser Pro
            180                 185                 190

Asp Phe Thr Phe Gly Phe Glu Glu Ser Leu Glu Val Asp Thr Asn Pro
        195                 200                 205

Leu Leu Gly Ala Gly Lys Phe Ala Thr Asp Pro Ala Val Thr Leu Ala
210                 215                 220

His Glu Leu Ile His Ala Gly His Arg Leu Tyr Gly Ile Ala Ile Asn
225                 230                 235                 240

Pro Asn Arg Val Phe Lys Val Asn Thr Asn Ala Tyr Tyr Glu Met Ser
                245                 250                 255

Gly Leu Glu Val Ser Phe Glu Glu Leu Arg Thr Phe Gly Gly His Asp
            260                 265                 270

Ala Lys Phe Ile Asp Ser Leu Gln Glu Asn Glu Phe Arg Leu Tyr Tyr
        275                 280                 285

Tyr Asn Lys Phe Lys Asp Ile Ala Ser Thr Leu Asn Lys Ala Lys Ser
    290                 295                 300

Ile Val Gly Thr Thr Ala Ser Leu Gln Tyr Met Lys Asn Val Phe Lys
305                 310                 315                 320

Glu Lys Tyr Leu Leu Ser Glu Asp Thr Ser Gly Lys Phe Ser Val Asp
                325                 330                 335

Lys Leu Lys Phe Asp Lys Leu Tyr Lys Met Leu Thr Glu Ile Tyr Thr
            340                 345                 350

Glu Asp Asn Phe Val Lys Phe Phe Lys Val Leu Asn Arg Lys Thr Tyr
        355                 360                 365

Leu Asn Phe Asp Lys Ala Val Phe Lys Ile Asn Ile Val Pro Lys Val
    370                 375                 380

Asn Tyr Thr Ile Tyr Asp Gly Phe Asn Leu Arg Asn Thr Asn Leu Ala
385                 390                 395                 400

Ala Asn Phe Asn Gly Gln Asn Thr Glu Ile Asn Asn Met Asn Phe Thr
                405                 410                 415

Lys Leu Lys Asn Phe Thr Gly Leu Phe Glu Phe Tyr Lys Leu Leu Cys
            420                 425                 430

Val Asp Gly Ile Ile Thr Ser Lys Thr Lys Ser Leu Ile Glu Gly Arg
        435                 440                 445

Phe Gly Gly Phe Thr Gly Ala Arg Lys Ser Ala Ala Leu Ala Gly Gly
    450                 455                 460

Gly Gly Ser Gly Gly Gly Ser Gly Gly Gly Ser Ala Leu Val
465                 470                 475                 480

Leu Gln Cys Ile Lys Val Asn Asn Trp Asp Leu Phe Phe Ser Pro Ser
                485                 490                 495

Glu Asp Asn Phe Thr Asn Asp Leu Asn Lys Gly Glu Glu Ile Thr Ser
            500                 505                 510

Asp Thr Asn Ile Glu Ala Ala Glu Glu Asn Ile Ser Leu Asp Leu Ile
```

515                 520                 525

Gln Gln Tyr Tyr Leu Thr Phe Asn Phe Asp Asn Glu Pro Glu Asn Ile
            530                 535                 540

Ser Ile Glu Asn Leu Ser Ser Asp Ile Ile Gly Gln Leu Glu Leu Met
545                 550                 555                 560

Pro Asn Ile Glu Arg Phe Pro Asn Gly Lys Lys Tyr Glu Leu Asp Lys
                565                 570                 575

Tyr Thr Met Phe His Tyr Leu Arg Ala Gln Glu Phe Glu His Gly Lys
            580                 585                 590

Ser Arg Ile Ala Leu Thr Asn Ser Val Asn Glu Ala Leu Leu Asn Pro
                595                 600                 605

Ser Arg Val Tyr Thr Phe Phe Ser Ser Asp Tyr Val Lys Lys Val Asn
            610                 615                 620

Lys Ala Thr Glu Ala Ala Met Phe Leu Gly Trp Val Glu Gln Leu Val
625                 630                 635                 640

Tyr Asp Phe Thr Asp Glu Thr Ser Glu Val Ser Thr Thr Asp Lys Ile
                645                 650                 655

Ala Asp Ile Thr Ile Ile Ile Pro Tyr Ile Gly Pro Ala Leu Asn Ile
            660                 665                 670

Gly Asn Met Leu Tyr Lys Asp Asp Phe Val Gly Ala Leu Ile Phe Ser
                675                 680                 685

Gly Ala Val Ile Leu Leu Glu Phe Ile Pro Glu Ile Ala Ile Pro Val
            690                 695                 700

Leu Gly Thr Phe Ala Leu Val Ser Tyr Ile Ala Asn Lys Val Leu Thr
705                 710                 715                 720

Val Gln Thr Ile Asp Asn Ala Leu Ser Lys Arg Asn Glu Lys Trp Asp
                725                 730                 735

Glu Val Tyr Lys Tyr Ile Val Thr Asn Trp Leu Ala Lys Val Asn Thr
            740                 745                 750

Gln Ile Asp Leu Ile Arg Lys Lys Met Lys Glu Ala Leu Glu Asn Gln
                755                 760                 765

Ala Glu Ala Thr Lys Ala Ile Ile Asn Tyr Gln Tyr Asn Gln Tyr Thr
            770                 775                 780

Glu Glu Glu Lys Asn Asn Ile Asn Phe Asn Ile Asp Asp Leu Ser Ser
785                 790                 795                 800

Lys Leu Asn Glu Ser Ile Asn Lys Ala Met Ile Asn Ile Asn Lys Phe
                805                 810                 815

Leu Asn Gln Cys Ser Val Ser Tyr Leu Met Asn Ser Met Ile Pro Tyr
            820                 825                 830

Gly Val Lys Arg Leu Glu Asp Phe Asp Ala Ser Leu Lys Asp Ala Leu
            835                 840                 845

Leu Lys Tyr Ile Tyr Asp Asn Arg Gly Thr Leu Ile Gly Gln Val Asp
850                 855                 860

Arg Leu Lys Asp Lys Val Asn Asn Thr Leu Ser Thr Asp Ile Pro Phe
865                 870                 875                 880

Gln Leu Ser Lys Tyr Val Asp Asn Gln Arg Leu Leu Ser Thr Leu Asp
            885                 890                 895

<210> SEQ ID NO 29
<211> LENGTH: 2691
<212> TYPE: DNA
<213> ORGANISM: Artificial Sequence
<220> FEATURE:
<223> OTHER INFORMATION: chemically synthesized polynucleotide encoding
      fusion protein

<400> SEQUENCE: 29

```
ggatccatgg agttcgttaa caaacagttc aactataaag acccagttaa cggtgttgac      60
attgcttaca tcaaaatccc gaacgctggc cagatgcagc cggtaaaggc attcaaaatc     120
cacaacaaaa tctgggttat cccggaacgt gataccttta ctaacccgga agaaggtgac     180
ctgaacccgc caccggaagc gaaacaggtg ccggtatctt actatgactc cacctacctg     240
tctaccgata cgaaaagga caactacctg aaaggtgtta ctaaactgtt cgagcgtatt     300
tactccaccg acctgggccg tatgctgctg actagcatcg ttcgcggtat cccgttctgg     360
ggcggttcta ccatcgatac cgaactgaaa gtaatcgaca ctaactgcat caacgttatt     420
cagccggacg gttcctatcg ttccgaagaa ctgaacctgg tgatcatcgg cccgtctgct     480
gatatcatcc agttcgagtg taagagcttt ggtcacgaag ttctgaacct cacccgtaac     540
ggctacggtt ccactcagta catccgtttc tctccggact tcaccttcgg ttttgaagaa     600
tccctggaag tagacacgaa cccactgctg gcgctggta aattcgcaac tgatcctgcg      660
gttaccctgg ctcacgaact gattcatgca ggccaccgcc tgtacggtat cgccatcaat     720
ccgaaccgtg tcttcaaagt taacaccaac gcgtattacg agatgtccgg tctggaagtt     780
agcttcgaag aactgcgtac ttttggcggt cacgacgcta aattcatcga ctctctgcaa     840
gaaaacgagt ccgtctgta ctactataac aagttcaaag atatcgcatc cacccctgaac     900
aaagcgaaat ccatcgtggg taccactgct tctctccagt acatgaagaa cgttttaaa     960
gaaaaatacc tgctcagcga agacacctcc ggcaaattct ctgtagacaa gttgaaattc    1020
gataaacttt acaaaatgct gactgaaatt tacaccgaag acaacttcgt taagttcttt    1080
aaagttctga accgcaaaac ctatctgaac ttcgacaagg cagtattcaa aatcaacatc    1140
gtgccgaaag ttaactacac tatctacgat ggtttcaacc tgcgtaacac caacctggct    1200
gctaattta acggccagaa cacggaaatc aacaacatga acttcacaaa actgaaaaac    1260
ttcactggtc tgttcgagtt ttacaagctg ctgtgcgtcg acggcatcat tacctccaaa    1320
actaaatctc tgatagaagg tagatttggc ggtttcacgg gcgcacgcaa atatgcggcg    1380
ctagcgggcg gtggcggtag cggcggtggc ggtagcggcg gtggcggtag cgcactagtg    1440
ctgcagtgta tcaaggttaa caactgggat ttattcttca gcccgagtga agacaacttc    1500
accaacgacc tgaacaaagg tgaagaaatc acctcagata ctaacatcga agcagccgaa    1560
gaaacatctc gctggacct gatccagcag tactacctga cctttaattt cgacaacgag    1620
ccggaaaaca tttctatcga aaacctgagc tctgatatca tcggccagct ggaactgatg    1680
ccgaacatcg aacgtttccc aaacggtaaa agtacgagc tggacaaata ccatgttc     1740
cactacctgc gcgcgcagga atttgaacac ggcaaatccc gtatcgcact gactaactcc    1800
gttaacgaag ctctgctcaa cccgtcccgt gtatacacct tcttctctag cgactacgtg    1860
aaaaaggtca caaagcgac tgaagctgca atgttcttgg gttgggttga acagcttgtt    1920
tatgatttta ccgacgagac gtccgaagta tctactaccg acaaaattgc ggatatcact    1980
atcatcatcc cgtacatcgg tccggctctg aacattggca acatgctgta caaagacgac    2040
ttcgttggcg cactgatctt ctccggtgcg gtgatcctgc tggagttcat cccggaaatc    2100
gccatcccgg tactgggcac cttttgctctg gttttcttaca ttgcaaacaa ggttctgact    2160
gtacaaacca tcgacaacgc gctgagcaaa cgtaacgaaa atgggatgaa gtttacaaa    2220
tatatcgtga ccaactggct ggctaaggtt aatactcaga tcgacctcat ccgcaaaaa    2280
atgaaagaag cactggaaaa ccaggcggaa gctaccaagg caatcattaa ctaccagtac    2340
```

-continued

```
aaccagtaca ccgaggaaga aaaaaacaac atcaacttca acatcgacga tctgtcctct      2400
aaactgaacg aatccatcaa caaagctatg atcaacatca acaagttcct gaaccagtgc      2460
tctgtaagct atctgatgaa ctccatgatc ccgtacggtg ttaaacgtct ggaggacttc      2520
gatgcgtctc tgaaagacgc cctgctgaaa tacatttacg acaaccgtgg cactctgatc      2580
ggtcaggttg atcgtctgaa ggacaaagtg aacaatacct tatcgaccga catccctttt      2640
cagctcagta aatatgtcga taaccaacgc cttttgtcca ctctagacta g               2691
```

<210> SEQ ID NO 30
<211> LENGTH: 896
<212> TYPE: PRT
<213> ORGANISM: Artificial Sequence
<220> FEATURE:
<223> OTHER INFORMATION: chemically synthesized fusion protein

<400> SEQUENCE: 30

```
Gly Ser Met Glu Phe Val Asn Lys Gln Phe Asn Tyr Lys Asp Pro Val
1               5                   10                  15

Asn Gly Val Asp Ile Ala Tyr Ile Lys Ile Pro Asn Ala Gly Gln Met
            20                  25                  30

Gln Pro Val Lys Ala Phe Lys Ile His Asn Lys Ile Trp Val Ile Pro
        35                  40                  45

Glu Arg Asp Thr Phe Thr Asn Pro Glu Glu Gly Asp Leu Asn Pro Pro
    50                  55                  60

Pro Glu Ala Lys Gln Val Pro Val Ser Tyr Tyr Asp Ser Thr Tyr Leu
65                  70                  75                  80

Ser Thr Asp Asn Glu Lys Asp Asn Tyr Leu Lys Gly Val Thr Lys Leu
                85                  90                  95

Phe Glu Arg Ile Tyr Ser Thr Asp Leu Gly Arg Met Leu Leu Thr Ser
            100                 105                 110

Ile Val Arg Gly Ile Pro Phe Trp Gly Gly Ser Thr Ile Asp Thr Glu
        115                 120                 125

Leu Lys Val Ile Asp Thr Asn Cys Ile Asn Val Ile Gln Pro Asp Gly
    130                 135                 140

Ser Tyr Arg Ser Glu Glu Leu Asn Leu Val Ile Ile Gly Pro Ser Ala
145                 150                 155                 160

Asp Ile Ile Gln Phe Glu Cys Lys Ser Phe Gly His Glu Val Leu Asn
                165                 170                 175

Leu Thr Arg Asn Gly Tyr Gly Ser Thr Gln Tyr Ile Arg Phe Ser Pro
            180                 185                 190

Asp Phe Thr Phe Gly Phe Glu Glu Ser Leu Glu Val Asp Thr Asn Pro
        195                 200                 205

Leu Leu Gly Ala Gly Lys Phe Ala Thr Asp Pro Ala Val Thr Leu Ala
    210                 215                 220

His Glu Leu Ile His Ala Gly His Arg Leu Tyr Gly Ile Ala Ile Asn
225                 230                 235                 240

Pro Asn Arg Val Phe Lys Val Asn Thr Asn Ala Tyr Tyr Glu Met Ser
                245                 250                 255

Gly Leu Glu Val Ser Phe Glu Glu Leu Arg Thr Phe Gly Gly His Asp
            260                 265                 270

Ala Lys Phe Ile Asp Ser Leu Gln Glu Asn Glu Phe Arg Leu Tyr Tyr
        275                 280                 285

Tyr Asn Lys Phe Lys Asp Ile Ala Ser Thr Leu Asn Lys Ala Lys Ser
    290                 295                 300

Ile Val Gly Thr Thr Ala Ser Leu Gln Tyr Met Lys Asn Val Phe Lys
```

```
            305                 310                 315                 320
Glu Lys Tyr Leu Leu Ser Glu Asp Thr Ser Gly Lys Phe Ser Val Asp
                    325                 330                 335

Lys Leu Lys Phe Asp Lys Leu Tyr Lys Met Leu Thr Glu Ile Tyr Thr
                    340                 345                 350

Glu Asp Asn Phe Val Lys Phe Lys Val Leu Asn Arg Lys Thr Tyr
                    355                 360                 365

Leu Asn Phe Asp Lys Ala Val Phe Lys Ile Asn Ile Val Pro Lys Val
                370                 375                 380

Asn Tyr Thr Ile Tyr Asp Gly Phe Asn Leu Arg Asn Thr Asn Leu Ala
385                 390                 395                 400

Ala Asn Phe Asn Gly Gln Asn Thr Glu Ile Asn Asn Met Asn Phe Thr
                    405                 410                 415

Lys Leu Lys Asn Phe Thr Gly Leu Phe Glu Phe Tyr Lys Leu Leu Cys
                    420                 425                 430

Val Asp Gly Ile Ile Thr Ser Lys Thr Lys Ser Leu Ile Glu Gly Arg
                    435                 440                 445

Phe Gly Gly Phe Thr Gly Ala Arg Lys Tyr Ala Ala Leu Ala Gly Gly
                    450                 455                 460

Gly Gly Ser Gly Gly Gly Ser Gly Gly Gly Ser Ala Leu Val
465                 470                 475                 480

Leu Gln Cys Ile Lys Val Asn Asn Trp Asp Leu Phe Phe Ser Pro Ser
                    485                 490                 495

Glu Asp Asn Phe Thr Asn Asp Leu Asn Lys Gly Glu Glu Ile Thr Ser
                    500                 505                 510

Asp Thr Asn Ile Glu Ala Ala Glu Glu Asn Ile Ser Leu Asp Leu Ile
                    515                 520                 525

Gln Gln Tyr Tyr Leu Thr Phe Asn Phe Asp Asn Glu Pro Glu Asn Ile
                    530                 535                 540

Ser Ile Glu Asn Leu Ser Ser Asp Ile Ile Gly Gln Leu Glu Leu Met
545                 550                 555                 560

Pro Asn Ile Glu Arg Phe Pro Asn Gly Lys Lys Tyr Glu Leu Asp Lys
                    565                 570                 575

Tyr Thr Met Phe His Tyr Leu Arg Ala Gln Glu Phe Glu His Gly Lys
                    580                 585                 590

Ser Arg Ile Ala Leu Thr Asn Ser Val Asn Glu Ala Leu Leu Asn Pro
                    595                 600                 605

Ser Arg Val Tyr Thr Phe Phe Ser Ser Asp Tyr Val Lys Lys Val Asn
                    610                 615                 620

Lys Ala Thr Glu Ala Ala Met Phe Leu Gly Trp Val Glu Gln Leu Val
625                 630                 635                 640

Tyr Asp Phe Thr Asp Glu Thr Ser Glu Val Ser Thr Thr Asp Lys Ile
                    645                 650                 655

Ala Asp Ile Thr Ile Ile Pro Tyr Ile Gly Pro Ala Leu Asn Ile
                    660                 665                 670

Gly Asn Met Leu Tyr Lys Asp Asp Phe Val Gly Ala Leu Ile Phe Ser
                    675                 680                 685

Gly Ala Val Ile Leu Leu Glu Phe Ile Pro Glu Ile Ala Ile Pro Val
                    690                 695                 700

Leu Gly Thr Phe Ala Leu Val Ser Tyr Ile Ala Asn Lys Val Leu Thr
705                 710                 715                 720

Val Gln Thr Ile Asp Asn Ala Leu Ser Lys Arg Asn Glu Lys Trp Asp
                    725                 730                 735
```

```
Glu Val Tyr Lys Tyr Ile Val Thr Asn Trp Leu Ala Lys Val Asn Thr
                740                 745                 750

Gln Ile Asp Leu Ile Arg Lys Met Lys Glu Ala Leu Glu Asn Gln
            755                 760                 765

Ala Glu Ala Thr Lys Ala Ile Ile Asn Tyr Gln Tyr Asn Gln Tyr Thr
770                 775                 780

Glu Glu Glu Lys Asn Asn Ile Asn Phe Asn Ile Asp Asp Leu Ser Ser
785                 790                 795                 800

Lys Leu Asn Glu Ser Ile Asn Lys Ala Met Ile Asn Ile Asn Lys Phe
                805                 810                 815

Leu Asn Gln Cys Ser Val Ser Tyr Leu Met Asn Ser Met Ile Pro Tyr
            820                 825                 830

Gly Val Lys Arg Leu Glu Asp Phe Asp Ala Ser Leu Lys Asp Ala Leu
        835                 840                 845

Leu Lys Tyr Ile Tyr Asp Asn Arg Gly Thr Leu Ile Gly Gln Val Asp
    850                 855                 860

Arg Leu Lys Asp Lys Val Asn Asn Thr Leu Ser Thr Asp Ile Pro Phe
865                 870                 875                 880

Gln Leu Ser Lys Tyr Val Asp Asn Gln Arg Leu Leu Ser Thr Leu Asp
                885                 890                 895

<210> SEQ ID NO 31
<211> LENGTH: 2691
<212> TYPE: DNA
<213> ORGANISM: Artificial Sequence
<220> FEATURE:
<223> OTHER INFORMATION: chemically synthesized polynucleotide encoding
      fusion protein

<400> SEQUENCE: 31
ggatccatgg agttcgttaa caaacagttc aactataaag acccagttaa cggtgttgac        60
attgcttaca tcaaaatccc gaacgctggc cagatgcagc cggtaaaggc attcaaaatc       120
cacaacaaaa tctgggttat cccggaacgt gataccttta ctaacccgga agaaggtgac       180
ctgaacccgc accggaagc gaaacaggtg ccggtatctt actatgactc cacctacctg        240
tctaccgata acgaaaagga caactacctg aaaggtgtta ctaaactgtt cgagcgtatt       300
tactccaccg acctgggccg tatgctgctg actagcatcg ttcgcggtat cccgttctgg       360
ggcggttcta ccatcgatac cgaactgaaa gtaatcgaca ctaactgcat caacgttatt       420
cagccggacg ttcctatcg ttccgaagaa ctgaacctgg tgatcatcgg cccgtctgct        480
gatatcatcc agttcgagtg taagagcttt ggtcacgaag ttctgaacct cacccgtaac       540
ggctacggtt ccactcagta catccgtttc tctccggact tcaccttcgg ttttgaagaa       600
tccctggaag tagacacgaa cccactgctg ggcgctggta attcgcaac tgatcctgcg        660 gttaccctgg ctcacgaact gattcatgca ggccaccgcc tgtacggtat cgccatcaat       720
ccgaaccgtg tcttcaaagt taacaccaac gcgtattacg agatgtccgg tctggaagtt       780
agcttcgaag aactgcgtac ttttggcggt cacgacgcta aattcatcga ctctctgcaa       840
gaaaacgagt tccgtctgta ctactataac aagttcaaag atatcgcatc caccctgaac       900
aaagcgaaat ccatcgtggg taccactgct ctctccagt acatgaagaa cgttttaaa        960 gaaaatatacc tgctcagcga agacacctcc ggcaaattct ctgtagacaa gttgaaattc      1020
gataactttt acaaaatgct gactgaaatt tacaccgaag acaacttcgt taagttcttt      1080
aaagttctga accgcaaaac ctatctgaac ttcgacaagg cagtattcaa atcaacatc       1140 gtgccgaaag ttaactacac tatctacgat ggtttcaacc tgcgtaacac caacctggct      1200
```

```
gctaatttta acggccagaa cacggaaatc aacaacatga acttcacaaa actgaaaaac    1260
ttcactggtc tgttcgagtt ttacaagctg ctgtgcgtcg acggcatcat tacctccaaa    1320
actaaatctc tgatagaagg tagatttggc ggtttcacgg gcgcacgcaa atcatatgcg    1380
ctagcgggcg gtggcggtag cggcggtggc ggtagcggcg gtggcggtag cgcactagtg    1440
ctgcagtgta tcaaggttaa caactgggat ttattcttca gcccgagtga agacaacttc    1500
accaacgacc tgaacaaagg tgaagaaatc acctcagata ctaacatcga agcagccgaa    1560
gaaaacatct cgctggacct gatccagcag tactacctga cctttaattt cgacaacgag    1620
ccggaaaaca tttctatcga aaacctgagc tctgatatca tcggccagct ggaactgatg    1680
ccgaacatcg aacgtttccc aaacggtaaa aagtacgagc tggacaaata taccatgttc    1740
cactacctgc gcgcgcagga atttgaacac ggcaaatccc gtatcgcact gactaactcc    1800
gttaacgaag ctctgctcaa cccgtcccgt gtatacacct tcttctctag cgactacgtg    1860
aaaaaggtca caaagcgac tgaagctgca atgttcttgg gttgggttga acagcttgtt    1920
tatgatttta ccgacgagac gtccgaagta tctactaccg acaaaattgc ggatatcact    1980
atcatcatcc cgtacatcgg tccggctctg aacattggca acatgctgta caaagacgac    2040
ttcgttggcg cactgatctt ctccggtgcg gtgatcctgc tggagttcat cccggaaatc    2100
gccatcccgg tactgggcac cttttgctctg gtttcttaca ttgcaaacaa ggttctgact    2160
gtacaaacca tcgacaacgc gctgagcaaa cgtaacgaaa aatgggatga agtttacaaa    2220
tatatcgtga ccaactggct ggctaaggtt aatactcaga tcgacctcat ccgcaaaaaa    2280
atgaaagaag cactggaaaa ccaggcggaa gctaccaagg caatcattaa ctaccagtac    2340
aaccagtaca ccgaggaaga aaaaacaac atcaacttca acatcgacga tctgtcctct    2400
aaactgaacg aatccatcaa caaagctatg atcaacatca caagttcct gaaccagtgc    2460 tctgtaagct atctgatgaa ctccatgatc ccgtacggtg ttaaacgtct ggaggacttc    2520
gatgcgtctc tgaaagacgc cctgctgaaa tacatttacg acaaccgtgg cactctgatc    2580
ggtcaggttg atcgtctgaa ggacaaagtg aacaatacct atcgaccga catcccttt    2640 cagctcagta aatatgtcga taaccaacgc cttttgtcca ctctagacta g             2691
```

<210> SEQ ID NO 32
<211> LENGTH: 896
<212> TYPE: PRT
<213> ORGANISM: Artificial Sequence
<220> FEATURE:
<223> OTHER INFORMATION: chemically synthesized fusion protein

<400> SEQUENCE: 32

```
Gly Ser Met Glu Phe Val Asn Lys Gln Phe Asn Tyr Lys Asp Pro Val
1               5                   10                  15

Asn Gly Val Asp Ile Ala Tyr Ile Lys Ile Pro Asn Ala Gly Gln Met
            20                  25                  30

Gln Pro Val Lys Ala Phe Lys Ile His Asn Lys Ile Trp Val Ile Pro
        35                  40                  45

Glu Arg Asp Thr Phe Thr Asn Pro Glu Glu Gly Asp Leu Asn Pro Pro
    50                  55                  60

Pro Glu Ala Lys Gln Val Pro Val Ser Tyr Tyr Asp Ser Thr Tyr Leu
65                  70                  75                  80

Ser Thr Asp Asn Glu Lys Asp Asn Tyr Leu Lys Gly Val Thr Lys Leu
                85                  90                  95

Phe Glu Arg Ile Tyr Ser Thr Asp Leu Gly Arg Met Leu Leu Thr Ser
```

-continued

```
            100                 105                 110
Ile Val Arg Gly Ile Pro Phe Trp Gly Gly Ser Thr Ile Asp Thr Glu
        115                 120                 125

Leu Lys Val Ile Asp Thr Asn Cys Ile Asn Val Ile Gln Pro Asp Gly
    130                 135                 140

Ser Tyr Arg Ser Glu Glu Leu Asn Leu Val Ile Ile Gly Pro Ser Ala
145                 150                 155                 160

Asp Ile Ile Gln Phe Glu Cys Lys Ser Phe Gly His Glu Val Leu Asn
                165                 170                 175

Leu Thr Arg Asn Gly Tyr Gly Ser Thr Gln Tyr Ile Arg Phe Ser Pro
            180                 185                 190

Asp Phe Thr Phe Gly Phe Glu Glu Ser Leu Glu Val Asp Thr Asn Pro
        195                 200                 205

Leu Leu Gly Ala Gly Lys Phe Ala Thr Asp Pro Ala Val Thr Leu Ala
    210                 215                 220

His Glu Leu Ile His Ala Gly His Arg Leu Tyr Gly Ile Ala Ile Asn
225                 230                 235                 240

Pro Asn Arg Val Phe Lys Val Asn Thr Asn Ala Tyr Tyr Glu Met Ser
                245                 250                 255

Gly Leu Glu Val Ser Phe Glu Glu Leu Arg Thr Phe Gly Gly His Asp
            260                 265                 270

Ala Lys Phe Ile Asp Ser Leu Gln Glu Asn Glu Phe Arg Leu Tyr Tyr
        275                 280                 285

Tyr Asn Lys Phe Lys Asp Ile Ala Ser Thr Leu Asn Lys Ala Lys Ser
    290                 295                 300

Ile Val Gly Thr Thr Ala Ser Leu Gln Tyr Met Lys Asn Val Phe Lys
305                 310                 315                 320

Glu Lys Tyr Leu Leu Ser Glu Asp Thr Ser Gly Lys Phe Ser Val Asp
                325                 330                 335

Lys Leu Lys Phe Asp Lys Leu Tyr Lys Met Leu Thr Glu Ile Tyr Thr
            340                 345                 350

Glu Asp Asn Phe Val Lys Phe Phe Lys Val Leu Asn Arg Lys Thr Tyr
        355                 360                 365

Leu Asn Phe Asp Lys Ala Val Phe Lys Ile Asn Ile Val Pro Lys Val
    370                 375                 380

Asn Tyr Thr Ile Tyr Asp Gly Phe Asn Leu Arg Asn Thr Asn Leu Ala
385                 390                 395                 400

Ala Asn Phe Asn Gly Gln Asn Thr Glu Ile Asn Asn Met Asn Phe Thr
                405                 410                 415

Lys Leu Lys Asn Phe Thr Gly Leu Phe Glu Phe Tyr Lys Leu Leu Cys
            420                 425                 430

Val Asp Gly Ile Ile Thr Ser Lys Thr Lys Ser Leu Ile Glu Gly Arg
        435                 440                 445

Phe Gly Gly Phe Thr Gly Ala Arg Lys Ser Tyr Ala Leu Ala Gly Gly
    450                 455                 460

Gly Gly Ser Gly Gly Gly Gly Ser Gly Gly Gly Gly Ser Ala Leu Val
465                 470                 475                 480

Leu Gln Cys Ile Lys Val Asn Asn Trp Asp Leu Phe Phe Ser Pro Ser
                485                 490                 495

Glu Asp Asn Phe Thr Asn Asp Leu Asn Lys Gly Glu Ile Thr Ser
            500                 505                 510

Asp Thr Asn Ile Glu Ala Ala Glu Glu Asn Ile Ser Leu Asp Leu Ile
        515                 520                 525
```

```
Gln Gln Tyr Tyr Leu Thr Phe Asn Phe Asp Asn Glu Pro Glu Asn Ile
            530                 535                 540

Ser Ile Glu Asn Leu Ser Ser Asp Ile Ile Gly Gln Leu Glu Leu Met
545                 550                 555                 560

Pro Asn Ile Glu Arg Phe Pro Asn Gly Lys Lys Tyr Glu Leu Asp Lys
                565                 570                 575

Tyr Thr Met Phe His Tyr Leu Arg Ala Gln Glu Phe Glu His Gly Lys
                580                 585                 590

Ser Arg Ile Ala Leu Thr Asn Ser Val Asn Glu Ala Leu Leu Asn Pro
                595                 600                 605

Ser Arg Val Tyr Thr Phe Phe Ser Ser Asp Tyr Val Lys Lys Val Asn
610                 615                 620

Lys Ala Thr Glu Ala Ala Met Phe Leu Gly Trp Val Glu Gln Leu Val
625                 630                 635                 640

Tyr Asp Phe Thr Asp Glu Thr Ser Glu Val Ser Thr Thr Asp Lys Ile
                645                 650                 655

Ala Asp Ile Thr Ile Ile Ile Pro Tyr Ile Gly Pro Ala Leu Asn Ile
                660                 665                 670

Gly Asn Met Leu Tyr Lys Asp Asp Phe Val Gly Ala Leu Ile Phe Ser
                675                 680                 685

Gly Ala Val Ile Leu Leu Glu Phe Ile Pro Glu Ile Ala Ile Pro Val
690                 695                 700

Leu Gly Thr Phe Ala Leu Val Ser Tyr Ile Ala Asn Lys Val Leu Thr
705                 710                 715                 720

Val Gln Thr Ile Asp Asn Ala Leu Ser Lys Arg Asn Glu Lys Trp Asp
                725                 730                 735

Glu Val Tyr Lys Tyr Ile Val Thr Asn Trp Leu Ala Lys Val Asn Thr
                740                 745                 750

Gln Ile Asp Leu Ile Arg Lys Lys Met Lys Glu Ala Leu Glu Asn Gln
                755                 760                 765

Ala Glu Ala Thr Lys Ala Ile Ile Asn Tyr Gln Tyr Asn Gln Tyr Thr
                770                 775                 780

Glu Glu Glu Lys Asn Asn Ile Asn Phe Asn Ile Asp Asp Leu Ser Ser
785                 790                 795                 800

Lys Leu Asn Glu Ser Ile Asn Lys Ala Met Ile Asn Ile Asn Lys Phe
                805                 810                 815

Leu Asn Gln Cys Ser Val Ser Tyr Leu Met Asn Ser Met Ile Pro Tyr
                820                 825                 830

Gly Val Lys Arg Leu Glu Asp Phe Asp Ala Ser Leu Lys Asp Ala Leu
                835                 840                 845

Leu Lys Tyr Ile Tyr Asp Asn Arg Gly Thr Leu Ile Gly Gln Val Asp
850                 855                 860

Arg Leu Lys Asp Lys Val Asn Asn Thr Leu Ser Thr Asp Ile Pro Phe
865                 870                 875                 880

Gln Leu Ser Lys Tyr Val Asp Asn Gln Arg Leu Leu Ser Thr Leu Asp
                885                 890                 895

<210> SEQ ID NO 33
<211> LENGTH: 2709
<212> TYPE: DNA
<213> ORGANISM: Artificial Sequence
<220> FEATURE:
<223> OTHER INFORMATION: chemically synthesized polynucleotide encoding
      fusion protein

<400> SEQUENCE: 33
```

```
ggatccatgg agttcgttaa caaacagttc aactataaag acccagttaa cggtgttgac      60
attgcttaca tcaaaatccc gaacgctggc cagatgcagc cggtaaaggc attcaaaatc     120
cacaacaaaa tctgggttat cccggaacgt gatacctta ctaacccgga agaaggtgac     180
ctgaacccgc caccgaagc gaaacaggtg ccggtatctt actatgactc cacctacctg     240
tctaccgata acgaaaagga caactacctg aaaggtgtta ctaaactgtt cgagcgtatt     300
tactccaccg acctgggccg tatgctgctg actagcatcg ttcgcggtat cccgttctgg     360
ggcggttcta ccatcgatac cgaactgaaa gtaatcgaca ctaactgcat caacgttatt     420
cagccggacg gttcctatcg ttccgaagaa ctgaacctgg tgatcatcgg cccgtctgct     480
gatatcatcc agttcgagtg taagagcttt ggtcacgaag ttctgaacct cacccgtaac     540
ggctacggtt ccactcagta catccgtttc tctccggact tcaccttcgg ttttgaagaa     600
tccctggaag tagacacgaa cccactgctg ggcgctggta aattcgcaac tgatcctgcg     660
gttaccctgg ctcacgaact gattcatgca ggccaccgcc tgtacggtat cgccatcaat     720
ccgaaccgtg tcttcaaagt taacaccaac gcgtattacg agatgtccgg tctggaagtt     780
agcttcgaag aactgcgtac ttttggcggt cacgacgcta aattcatcga ctctctgcaa     840
gaaaacgagt ccgtctgta ctactataac aagttcaaag atatcgcatc caccctgaac     900
aaagcgaaat ccatcgtggg taccactgct tctctccagt acatgaagaa cgttttaaa     960 gaaaaatacc tgctcagcga agacacctcc ggcaaattct ctgtagacaa gttgaaattc    1020 gataaactt acaaaatgct gactgaaatt tacaccgaag acaacttcgt taagttcttt    1080
aaagttctga accgcaaaac ctatctgaac ttcgacaagg cagtattcaa aatcaacatc    1140
gtgccgaaag ttaactacac tatctacgat ggtttcaacc tgcgtaacac caacctggct    1200
gctaatttta acggccagaa cacggaaatc aacaacatga acttcacaaa actgaaaaac    1260
ttcactggtc tgttcgagtt ttacaagctg ctgtgcgtcg acggcatcat tacctccaaa    1320
actaaatctc tgatagaagg tagatttggc ggtttcacgg gcgcacgcaa atcagcgcgt    1380
aaatatgcta accaggcgct agcgggcggt ggcggtagcg gcggtggcgg tagcggcggt    1440
ggcggtagcg cactagtgct gcagtgtatc aaggttaaca actgggattt attcttcagc    1500
ccgagtgaag acaacttcac caacgacctg aacaaaggtg aagaaatcac ctcagatact    1560
aacatcgaag cagccgaaga aacatctcg ctggacctga tccagcagta ctacctgacc    1620
tttaatttcg acaacgagcc ggaaaacatt tctatcgaaa acctgagctc tgatatcatc    1680
ggccagctga aactgatgcc gaacatcgaa cgtttcccaa acgtaaaaaa gtacgagctg    1740
gacaaatata ccatgttcca ctacctgcgc gcgcaggaat ttgaacacgg caaatcccgt    1800
atcgcactga ctaactccgt taacgaagct ctgctcaacc cgtcccgtgt atacaccttc    1860
ttctctagcg actacgtgaa aaaggtcaac aaagcgactg aagctgcaat gttcttgggt    1920
tgggttgaac agcttgttta tgattttacc gacgagacgt ccgaagtatc tactaccgac    1980
aaaattgcgg atatcactat catcatcccg tacatcggtc cggctctgaa cattggcaac    2040
atgctgtaca agacgactt cgttggcgca ctgatcttct ccggtgcggt gatcctgctg    2100
gagttcatcc cggaaatcgc catcccggta ctgggcacct ttgctctggt tcttacattt    2160
gcaaacaagg ttctgactgt acaaaccatc gacaacgcgc tgagcaaacg taacgaaaaa    2220
tgggatgaag tttacaaata tatcgtgacc aactggctgg ctaaggttaa tactcagatc    2280
gacctcatcc gcaaaaaaat gaagaagca ctggaaaacc aggcggaagc taccaaggca    2340
atcattaact accagtacaa ccagtacacc gaggaagaaa aaaacaacat caacttcaac    2400
```

```
atcgacgatc tgtcctctaa actgaacgaa tccatcaaca aagctatgat caacatcaac   2460
aagttcctga accagtgctc tgtaagctat ctgatgaact ccatgatccc gtacggtgtt   2520
aaacgtctgg aggacttcga tgcgtctctg aaagacgccc tgctgaaata catttacgac   2580
aaccgtggca ctctgatcgg tcaggttgat cgtctgaagg acaaagtgaa caataccttg   2640
tcgaccgaca tcccttttca gctcagtaaa tatgtcgata ccaacgcct tttgtccact   2700 ctagactag                                                           2709
```

<210> SEQ ID NO 34
<211> LENGTH: 902
<212> TYPE: PRT
<213> ORGANISM: Artificial Sequence
<220> FEATURE:
<223> OTHER INFORMATION: chemically synthesized fusion protein

<400> SEQUENCE: 34

```
Gly Ser Met Glu Phe Val Asn Lys Gln Phe Asn Tyr Lys Asp Pro Val
1               5                   10                  15

Asn Gly Val Asp Ile Ala Tyr Ile Lys Ile Pro Asn Ala Gly Gln Met
            20                  25                  30

Gln Pro Val Lys Ala Phe Lys Ile His Asn Lys Ile Trp Val Ile Pro
        35                  40                  45

Glu Arg Asp Thr Phe Thr Asn Pro Glu Gly Asp Leu Asn Pro Pro
    50                  55                  60

Pro Glu Ala Lys Gln Val Pro Val Ser Tyr Tyr Asp Ser Thr Tyr Leu
65                  70                  75                  80

Ser Thr Asp Asn Glu Lys Asp Asn Tyr Leu Lys Gly Val Thr Lys Leu
                85                  90                  95

Phe Glu Arg Ile Tyr Ser Thr Asp Leu Gly Arg Met Leu Leu Thr Ser
            100                 105                 110

Ile Val Arg Gly Ile Pro Phe Trp Gly Gly Ser Thr Ile Asp Thr Glu
        115                 120                 125

Leu Lys Val Ile Asp Thr Asn Cys Ile Asn Val Ile Gln Pro Asp Gly
    130                 135                 140

Ser Tyr Arg Ser Glu Glu Leu Asn Leu Val Ile Ile Gly Pro Ser Ala
145                 150                 155                 160

Asp Ile Ile Gln Phe Glu Cys Lys Ser Phe Gly His Glu Val Leu Asn
                165                 170                 175

Leu Thr Arg Asn Gly Tyr Gly Ser Thr Gln Tyr Ile Arg Phe Ser Pro
            180                 185                 190

Asp Phe Thr Phe Gly Phe Glu Glu Ser Leu Glu Val Asp Thr Asn Pro
        195                 200                 205

Leu Leu Gly Ala Gly Lys Phe Ala Thr Asp Pro Ala Val Thr Leu Ala
    210                 215                 220

His Glu Leu Ile His Ala Gly His Arg Leu Tyr Gly Ile Ala Ile Asn
225                 230                 235                 240

Pro Asn Arg Val Phe Lys Val Asn Thr Asn Ala Tyr Tyr Glu Met Ser
                245                 250                 255

Gly Leu Glu Val Ser Phe Glu Glu Leu Arg Thr Phe Gly Gly His Asp
            260                 265                 270

Ala Lys Phe Ile Asp Ser Leu Gln Glu Asn Glu Phe Arg Leu Tyr Tyr
        275                 280                 285

Tyr Asn Lys Phe Lys Asp Ile Ala Ser Thr Leu Asn Lys Ala Lys Ser
    290                 295                 300

Ile Val Gly Thr Thr Ala Ser Leu Gln Tyr Met Lys Asn Val Phe Lys
```

```
                305                 310                 315                 320
Glu Lys Tyr Leu Leu Ser Glu Asp Thr Ser Gly Lys Phe Ser Val Asp
                    325                 330                 335

Lys Leu Lys Phe Asp Lys Leu Tyr Lys Met Leu Thr Glu Ile Tyr Thr
                340                 345                 350

Glu Asp Asn Phe Val Lys Phe Phe Lys Val Leu Asn Arg Lys Thr Tyr
            355                 360                 365

Leu Asn Phe Asp Lys Ala Val Phe Lys Ile Asn Ile Val Pro Lys Val
        370                 375                 380

Asn Tyr Thr Ile Tyr Asp Gly Phe Asn Leu Arg Asn Thr Asn Leu Ala
385                 390                 395                 400

Ala Asn Phe Asn Gly Gln Asn Thr Glu Ile Asn Asn Met Asn Phe Thr
                405                 410                 415

Lys Leu Lys Asn Phe Thr Gly Leu Phe Glu Phe Tyr Lys Leu Leu Cys
                420                 425                 430

Val Asp Gly Ile Ile Thr Ser Lys Thr Lys Ser Leu Ile Glu Gly Arg
            435                 440                 445

Phe Gly Gly Phe Thr Gly Ala Arg Lys Ser Ala Arg Lys Tyr Ala Asn
        450                 455                 460

Gln Ala Leu Ala Gly Gly Gly Ser Gly Gly Gly Ser Gly Gly
465                 470                 475                 480

Gly Gly Ser Ala Leu Val Leu Gln Cys Ile Lys Val Asn Asn Trp Asp
                485                 490                 495

Leu Phe Phe Ser Pro Ser Glu Asp Asn Phe Thr Asn Asp Leu Asn Lys
                500                 505                 510

Gly Glu Glu Ile Thr Ser Asp Thr Asn Ile Glu Ala Ala Glu Glu Asn
                515                 520                 525

Ile Ser Leu Asp Leu Ile Gln Gln Tyr Tyr Leu Thr Phe Asn Phe Asp
            530                 535                 540

Asn Glu Pro Glu Asn Ile Ser Ile Glu Asn Leu Ser Ser Asp Ile Ile
545                 550                 555                 560

Gly Gln Leu Glu Leu Met Pro Asn Ile Glu Arg Phe Pro Asn Gly Lys
                565                 570                 575

Lys Tyr Glu Leu Asp Lys Tyr Thr Met Phe His Tyr Leu Arg Ala Gln
                580                 585                 590

Glu Phe Glu His Gly Lys Ser Arg Ile Ala Leu Thr Asn Ser Val Asn
            595                 600                 605

Glu Ala Leu Leu Asn Pro Ser Arg Val Tyr Thr Phe Phe Ser Ser Asp
        610                 615                 620

Tyr Val Lys Lys Val Asn Lys Ala Thr Glu Ala Ala Met Phe Leu Gly
625                 630                 635                 640

Trp Val Glu Gln Leu Val Tyr Asp Phe Thr Asp Glu Thr Ser Glu Val
                645                 650                 655

Ser Thr Thr Asp Lys Ile Ala Asp Ile Thr Ile Ile Pro Tyr Ile
                660                 665                 670

Gly Pro Ala Leu Asn Ile Gly Asn Met Leu Tyr Lys Asp Asp Phe Val
            675                 680                 685

Gly Ala Leu Ile Phe Ser Gly Ala Val Ile Leu Leu Glu Phe Ile Pro
        690                 695                 700

Glu Ile Ala Ile Pro Val Leu Gly Thr Phe Ala Leu Val Ser Tyr Ile
705                 710                 715                 720

Ala Asn Lys Val Leu Thr Val Gln Thr Ile Asp Asn Ala Leu Ser Lys
                725                 730                 735
```

```
Arg Asn Glu Lys Trp Asp Glu Val Tyr Lys Tyr Ile Val Thr Asn Trp
            740                 745                 750

Leu Ala Lys Val Asn Thr Gln Ile Asp Leu Ile Arg Lys Lys Met Lys
            755                 760                 765

Glu Ala Leu Glu Asn Gln Ala Glu Ala Thr Lys Ala Ile Ile Asn Tyr
            770                 775                 780

Gln Tyr Asn Gln Tyr Thr Glu Glu Lys Asn Asn Ile Asn Phe Asn
785                 790                 795                 800

Ile Asp Asp Leu Ser Ser Lys Leu Asn Glu Ser Ile Asn Lys Ala Met
                805                 810                 815

Ile Asn Ile Asn Lys Phe Leu Asn Gln Cys Ser Val Ser Tyr Leu Met
            820                 825                 830

Asn Ser Met Ile Pro Tyr Gly Val Lys Arg Leu Glu Asp Phe Asp Ala
            835                 840                 845

Ser Leu Lys Asp Ala Leu Leu Lys Tyr Ile Tyr Asp Asn Arg Gly Thr
850                 855                 860

Leu Ile Gly Gln Val Asp Arg Leu Lys Asp Lys Val Asn Asn Thr Leu
865                 870                 875                 880

Ser Thr Asp Ile Pro Phe Gln Leu Ser Lys Tyr Val Asp Asn Gln Arg
            885                 890                 895

Leu Leu Ser Thr Leu Asp
            900

<210> SEQ ID NO 35
<211> LENGTH: 2697
<212> TYPE: DNA
<213> ORGANISM: Artificial Sequence
<220> FEATURE:
<223> OTHER INFORMATION: chemically synthesized polynucleotide encoding
      fusion protein

<400> SEQUENCE: 35
ggatccatgg agttcgttaa caaacagttc aactataaag acccagttaa cggtgttgac      60
attgcttaca tcaaaatccc gaacgctggc cagatgcagc cggtaaaggc attcaaaatc    120
cacaacaaaa tctgggttat cccggaacgt gataccttta ctaacccgga agaaggtgac    180
ctgaacccgc caccggaagc gaaacaggtg ccggtatctt actatgactc cacctacctg    240
tctaccgata cgaaaagga caactacctg aaaggtgtta ctaaactgtt cgagcgtatt    300
tactccaccg acctgggccg tatgctgctg actagcatcg ttcgcggtat cccgttctgg    360
ggcggttcta ccatcgatac cgaactgaaa gtaatcgaca ctaactgcat caacgttatt    420
cagccggacg gttcctatcg ttccgaagaa ctgaacctgg tgatcatcgg cccgtctgct    480
gatatcatcc agttcgagtg taagagcttt ggtcacgaag ttctgaacct cacccgtaac    540
ggctacggtt ccactcagta catccgtttc tctccggact tcaccttcgg ttttgaagaa    600
tccctggaag tagacacgaa cccactgctg ggcgctggta aattcgcaac tgatcctgcg    660
gttaccctgg ctcacgaact gattcatgca ggccaccgcc tgtacggtat cgccatcaat    720
ccgaaccgtg tcttcaaagt taacaccaac gcgtattacg agatgtccgg tctggaagtt    780
agcttcgaag aactgcgtac ttttggcggt cacgacgcta aattcatcga ctctctgcaa    840
gaaaacgagt ccgtctgtac tactataaac aagttcaaag atatcgcatc caccctgaac    900
aaagcgaaat ccatcgtggg taccactgct tctctccagt acatgaagaa cgttttaaa     960 gaaaatacc tgctcagcga agacacctcc ggcaaattct ctgtagacaa gttgaaattc   1020 gataaactt acaaaatgct gactgaaatt tacaccgaag caacttcgt taagttcttt   1080
```

```
aaagttctga accgcaaaac ctatctgaac ttcgacaagg cagtattcaa aatcaacatc    1140
gtgccgaaag ttaactacac tatctacgat ggtttcaacc tgcgtaacac caacctggct    1200
gctaatttta acggccagaa cacggaaatc aacaacatga acttcacaaa actgaaaaac    1260
ttcactggtc tgttcgagtt ttacaagctg ctgtgcgtcg acggcatcat tacctccaaa    1320
actaaatctc tgatagaagg tagatttggc ggtttcacgg gcgcacgcaa atcagcgcgt    1380
aaagcgctag cgggcggtgg cggtagcggc ggtggcggta gcggcggtgg cggtagcgca    1440
ctagtgctgc agtgtatcaa ggttaacaac tgggatttat tcttcagccc gagtgaagac    1500
aacttcacca acgacctgaa caaaggtgaa gaaatcaccc cagatactaa catcgaagca    1560
gccgaagaaa acatctcgct ggacctgatc cagcagtact acctgacctt taatttcgac    1620
aacgagccgg aaaacatttc tatcgaaaac ctgagctctg atatcatcgg ccagctggaa    1680
ctgatgccga acatcgaacg tttcccaaac ggtaaaaagt acgagctgga caaatatacc    1740
atgttccact acctgcgcgc gcaggaattt gaacacggca atcccgtat cgcactgact    1800 aactccgtta acgaagctct gctcaacccg tcccgtgtat acaccttctt ctctagcgac    1860
tacgtgaaaa aggtcaacaa agcgactgaa gctgcaatgt tcttggggttg ggttgaacag    1920 cttgtttatg attttaccga cgagacgtcc gaagtatcta ctaccgacaa aattgcggat    1980
atcactatca tcatcccgta catcggtccg gctctgaaca ttggcaacat gctgtacaaa    2040
gacgacttcg ttggcgcact gatcttctcc ggtgcggtga tcctgctgga gttcatcccg    2100
gaaatcgcca tcccggtact gggcaccttt gctctggttt cttacattgc aaacaaggtt    2160
ctgactgtac aaaccatcga caacgcgctg agcaaacgta acgaaaaatg ggatgaagtt    2220
tacaaatata tcgtgaccaa ctggctggct aaggttaata tcagatcga cctcatccgc    2280 aaaaaaatga agaagcact ggaaaccag gcggaagcta ccaaggcaat cattaactac    2340
cagtacaacc agtacaccga ggaagaaaaa aacaacatca acttcaacat cgacgatctg    2400
tcctctaaac tgaacgaatc catcaacaaa gctatgatca acatcaacaa gttcctgaac    2460
cagtgctctg taagctatct gatgaactcc atgatcccgt acggtgttaa acgtctggag    2520
gacttcgatg cgtctctgaa agacgccctg ctgaaataca tttacgacaa ccgtggcact    2580
ctgatcggtc aggttgatcg tctgaaggac aaagtgaaca ataccttatc gaccgacatc    2640
ccttttcagc tcagtaaata tgtcgataac caacgccttt tgtccactct agactag      2697
```

<210> SEQ ID NO 36
<211> LENGTH: 898
<212> TYPE: PRT
<213> ORGANISM: Artificial Sequence
<220> FEATURE:
<223> OTHER INFORMATION: chemically synthesized fusion protein

<400> SEQUENCE: 36

```
Gly Ser Met Glu Phe Val Asn Lys Gln Phe Asn Tyr Lys Asp Pro Val
1               5                   10                  15

Asn Gly Val Asp Ile Ala Tyr Ile Lys Ile Pro Asn Ala Gly Gln Met
            20                  25                  30

Gln Pro Val Lys Ala Phe Lys Ile His Asn Lys Ile Trp Val Ile Pro
        35                  40                  45

Glu Arg Asp Thr Phe Thr Asn Pro Glu Glu Gly Asp Leu Asn Pro Pro
    50                  55                  60

Pro Glu Ala Lys Gln Val Pro Val Ser Tyr Tyr Asp Ser Thr Tyr Leu
65                  70                  75                  80

Ser Thr Asp Asn Glu Lys Asp Asn Tyr Leu Lys Gly Val Thr Lys Leu
```

```
            85                  90                  95
Phe Glu Arg Ile Tyr Ser Thr Asp Leu Gly Arg Met Leu Leu Thr Ser
                100                 105                 110

Ile Val Arg Gly Ile Pro Phe Trp Gly Gly Ser Thr Ile Asp Thr Glu
                115                 120                 125

Leu Lys Val Ile Asp Thr Asn Cys Ile Asn Val Ile Gln Pro Asp Gly
                130                 135                 140

Ser Tyr Arg Ser Glu Glu Leu Asn Leu Val Ile Ile Gly Pro Ser Ala
145                 150                 155                 160

Asp Ile Ile Gln Phe Glu Cys Lys Ser Phe Gly His Glu Val Leu Asn
                165                 170                 175

Leu Thr Arg Asn Gly Tyr Gly Ser Thr Gln Tyr Ile Arg Phe Ser Pro
                180                 185                 190

Asp Phe Thr Phe Gly Phe Glu Glu Ser Leu Glu Val Asp Thr Asn Pro
                195                 200                 205

Leu Leu Gly Ala Gly Lys Phe Ala Thr Asp Pro Ala Val Thr Leu Ala
                210                 215                 220

His Glu Leu Ile His Ala Gly His Arg Leu Tyr Gly Ile Ala Ile Asn
225                 230                 235                 240

Pro Asn Arg Val Phe Lys Val Asn Thr Asn Ala Tyr Tyr Glu Met Ser
                245                 250                 255

Gly Leu Glu Val Ser Phe Glu Glu Leu Arg Thr Phe Gly Gly His Asp
                260                 265                 270

Ala Lys Phe Ile Asp Ser Leu Gln Glu Asn Glu Phe Arg Leu Tyr Tyr
                275                 280                 285

Tyr Asn Lys Phe Lys Asp Ile Ala Ser Thr Leu Asn Lys Ala Lys Ser
                290                 295                 300

Ile Val Gly Thr Thr Ala Ser Leu Gln Tyr Met Lys Asn Val Phe Lys
305                 310                 315                 320

Glu Lys Tyr Leu Leu Ser Glu Asp Thr Ser Gly Lys Phe Ser Val Asp
                325                 330                 335

Lys Leu Lys Phe Asp Lys Leu Tyr Lys Met Leu Thr Glu Ile Tyr Thr
                340                 345                 350

Glu Asp Asn Phe Val Lys Phe Phe Lys Val Leu Asn Arg Lys Thr Tyr
                355                 360                 365

Leu Asn Phe Asp Lys Ala Val Phe Lys Ile Asn Ile Val Pro Lys Val
                370                 375                 380

Asn Tyr Thr Ile Tyr Asp Gly Phe Asn Leu Arg Asn Thr Asn Leu Ala
385                 390                 395                 400

Ala Asn Phe Asn Gly Gln Asn Thr Glu Ile Asn Asn Met Asn Phe Thr
                405                 410                 415

Lys Leu Lys Asn Phe Thr Gly Leu Phe Glu Phe Tyr Lys Leu Leu Cys
                420                 425                 430

Val Asp Gly Ile Ile Thr Ser Lys Thr Lys Ser Leu Ile Glu Gly Arg
                435                 440                 445

Phe Gly Gly Phe Thr Gly Ala Arg Lys Ser Ala Arg Lys Ala Leu Ala
                450                 455                 460

Gly Gly Gly Gly Ser Gly Gly Gly Ser Gly Gly Gly Gly Ser Ala
465                 470                 475                 480

Leu Val Leu Gln Cys Ile Lys Val Asn Asn Trp Asp Leu Phe Phe Ser
                485                 490                 495

Pro Ser Glu Asp Asn Phe Thr Asn Asp Leu Asn Lys Gly Glu Glu Ile
                500                 505                 510
```

```
Thr Ser Asp Thr Asn Ile Glu Ala Glu Glu Asn Ile Ser Leu Asp
    515                 520                 525

Leu Ile Gln Gln Tyr Tyr Leu Thr Phe Asn Phe Asp Asn Glu Pro Glu
530                 535                 540

Asn Ile Ser Ile Glu Asn Leu Ser Ser Asp Ile Ile Gly Gln Leu Glu
545                 550                 555                 560

Leu Met Pro Asn Ile Glu Arg Phe Pro Asn Gly Lys Lys Tyr Glu Leu
                565                 570                 575

Asp Lys Tyr Thr Met Phe His Tyr Leu Arg Ala Gln Glu Phe Glu His
            580                 585                 590

Gly Lys Ser Arg Ile Ala Leu Thr Asn Ser Val Asn Glu Ala Leu Leu
        595                 600                 605

Asn Pro Ser Arg Val Tyr Thr Phe Phe Ser Ser Asp Tyr Val Lys Lys
    610                 615                 620

Val Asn Lys Ala Thr Glu Ala Ala Met Phe Leu Gly Trp Val Glu Gln
625                 630                 635                 640

Leu Val Tyr Asp Phe Thr Asp Glu Thr Ser Glu Val Ser Thr Thr Asp
                645                 650                 655

Lys Ile Ala Asp Ile Thr Ile Ile Pro Tyr Ile Gly Pro Ala Leu
            660                 665                 670

Asn Ile Gly Asn Met Leu Tyr Lys Asp Asp Phe Val Gly Ala Leu Ile
        675                 680                 685

Phe Ser Gly Ala Val Ile Leu Leu Glu Phe Ile Pro Glu Ile Ala Ile
    690                 695                 700

Pro Val Leu Gly Thr Phe Ala Leu Val Ser Tyr Ile Ala Asn Lys Val
705                 710                 715                 720

Leu Thr Val Gln Thr Ile Asp Asn Ala Leu Ser Lys Arg Asn Glu Lys
                725                 730                 735

Trp Asp Glu Val Tyr Lys Tyr Ile Val Thr Asn Trp Leu Ala Lys Val
            740                 745                 750

Asn Thr Gln Ile Asp Leu Ile Arg Lys Lys Met Lys Glu Ala Leu Glu
        755                 760                 765

Asn Gln Ala Glu Ala Thr Lys Ala Ile Ile Asn Tyr Gln Tyr Asn Gln
    770                 775                 780

Tyr Thr Glu Glu Glu Lys Asn Asn Ile Asn Phe Asn Ile Asp Asp Leu
785                 790                 795                 800

Ser Ser Lys Leu Asn Glu Ser Ile Asn Lys Ala Met Ile Asn Ile Asn
                805                 810                 815

Lys Phe Leu Asn Gln Cys Ser Val Ser Tyr Leu Met Asn Ser Met Ile
            820                 825                 830

Pro Tyr Gly Val Lys Arg Leu Glu Asp Phe Asp Ala Ser Leu Lys Asp
        835                 840                 845

Ala Leu Leu Lys Tyr Ile Tyr Asp Asn Arg Gly Thr Leu Ile Gly Gln
    850                 855                 860

Val Asp Arg Leu Lys Asp Lys Val Asn Asn Thr Leu Ser Thr Asp Ile
865                 870                 875                 880

Pro Phe Gln Leu Ser Lys Tyr Val Asp Asn Gln Arg Leu Leu Ser Thr
                885                 890                 895

Leu Asp

<210> SEQ ID NO 37
<211> LENGTH: 51
<212> TYPE: DNA
<213> ORGANISM: Artificial Sequence
<220> FEATURE:
```

```
<223> OTHER INFORMATION: chemically synthesized polynucleotide encoding
      a targeting moiety

<400> SEQUENCE: 37
tttggcggtt tcacgggcgc acgcaaatca gcgcgtaaat tagctaacca g            51

<210> SEQ ID NO 38
<211> LENGTH: 17
<212> TYPE: PRT
<213> ORGANISM: Artificial Sequence
<220> FEATURE:
<223> OTHER INFORMATION: chemically synthesized targeting moiety

<400> SEQUENCE: 38

Phe Gly Gly Phe Thr Gly Ala Arg Lys Ser Ala Arg Lys Leu Ala Asn
1               5                   10                  15

Gln

<210> SEQ ID NO 39
<211> LENGTH: 33
<212> TYPE: DNA
<213> ORGANISM: Artificial Sequence
<220> FEATURE:
<223> OTHER INFORMATION: chemically synthesized polynucleotide encoding
      a targeting moiety

<400> SEQUENCE: 39
tttggcggtt tcacgggcgc acgcaaatca gcg                               33

<210> SEQ ID NO 40
<211> LENGTH: 11
<212> TYPE: PRT
<213> ORGANISM: Artificial Sequence
<220> FEATURE:
<223> OTHER INFORMATION: chemically synthesized targeting moiety

<400> SEQUENCE: 40

Phe Gly Gly Phe Thr Gly Ala Arg Lys Ser Ala
1               5                   10

<210> SEQ ID NO 41
<211> LENGTH: 33
<212> TYPE: DNA
<213> ORGANISM: Artificial Sequence
<220> FEATURE:
<223> OTHER INFORMATION: chemically synthesized polynucleotide encoding
      a targeting moiety

<400> SEQUENCE: 41
tttggcggtt tcacgggcgc acgcaaatat gcg                               33

<210> SEQ ID NO 42
<211> LENGTH: 11
<212> TYPE: PRT
<213> ORGANISM: Artificial Sequence
<220> FEATURE:
<223> OTHER INFORMATION: chemically synthesized targeting moiety

<400> SEQUENCE: 42

Phe Gly Gly Phe Thr Gly Ala Arg Lys Tyr Ala
1               5                   10

<210> SEQ ID NO 43
<211> LENGTH: 33
<212> TYPE: DNA
<213> ORGANISM: Artificial Sequence
<220> FEATURE:
```

-continued

<223> OTHER INFORMATION: chemically synthesized polynucleotide encoding
     a targeting moiety

<400> SEQUENCE: 43
tttggcggtt tcacgggcgc acgcaaatca tat                               33

<210> SEQ ID NO 44
<211> LENGTH: 11
<212> TYPE: PRT
<213> ORGANISM: Artificial Sequence
<220> FEATURE:
<223> OTHER INFORMATION: chemically synthesized targeting moiety

<400> SEQUENCE: 44

Phe Gly Gly Phe Thr Gly Ala Arg Lys Ser Tyr
1               5                   10

<210> SEQ ID NO 45
<211> LENGTH: 51
<212> TYPE: DNA
<213> ORGANISM: Artificial Sequence
<220> FEATURE:
<223> OTHER INFORMATION: chemically synthesized polynucleotide encoding
     a targeting moiety

<400> SEQUENCE: 45
tttggcggtt tcacgggcgc acgcaaatca gcgcgtaaat atgctaacca g           51

<210> SEQ ID NO 46
<211> LENGTH: 17
<212> TYPE: PRT
<213> ORGANISM: Artificial Sequence
<220> FEATURE:
<223> OTHER INFORMATION: chemically synthesized targeting moiety

<400> SEQUENCE: 46

Phe Gly Gly Phe Thr Gly Ala Arg Lys Ser Ala Arg Lys Tyr Ala Asn
1               5                   10                  15

Gln

<210> SEQ ID NO 47
<211> LENGTH: 39
<212> TYPE: DNA
<213> ORGANISM: Artificial Sequence
<220> FEATURE:
<223> OTHER INFORMATION: chemically synthesized polynucleotide encoding
     a targeting moiety

<400> SEQUENCE: 47
tttggcggtt tcacgggcgc acgcaaatca gcgcgtaaa                         39

<210> SEQ ID NO 48
<211> LENGTH: 13
<212> TYPE: PRT
<213> ORGANISM: Artificial Sequence
<220> FEATURE:
<223> OTHER INFORMATION: chemically synthesized targeting moiety

<400> SEQUENCE: 48

Phe Gly Gly Phe Thr Gly Ala Arg Lys Ser Ala Arg Lys
1               5                   10

<210> SEQ ID NO 49
<211> LENGTH: 51
<212> TYPE: DNA
<213> ORGANISM: Artificial Sequence
<220> FEATURE:

```
<223> OTHER INFORMATION: chemically synthesized polynucleotide encoding
      a targeting moiety

<400> SEQUENCE: 49
tttggcggtt tcacgggcgc acgcaaatca gcgcgtaaac gcaaaaacca g            51

<210> SEQ ID NO 50
<211> LENGTH: 17
<212> TYPE: PRT
<213> ORGANISM: Artificial Sequence
<220> FEATURE:
<223> OTHER INFORMATION: chemically synthesized targeting moiety

<400> SEQUENCE: 50

Phe Gly Gly Phe Thr Gly Ala Arg Lys Ser Ala Arg Lys Arg Lys Asn
1               5                   10                  15

Gln

<210> SEQ ID NO 51
<211> LENGTH: 2736
<212> TYPE: DNA
<213> ORGANISM: Artificial Sequence
<220> FEATURE:
<223> OTHER INFORMATION: chemically synthesized polynucleotide encoding
      a fusion protein

<400> SEQUENCE: 51
ctcgggattg agggtcgttt tggcggtttc acgggcgcac gcaaatcagc gcgtaaatta      60
gctaaccaga ctagtggcgg tggggtagt ggcggtggcg ttcgggcgg gggtgggagc       120 cctaggggat ccatggagtt cgttaacaaa cagttcaact ataaagaccc agttaacggt     180
gttgacattg cttacatcaa aatcccgaac gctggccaga tgcagccggt aaaggcattc    240
aaaatccaca acaaaatctg ggttatcccg gaacgtgata cctttactaa cccggaagaa    300
ggtgacctga acccgccacc ggaagcgaaa caggtgccgg tatcttacta tgactccacc    360
tacctgtcta ccgataacga aaaggacaac tacctgaaag gtgttactaa actgttcgag    420
cgtatttact ccaccgacct gggccgtatg ctgctgacta gcatcgttcg cggtatcccg    480
ttctggggcg gttctaccat cgataccgaa ctgaaagtaa tcgacactaa ctgcatcaac    540
gttattcagc cggacggttc ctatcgttcc gaagaactga acctggtgat catcggcccg    600
tctgctgata tcatccagtt cgagtgtaag agctttggtc acgaagttct gaacctcacc    660
cgtaacggct acggttccac tcagtacatc cgtttctctc cggacttcac cttcggtttt    720
gaagaatccc tggaagtaga cacgaaccca ctgctgggcg ctggtaaatt cgcaactgat    780
cctgcggtta ccctggctca cgaactgatt catgcaggcc accgcctgta cggtatcgcc    840
atcaatccga accgtgtctt caaagttaac accaacgcgt attacgagat gtccggtctg    900
gaagttagct tcgaagaact gcgtactttt ggcggtcacg acgctaaatt catcgactct    960
ctgcaagaaa acgagttccg tctgtactac tataacaagt tcaaagatat cgcatccacc   1020
ctgaacaaag cgaaatccat cgtgggtacc actgcttctc tccagtacat gaagaacgtt   1080 tttaagaaa aatacctgct cagcgaagac acctccggca aattctctgt agacaagttg    1140
aaattcgata aactttacaa aatgctgact gaaatttaca ccgaagacaa cttcgttaag   1200
ttctttaaag ttctgaaccg caaaacctat ctgaacttcg acaaggcagt attcaaaatc   1260
aacatcgtgc cgaaagttaa ctacactatc tacgatggtt tcaacctgcg taacaccaac   1320
ctggctgcta ttttaacgg ccagaacacg gaaatcaaca acatgaactt cacaaaactg    1380
aaaaacttca ctggtctgtt cgagttttac aagctgctgt gcgtcgacgg catcattacc   1440
```

```
tccaaaacta atctctgat agaaggtaga aacaaagcgc tgaacctgca gtgtatcaag    1500
gttaacaact gggatttatt cttcagcccg agtgaagaca acttcaccaa cgacctgaac    1560
aaaggtgaag aaatcacctc agatactaac atcgaagcag ccgaagaaaa catctcgctg    1620
gacctgatcc agcagtacta cctgaccttt aatttcgaca acgagccgga aaacatttct    1680
atcgaaaacc tgagctctga tatcatcggc cagctggaac tgatgccgaa catcgaacgt    1740
ttcccaaacg gtaaaaagta cgagctggac aaatatacca tgttccacta cctgcgcgcg    1800
caggaatttg aacacggcaa atcccgtatc gcactgacta actccgttaa cgaagctctg    1860
ctcaacccgt cccgtgtata caccttcttc tctagcgact acgtgaaaaa ggtcaacaaa    1920
gcgactgaag ctgcaatgtt cttgggttgg gttaacagc ttgtttatga ttttaccgac    1980
gagacgtccg aagtatctac taccgacaaa attgcggata tcactatcat catcccgtac    2040
atcggtccgg ctctgaacat tggcaacatg ctgtacaaag acgacttcgt tggcgcactg    2100
atcttctccg gtgcggtgat cctgctggag ttcatcccgg aaatcgccat cccggtactg    2160
ggcacctttg ctctggtttc ttacattgca aacaaggttc tgactgtaca aaccatcgac    2220
aacgcgctga gcaaacgtaa cgaaaaatgg gatgaagttt acaaatatat cgtgaccaac    2280
tggctggcta aggttaatac tcagatcgac ctcatccgca aaaaatgaa gaagcactg    2340 gaaaaccagg cggaagctac caaggcaatc attaactacc agtacaacca gtacaccgag    2400
gaagaaaaaa acaacatcaa cttcaacatc gacgatctgt cctctaaact gaacgaatcc    2460
atcaacaaag ctatgatcaa catcaacaag ttcctgaacc agtgctctgt aagctatctg    2520
atgaactcca tgatcccgta cggtgttaaa cgtctggagg acttcgatgc gtctctgaaa    2580
gacgccctgc tgaaatacat ttacgacaac cgtggcactc tgatcggtca ggttgatcgt    2640
ctgaaggaca aagtgaacaa taccttatcg accgacatcc cttttcagct cagtaaatat    2700
gtcgataacc aacgcctttt gtccactcta gactag                              2736
```

<210> SEQ ID NO 52
<211> LENGTH: 911
<212> TYPE: PRT
<213> ORGANISM: Artificial Sequence
<220> FEATURE:
<223> OTHER INFORMATION: chemically synthesized fusion protein

<400> SEQUENCE: 52

```
Leu Gly Ile Glu Gly Arg Phe Gly Gly Phe Thr Gly Ala Arg Lys Ser
1               5                   10                  15

Ala Arg Lys Leu Ala Asn Gln Thr Ser Gly Gly Gly Ser Gly Gly
            20                  25                  30

Gly Gly Ser Gly Gly Gly Gly Ser Pro Arg Gly Ser Met Glu Phe Val
        35                  40                  45

Asn Lys Gln Phe Asn Tyr Lys Asp Pro Val Asn Gly Val Asp Ile Ala
    50                  55                  60

Tyr Ile Lys Ile Pro Asn Ala Gly Gln Met Gln Pro Val Lys Ala Phe
65                  70                  75                  80

Lys Ile His Asn Lys Ile Trp Val Ile Pro Glu Arg Asp Thr Phe Thr
                85                  90                  95

Asn Pro Glu Glu Gly Asp Leu Asn Pro Pro Glu Ala Lys Gln Val
            100                 105                 110

Pro Val Ser Tyr Tyr Asp Ser Thr Tyr Leu Ser Thr Asp Asn Glu Lys
        115                 120                 125

Asp Asn Tyr Leu Lys Gly Val Thr Lys Leu Phe Glu Arg Ile Tyr Ser
```

-continued

```
                130                 135                 140
Thr Asp Leu Gly Arg Met Leu Leu Thr Ser Ile Val Arg Gly Ile Pro
145                 150                 155                 160

Phe Trp Gly Gly Ser Thr Ile Asp Thr Glu Leu Lys Val Ile Asp Thr
                165                 170                 175

Asn Cys Ile Asn Val Ile Gln Pro Asp Gly Ser Tyr Arg Ser Glu
            180                 185                 190

Leu Asn Leu Val Ile Ile Gly Pro Ser Ala Asp Ile Ile Gln Phe Glu
                195                 200                 205

Cys Lys Ser Phe Gly His Glu Val Leu Asn Leu Thr Arg Asn Gly Tyr
            210                 215                 220

Gly Ser Thr Gln Tyr Ile Arg Phe Ser Pro Asp Phe Thr Phe Gly Phe
225                 230                 235                 240

Glu Glu Ser Leu Glu Val Asp Thr Asn Pro Leu Leu Gly Ala Gly Lys
                245                 250                 255

Phe Ala Thr Asp Pro Ala Val Thr Leu Ala His Glu Leu Ile His Ala
                260                 265                 270

Gly His Arg Leu Tyr Gly Ile Ala Ile Asn Pro Asn Arg Val Phe Lys
            275                 280                 285

Val Asn Thr Asn Ala Tyr Tyr Glu Met Ser Gly Leu Glu Val Ser Phe
            290                 295                 300

Glu Glu Leu Arg Thr Phe Gly Gly His Asp Ala Lys Phe Ile Asp Ser
305                 310                 315                 320

Leu Gln Glu Asn Glu Phe Arg Leu Tyr Tyr Tyr Asn Lys Phe Lys Asp
                325                 330                 335

Ile Ala Ser Thr Leu Asn Lys Ala Lys Ser Ile Val Gly Thr Thr Ala
            340                 345                 350

Ser Leu Gln Tyr Met Lys Asn Val Phe Lys Glu Lys Tyr Leu Leu Ser
            355                 360                 365

Glu Asp Thr Ser Gly Lys Phe Ser Val Asp Lys Leu Lys Phe Asp Lys
370                 375                 380

Leu Tyr Lys Met Leu Thr Glu Ile Tyr Thr Glu Asp Asn Phe Val Lys
385                 390                 395                 400

Phe Phe Lys Val Leu Asn Arg Lys Thr Tyr Leu Asn Phe Asp Lys Ala
                405                 410                 415

Val Phe Lys Ile Asn Ile Val Pro Lys Val Asn Tyr Thr Ile Tyr Asp
                420                 425                 430

Gly Phe Asn Leu Arg Asn Thr Asn Leu Ala Ala Asn Phe Asn Gly Gln
            435                 440                 445

Asn Thr Glu Ile Asn Asn Met Asn Phe Thr Lys Leu Lys Asn Phe Thr
450                 455                 460

Gly Leu Phe Glu Phe Tyr Lys Leu Leu Cys Val Asp Gly Ile Ile Thr
465                 470                 475                 480

Ser Lys Thr Lys Ser Leu Ile Glu Gly Arg Asn Lys Ala Leu Asn Leu
                485                 490                 495

Gln Cys Ile Lys Val Asn Asn Trp Asp Leu Phe Phe Ser Pro Ser Glu
            500                 505                 510

Asp Asn Phe Thr Asn Asp Leu Asn Lys Gly Glu Glu Ile Thr Ser Asp
            515                 520                 525

Thr Asn Ile Glu Ala Ala Glu Glu Asn Ile Ser Leu Asp Leu Ile Gln
            530                 535                 540

Gln Tyr Tyr Leu Thr Phe Asn Phe Asp Asn Glu Pro Glu Asn Ile Ser
545                 550                 555                 560
```

```
Ile Glu Asn Leu Ser Ser Asp Ile Ile Gly Gln Leu Glu Leu Met Pro
                565                 570                 575
Asn Ile Glu Arg Phe Pro Asn Gly Lys Lys Tyr Glu Leu Asp Lys Tyr
            580                 585                 590
Thr Met Phe His Tyr Leu Arg Ala Gln Glu Phe Glu His Gly Lys Ser
        595                 600                 605
Arg Ile Ala Leu Thr Asn Ser Val Asn Glu Ala Leu Leu Asn Pro Ser
    610                 615                 620
Arg Val Tyr Thr Phe Phe Ser Ser Asp Tyr Val Lys Lys Val Asn Lys
625                 630                 635                 640
Ala Thr Glu Ala Ala Met Phe Leu Gly Trp Val Glu Gln Leu Val Tyr
                645                 650                 655
Asp Phe Thr Asp Glu Thr Ser Glu Val Ser Thr Thr Asp Lys Ile Ala
            660                 665                 670
Asp Ile Thr Ile Ile Ile Pro Tyr Ile Gly Pro Ala Leu Asn Ile Gly
        675                 680                 685
Asn Met Leu Tyr Lys Asp Asp Phe Val Gly Ala Leu Ile Phe Ser Gly
    690                 695                 700
Ala Val Ile Leu Leu Glu Phe Ile Pro Glu Ile Ala Ile Pro Val Leu
705                 710                 715                 720
Gly Thr Phe Ala Leu Val Ser Tyr Ile Ala Asn Lys Val Leu Thr Val
                725                 730                 735
Gln Thr Ile Asp Asn Ala Leu Ser Lys Arg Asn Glu Lys Trp Asp Glu
            740                 745                 750
Val Tyr Lys Tyr Ile Val Thr Asn Trp Leu Ala Lys Val Asn Thr Gln
        755                 760                 765
Ile Asp Leu Ile Arg Lys Lys Met Lys Glu Ala Leu Glu Asn Gln Ala
    770                 775                 780
Glu Ala Thr Lys Ala Ile Ile Asn Tyr Gln Tyr Asn Gln Tyr Thr Glu
785                 790                 795                 800
Glu Glu Lys Asn Asn Ile Asn Phe Asn Ile Asp Asp Leu Ser Ser Lys
                805                 810                 815
Leu Asn Glu Ser Ile Asn Lys Ala Met Ile Asn Ile Asn Lys Phe Leu
            820                 825                 830
Asn Gln Cys Ser Val Ser Tyr Leu Met Asn Ser Met Ile Pro Tyr Gly
        835                 840                 845
Val Lys Arg Leu Glu Asp Phe Asp Ala Ser Leu Lys Asp Ala Leu Leu
    850                 855                 860
Lys Tyr Ile Tyr Asp Asn Arg Gly Thr Leu Ile Gly Gln Val Asp Arg
865                 870                 875                 880
Leu Lys Asp Lys Val Asn Asn Thr Leu Ser Thr Asp Ile Pro Phe Gln
                885                 890                 895
Leu Ser Lys Tyr Val Asp Asn Gln Arg Leu Leu Ser Thr Leu Asp
            900                 905                 910

<210> SEQ ID NO 53
<211> LENGTH: 177
<212> TYPE: DNA
<213> ORGANISM: Artificial Sequence
<220> FEATURE:
<223> OTHER INFORMATION: chemically synthesized polynucleotide encoding
      a linker

<400> SEQUENCE: 53
ggatccacgc acgtcgacgg catcattacc tccaaaacta aatctctgat agaaggtaga      60
tttggcggtt tcacgggcgc acgcaaatca gcgcgtaaat tagctaacca ggcgctagcg     120
```

```
ggtggtggtg gttctgcact agtgctgcag acgcacggtc tagaatgata aaagctt      177
```

<210> SEQ ID NO 54
<211> LENGTH: 192
<212> TYPE: DNA
<213> ORGANISM: Artificial Sequence
<220> FEATURE:
<223> OTHER INFORMATION: chemically synthesized polynucleotide encoding
      a linker

<400> SEQUENCE: 54

```
ggatccacgc acgtcgacgg catcattacc tccaaaacta aatctctgat agaaggtaga      60
tttggcggtt tcacgggcgc acgcaaatca gcgcgtaaat tagctaacca ggcgctagcg     120
ggtggtggtg gttctggtgg tggtggttct gcactagtgc tgcagacgca cggtctagaa     180
tgataaaagc tt                                                          192
```

<210> SEQ ID NO 55
<211> LENGTH: 222
<212> TYPE: DNA
<213> ORGANISM: Artificial Sequence
<220> FEATURE:
<223> OTHER INFORMATION: chemically synthesized polynucleotide encoding
      a linker

<400> SEQUENCE: 55

```
ggatccacgc acgtcgacgg catcattacc tccaaaacta aatctctgat agaaggtaga      60
tttggcggtt tcacgggcgc acgcaaatca gcgcgtaaat tagctaacca ggcgctagcg     120
ggtggtggtg gttctggtgg tggtggttct ggtggtggtg gttctggtgg tggtggttct     180
gcactagtgc tgcagacgca cggtctagaa tgataaaagc tt                        222
```

<210> SEQ ID NO 56
<211> LENGTH: 237
<212> TYPE: DNA
<213> ORGANISM: Artificial Sequence
<220> FEATURE:
<223> OTHER INFORMATION: chemically synthesized polynucleotide encoding
      a linker

<400> SEQUENCE: 56

```
ggatccacgc acgtcgacgg catcattacc tccaaaacta aatctctgat agaaggtaga      60
tttggcggtt tcacgggcgc acgcaaatca gcgcgtaaat tagctaacca ggcgctagcg     120
ggtggtggtg gttctggtgg tggtggttct ggtggtggtg gttctggtgg tggtggttct     180
ggtggtggtg gttctgcact agtgctgcag acgcacggtc tagaatgata aaagctt        237
```

<210> SEQ ID NO 57
<211> LENGTH: 228
<212> TYPE: DNA
<213> ORGANISM: Artificial Sequence
<220> FEATURE:
<223> OTHER INFORMATION: chemically synthesized polynucleotide encoding
      a linker

<400> SEQUENCE: 57

```
ggatccacgc acgtcgacgg catcattacc tccaaaacta aatctctgat agaaggtaga      60
tttggcggtt tcacgggcgc acgcaaatca gcgcgtaaat tagctaacca ggcgctagcg     120
gctgaagctg ctgctaaaga agctgctgct aaagaagctg ctgctaaagc tggtggcggt     180
ggttccgcac tagtgctgca gacgcacggt ctagaatgat aaaagctt                  228
```

<210> SEQ ID NO 58
<211> LENGTH: 2694
<212> TYPE: DNA
<213> ORGANISM: Artificial Sequence
<220> FEATURE:
<223> OTHER INFORMATION: chemically synthesized polynucleotide encoding a fusion protein

<400> SEQUENCE: 58

```
ggatccatgg agttcgttaa caaacagttc aactataaag acccagttaa cggtgttgac      60
attgcttaca tcaaaatccc gaacgctggc cagatgcagc cggtaaaggc attcaaaatc     120
cacaacaaaa tctgggttat cccggaacgt gataccttta ctaacccgga agaaggtgac     180
ctgaacccgc accggaagc gaaacaggtg ccggtatctt actatgactc cacctacctg     240
tctaccgata cgaaaagga caactacctg aaaggtgtta ctaaactgtt cgagcgtatt     300
tactccaccg acctgggccg tatgctgctg actagcatcg ttcgcggtat cccgttctgg     360
ggcggttcta ccatcgatac cgaactgaaa gtaatcgaca ctaactgcat caacgttatt     420
cagccggacg gttcctatcg ttccgaagaa ctgaacctgg tgatcatcgg cccgtctgct     480
gatatcatcc agttcgagtg taagagcttt ggtcacgaag ttctgaacct cacccgtaac     540
ggctacggtt ccactcagta catccgtttc tctccggact tcaccttcgg ttttgaagaa     600
tccctggaag tagacacgaa cccactgctg ggcgctggta aattcgcaac tgatcctgcg     660
gttaccctgg ctcacgaact gattcatgca ggccaccgcc tgtacggtat cgccatcaat     720
ccgaaccgtg tcttcaaagt taacaccaac gcgtattacg agatgtccgg tctggaagtt     780
agcttcgaag aactgcgtac ttttggcggt cacgacgcta aattcatcga ctctctgcaa     840
gaaaacgagt ccgtctgta ctactataac aagttcaaag atatcgcatc cacccctgaac     900
aaagcgaaat ccatcgtggg taccactgct tctctccagt acatgaagaa cgttttaaa     960
gaaaatacc tgctcagcga agacacctcc ggcaaattct ctgtagacaa gttgaaattc    1020
gataaacttt acaaaatgct gactgaaatt tacaccgaag acaacttcgt taagttcttt    1080
aaagttctga accgcaaaac ctatctgaac ttcgacaagg cagtattcaa aatcaacatc    1140
gtgccgaaag ttaactacac tatctacgat ggtttcaacc tgcgtaacac caacctggct    1200
gctaattta acggccagaa cacggaaatc aacaacatga cttcacaaa actgaaaaac    1260
ttcactggtc tgttcgagtt ttacaagctg ctgtgcgtcg acggcatcat acctccaaa    1320
actaaatctc tgatagaagg tagatttggc ggtttcacgg gcgcacgcaa atcagcgcgt    1380
aaattagcta accaggcgct agcgggtggt ggtggttctg gtggtggtgg ttctgcacta    1440
gtgctgcagt gtatcaaggt taacaactgg gatttattct tcagcccgag tgaagacaac    1500
ttcaccaacg acctgaacaa aggtgaagaa atcacctcag atactaacat cgaagcagcc    1560
gaagaaaaca tctcgctgga cctgatccag cagtactacc tgacctttaa tttcgacaac    1620
gagccggaaa acatttctat cgaaaacctg agctctgata tcatcggcca gctggaactg    1680
atgccgaaca tcgaacgttt cccaaacggt aaaaagtacg agctggacaa atatcaccatg    1740
ttccactacc tgcgcgcgca ggaatttgaa cacggcaaat cccgtatcgc actgactaac    1800
tccgttaacg aagctctgct caacccgtcc cgtgtataca ccttcttctc tagcgactac    1860
gtgaaaaagg tcaacaaagc gactgaagct gcaatgttct tgggttgggt tgaacagctt    1920
gtttatgatt ttaccgacga cgtccgaa gtatctacta ccgacaaaat tgcggatatc    1980
actatcatca tcccgtacat cggtccggct ctgaacattg caacatgct gtacaaagac    2040
gacttcgttg gcgcactgat cttctccggt gcggtgatcc tgctggagtt catcccggaa    2100
```

```
atcgccatcc cggtactggg cacctttgct ctggtttctt acattgcaaa caaggttctg   2160
actgtacaaa ccatcgacaa cgcgctgagc aaacgtaacg aaaaatggga tgaagtttac   2220
aaatatatcg tgaccaactg gctggctaag gttaatactc agatcgacct catccgcaaa   2280
aaaatgaaag aagcactgga aaaccaggcg gaagctacca aggcaatcat taactaccag   2340
tacaaccagt acaccgagga agaaaaaaac aacatcaact tcaacatcga cgatctgtcc   2400
tctaaactga cgaatccat caacaaagct atgatcaaca tcaacaagtt cctgaaccag   2460
tgctctgtaa gctatctgat gaactccatg atcccgtacg gtgttaaacg tctggaggac   2520
ttcgatgcgt ctctgaaaga cgccctgctg aaatacattt acgacaaccg tggcactctg   2580
atcggtcagg ttgatcgtct gaaggacaaa gtgaacaata ccttatcgac cgacatccct   2640
tttcagctca gtaaatatgt cgataaccaa cgccttttgt ccactctaga ctag         2694
```

<210> SEQ ID NO 59
<211> LENGTH: 897
<212> TYPE: PRT
<213> ORGANISM: Artificial Sequence
<220> FEATURE:
<223> OTHER INFORMATION: chemically synthesized fusion protein

<400> SEQUENCE: 59

```
Gly Ser Met Glu Phe Val Asn Lys Gln Phe Asn Tyr Lys Asp Pro Val
1               5                   10                  15

Asn Gly Val Asp Ile Ala Tyr Ile Lys Ile Pro Asn Ala Gly Gln Met
            20                  25                  30

Gln Pro Val Lys Ala Phe Lys Ile His Asn Lys Ile Trp Val Ile Pro
        35                  40                  45

Glu Arg Asp Thr Phe Thr Asn Pro Glu Glu Gly Asp Leu Asn Pro Pro
    50                  55                  60

Pro Glu Ala Lys Gln Val Pro Val Ser Tyr Tyr Asp Ser Thr Tyr Leu
65                  70                  75                  80

Ser Thr Asp Asn Glu Lys Asp Asn Tyr Leu Lys Gly Val Thr Lys Leu
                85                  90                  95

Phe Glu Arg Ile Tyr Ser Thr Asp Leu Gly Arg Met Leu Leu Thr Ser
            100                 105                 110

Ile Val Arg Gly Ile Pro Phe Trp Gly Gly Ser Thr Ile Asp Thr Glu
        115                 120                 125

Leu Lys Val Ile Asp Thr Asn Cys Ile Asn Val Ile Gln Pro Asp Gly
    130                 135                 140

Ser Tyr Arg Ser Glu Glu Leu Asn Leu Val Ile Ile Gly Pro Ser Ala
145                 150                 155                 160

Asp Ile Ile Gln Phe Glu Cys Lys Ser Phe Gly His Glu Val Leu Asn
                165                 170                 175

Leu Thr Arg Asn Gly Tyr Gly Ser Thr Gln Tyr Ile Arg Phe Ser Pro
            180                 185                 190

Asp Phe Thr Phe Gly Phe Glu Glu Ser Leu Glu Val Asp Thr Asn Pro
        195                 200                 205

Leu Leu Gly Ala Gly Lys Phe Ala Thr Asp Pro Ala Val Thr Leu Ala
    210                 215                 220

His Glu Leu Ile His Ala Gly His Arg Leu Tyr Gly Ile Ala Ile Asn
225                 230                 235                 240

Pro Asn Arg Val Phe Lys Val Asn Thr Asn Ala Tyr Tyr Glu Met Ser
                245                 250                 255

Gly Leu Glu Val Ser Phe Glu Glu Leu Arg Thr Phe Gly Gly His Asp
            260                 265                 270
```

Ala Lys Phe Ile Asp Ser Leu Gln Glu Asn Glu Phe Arg Leu Tyr Tyr
            275                 280                 285

Tyr Asn Lys Phe Lys Asp Ile Ala Ser Thr Leu Asn Lys Ala Lys Ser
        290                 295                 300

Ile Val Gly Thr Thr Ala Ser Leu Gln Tyr Met Lys Asn Val Phe Lys
305                 310                 315                 320

Glu Lys Tyr Leu Leu Ser Glu Asp Thr Ser Gly Lys Phe Ser Val Asp
                325                 330                 335

Lys Leu Lys Phe Asp Lys Leu Tyr Lys Met Leu Thr Glu Ile Tyr Thr
            340                 345                 350

Glu Asp Asn Phe Val Lys Phe Lys Val Leu Asn Arg Lys Thr Tyr
        355                 360                 365

Leu Asn Phe Asp Lys Ala Val Phe Lys Ile Asn Ile Val Pro Lys Val
    370                 375                 380

Asn Tyr Thr Ile Tyr Asp Gly Phe Asn Leu Arg Asn Thr Asn Leu Ala
385                 390                 395                 400

Ala Asn Phe Asn Gly Gln Asn Thr Glu Ile Asn Asn Met Asn Phe Thr
                405                 410                 415

Lys Leu Lys Asn Phe Thr Gly Leu Phe Glu Phe Tyr Lys Leu Leu Cys
            420                 425                 430

Val Asp Gly Ile Ile Thr Ser Lys Thr Lys Ser Leu Ile Glu Gly Arg
        435                 440                 445

Phe Gly Gly Phe Thr Gly Ala Arg Lys Ser Ala Arg Lys Leu Ala Asn
    450                 455                 460

Gln Ala Leu Ala Gly Gly Gly Ser Gly Gly Gly Ser Ala Leu
465                 470                 475                 480

Val Leu Gln Cys Ile Lys Val Asn Asn Trp Asp Leu Phe Phe Ser Pro
                485                 490                 495

Ser Glu Asp Asn Phe Thr Asn Asp Leu Asn Lys Gly Glu Glu Ile Thr
            500                 505                 510

Ser Asp Thr Asn Ile Glu Ala Ala Glu Glu Asn Ile Ser Leu Asp Leu
        515                 520                 525

Ile Gln Gln Tyr Tyr Leu Thr Phe Asn Phe Asp Asn Glu Pro Glu Asn
    530                 535                 540

Ile Ser Ile Glu Asn Leu Ser Ser Asp Ile Ile Gly Gln Leu Glu Leu
545                 550                 555                 560

Met Pro Asn Ile Glu Arg Phe Pro Asn Gly Lys Lys Tyr Glu Leu Asp
                565                 570                 575

Lys Tyr Thr Met Phe His Tyr Leu Arg Ala Gln Glu Phe Glu His Gly
            580                 585                 590

Lys Ser Arg Ile Ala Leu Thr Asn Ser Val Asn Glu Ala Leu Leu Asn
        595                 600                 605

Pro Ser Arg Val Tyr Thr Phe Phe Ser Ser Asp Tyr Val Lys Lys Val
    610                 615                 620

Asn Lys Ala Thr Glu Ala Ala Met Phe Leu Gly Trp Val Glu Gln Leu
625                 630                 635                 640

Val Tyr Asp Phe Thr Asp Glu Thr Ser Glu Val Ser Thr Thr Asp Lys
                645                 650                 655

Ile Ala Asp Ile Thr Ile Ile Pro Tyr Ile Gly Pro Ala Leu Asn
            660                 665                 670

Ile Gly Asn Met Leu Tyr Lys Asp Asp Phe Val Gly Ala Leu Ile Phe
        675                 680                 685

Ser Gly Ala Val Ile Leu Leu Glu Phe Ile Pro Glu Ile Ala Ile Pro

```
                690                 695                 700
Val Leu Gly Thr Phe Ala Leu Val Ser Tyr Ile Ala Asn Lys Val Leu
705                 710                 715                 720

Thr Val Gln Thr Ile Asp Asn Ala Leu Ser Lys Arg Asn Glu Lys Trp
                725                 730                 735

Asp Glu Val Tyr Lys Tyr Ile Val Thr Asn Trp Leu Ala Lys Val Asn
                740                 745                 750

Thr Gln Ile Asp Leu Ile Arg Lys Lys Met Lys Glu Ala Leu Glu Asn
                755                 760                 765

Gln Ala Glu Ala Thr Lys Ala Ile Ile Asn Tyr Gln Tyr Asn Gln Tyr
770                 775                 780

Thr Glu Glu Lys Asn Asn Ile Asn Phe Asn Ile Asp Asp Leu Ser
785                 790                 795                 800

Ser Lys Leu Asn Glu Ser Ile Asn Lys Ala Met Ile Asn Ile Asn Lys
                805                 810                 815

Phe Leu Asn Gln Cys Ser Val Ser Tyr Leu Met Asn Ser Met Ile Pro
                820                 825                 830

Tyr Gly Val Lys Arg Leu Glu Asp Phe Asp Ala Ser Leu Lys Asp Ala
                835                 840                 845

Leu Leu Lys Tyr Ile Tyr Asp Asn Arg Gly Thr Leu Ile Gly Gln Val
850                 855                 860

Asp Arg Leu Lys Asp Lys Val Asn Asn Thr Leu Ser Thr Asp Ile Pro
865                 870                 875                 880

Phe Gln Leu Ser Lys Tyr Val Asp Asn Gln Arg Leu Leu Ser Thr Leu
                885                 890                 895

Asp

<210> SEQ ID NO 60
<211> LENGTH: 2724
<212> TYPE: DNA
<213> ORGANISM: Artificial Sequence
<220> FEATURE:
<223> OTHER INFORMATION: chemically synthesized polynucleotide encoding
      a fusion protein

<400> SEQUENCE: 60
ggatccatgg agttcgttaa caaacagttc aactataaag acccagttaa cggtgttgac      60
attgcttaca tcaaaatccc gaacgctggc cagatgcagc cggtaaaggc attcaaaatc     120
cacaacaaaa tctgggttat cccggaacgt gataccttta ctaacccgga agaaggtgac     180
ctgaacccgc accggaagc gaaacaggtg ccggtatctt actatgactc cacctacctg     240
tctaccgata cgaaaagga caactacctg aaaggtgtta ctaaactgtt cgagcgtatt     300
tactccaccg acctgggccg tatgctgctg actagcatcg ttcgcggtat cccgttctgg     360
ggcggttcta ccatcgatac cgaactgaaa gtaatcgaca ctaactgcat caacgttatt     420
cagccggacg gttcctatcg ttccgaagaa ctgaacctgg tgatcatcgg cccgtctgct     480
gatatcatcc agttcgagtg taagagcttt ggtcacgaag ttctgaacct cacccgtaac     540
ggctacggtt ccactcagta catccgtttc tctccggact tcaccttcgg ttttgaagaa     600
tccctggaag tagacacgaa cccactgctg ggcgctggta aattcgcaac tgatcctgcg     660
gttaccctgg ctcacgaact gattcatgca ggccaccgcc tgtacggtat cgccatcaat     720
ccgaaccgtg tcttcaaagt taacaccaac gcgtattacg agatgtccgg tctggaagtt     780
agcttcgaag aactgcgtac ttttggcggt cacgacgcta aattcatcga ctctctgcaa     840
gaaaacgagt tccgtctgta ctactataac aagttcaaag atatcgcatc cacccctgaac     900
```

```
aaagcgaaat ccatcgtggg taccactgct tctctccagt acatgaagaa cgtttttaaa    960
gaaaatacc tgctcagcga agacacctcc ggcaaattct ctgtagacaa gttgaaattc    1020
gataaacttt acaaaatgct gactgaaatt tacaccgaag acaacttcgt taagttcttt    1080
aaagttctga accgcaaaac ctatctgaac ttcgacaagg cagtattcaa aatcaacatc    1140
gtgccgaaag ttaactacac tatctacgat ggtttcaacc tgcgtaacac caacctggct    1200
gctaatttta acggccagaa cacggaaatc aacaacatga acttcacaaa actgaaaaac    1260
ttcactggtc tgttcgagtt ttacaagctg ctgtgcgtcg acggcatcat acctccaaa     1320
actaaatctc tgatagaagg tagatttggc ggtttcacgg gcgcacgcaa atcagcgcgt    1380
aaattagcta accaggcgct agcgggtggt ggtggttctg gtggtggtgg ttctggtggt    1440
ggtggttctg gtggtggtgg ttctgcacta gtgctgcagt gtatcaaggt taacaactgg    1500
gatttattct tcagcccgag tgaagacaac ttcaccaacg acctgaacaa aggtgaagaa    1560
atcacctcag atactaacat cgaagcagcc gaagaaaaca tctcgctgga cctgatccag    1620
cagtactacc tgacctttaa tttcgacaac gagccggaaa acatttctat cgaaaacctg    1680
agctctgata tcatcggcca gctggaactg atgccgaaca tcgaacgttt cccaaacggt    1740
aaaaagtacg agctggacaa atataccatg ttccactacc tgcgcgcgca ggaatttgaa    1800
cacggcaaat cccgtatcgc actgactaac tccgttaacg aagctctgct caacccgtcc    1860
cgtgtataca ccttcttctc tagcgactac gtgaaaaagg tcaacaaagc gactgaagct    1920
gcaatgttct gggttgggt tgaacagctt gtttatgatt ttaccgacga acgtccgaa      1980
gtatctacta ccgacaaaat tgcggatatc actatcatca tcccgtacat cggtccggct    2040
ctgaacattg caacatgct gtacaaagac gacttcgttg gcgcactgat cttctccggt     2100
gcggtgatcc tgctggagtt catcccggaa atcgccatcc cggtactggg cacctttgct    2160
ctggtttctt acattgcaaa caaggttctg actgtacaaa ccatcgacaa cgcgctgagc    2220
aaacgtaacg aaaaatggga tgaagtttac aaatatatcg tgaccaactg gctggctaag    2280
gttaatactc agatcgacct catccgcaaa aaaatgaaag aagcactgga aaaccaggcg    2340
gaagctacca aggcaatcat taactaccag tacaaccagt acaccgagga agaaaaaaac    2400
aacatcaact tcaacatcga cgatctgtcc tctaaactga cgaatccat caacaaagct     2460
atgatcaaca tcaacaagtt cctgaaccag tgctctgtaa gctatctgat gaactccatg    2520
atcccgtacg tgttaaacg tctggaggac ttcgatgcgt ctctgaaaga cgccctgctg     2580
aaatacattt acgacaaccg tggcactctg atcggtcagg ttgatcgtct gaaggacaaa    2640
gtgaacaata ccttatcgac cgacatccct tttcagctca gtaaatatgt cgataaccaa    2700
cgcctttgt ccactctaga ctag                                              2724
```

<210> SEQ ID NO 61
<211> LENGTH: 907
<212> TYPE: PRT
<213> ORGANISM: Artificial Sequence
<220> FEATURE:
<223> OTHER INFORMATION: chemically synthesized fusion protein

<400> SEQUENCE: 61

Gly Ser Met Glu Phe Val Asn Lys Gln Phe Asn Tyr Lys Asp Pro Val
1               5                   10                  15

Asn Gly Val Asp Ile Ala Tyr Ile Lys Ile Pro Asn Ala Gly Gln Met
            20                  25                  30

Gln Pro Val Lys Ala Phe Lys Ile His Asn Lys Ile Trp Val Ile Pro

-continued

```
                 35                  40                  45
Glu Arg Asp Thr Phe Thr Asn Pro Glu Glu Gly Asp Leu Asn Pro Pro
 50                  55                  60

Pro Glu Ala Lys Gln Val Pro Val Ser Tyr Tyr Asp Ser Thr Tyr Leu
 65                  70                  75                  80

Ser Thr Asp Asn Glu Lys Asp Asn Tyr Leu Lys Gly Val Thr Lys Leu
                 85                  90                  95

Phe Glu Arg Ile Tyr Ser Thr Asp Leu Gly Arg Met Leu Leu Thr Ser
                100                 105                 110

Ile Val Arg Gly Ile Pro Phe Trp Gly Gly Ser Thr Ile Asp Thr Glu
            115                 120                 125

Leu Lys Val Ile Asp Thr Asn Cys Ile Asn Val Ile Gln Pro Asp Gly
            130                 135                 140

Ser Tyr Arg Ser Glu Glu Leu Asn Leu Val Ile Ile Gly Pro Ser Ala
145                 150                 155                 160

Asp Ile Ile Gln Phe Glu Cys Lys Ser Phe Gly His Glu Val Leu Asn
                165                 170                 175

Leu Thr Arg Asn Gly Tyr Gly Ser Thr Gln Tyr Ile Arg Phe Ser Pro
            180                 185                 190

Asp Phe Thr Phe Gly Phe Glu Glu Ser Leu Glu Val Asp Thr Asn Pro
        195                 200                 205

Leu Leu Gly Ala Gly Lys Phe Ala Thr Asp Pro Ala Val Thr Leu Ala
210                 215                 220

His Glu Leu Ile His Ala Gly His Arg Leu Tyr Gly Ile Ala Ile Asn
225                 230                 235                 240

Pro Asn Arg Val Phe Lys Val Asn Thr Asn Ala Tyr Tyr Glu Met Ser
                245                 250                 255

Gly Leu Glu Val Ser Phe Glu Glu Leu Arg Thr Phe Gly Gly His Asp
            260                 265                 270

Ala Lys Phe Ile Asp Ser Leu Gln Glu Asn Glu Phe Arg Leu Tyr Tyr
        275                 280                 285

Tyr Asn Lys Phe Lys Asp Ile Ala Ser Thr Leu Asn Lys Ala Lys Ser
290                 295                 300

Ile Val Gly Thr Thr Ala Ser Leu Gln Tyr Met Lys Asn Val Phe Lys
305                 310                 315                 320

Glu Lys Tyr Leu Leu Ser Glu Asp Thr Ser Gly Lys Phe Ser Val Asp
                325                 330                 335

Lys Leu Lys Phe Asp Lys Leu Tyr Lys Met Leu Thr Glu Ile Tyr Thr
            340                 345                 350

Glu Asp Asn Phe Val Lys Phe Phe Lys Val Leu Asn Arg Lys Thr Tyr
        355                 360                 365

Leu Asn Phe Asp Lys Ala Val Phe Lys Ile Asn Ile Val Pro Lys Val
370                 375                 380

Asn Tyr Thr Ile Tyr Asp Gly Phe Asn Leu Arg Asn Thr Asn Leu Ala
385                 390                 395                 400

Ala Asn Phe Asn Gly Gln Asn Thr Glu Ile Asn Asn Met Asn Phe Thr
                405                 410                 415

Lys Leu Lys Asn Phe Thr Gly Leu Phe Glu Phe Tyr Lys Leu Leu Cys
            420                 425                 430

Val Asp Gly Ile Ile Thr Ser Lys Thr Lys Ser Leu Ile Glu Gly Arg
        435                 440                 445

Phe Gly Gly Phe Thr Gly Ala Arg Lys Ser Ala Arg Lys Leu Ala Asn
450                 455                 460
```

```
Gln Ala Leu Ala Gly Gly Gly Ser Gly Gly Gly Ser Gly Gly
465                 470                 475                 480

Gly Gly Ser Gly Gly Gly Ser Ala Leu Val Leu Gln Cys Ile Lys
            485                 490                 495

Val Asn Asn Trp Asp Leu Phe Phe Ser Pro Ser Glu Asp Asn Phe Thr
                500                 505                 510

Asn Asp Leu Asn Lys Gly Glu Ile Thr Ser Asp Thr Asn Ile Glu
            515                 520                 525

Ala Ala Glu Glu Asn Ile Ser Leu Asp Leu Ile Gln Gln Tyr Tyr Leu
530                 535                 540

Thr Phe Asn Phe Asp Asn Glu Pro Glu Asn Ile Ser Ile Glu Asn Leu
545                 550                 555                 560

Ser Ser Asp Ile Ile Gly Gln Leu Glu Leu Met Pro Asn Ile Glu Arg
                565                 570                 575

Phe Pro Asn Gly Lys Lys Tyr Glu Leu Asp Lys Tyr Thr Met Phe His
                580                 585                 590

Tyr Leu Arg Ala Gln Glu Phe Glu His Gly Lys Ser Arg Ile Ala Leu
            595                 600                 605

Thr Asn Ser Val Asn Glu Ala Leu Leu Asn Pro Ser Arg Val Tyr Thr
610                 615                 620

Phe Phe Ser Ser Asp Tyr Val Lys Lys Val Asn Lys Ala Thr Glu Ala
625                 630                 635                 640

Ala Met Phe Leu Gly Trp Val Glu Gln Leu Val Tyr Asp Phe Thr Asp
                645                 650                 655

Glu Thr Ser Glu Val Ser Thr Thr Asp Lys Ile Ala Asp Ile Thr Ile
            660                 665                 670

Ile Ile Pro Tyr Ile Gly Pro Ala Leu Asn Ile Gly Asn Met Leu Tyr
            675                 680                 685

Lys Asp Asp Phe Val Gly Ala Leu Ile Phe Ser Gly Ala Val Ile Leu
690                 695                 700

Leu Glu Phe Ile Pro Glu Ile Ala Ile Pro Val Leu Gly Thr Phe Ala
705                 710                 715                 720

Leu Val Ser Tyr Ile Ala Asn Lys Val Leu Thr Val Gln Thr Ile Asp
                725                 730                 735

Asn Ala Leu Ser Lys Arg Asn Glu Lys Trp Asp Glu Val Tyr Lys Tyr
            740                 745                 750

Ile Val Thr Asn Trp Leu Ala Lys Val Asn Thr Gln Ile Asp Leu Ile
            755                 760                 765

Arg Lys Lys Met Lys Glu Ala Leu Glu Asn Gln Ala Glu Ala Thr Lys
770                 775                 780

Ala Ile Ile Asn Tyr Gln Tyr Asn Gln Tyr Thr Glu Glu Glu Lys Asn
785                 790                 795                 800

Asn Ile Asn Phe Asn Ile Asp Asp Leu Ser Ser Lys Leu Asn Glu Ser
                805                 810                 815

Ile Asn Lys Ala Met Ile Asn Ile Asn Lys Phe Leu Asn Gln Cys Ser
            820                 825                 830

Val Ser Tyr Leu Met Asn Ser Met Ile Pro Tyr Gly Val Lys Arg Leu
            835                 840                 845

Glu Asp Phe Asp Ala Ser Leu Lys Asp Ala Leu Leu Lys Tyr Ile Tyr
850                 855                 860

Asp Asn Arg Gly Thr Leu Ile Gly Gln Val Asp Arg Leu Lys Asp Lys
865                 870                 875                 880

Val Asn Asn Thr Leu Ser Thr Asp Ile Pro Phe Gln Leu Ser Lys Tyr
                885                 890                 895
```

Val Asp Asn Gln Arg Leu Leu Ser Thr Leu Asp
         900                 905

<210> SEQ ID NO 62
<211> LENGTH: 207
<212> TYPE: DNA
<213> ORGANISM: Artificial Sequence
<220> FEATURE:
<223> OTHER INFORMATION: chemically synthesized polynucleotide encoding
      a linker

<400> SEQUENCE: 62
ggatccacgc acgtcgacgg catcattacc tccaaaacta aatctgacga tgacgataaa      60
tttggcggtt tcacgggcgc acgcaaatca gcgcgtaaac gtaagaacca ggcgctagcg     120
ggcggtggcg gtagcggcgg tggcggtagc ggcggtggcg gtagcgcact agtgctgcag     180
acgcacggtc tagaatgata aagctt                                          207

<210> SEQ ID NO 63
<211> LENGTH: 2709
<212> TYPE: DNA
<213> ORGANISM: Artificial Sequence
<220> FEATURE:
<223> OTHER INFORMATION: chemically synthesized polynucleotide encoding
      a fusion protein

<400> SEQUENCE: 63
ggatccatgg agttcgttaa caaacagttc aactataaag acccagttaa cggtgttgac      60
attgcttaca tcaaaatccc gaacgctggc cagatgcagc cggtaaaggc attcaaaatc     120
cacaacaaaa tctgggttat cccggaacgt gataccttta ctaacccgga agaaggtgac     180
ctgaacccgc accggaagc gaaacaggtg ccggtatctt actatgactc cacctacctg     240
tctaccgata cgaaaagga caactacctg aaaggtgtta ctaaactgtt cgagcgtatt     300
tactccaccg acctgggccg tatgctgctg actagcatcg ttcgcggtat cccgttctgg     360
ggcggttcta ccatcgatac cgaactgaaa gtaatcgaca ctaactgcat caacgttatt     420
cagccggacg gttcctatcg ttccgaagaa ctgaacctgg tgatcatcgg cccgtctgct     480
gatatcatcc agttcgagtg taagagcttt ggtcacgaag ttctgaacct cacccgtaac     540
ggctacggtt ccactcagta catccgtttc tctccggact tcaccttcgg ttttgaagaa     600
tccctggaag tagacacgaa cccactgctg ggcgctggta aattcgcaac tgatcctgcg     660
gttaccctgg ctcacgaact gattcatgca ggccaccgcc tgtacggtat cgccatcaat     720
ccgaaccgtg tcttcaaagt taacaccaac gcgtattacg agatgtccgg tctggaagtt     780
agcttcgaag aactgcgtac ttttggcggt cacgacgcta aattcatcga ctctctgcaa     840
gaaaacgagt ccgtctgta ctactataac aagttcaaag atatcgcatc caccctgaac     900
aaagcgaaat ccatcgtggg taccactgct tctctccagt acatgaagaa cgttttttaaa     960 gaaaaatacc tgctcagcga agacacctcc ggcaaattct ctgtagacaa gttgaaattc    1020
gataaacttt acaaaatgct gactgaaatt tacaccgaag caacttcgt taagttctt     1080 aaagttctga ccgcaaaac ctatctgaac ttcgacaagg cagtattcaa aatcaacatc    1140
gtgccgaaag ttaactacac tatctacgat ggtttcaacc tgcgtaacac caacctggct    1200
gctaatttta acggccagaa cacggaaatc aacaacatga acttcacaaa actgaaaaac    1260
ttcactggtc tgttcgagtt ttacaagctg ctgtgcgtcg acggcatcat acctccaaa    1320 actaaatctg acgatgacga taaatttggc ggtttcacgg gcgcacgcaa atcagcgcgt    1380

```
aaacgtaaga accaggcgct agcgggcggt ggcggtagcg gcggtggcgg tagcggcggt    1440
ggcggtagcg cactagtgct gcagtgtatc aaggttaaca actgggattt attcttcagc    1500
ccgagtgaag acaacttcac caacgacctg aacaaggtg aagaaatcac ctcagatact    1560
aacatcgaag cagccgaaga aaacatctcg ctggacctga tccagcagta ctacctgacc    1620
tttaatttcg acaacgagcc ggaaaacatt tctatcgaaa acctgagctc tgatatcatc    1680
ggccagctgg aactgatgcc gaacatcgaa cgtttcccaa cggtaaaaa gtacgagctg    1740 gacaaatata ccatgttcca ctacctgcgc gcgcaggaat ttgaacacgg caaatcccgt    1800
atcgcactga ctaactccgt taacgaagct ctgctcaacc cgtcccgtgt ataccttc      1860 ttctctagcg actacgtgaa aaaggtcaac aaagcgactg aagctgcaat gttcttgggt    1920
tgggttgaac agcttgttta tgattttacc gacgagacgt ccgaagtatc tactaccgac    1980
aaaattgcgg atatcactat catcatcccg tacatcggtc cggctctgaa cattggcaac    2040
atgctgtaca agacgacttt cgttggcgca ctgatcttct ccggtgcggt gatcctgctg    2100
gagttcatcc cggaaatcgc catcccggta ctgggcacct ttgctctggt tcttacatt     2160 gcaaacaagg ttctgactgt acaaaccatc gacaacgcgc tgagcaaacg taacgaaaaa    2220
tgggatgaag tttacaaata tatcgtgacc aactggctgg ctaaggttaa tactcagatc    2280
gacctcatcc gcaaaaaaat gaagaagca ctggaaaacc aggcggaagc taccaaggca     2340
atcattaact accagtacaa ccagtacacc gaggaagaaa aaacaacat caacttcaac     2400 atcgacgatc tgtcctctaa actgaacgaa tccatcaaca aagctatgat caacatcaac    2460
aagttcctga ccagtgctc tgtaagctat ctgatgaact ccatgatccc gtacggtgtt     2520
aaacgtctgg aggacttcga tgcgtctctg aaagacgccc tgctgaaata catttacgac    2580
aaccgtggca ctctgatcgg tcaggttgat cgtctgaagg acaaagtgaa caataccta    2640 tcgaccgaca tccctttca gctcagtaaa tatgtcgata ccaacgcct tttgtccact      2700 ctagactag                                                             2709
```

<210> SEQ ID NO 64
<211> LENGTH: 902
<212> TYPE: PRT
<213> ORGANISM: Artificial Sequence
<220> FEATURE:
<223> OTHER INFORMATION: chemically synthesized fusion protein

<400> SEQUENCE: 64

```
Gly Ser Met Glu Phe Val Asn Lys Gln Phe Asn Tyr Lys Asp Pro Val
1               5                   10                  15

Asn Gly Val Asp Ile Ala Tyr Ile Lys Ile Pro Asn Ala Gly Gln Met
            20                  25                  30

Gln Pro Val Lys Ala Phe Lys Ile His Asn Lys Ile Trp Val Ile Pro
        35                  40                  45

Glu Arg Asp Thr Phe Thr Asn Pro Glu Glu Gly Asp Leu Asn Pro Pro
    50                  55                  60

Pro Glu Ala Lys Gln Val Pro Val Ser Tyr Tyr Asp Ser Thr Tyr Leu
65                  70                  75                  80

Ser Thr Asp Asn Glu Lys Asp Asn Tyr Leu Lys Gly Val Thr Lys Leu
                85                  90                  95

Phe Glu Arg Ile Tyr Ser Thr Asp Leu Gly Arg Met Leu Leu Thr Ser
            100                 105                 110

Ile Val Arg Gly Ile Pro Phe Trp Gly Gly Ser Thr Ile Asp Thr Glu
        115                 120                 125
```

```
Leu Lys Val Ile Asp Thr Asn Cys Ile Asn Val Ile Gln Pro Asp Gly
130                 135                 140

Ser Tyr Arg Ser Glu Glu Leu Asn Leu Val Ile Gly Pro Ser Ala
145                 150                 155                 160

Asp Ile Ile Gln Phe Glu Cys Lys Ser Phe Gly His Glu Val Leu Asn
                    165                 170                 175

Leu Thr Arg Asn Gly Tyr Gly Ser Thr Gln Tyr Ile Arg Phe Ser Pro
            180                 185                 190

Asp Phe Thr Phe Gly Phe Glu Glu Ser Leu Glu Val Asp Thr Asn Pro
                195                 200                 205

Leu Leu Gly Ala Gly Lys Phe Ala Thr Asp Pro Ala Val Thr Leu Ala
210                 215                 220

His Glu Leu Ile His Ala Gly His Arg Leu Tyr Gly Ile Ala Ile Asn
225                 230                 235                 240

Pro Asn Arg Val Phe Lys Val Asn Thr Asn Ala Tyr Tyr Glu Met Ser
                    245                 250                 255

Gly Leu Glu Val Ser Phe Glu Glu Leu Arg Thr Phe Gly Gly His Asp
                260                 265                 270

Ala Lys Phe Ile Asp Ser Leu Gln Glu Asn Glu Phe Arg Leu Tyr Tyr
            275                 280                 285

Tyr Asn Lys Phe Lys Asp Ile Ala Ser Thr Leu Asn Lys Ala Lys Ser
290                 295                 300

Ile Val Gly Thr Thr Ala Ser Leu Gln Tyr Met Lys Asn Val Phe Lys
305                 310                 315                 320

Glu Lys Tyr Leu Leu Ser Glu Asp Thr Ser Gly Lys Phe Ser Val Asp
                    325                 330                 335

Lys Leu Lys Phe Asp Lys Leu Tyr Lys Met Leu Thr Glu Ile Tyr Thr
            340                 345                 350

Glu Asp Asn Phe Val Lys Phe Phe Lys Val Leu Asn Arg Lys Thr Tyr
                355                 360                 365

Leu Asn Phe Asp Lys Ala Val Phe Lys Ile Asn Ile Val Pro Lys Val
            370                 375                 380

Asn Tyr Thr Ile Tyr Asp Gly Phe Asn Leu Arg Asn Thr Asn Leu Ala
385                 390                 395                 400

Ala Asn Phe Asn Gly Gln Asn Thr Glu Ile Asn Asn Met Asn Phe Thr
                    405                 410                 415

Lys Leu Lys Asn Phe Thr Gly Leu Phe Glu Phe Tyr Lys Leu Leu Cys
                420                 425                 430

Val Asp Gly Ile Ile Thr Ser Lys Thr Lys Ser Asp Asp Asp Lys
            435                 440                 445

Phe Gly Gly Phe Thr Gly Ala Arg Lys Ser Ala Arg Lys Arg Lys Asn
450                 455                 460

Gln Ala Leu Ala Gly Gly Gly Ser Gly Gly Gly Ser Gly Gly
465                 470                 475                 480

Gly Gly Ser Ala Leu Val Leu Gln Cys Ile Lys Val Asn Asn Trp Asp
                485                 490                 495

Leu Phe Phe Ser Pro Ser Glu Asp Asn Phe Thr Asn Asp Leu Asn Lys
                500                 505                 510

Gly Glu Glu Ile Thr Ser Asp Thr Asn Ile Glu Ala Ala Glu Glu Asn
                515                 520                 525

Ile Ser Leu Asp Leu Ile Gln Gln Tyr Tyr Leu Thr Phe Asn Phe Asp
530                 535                 540

Asn Glu Pro Glu Asn Ile Ser Ile Glu Asn Leu Ser Ser Asp Ile Ile
545                 550                 555                 560
```

Gly Gln Leu Glu Leu Met Pro Asn Ile Glu Arg Phe Pro Asn Gly Lys
                565                 570                 575

Lys Tyr Glu Leu Asp Lys Tyr Thr Met Phe His Tyr Leu Arg Ala Gln
            580                 585                 590

Glu Phe Glu His Gly Lys Ser Arg Ile Ala Leu Thr Asn Ser Val Asn
        595                 600                 605

Glu Ala Leu Leu Asn Pro Ser Arg Val Tyr Thr Phe Phe Ser Ser Asp
    610                 615                 620

Tyr Val Lys Lys Val Asn Lys Ala Thr Glu Ala Ala Met Phe Leu Gly
625                 630                 635                 640

Trp Val Glu Gln Leu Val Tyr Asp Phe Thr Asp Glu Thr Ser Glu Val
                645                 650                 655

Ser Thr Thr Asp Lys Ile Ala Asp Ile Thr Ile Ile Pro Tyr Ile
            660                 665                 670

Gly Pro Ala Leu Asn Ile Gly Asn Met Leu Tyr Lys Asp Asp Phe Val
        675                 680                 685

Gly Ala Leu Ile Phe Ser Gly Ala Val Ile Leu Leu Glu Phe Ile Pro
    690                 695                 700

Glu Ile Ala Ile Pro Val Leu Gly Thr Phe Ala Leu Val Ser Tyr Ile
705                 710                 715                 720

Ala Asn Lys Val Leu Thr Val Gln Thr Ile Asp Asn Ala Leu Ser Lys
                725                 730                 735

Arg Asn Glu Lys Trp Asp Glu Val Tyr Lys Tyr Ile Val Thr Asn Trp
            740                 745                 750

Leu Ala Lys Val Asn Thr Gln Ile Asp Leu Ile Arg Lys Lys Met Lys
        755                 760                 765

Glu Ala Leu Glu Asn Gln Ala Glu Ala Thr Lys Ala Ile Ile Asn Tyr
    770                 775                 780

Gln Tyr Asn Gln Tyr Thr Glu Glu Lys Asn Asn Ile Asn Phe Asn
785                 790                 795                 800

Ile Asp Asp Leu Ser Ser Lys Leu Asn Glu Ser Ile Asn Lys Ala Met
                805                 810                 815

Ile Asn Ile Asn Lys Phe Leu Asn Gln Cys Ser Val Ser Tyr Leu Met
            820                 825                 830

Asn Ser Met Ile Pro Tyr Gly Val Lys Arg Leu Glu Asp Phe Asp Ala
        835                 840                 845

Ser Leu Lys Asp Ala Leu Leu Lys Tyr Ile Tyr Asp Asn Arg Gly Thr
    850                 855                 860

Leu Ile Gly Gln Val Asp Arg Leu Lys Asp Lys Val Asn Asn Thr Leu
865                 870                 875                 880

Ser Thr Asp Ile Pro Phe Gln Leu Ser Lys Tyr Val Asp Asn Gln Arg
                885                 890                 895

Leu Leu Ser Thr Leu Asp
            900

<210> SEQ ID NO 65
<211> LENGTH: 207
<212> TYPE: DNA
<213> ORGANISM: Artificial Sequence
<220> FEATURE:
<223> OTHER INFORMATION: chemically synthesized polynucleotide encoding
      a linker

<400> SEQUENCE: 65
ggatccacgc acgtcgacgg catcattacc tccaaaacta aatctctgat agaaggtaga    60

-continued

```
tttggcggtt tcacgggcgc acgcaaatca gcgcgtaaac gtaagaacca ggcgctagcg       120
ggcggtggcg gtagcggcgg tggcggtagc ggcggtggcg gtagcgcact agtgctgcag       180
acgcacggtc tagaatgata aaagctt                                          207
```

<210> SEQ ID NO 66
<211> LENGTH: 2742
<212> TYPE: DNA
<213> ORGANISM: Artificial Sequence
<220> FEATURE:
<223> OTHER INFORMATION: chemically synthesized polynucleotide encoding
    a fusion protein

<400> SEQUENCE: 66

```
ggatccgaat tcatgccgat caccatcaac aacttcaact acagcgatcc ggtggataac        60
aaaaacatcc tgtacctgga tacccatctg aatccctgg cgaacgaacc ggaaaaagcg       120
tttcgtatca ccggcaacat tgggttatt ccggatcgtt ttagccgtaa cagcaacccg       180
aatctgaata accgccgcg tgttaccagc ccgaaaagcg gttattacga tccgaactat       240
ctgagcaccg atagcgataa agataccttc ctgaaagaaa tcatcaaact gttcaaacgc       300
atcaacagcc gtgaaattgg cgaagaactg atctatcgcc tgagcaccga tattccgttt       360
ccgggcaaca caacacccc gatcaacacc tttgatttcg atgtggattt caacagcgtt       420
gatgttaaaa cccgccaggg taacaattgg gtgaaaaccg gcagcattaa cccgagcgtg       480
attattaccg gtccgcgcga aacattatt gatccggaaa ccagcacctt taaactgacc       540
aacaacacct tgcggcgca ggaaggtttt ggcgcgctga gcattattag cattagcccg       600
cgctttatgc tgacctatag caacgcgacc aacgatgttg gtgaaggccg tttcagcaaa       660
agcgaatttt gcatggaccc gatcctgatc ctgatgcatg aactgaacca tgcgatgcat       720
aacctgtatg gcatcgcgat tccgaacgat cagaccatta gcagcgtgac cagcaacatc       780 tttacagcc agtacaacgt gaaactggaa tatgcggaaa tctatgcgtt tggcggtccg       840
accattgatc tgattccgaa aagcgcgcgc aaatacttcg aagaaaaagc gctggattac       900
tatcgcagca ttgcgaaacg tctgaacagc attaccaccg cgaatccgag cagcttcaac       960
aaatatatcg gcgaatataa acagaaactg atccgcaaat atcgctttgt ggtggaaagc      1020
agcggcgaag ttaccgttaa ccgcaataaa ttcgtggaac tgtacaacga actgacccag      1080
atcttcaccg aatttaacta tgcgaaaatc tataacgtgc agaaccgtaa atctacctg       1140 agcaacgtgt ataccccggt gaccgcgaat attctggatg ataacgtgta cgatatccag      1200
aacggcttta acatcccgaa aagcaacctg aacgttctgt ttatgggcca gaacctgagc      1260
cgtaatccgg cgctgcgtaa agtgaacccg gaaaacatgc tgtacctgtt caccaaattt      1320
tgcgtcgacg gcatcattac ctccaaaact aaatctctga tagaaggtag atttggcggt      1380
ttcacgggcg cacgcaaatc agcgcgtaaa cgtaagaacc aggcgctagc gggcggtggc      1440
ggtagcggcg gtggcggtag cggcggtggc ggtagcgcac tagtgctgca gtgtcgtgaa      1500
ctgctggtga aaacaccga tctgccgttt attggcgata tcagcgatgt gaaaaccgat      1560
atcttcctgc gcaaagatat caacgaagaa accgaagtga tctactaccc ggataacgtg      1620
agcgttgatc aggtgatcct gagcaaaaac accagcgaac atggtcagct ggatctgctg      1680
tatccgagca ttgatagcga aagcgaaatt ctgccgggcg aaaaccaggt ttttacgat       1740 aaccgtaccc agaacgtgga ttacctgaac agctattact acctggaaag ccagaaactg      1800
agcgataacg tggaagattt tacctttacc cgcagcattg aagaagcgct ggataacagc      1860
gcgaaagttt acacctattt tccgacccg gcgaacaaag ttaatgcggg tgttcagggc      1920
```

```
ggtctgtttc tgatgtgggc gaacgatgtg gtggaagatt tcaccaccaa catcctgcgt    1980
aaagataccc tggataaaat cagcgatgtt agcgcgatta ttccgtatat tggtccggcg    2040
ctgaacatta gcaatagcgt gcgtcgtggc aattttaccg aagcgtttgc ggttaccggt    2100
gtgaccattc tgctggaagc gtttccggaa tttaccattc cggcgctggg tgcgtttgtg    2160
atctatagca aagtgcagga acgcaacgaa atcatcaaaa ccatcgataa ctgcctggaa    2220
cagcgtatta aacgctggaa agatagctat gaatggatga tgggcacctg gctgagccgt    2280
attatcaccc agttcaacaa catcagctac cagatgtacg atagcctgaa ctatcaggcg    2340
ggtgcgatta aagcgaaaat cgatctggaa tacaaaaaat acagcggcag cgataaagaa    2400
aacatcaaaa gccaggttga aaacctgaaa aacagcctgg atgtgaaaat tagcgaagcg    2460
atgaataaca tcaacaaatt catccgcgaa tgcagcgtga cctacctgtt caaaaacatg    2520
ctgccgaaag tgatcgatga actgaacgaa tttgatcgca acaccaaagc gaaactgatc    2580
aacctgatcg atagccacaa cattattctg gtgggcgaag tggataaact gaaagcgaaa    2640
gttaacaaca gcttccagaa caccatcccg tttaacatct tcagctatac caacaacagc    2700
ctgctgaaag atatcatcaa cgaatacttc aatctagact ag                      2742
```

<210> SEQ ID NO 67
<211> LENGTH: 913
<212> TYPE: PRT
<213> ORGANISM: Artificial Sequence
<220> FEATURE:
<223> OTHER INFORMATION: chemically synthesized fusion protein

<400> SEQUENCE: 67

```
Gly Ser Glu Phe Met Pro Ile Thr Ile Asn Asn Phe Asn Tyr Ser Asp
  1               5                  10                  15

Pro Val Asp Asn Lys Asn Ile Leu Tyr Leu Asp Thr His Leu Asn Thr
             20                  25                  30

Leu Ala Asn Glu Pro Glu Lys Ala Phe Arg Ile Thr Gly Asn Ile Trp
         35                  40                  45

Val Ile Pro Asp Arg Phe Ser Arg Asn Ser Asn Pro Asn Leu Asn Lys
     50                  55                  60

Pro Pro Arg Val Thr Ser Pro Lys Ser Gly Tyr Tyr Asp Pro Asn Tyr
 65                  70                  75                  80

Leu Ser Thr Asp Ser Asp Lys Asp Thr Phe Leu Lys Glu Ile Ile Lys
                 85                  90                  95

Leu Phe Lys Arg Ile Asn Ser Arg Glu Ile Gly Glu Glu Leu Ile Tyr
            100                 105                 110

Arg Leu Ser Thr Asp Ile Pro Phe Pro Gly Asn Asn Asn Thr Pro Ile
        115                 120                 125

Asn Thr Phe Asp Phe Asp Val Asp Phe Asn Ser Val Asp Val Lys Thr
    130                 135                 140

Arg Gln Gly Asn Asn Trp Val Lys Thr Gly Ser Ile Asn Pro Ser Val
145                 150                 155                 160

Ile Ile Thr Gly Pro Arg Glu Asn Ile Ile Asp Pro Glu Thr Ser Thr
                165                 170                 175

Phe Lys Leu Thr Asn Asn Thr Phe Ala Ala Gln Glu Gly Phe Gly Ala
            180                 185                 190

Leu Ser Ile Ile Ser Ile Ser Pro Arg Phe Met Leu Thr Tyr Ser Asn
        195                 200                 205

Ala Thr Asn Asp Val Gly Glu Gly Arg Phe Ser Lys Ser Glu Phe Cys
    210                 215                 220
```

```
Met Asp Pro Ile Leu Ile Leu Met His Glu Leu Asn His Ala Met His
225                 230                 235                 240

Asn Leu Tyr Gly Ile Ala Ile Pro Asn Asp Gln Thr Ile Ser Ser Val
                245                 250                 255

Thr Ser Asn Ile Phe Tyr Ser Gln Tyr Asn Val Lys Leu Glu Tyr Ala
                260                 265                 270

Glu Ile Tyr Ala Phe Gly Gly Pro Thr Ile Asp Leu Ile Pro Lys Ser
            275                 280                 285

Ala Arg Lys Tyr Phe Glu Glu Lys Ala Leu Asp Tyr Tyr Arg Ser Ile
        290                 295                 300

Ala Lys Arg Leu Asn Ser Ile Thr Thr Ala Asn Pro Ser Ser Phe Asn
305                 310                 315                 320

Lys Tyr Ile Gly Glu Tyr Lys Gln Lys Leu Ile Arg Lys Tyr Arg Phe
                325                 330                 335

Val Val Glu Ser Ser Gly Glu Val Thr Val Asn Arg Asn Lys Phe Val
                340                 345                 350

Glu Leu Tyr Asn Glu Leu Thr Gln Ile Phe Thr Glu Phe Asn Tyr Ala
            355                 360                 365

Lys Ile Tyr Asn Val Gln Asn Arg Lys Ile Tyr Leu Ser Asn Val Tyr
        370                 375                 380

Thr Pro Val Thr Ala Asn Ile Leu Asp Asp Asn Val Tyr Asp Ile Gln
385                 390                 395                 400

Asn Gly Phe Asn Ile Pro Lys Ser Asn Leu Asn Val Leu Phe Met Gly
                405                 410                 415

Gln Asn Leu Ser Arg Asn Pro Ala Leu Arg Lys Val Asn Pro Glu Asn
                420                 425                 430

Met Leu Tyr Leu Phe Thr Lys Phe Cys Val Asp Gly Ile Ile Thr Ser
            435                 440                 445

Lys Thr Lys Ser Leu Ile Glu Gly Arg Phe Gly Phe Thr Gly Ala
        450                 455                 460

Arg Lys Ser Ala Arg Lys Arg Lys Asn Gln Ala Leu Ala Gly Gly Gly
465                 470                 475                 480

Gly Ser Gly Gly Gly Ser Gly Gly Gly Ser Ala Leu Val Leu
                485                 490                 495

Gln Cys Arg Glu Leu Leu Val Lys Asn Thr Asp Leu Pro Phe Ile Gly
                500                 505                 510

Asp Ile Ser Asp Val Lys Thr Asp Ile Phe Leu Arg Lys Asp Ile Asn
            515                 520                 525

Glu Glu Thr Glu Val Ile Tyr Tyr Pro Asp Asn Val Ser Val Asp Gln
            530                 535                 540

Val Ile Leu Ser Lys Asn Thr Ser Glu His Gly Gln Leu Asp Leu Leu
545                 550                 555                 560

Tyr Pro Ser Ile Asp Ser Glu Ser Glu Ile Leu Pro Gly Glu Asn Gln
                565                 570                 575

Val Phe Tyr Asp Asn Arg Thr Gln Asn Val Asp Tyr Leu Asn Ser Tyr
            580                 585                 590

Tyr Tyr Leu Glu Ser Gln Lys Leu Ser Asp Asn Val Glu Asp Phe Thr
        595                 600                 605

Phe Thr Arg Ser Ile Glu Glu Ala Leu Asp Asn Ser Ala Lys Val Tyr
        610                 615                 620

Thr Tyr Phe Pro Thr Leu Ala Asn Lys Val Asn Ala Gly Val Gln Gly
625                 630                 635                 640

Gly Leu Phe Leu Met Trp Ala Asn Asp Val Val Glu Asp Phe Thr Thr
```

645                 650                 655
Asn Ile Leu Arg Lys Asp Thr Leu Asp Lys Ile Ser Asp Val Ser Ala
                660                 665                 670

Ile Ile Pro Tyr Ile Gly Pro Ala Leu Asn Ile Ser Asn Ser Val Arg
            675                 680                 685

Arg Gly Asn Phe Thr Glu Ala Phe Ala Val Thr Gly Val Thr Ile Leu
        690                 695                 700

Leu Glu Ala Phe Pro Glu Phe Thr Ile Pro Ala Leu Gly Ala Phe Val
705                 710                 715                 720

Ile Tyr Ser Lys Val Gln Glu Arg Asn Glu Ile Ile Lys Thr Ile Asp
                725                 730                 735

Asn Cys Leu Glu Gln Arg Ile Lys Arg Trp Lys Asp Ser Tyr Glu Trp
            740                 745                 750

Met Met Gly Thr Trp Leu Ser Arg Ile Ile Thr Gln Phe Asn Asn Ile
        755                 760                 765

Ser Tyr Gln Met Tyr Asp Ser Leu Asn Tyr Gln Ala Gly Ala Ile Lys
    770                 775                 780

Ala Lys Ile Asp Leu Glu Tyr Lys Lys Tyr Ser Gly Ser Asp Lys Glu
785                 790                 795                 800

Asn Ile Lys Ser Gln Val Glu Asn Leu Lys Asn Ser Leu Asp Val Lys
                805                 810                 815

Ile Ser Glu Ala Met Asn Asn Ile Asn Lys Phe Ile Arg Glu Cys Ser
            820                 825                 830

Val Thr Tyr Leu Phe Lys Asn Met Leu Pro Lys Val Ile Asp Glu Leu
        835                 840                 845

Asn Glu Phe Asp Arg Asn Thr Lys Ala Lys Leu Ile Asn Leu Ile Asp
    850                 855                 860

Ser His Asn Ile Ile Leu Val Gly Glu Val Asp Lys Leu Lys Ala Lys
865                 870                 875                 880

Val Asn Asn Ser Phe Gln Asn Thr Ile Pro Phe Asn Ile Phe Ser Tyr
                885                 890                 895

Thr Asn Asn Ser Leu Leu Lys Asp Ile Ile Asn Glu Tyr Phe Asn Leu
            900                 905                 910

Asp

<210> SEQ ID NO 68
<211> LENGTH: 2673
<212> TYPE: DNA
<213> ORGANISM: Artificial Sequence
<220> FEATURE:
<223> OTHER INFORMATION: chemically synthesized polynucleotide encoding
      a fusion protein

<400> SEQUENCE: 68
ggatccatgg agttcgttaa caaacagttc aactataaag acccagttaa cggtgttgac     60
attgcttaca tcaaaatccc gaacgctggc cagatgcagc cggtaaaggc attcaaaatc    120
cacaacaaaa tctgggttat cccggaacgt gataccttta ctaacccgga agaaggtgac    180 ctgaaccccgc accggaagc gaaacaggtg ccggtatctt actatgactc cacctacctg    240
tctaccgata cgaaaagga caactacctg aaaggtgtta ctaaactgtt cgagcgtatt    300
tactccaccg acctgggccg tatgctgctg actagcatcg ttcgcggtat cccgttctgg    360
ggcggttcta ccatcgatac cgaactgaaa gtaatcgaca ctaactgcat caacgttatt    420
cagccggacg ttcctatcg ttccgaagaa ctgaacctgg tgatcatcgg cccgtctgct    480
gatatcatcc agttcgagtg taagagcttt ggtcacgaag ttctgaacct cacccgtaac    540

```
ggctacggtt ccactcagta catccgtttc tctccggact tcaccttcgg ttttgaagaa    600
tccctggaag tagacacgaa cccactgctg ggcgctggta aattcgcaac tgatcctgcg    660
gttaccctgg ctcacgaact gattcatgca ggccaccgcc tgtacggtat cgccatcaat    720
ccgaaccgtg tcttcaaagt taacaccaac gcgtattacg agatgtccgg tctggaagtt    780
agcttcgaag aactgcgtac ttttggcggt cacgacgcta aattcatcga ctctctgcaa    840
gaaaacgagt tccgtctgta ctactataac aagttcaaag atatcgcatc caccctgaac    900
aaagcgaaat ccatcgtggg taccactgct tctctccagt acatgaagaa cgttttaaa     960
gaaaaatacc tgctcagcga agacacctcc ggcaaattct ctgtagacaa gttgaaattc   1020
gataaacttt acaaaatgct gactgaaatt tacaccgaag acaacttcgt taagttcttt   1080
aaagttctga accgcaaaac ctatctgaac ttcgacaagg cagtattcaa aatcaacatc   1140
gtgccgaaag ttaactacac tatctacgat ggtttcaacc tgcgtaacac caacctggct   1200
gctaattta acggccagaa cacggaaatc aacaacatga acttcacaaa actgaaaaac   1260
ttcactggtc tgttcgagtt ttacaagctg ctgtgcgtcg acggcatcat tacctccaaa   1320
actaaatctc tgatagaagg tagatacggt ggtttcctgg cgctagcggg cggtggcggt   1380
agcggcggtg gcggtagcgg cggtggcggt agcgcactag tgctgcagtg tatcaaggtt   1440
aacaactggg atttattctt cagcccgagt gaagacaact tcaccaacga cctgaacaaa   1500
ggtgaagaaa tcacctcaga tactaacatc gaagcagccg aagaaaacat ctcgctggac   1560
ctgatccagc agtactacct gacctttaat ttcgacaacg agccggaaaa catttctatc   1620
gaaaacctga gctctgatat catcggccag ctggaactga tgccgaacat cgaacgtttc   1680
ccaaacggta aaaagtacga gctggacaaa tataccatgt tccactacct gcgcgcgcag   1740
gaatttgaac acggcaaatc ccgtatcgca ctgactaact ccgttaacga agctctgctc   1800
aacccgtccc gtgtatacac cttcttctct agcgactacg tgaaaaaggt caacaaagcg   1860
actgaagctg caatgttctt gggttgggtt gaacagcttg tttatgattt taccgacgag   1920
acgtccgaag tatctactac cgacaaaatt gcggatatca ctatcatcat cccgtacatc   1980
ggtccggctc tgaacattgg caacatgctg tacaaagacg acttcgttgg cgcactgatc   2040
ttctccggtg cggtgatcct gctggagttc atcccggaaa tcgccatccc ggtactgggc   2100
acctttgctc tggtttctta cattgcaaac aaggttctga ctgtacaaac catcgacaac   2160
gcgctgagca acgtaacga aaaatgggat gaagtttaca atatatcgt gaccaactgg   2220
ctggctaagg ttaatactca gatcgacctc atccgcaaaa aaatgaaaga agcactggaa   2280
aaccaggcgg aagctaccaa ggcaatcatt aactaccagt acaaccagta caccgaggaa   2340
gaaaaaaaca acatcaactt caacatcgac gatctgtcct ctaaactgaa cgaatccatc   2400
aacaaagcta tgatcaacat caacaagttc ctgaaccagt gctctgtaag ctatctgatg   2460
aactccatga tcccgtacgg tgttaaacgt ctggaggact tcgatgcgtc tctgaaagac   2520
gccctgctga aatacattta cgacaaccgt ggcactctga tcggtcaggt tgatcgtctg   2580
aaggacaaag tgaacaatac cttatcgacc gacatccctt ttcagctcag taaatatgtc   2640
gataaccaac gccttttgtc cactctagac tag                               2673
```

<210> SEQ ID NO 69
<211> LENGTH: 890
<212> TYPE: PRT
<213> ORGANISM: Artificial Sequence
<220> FEATURE:
<223> OTHER INFORMATION: chemically synthesized fusion protein

<400> SEQUENCE: 69

```
Gly Ser Met Glu Phe Val Asn Lys Gln Phe Asn Tyr Lys Asp Pro Val
1               5                   10                  15

Asn Gly Val Asp Ile Ala Tyr Ile Lys Ile Pro Asn Ala Gly Gln Met
            20                  25                  30

Gln Pro Val Lys Ala Phe Lys Ile His Asn Lys Ile Trp Val Ile Pro
        35                  40                  45

Glu Arg Asp Thr Phe Thr Asn Pro Glu Glu Gly Asp Leu Asn Pro Pro
50                  55                  60

Pro Glu Ala Lys Gln Val Pro Val Ser Tyr Tyr Asp Ser Thr Tyr Leu
65                  70                  75                  80

Ser Thr Asp Asn Glu Lys Asp Asn Tyr Leu Lys Gly Val Thr Lys Leu
                85                  90                  95

Phe Glu Arg Ile Tyr Ser Thr Asp Leu Gly Arg Met Leu Leu Thr Ser
            100                 105                 110

Ile Val Arg Gly Ile Pro Phe Trp Gly Gly Ser Thr Ile Asp Thr Glu
        115                 120                 125

Leu Lys Val Ile Asp Thr Asn Cys Ile Asn Val Ile Gln Pro Asp Gly
130                 135                 140

Ser Tyr Arg Ser Glu Glu Leu Asn Leu Val Ile Ile Gly Pro Ser Ala
145                 150                 155                 160

Asp Ile Ile Gln Phe Glu Cys Lys Ser Phe Gly His Glu Val Leu Asn
                165                 170                 175

Leu Thr Arg Asn Gly Tyr Gly Ser Thr Gln Tyr Ile Arg Phe Ser Pro
            180                 185                 190

Asp Phe Thr Phe Gly Phe Glu Glu Ser Leu Glu Val Asp Thr Asn Pro
        195                 200                 205

Leu Leu Gly Ala Gly Lys Phe Ala Thr Asp Pro Ala Val Thr Leu Ala
210                 215                 220

His Glu Leu Ile His Ala Gly His Arg Leu Tyr Gly Ile Ala Ile Asn
225                 230                 235                 240

Pro Asn Arg Val Phe Lys Val Asn Thr Asn Ala Tyr Tyr Glu Met Ser
                245                 250                 255

Gly Leu Glu Val Ser Phe Glu Glu Leu Arg Thr Phe Gly Gly His Asp
            260                 265                 270

Ala Lys Phe Ile Asp Ser Leu Gln Glu Asn Glu Phe Arg Leu Tyr Tyr
        275                 280                 285

Tyr Asn Lys Phe Lys Asp Ile Ala Ser Thr Leu Asn Lys Ala Lys Ser
290                 295                 300

Ile Val Gly Thr Thr Ala Ser Leu Gln Tyr Met Lys Asn Val Phe Lys
305                 310                 315                 320

Glu Lys Tyr Leu Leu Ser Glu Asp Thr Ser Gly Lys Phe Ser Val Asp
                325                 330                 335

Lys Leu Lys Phe Asp Lys Leu Tyr Lys Met Leu Thr Glu Ile Tyr Thr
            340                 345                 350

Glu Asp Asn Phe Val Lys Phe Lys Val Leu Asn Arg Lys Thr Tyr
        355                 360                 365

Leu Asn Phe Asp Lys Ala Val Phe Lys Ile Asn Ile Val Pro Lys Val
370                 375                 380

Asn Tyr Thr Ile Tyr Asp Gly Phe Asn Leu Arg Asn Thr Asn Leu Ala
385                 390                 395                 400

Ala Asn Phe Asn Gly Gln Asn Thr Glu Ile Asn Asn Met Asn Phe Thr
                405                 410                 415
```

```
Lys Leu Lys Asn Phe Thr Gly Leu Phe Glu Phe Tyr Lys Leu Leu Cys
            420                 425                 430

Val Asp Gly Ile Ile Thr Ser Lys Thr Lys Ser Leu Ile Glu Gly Arg
        435                 440                 445

Tyr Gly Gly Phe Leu Ala Leu Ala Gly Gly Gly Ser Gly Gly Gly
    450                 455                 460

Gly Ser Gly Gly Gly Gly Ser Ala Leu Val Leu Gln Cys Ile Lys Val
465                 470                 475                 480

Asn Asn Trp Asp Leu Phe Phe Ser Pro Ser Glu Asp Asn Phe Thr Asn
            485                 490                 495

Asp Leu Asn Lys Gly Glu Ile Thr Ser Asp Thr Asn Ile Glu Ala
        500                 505                 510

Ala Glu Glu Asn Ile Ser Leu Asp Leu Ile Gln Gln Tyr Tyr Leu Thr
            515                 520                 525

Phe Asn Phe Asp Asn Glu Pro Glu Asn Ile Ser Ile Glu Asn Leu Ser
    530                 535                 540

Ser Asp Ile Ile Gly Gln Leu Glu Leu Met Pro Asn Ile Glu Arg Phe
545                 550                 555                 560

Pro Asn Gly Lys Lys Tyr Glu Leu Asp Lys Tyr Thr Met Phe His Tyr
                565                 570                 575

Leu Arg Ala Gln Glu Phe Glu His Gly Lys Ser Arg Ile Ala Leu Thr
            580                 585                 590

Asn Ser Val Asn Glu Ala Leu Leu Asn Pro Ser Arg Val Tyr Thr Phe
        595                 600                 605

Phe Ser Ser Asp Tyr Val Lys Lys Val Asn Lys Ala Thr Glu Ala Ala
    610                 615                 620

Met Phe Leu Gly Trp Val Glu Gln Leu Val Tyr Asp Phe Thr Asp Glu
625                 630                 635                 640

Thr Ser Glu Val Ser Thr Thr Asp Lys Ile Ala Asp Ile Thr Ile Ile
                645                 650                 655

Ile Pro Tyr Ile Gly Pro Ala Leu Asn Ile Gly Asn Met Leu Tyr Lys
            660                 665                 670

Asp Asp Phe Val Gly Ala Leu Ile Phe Ser Gly Ala Val Ile Leu Leu
        675                 680                 685

Glu Phe Ile Pro Glu Ile Ala Ile Pro Val Leu Gly Thr Phe Ala Leu
    690                 695                 700

Val Ser Tyr Ile Ala Asn Lys Val Leu Thr Val Gln Thr Ile Asp Asn
705                 710                 715                 720

Ala Leu Ser Lys Arg Asn Glu Lys Trp Asp Glu Val Tyr Lys Tyr Ile
                725                 730                 735

Val Thr Asn Trp Leu Ala Lys Val Asn Thr Gln Ile Asp Leu Ile Arg
            740                 745                 750

Lys Lys Met Lys Glu Ala Leu Glu Asn Gln Ala Glu Ala Thr Lys Ala
        755                 760                 765

Ile Ile Asn Tyr Gln Tyr Asn Gln Tyr Thr Glu Glu Glu Lys Asn Asn
    770                 775                 780

Ile Asn Phe Asn Ile Asp Asp Leu Ser Ser Lys Leu Asn Glu Ser Ile
785                 790                 795                 800

Asn Lys Ala Met Ile Asn Ile Asn Lys Phe Leu Asn Gln Cys Ser Val
                805                 810                 815

Ser Tyr Leu Met Asn Ser Met Ile Pro Tyr Gly Val Lys Arg Leu Glu
            820                 825                 830

Asp Phe Asp Ala Ser Leu Lys Asp Ala Leu Leu Lys Tyr Ile Tyr Asp
```

|     | 835 |     |     | 840 |     |     |     | 845 |     |

Asn Arg Gly Thr Leu Ile Gly Gln Val Asp Arg Leu Lys Asp Lys Val
       850                 855                 860

Asn Asn Thr Leu Ser Thr Asp Ile Pro Phe Gln Leu Ser Lys Tyr Val
865                 870                 875                 880

Asp Asn Gln Arg Leu Leu Ser Thr Leu Asp
                885                 890

<210> SEQ ID NO 70
<211> LENGTH: 2709
<212> TYPE: DNA
<213> ORGANISM: Artificial Sequence
<220> FEATURE:
<223> OTHER INFORMATION: chemically synthesized polynucleotide encoding
      a fusion protein

<400> SEQUENCE: 70

```
ggatccatgg agttcgttaa caaacagttc aactataaag acccagttaa cggtgttgac      60
attgcttaca tcaaaatccc gaacgctggc cagatgcagc cggtaaaggc attcaaaatc     120
cacaacaaaa tctgggttat cccggaacgt gataccttta ctaacccgga agaaggtgac     180
ctgaacccgc accggaagc gaaacaggtg ccggtatctt actatgactc cacctacctg      240
tctaccgata cgaaaagga caactacctg aaaggtgtta ctaaactgtt cgagcgtatt      300
tactccaccg acctgggccg tatgctgctg actagcatcg ttcgcggtat cccgttctgg      360
ggcggttcta ccatcgatac cgaactgaaa gtaatcgaca ctaactgcat caacgttatt      420
cagccggacg gttcctatcg ttccgaagaa ctgaacctgg tgatcatcgg cccgtctgct     480
gatatcatcc agttcgagtg taagagcttt ggtcacgaag ttctgaacct caccccgtaac    540 ggctacggtt ccactcagta catccgtttc tctccggact tcaccttcgg tttttgaagaa    600 tccctggaag tagacacgaa cccactgctg ggcgctggta aattcgcaac tgatcctgcg     660
gttaccctgg ctcacgaact gattcatgca ggccaccgcc tgtacggtat cgccatcaat    720
ccgaaccgtg tcttcaaagt taacaccaac gcgtattacg agatgtccgg tctggaagtt    780
agcttcgaag aactgcgtac ttttggcggt cacgacgcta aattcatcga ctctctgcaa    840
gaaaacgagt ccgtctgta ctactataac aagttcaaag atatcgcatc caccctgaac    900
aaagcgaaat ccatcgtggg taccactgct ctctctccagt acatgaagaa cgttttaaa    960 gaaaatacc tgctcagcga agacacctcc ggcaaattct ctgtagacaa gttgaaattc   1020
gataaacttt acaaaatgct gactgaaatt tacaccgaag caacttcgt taagttcttt    1080 aaagttctga ccgcaaaac ctatctgaac ttcgacaagg cagtattcaa aatcaacatc    1140
gtgccgaaag ttaactacac tatctacgat ggttttcaacc tgcgtaacac caacctggct   1200
gctaatttta cggccagaa cacggaaatc aacaacatga acttcacaaa actgaaaaac   1260
ttcactggtc tgttcgagtt ttacaagctg ctgtgcgtcg acggcatcat acctccaaa    1320 actaaatctc tgatagaagg tagatatggc ggtttcacgg gcgcacgcaa atcagcgcgt   1380
aaattagcta accaggcgct agcgggcggt ggcggtagcg gcgtggcgg tagcggcggt    1440 ggcggtagcg cactagtgct gcagtgtatc aaggttaaca ctgggatttt attcttcagc   1500
ccgagtgaag caacttcac caacgacctg aacaaaggtg aagaaatcac ctcagatact    1560
aacatcgaag cagccgaaga aaacatctcg ctggacctga tccagcagta ctacctgacc    1620
tttaatttcg acaacgagcc ggaaaacatt tctatcgaaa acctgagctc tgatatcatc    1680
ggccagctgg aactgatgcc gaacatcgaa cgtttcccaa acggtaaaaa gtacgagctg    1740
```

-continued

```
gacaaatata ccatgttcca ctacctgcgc gcgcaggaat ttgaacacgg caaatcccgt    1800
atcgcactga ctaactccgt taacgaagct ctgctcaacc cgtcccgtgt atacaccttc    1860
ttctctagcg actacgtgaa aaaggtcaac aaagcgactg aagctgcaat gttcttgggt    1920
tgggttgaac agcttgttta tgattttacc gacgagacgt ccgaagtatc tactaccgac    1980
aaaattgcgg atatcactat catcatcccg tacatcggtc cggctctgaa cattggcaac    2040
atgctgtaca agacgactt cgttggcgca ctgatcttct ccggtgcggt gatcctgctg    2100
gagttcatcc cggaaatcgc catcccggta ctgggcacct ttgctctggt ttcttacatt    2160
gcaaacaagg ttctgactgt acaaaccatc gacaacgcgc tgagcaaacg taacgaaaaa    2220
tgggatgaag tttacaaata tatcgtgacc aactggctgg ctaaggttaa tactcagatc    2280
gacctcatcc gcaaaaaaat gaaagaagca ctggaaaacc aggcggaagc taccaaggca    2340
atcattaact accagtacaa ccagtacacc gaggaagaaa aaacaacat caacttcaac    2400 atcgacgatc tgtcctctaa actgaacgaa tccatcaaca aagctatgat caacatcaac    2460
aagttcctga accagtgctc tgtaagctat ctgatgaact ccatgatccc gtacggtgtt    2520
aaacgtctgg aggacttcga tgcgtctctg aaagacgccc tgctgaaata catttacgac    2580
aaccgtggca ctctgatcgg tcaggttgat cgtctgaagg acaaagtgaa caataccta    2640 tcgaccgaca tcccttttca gctcagtaaa tatgtcgata ccaacgcct tttgtccact    2700 ctagactag                                                             2709
```

<210> SEQ ID NO 71
<211> LENGTH: 902
<212> TYPE: PRT
<213> ORGANISM: Artificial Sequence
<220> FEATURE:
<223> OTHER INFORMATION: chemically synthesized fusion protein

<400> SEQUENCE: 71

```
Gly Ser Met Glu Phe Val Asn Lys Gln Phe Asn Tyr Lys Asp Pro Val
1               5                   10                  15

Asn Gly Val Asp Ile Ala Tyr Ile Lys Ile Pro Asn Ala Gly Gln Met
            20                  25                  30

Gln Pro Val Lys Ala Phe Lys Ile His Asn Lys Ile Trp Val Ile Pro
        35                  40                  45

Glu Arg Asp Thr Phe Thr Asn Pro Glu Glu Gly Asp Leu Asn Pro Pro
    50                  55                  60

Pro Glu Ala Lys Gln Val Pro Val Ser Tyr Tyr Asp Ser Thr Tyr Leu
65                  70                  75                  80

Ser Thr Asp Asn Glu Lys Asp Asn Tyr Leu Lys Gly Val Thr Lys Leu
                85                  90                  95

Phe Glu Arg Ile Tyr Ser Thr Asp Leu Gly Arg Met Leu Leu Thr Ser
            100                 105                 110

Ile Val Arg Gly Ile Pro Phe Trp Gly Gly Ser Thr Ile Asp Thr Glu
        115                 120                 125

Leu Lys Val Ile Asp Thr Asn Cys Ile Asn Val Ile Gln Pro Asp Gly
    130                 135                 140

Ser Tyr Arg Ser Glu Glu Leu Asn Leu Val Ile Gly Pro Ser Ala
145                 150                 155                 160

Asp Ile Ile Gln Phe Glu Cys Lys Ser Phe Gly His Glu Val Leu Asn
                165                 170                 175

Leu Thr Arg Asn Gly Tyr Gly Ser Thr Gln Tyr Ile Arg Phe Ser Pro
            180                 185                 190
```

-continued

Asp Phe Thr Phe Gly Phe Glu Glu Ser Leu Glu Val Asp Thr Asn Pro
    195                 200                 205

Leu Leu Gly Ala Gly Lys Phe Ala Thr Asp Pro Ala Val Thr Leu Ala
210                 215                 220

His Glu Leu Ile His Ala Gly His Arg Leu Tyr Gly Ile Ala Ile Asn
225                 230                 235                 240

Pro Asn Arg Val Phe Lys Val Asn Thr Asn Ala Tyr Tyr Glu Met Ser
                245                 250                 255

Gly Leu Glu Val Ser Phe Glu Glu Leu Arg Thr Phe Gly Gly His Asp
            260                 265                 270

Ala Lys Phe Ile Asp Ser Leu Gln Glu Asn Glu Phe Arg Leu Tyr Tyr
        275                 280                 285

Tyr Asn Lys Phe Lys Asp Ile Ala Ser Thr Leu Asn Lys Ala Lys Ser
    290                 295                 300

Ile Val Gly Thr Thr Ala Ser Leu Gln Tyr Met Lys Asn Val Phe Lys
305                 310                 315                 320

Glu Lys Tyr Leu Leu Ser Glu Asp Thr Ser Gly Lys Phe Ser Val Asp
                325                 330                 335

Lys Leu Lys Phe Asp Lys Leu Tyr Lys Met Leu Thr Glu Ile Tyr Thr
            340                 345                 350

Glu Asp Asn Phe Val Lys Phe Phe Lys Val Leu Asn Arg Lys Thr Tyr
        355                 360                 365

Leu Asn Phe Asp Lys Ala Val Phe Lys Ile Asn Ile Val Pro Lys Val
    370                 375                 380

Asn Tyr Thr Ile Tyr Asp Gly Phe Asn Leu Arg Asn Thr Asn Leu Ala
385                 390                 395                 400

Ala Asn Phe Asn Gly Gln Asn Thr Glu Ile Asn Asn Met Asn Phe Thr
                405                 410                 415

Lys Leu Lys Asn Phe Thr Gly Leu Phe Glu Phe Tyr Lys Leu Leu Cys
            420                 425                 430

Val Asp Gly Ile Ile Thr Ser Lys Thr Lys Ser Leu Ile Glu Gly Arg
        435                 440                 445

Tyr Gly Gly Phe Thr Gly Ala Arg Lys Ser Ala Arg Lys Leu Ala Asn
    450                 455                 460

Gln Ala Leu Ala Gly Gly Gly Ser Gly Gly Gly Ser Gly Gly
465                 470                 475                 480

Gly Gly Ser Ala Leu Val Leu Gln Cys Ile Lys Val Asn Asn Trp Asp
                485                 490                 495

Leu Phe Phe Ser Pro Ser Glu Asp Asn Phe Thr Asn Asp Leu Asn Lys
            500                 505                 510

Gly Glu Glu Ile Thr Ser Asp Thr Asn Ile Glu Ala Ala Glu Glu Asn
        515                 520                 525

Ile Ser Leu Asp Leu Ile Gln Gln Tyr Tyr Leu Thr Phe Asn Phe Asp
    530                 535                 540

Asn Glu Pro Glu Asn Ile Ser Ile Glu Asn Leu Ser Ser Asp Ile Ile
545                 550                 555                 560

Gly Gln Leu Glu Leu Met Pro Asn Ile Glu Arg Phe Pro Asn Gly Lys
                565                 570                 575

Lys Tyr Glu Leu Asp Lys Tyr Thr Met Phe His Tyr Leu Arg Ala Gln
            580                 585                 590

Glu Phe Glu His Gly Lys Ser Arg Ile Ala Leu Thr Asn Ser Val Asn
        595                 600                 605

Glu Ala Leu Leu Asn Pro Ser Arg Val Tyr Thr Phe Phe Ser Ser Asp
    610                 615                 620

Tyr Val Lys Lys Val Asn Lys Ala Thr Glu Ala Ala Met Phe Leu Gly
625                 630                 635                 640

Trp Val Glu Gln Leu Val Tyr Asp Phe Thr Asp Thr Ser Glu Val
            645                 650                 655

Ser Thr Thr Asp Lys Ile Ala Asp Ile Thr Ile Ile Pro Tyr Ile
            660                 665                 670

Gly Pro Ala Leu Asn Ile Gly Asn Met Leu Tyr Lys Asp Asp Phe Val
            675                 680                 685

Gly Ala Leu Ile Phe Ser Gly Ala Val Ile Leu Glu Phe Ile Pro
690                 695                 700

Glu Ile Ala Ile Pro Val Leu Gly Thr Phe Ala Leu Val Ser Tyr Ile
705                 710                 715                 720

Ala Asn Lys Val Leu Thr Val Gln Thr Ile Asp Asn Ala Leu Ser Lys
            725                 730                 735

Arg Asn Glu Lys Trp Asp Glu Val Tyr Lys Tyr Ile Val Thr Asn Trp
            740                 745                 750

Leu Ala Lys Val Asn Thr Gln Ile Asp Leu Ile Arg Lys Lys Met Lys
            755                 760                 765

Glu Ala Leu Glu Asn Gln Ala Glu Ala Thr Lys Ala Ile Ile Asn Tyr
770                 775                 780

Gln Tyr Asn Gln Tyr Thr Glu Glu Lys Asn Asn Ile Asn Phe Asn
785                 790                 795                 800

Ile Asp Asp Leu Ser Ser Lys Leu Asn Glu Ser Ile Asn Lys Ala Met
            805                 810                 815

Ile Asn Ile Asn Lys Phe Leu Asn Gln Cys Ser Val Ser Tyr Leu Met
            820                 825                 830

Asn Ser Met Ile Pro Tyr Gly Val Lys Arg Leu Glu Asp Phe Asp Ala
            835                 840                 845

Ser Leu Lys Asp Ala Leu Leu Lys Tyr Ile Tyr Asp Asn Arg Gly Thr
850                 855                 860

Leu Ile Gly Gln Val Asp Arg Leu Lys Asp Lys Val Asn Asn Thr Leu
865                 870                 875                 880

Ser Thr Asp Ile Pro Phe Gln Leu Ser Lys Tyr Val Asp Asn Gln Arg
            885                 890                 895

Leu Leu Ser Thr Leu Asp
            900

<210> SEQ ID NO 72
<211> LENGTH: 2709
<212> TYPE: DNA
<213> ORGANISM: Artificial Sequence
<220> FEATURE:
<223> OTHER INFORMATION: chemically synthesized polynucleotide encoding
      a fusion protein

<400> SEQUENCE: 72
ggatccatgg agttcgttaa caaacagttc aactataaag acccagttaa cggtgttgac      60
attgcttaca tcaaaatccc gaacgctggc cagatgcagc cggtaaaggc attcaaaatc     120
cacaacaaaa tctgggttat cccggaacgt gataccttta ctaacccgga agaaggtgac     180
ctgaacccgc caccggaagc gaaacaggtg ccggtatctt actatgactc cacctacctg     240
tctaccgata cgaaaagga caactacctg aaaggtgtta ctaaactgtt cgagcgtatt     300
tactccaccg acctgggccg tatgctgctg actagcatcg ttcgcggtat cccgttctgg     360
ggcggttcta ccatcgatac cgaactgaaa gtaatcgaca ctaactgcat caacgttatt     420

| | |
|---|---|
| cagccggacg gttcctatcg ttccgaagaa ctgaacctgg tgatcatcgg cccgtctgct | 480 |
| gatatcatcc agttcgagtg taagagcttt ggtcacgaag ttctgaacct cacccgtaac | 540 |
| ggctacggtt ccactcagta catccgtttc tctccggact tcaccttcgg ttttgaagaa | 600 |
| tccctggaag tagacacgaa cccactgctg ggcgctggta aattcgcaac tgatcctgcg | 660 |
| gttaccctgg ctcacgaact gattcatgca ggccaccgcc tgtacggtat cgccatcaat | 720 |
| ccgaaccgtg tcttcaaagt taacaccaac gcgtattacg agatgtccgg tctggaagtt | 780 |
| agcttcgaag aactgcgtac ttttggcggt cacgacgcta aattcatcga ctctctgcaa | 840 |
| gaaaacgagt tccgtctgta ctactataac aagttcaaag atatcgcatc cacccctgaac | 900 |
| aaagcgaaat ccatcgtggg taccactgct tctctccagt acatgaagaa cgttttaaa | 960 |
| gaaaaatacc tgctcagcga agacacctcc ggcaaattct ctgtagacaa gttgaaattc | 1020 |
| gataaacttt acaaaatgct gactgaaatt tacaccgaag acaacttcgt taagttcttt | 1080 |
| aaagttctga accgcaaaac ctatctgaac ttcgacaagg cagtattcaa atcaacatc | 1140 |
| gtgccgaaag ttaactacac tatctacgat ggtttcaacc tgcgtaacac caacctggct | 1200 |
| gctaatttta acggcagaa cacgaaatc aacaacatga acttcacaaa actgaaaaac | 1260 |
| ttcactggtc tgttcgagtt ttacaagctg ctgtgcgtcg acggcatcat acctccaaa | 1320 |
| actaaatctc tgatagaagg tagatatggc ggtttcacgg gcgcacgcaa atcagcgcgt | 1380 |
| aaacgtaaga accaggcgct agcgggcggt ggcggtagcg gcggtggcgg tagcggcggt | 1440 |
| ggcggtagcg cactagtgct gcagtgtatc aaggttaaca actgggattt attcttcagc | 1500 |
| ccgagtgaag acaacttcac caacgacctg aacaaaggtg aagaaatcac ctcagatact | 1560 |
| aacatcgaag cagccgaaga aaacatctcg ctggacctga tccagcagta ctacctgacc | 1620 |
| tttaatttcg acaacgagcc ggaaaacatt tctatcgaaa acctgagctc tgatatcatc | 1680 |
| ggccagctgg aactgatgcc gaacatcgaa cgtttcccaa acggtaaaaa gtacgagctg | 1740 |
| gacaaatata ccatgttcca ctacctgcgc gcgcaggaat ttgaacacgg caaatcccgt | 1800 |
| atcgcactga ctaactccgt taacgaagct ctgctcaacc cgtcccgtgt atacaccttc | 1860 |
| ttctctagcg actacgtgaa aaaggtcaac aaagcgactg aagctgcaat gttcttgggt | 1920 |
| tgggttgaac agcttgttta tgattttacc gacgagacgt ccgaagtatc tactaccgac | 1980 |
| aaaattgcgg atatcactat catcatcccg tacatcggtc cggctctgaa cattggcaac | 2040 |
| atgctgtaca agacgactt cgttggcgca ctgatcttct ccggtgcggt gatcctgctg | 2100 |
| gagttcatcc cggaaatcgc catcccggta ctgggcacct ttgctctggt ttcttacatt | 2160 |
| gcaaacaagg ttctgactgt acaaaccatc gacaacgcgc tgagcaaacg taacgaaaaa | 2220 |
| tgggatgaag tttacaaata tcgtgtgacc aactggctgg ctaaggttaa tactcagatc | 2280 |
| gacctcatcc gcaaaaaaat gaaagaagca ctggaaaacc aggcggaagc taccaaggca | 2340 |
| atcattaact accagtacaa ccagtacacc gaggaagaaa aaacaacat caacttcaac | 2400 |
| atcgacgatc tgtcctctaa actgaacgaa tccatcaaca agctatgat caacatcaac | 2460 |
| aagttcctga accagtgctc tgtaagctat ctgatgaact ccatgatccc gtacggtgtt | 2520 |
| aaacgtctgg aggacttcga tgcgtctctg aaagacgccc tgctgaaata catttacgac | 2580 |
| aaccgtggca ctctgatcgg tcaggttgat cgtctgaagg acaaagtgaa caatacctta | 2640 |
| tcgaccgaca tcccttttca gctcagtaaa tatgtcgata ccaacgcct tttgtccact | 2700 |
| ctagactag | 2709 |

<210> SEQ ID NO 73

<211> LENGTH: 902
<212> TYPE: PRT
<213> ORGANISM: Artificial Sequence
<220> FEATURE:
<223> OTHER INFORMATION: chemically synthesized fusion protein

<400> SEQUENCE: 73

| Gly | Ser | Met | Glu | Phe | Val | Asn | Lys | Gln | Phe | Asn | Tyr | Lys | Asp | Pro | Val |
|---|---|---|---|---|---|---|---|---|---|---|---|---|---|---|---|
| 1 | | | | 5 | | | | | 10 | | | | | 15 | |

| Asn | Gly | Val | Asp | Ile | Ala | Tyr | Ile | Lys | Ile | Pro | Asn | Ala | Gly | Gln | Met |
|---|---|---|---|---|---|---|---|---|---|---|---|---|---|---|---|
| | | | 20 | | | | | 25 | | | | | 30 | | |

| Gln | Pro | Val | Lys | Ala | Phe | Lys | Ile | His | Asn | Lys | Ile | Trp | Val | Ile | Pro |
|---|---|---|---|---|---|---|---|---|---|---|---|---|---|---|---|
| | | | 35 | | | | | 40 | | | | | 45 | | |

| Glu | Arg | Asp | Thr | Phe | Thr | Asn | Pro | Glu | Glu | Gly | Asp | Leu | Asn | Pro | Pro |
|---|---|---|---|---|---|---|---|---|---|---|---|---|---|---|---|
| | 50 | | | | | 55 | | | | | 60 | | | | |

| Pro | Glu | Ala | Lys | Gln | Val | Pro | Val | Ser | Tyr | Tyr | Asp | Ser | Thr | Tyr | Leu |
|---|---|---|---|---|---|---|---|---|---|---|---|---|---|---|---|
| 65 | | | | | 70 | | | | | 75 | | | | | 80 |

| Ser | Thr | Asp | Asn | Glu | Lys | Asp | Asn | Tyr | Leu | Lys | Gly | Val | Thr | Lys | Leu |
|---|---|---|---|---|---|---|---|---|---|---|---|---|---|---|---|
| | | | | 85 | | | | | 90 | | | | | 95 | |

| Phe | Glu | Arg | Ile | Tyr | Ser | Thr | Asp | Leu | Gly | Arg | Met | Leu | Leu | Thr | Ser |
|---|---|---|---|---|---|---|---|---|---|---|---|---|---|---|---|
| | | | 100 | | | | | 105 | | | | | 110 | | |

| Ile | Val | Arg | Gly | Ile | Pro | Phe | Trp | Gly | Gly | Ser | Thr | Ile | Asp | Thr | Glu |
|---|---|---|---|---|---|---|---|---|---|---|---|---|---|---|---|
| | | 115 | | | | | 120 | | | | | 125 | | | |

| Leu | Lys | Val | Ile | Asp | Thr | Asn | Cys | Ile | Asn | Val | Ile | Gln | Pro | Asp | Gly |
|---|---|---|---|---|---|---|---|---|---|---|---|---|---|---|---|
| | 130 | | | | | 135 | | | | | 140 | | | | |

| Ser | Tyr | Arg | Ser | Glu | Glu | Leu | Asn | Leu | Val | Ile | Ile | Gly | Pro | Ser | Ala |
|---|---|---|---|---|---|---|---|---|---|---|---|---|---|---|---|
| 145 | | | | | 150 | | | | | 155 | | | | | 160 |

| Asp | Ile | Ile | Gln | Phe | Glu | Cys | Lys | Ser | Phe | Gly | His | Glu | Val | Leu | Asn |
|---|---|---|---|---|---|---|---|---|---|---|---|---|---|---|---|
| | | | | 165 | | | | | 170 | | | | | 175 | |

| Leu | Thr | Arg | Asn | Gly | Tyr | Gly | Ser | Thr | Gln | Tyr | Ile | Arg | Phe | Ser | Pro |
|---|---|---|---|---|---|---|---|---|---|---|---|---|---|---|---|
| | | | 180 | | | | | 185 | | | | | 190 | | |

| Asp | Phe | Thr | Phe | Gly | Phe | Glu | Glu | Ser | Leu | Glu | Val | Asp | Thr | Asn | Pro |
|---|---|---|---|---|---|---|---|---|---|---|---|---|---|---|---|
| | | 195 | | | | | 200 | | | | | 205 | | | |

| Leu | Leu | Gly | Ala | Gly | Lys | Phe | Ala | Thr | Asp | Pro | Ala | Val | Thr | Leu | Ala |
|---|---|---|---|---|---|---|---|---|---|---|---|---|---|---|---|
| | 210 | | | | | 215 | | | | | 220 | | | | |

| His | Glu | Leu | Ile | His | Ala | Gly | His | Arg | Leu | Tyr | Gly | Ile | Ala | Ile | Asn |
|---|---|---|---|---|---|---|---|---|---|---|---|---|---|---|---|
| 225 | | | | | 230 | | | | | 235 | | | | | 240 |

| Pro | Asn | Arg | Val | Phe | Lys | Val | Asn | Thr | Asn | Ala | Tyr | Tyr | Glu | Met | Ser |
|---|---|---|---|---|---|---|---|---|---|---|---|---|---|---|---|
| | | | | 245 | | | | | 250 | | | | | 255 | |

| Gly | Leu | Glu | Val | Ser | Phe | Glu | Glu | Leu | Arg | Thr | Phe | Gly | Gly | His | Asp |
|---|---|---|---|---|---|---|---|---|---|---|---|---|---|---|---|
| | | | 260 | | | | | 265 | | | | | 270 | | |

| Ala | Lys | Phe | Ile | Asp | Ser | Leu | Gln | Glu | Asn | Glu | Phe | Arg | Leu | Tyr | Tyr |
|---|---|---|---|---|---|---|---|---|---|---|---|---|---|---|---|
| | | 275 | | | | | 280 | | | | | 285 | | | |

| Tyr | Asn | Lys | Phe | Lys | Asp | Ile | Ala | Ser | Thr | Leu | Asn | Lys | Ala | Lys | Ser |
|---|---|---|---|---|---|---|---|---|---|---|---|---|---|---|---|
| | 290 | | | | | 295 | | | | | 300 | | | | |

| Ile | Val | Gly | Thr | Thr | Ala | Ser | Leu | Gln | Tyr | Met | Lys | Asn | Val | Phe | Lys |
|---|---|---|---|---|---|---|---|---|---|---|---|---|---|---|---|
| 305 | | | | | 310 | | | | | 315 | | | | | 320 |

| Glu | Lys | Tyr | Leu | Leu | Ser | Glu | Asp | Thr | Ser | Gly | Lys | Phe | Ser | Val | Asp |
|---|---|---|---|---|---|---|---|---|---|---|---|---|---|---|---|
| | | | | 325 | | | | | 330 | | | | | 335 | |

| Lys | Leu | Lys | Phe | Asp | Lys | Leu | Tyr | Lys | Met | Leu | Thr | Glu | Ile | Tyr | Thr |
|---|---|---|---|---|---|---|---|---|---|---|---|---|---|---|---|
| | | | 340 | | | | | 345 | | | | | 350 | | |

| Glu | Asp | Asn | Phe | Val | Lys | Phe | Phe | Lys | Val | Leu | Asn | Arg | Lys | Thr | Tyr |
|---|---|---|---|---|---|---|---|---|---|---|---|---|---|---|---|
| | | 355 | | | | | 360 | | | | | 365 | | | |

| Leu | Asn | Phe | Asp | Lys | Ala | Val | Phe | Lys | Ile | Asn | Ile | Val | Pro | Lys | Val |
|---|---|---|---|---|---|---|---|---|---|---|---|---|---|---|---|
| | 370 | | | | | 375 | | | | | 380 | | | | |

-continued

Asn Tyr Thr Ile Tyr Asp Gly Phe Asn Leu Arg Asn Thr Asn Leu Ala
385                 390                 395                 400

Ala Asn Phe Asn Gly Gln Asn Thr Glu Ile Asn Asn Met Asn Phe Thr
            405                 410                 415

Lys Leu Lys Asn Phe Thr Gly Leu Phe Glu Phe Tyr Lys Leu Leu Cys
        420                 425                 430

Val Asp Gly Ile Ile Thr Ser Lys Thr Lys Ser Leu Ile Glu Gly Arg
    435                 440                 445

Tyr Gly Gly Phe Thr Gly Ala Arg Lys Ser Ala Arg Lys Arg Lys Asn
450                 455                 460

Gln Ala Leu Ala Gly Gly Gly Ser Gly Gly Gly Ser Gly Gly
465                 470                 475                 480

Gly Gly Ser Ala Leu Val Leu Gln Cys Ile Lys Val Asn Asn Trp Asp
            485                 490                 495

Leu Phe Phe Ser Pro Ser Glu Asp Asn Phe Thr Asn Asp Leu Asn Lys
        500                 505                 510

Gly Glu Glu Ile Thr Ser Asp Thr Asn Ile Glu Ala Ala Glu Glu Asn
    515                 520                 525

Ile Ser Leu Asp Leu Ile Gln Gln Tyr Tyr Leu Thr Phe Asn Phe Asp
530                 535                 540

Asn Glu Pro Glu Asn Ile Ser Ile Glu Asn Leu Ser Ser Asp Ile Ile
545                 550                 555                 560

Gly Gln Leu Glu Leu Met Pro Asn Ile Glu Arg Phe Pro Asn Gly Lys
            565                 570                 575

Lys Tyr Glu Leu Asp Lys Tyr Thr Met Phe His Tyr Leu Arg Ala Gln
        580                 585                 590

Glu Phe Glu His Gly Lys Ser Arg Ile Ala Leu Thr Asn Ser Val Asn
    595                 600                 605

Glu Ala Leu Leu Asn Pro Ser Arg Val Tyr Thr Phe Phe Ser Ser Asp
610                 615                 620

Tyr Val Lys Lys Val Asn Lys Ala Thr Glu Ala Ala Met Phe Leu Gly
625                 630                 635                 640

Trp Val Glu Gln Leu Val Tyr Asp Phe Thr Asp Glu Thr Ser Glu Val
            645                 650                 655

Ser Thr Thr Asp Lys Ile Ala Asp Ile Thr Ile Ile Pro Tyr Ile
        660                 665                 670

Gly Pro Ala Leu Asn Ile Gly Asn Met Leu Tyr Lys Asp Asp Phe Val
    675                 680                 685

Gly Ala Leu Ile Phe Ser Gly Ala Val Ile Leu Leu Glu Phe Ile Pro
690                 695                 700

Glu Ile Ala Ile Pro Val Leu Gly Thr Phe Ala Leu Val Ser Tyr Ile
705                 710                 715                 720

Ala Asn Lys Val Leu Thr Val Gln Thr Ile Asp Asn Ala Leu Ser Lys
            725                 730                 735

Arg Asn Glu Lys Trp Asp Glu Val Tyr Lys Tyr Ile Val Thr Asn Trp
        740                 745                 750

Leu Ala Lys Val Asn Thr Gln Ile Asp Leu Ile Arg Lys Lys Met Lys
    755                 760                 765

Glu Ala Leu Glu Asn Gln Ala Glu Ala Thr Lys Ala Ile Ile Asn Tyr
770                 775                 780

Gln Tyr Asn Gln Tyr Thr Glu Glu Lys Asn Asn Ile Asn Phe Asn
785                 790                 795                 800

Ile Asp Asp Leu Ser Ser Lys Leu Asn Glu Ser Ile Asn Lys Ala Met
            805                 810                 815

```
Ile Asn Ile Asn Lys Phe Leu Asn Gln Cys Ser Val Ser Tyr Leu Met
        820                 825                 830

Asn Ser Met Ile Pro Tyr Gly Val Lys Arg Leu Glu Asp Phe Asp Ala
        835                 840                 845

Ser Leu Lys Asp Ala Leu Leu Lys Tyr Ile Tyr Asp Asn Arg Gly Thr
850                 855                 860

Leu Ile Gly Gln Val Asp Arg Leu Lys Asp Lys Val Asn Asn Thr Leu
865                 870                 875                 880

Ser Thr Asp Ile Pro Phe Gln Leu Ser Lys Tyr Val Asp Asn Gln Arg
                885                 890                 895

Leu Leu Ser Thr Leu Asp
        900

<210> SEQ ID NO 74
<211> LENGTH: 2889
<212> TYPE: DNA
<213> ORGANISM: Artificial Sequence
<220> FEATURE:
<223> OTHER INFORMATION: chemically synthesized polynucleotide encoding
      IgA protease

<400> SEQUENCE: 74
ggatccttgg tacgagatga cgttgactat caaattttcc gcgactttgc ggaaaataaa        60
ggtaagtttt tcgtcggcgc cacagacctg tccgtcaaaa ataagagagg ccagaacatc       120
ggtaacgcac tgagcaacgt ccctatgatt gattttagtg tagcggacgt taataaacgg       180
attgcaaccg tcgttgatcc gcagtatgct gtcagcgtca acatgctaaa gcggaagtt        240 catacgttct attacgggca atataacggc ataacgatg tggctgataa agaaaatgaa        300
tatcgcgtgg tcgagcagaa caattacgaa ccgcacaaag cgtggggcgc gagtaattta       360
ggccgcctgg aggactataa catggcccgt ttcaataaat tcgtgaccga ggtagcaccg       420
atcgccccca cagatgctgg tgggggcctg gatacctaca agataaaaaa ccgcttctct       480
agcttcgtgc gcattggcgc cggtcgtcag ctcgtgtacg agaagggtgt ctatcaccag       540
gaaggtaatg aaaaggggta cgacctccgt gatttgtccc aggcgtatcg ctacgctatt       600
gccggaaccc cgtataaaga tattaatatc gatcaaacca tgaataccga aggcctaatt       660
ggtttcggga atcataataa gcaatatagc gcagaagagc taaagcaggc cctcagccaa       720
gatgcgttaa ccaattacgg agtgttaggc gatagcggca gtccgctgtt tgccttcgat       780
aaacagaaaa atcaatgggt gtttctgggc acttatgatt attgggccgg atatggtaaa       840
aagagctggc aggaatggaa tatttataaa aaggaattcg cagacaaaat caagcagcat       900
gacaacgcag gtacggtgaa ggggaacggc gaacatcact ggaagacgac cggcacgaat       960
agtcatatcg gatcgacggc cgttcgcctg gcgaacaatg agggcgatgc aaacaatggg      1020
caaaacgtga cctttgagga caacggtacc ctggtcctta accagaacat aaatcagggc      1080
gcgggaggct tgttctttaa aggcgactat actgttaagg gagcaaacaa tgacatcacc      1140
tggttagggg ccgtattga cgttgcggat ggaaaaaagg tggtttggca ggttaaaaac      1200
cctaacgggg accggctggc aaaaatcggc aaagggacat ggaaattaa tggtaccggt      1260 gtgaatcagg gtcagctgaa agtgggagat gggaccgtga ttctgaacca gaaagcagac      1320
gctgacaaaa aggtgcaagc ctttagccaa gtaggaattg ttagtggtcg tggcacactc      1380
gtcttgaact caagcaacca aataaatccg ataacctgt actttggatt tcgtggcgga      1440
cgcctggatg ctaacgggaa tgatctgacc tttgaacata tccgtaacgt tgacgagggt      1500
```

-continued

| | |
|---|---|
| gcgcgcatag ttaatcataa tactgaccat gcatcaacta tcaccttgac cgggaaaagt | 1560 |
| ctgattacaa acccaaactc tctgtcagta cattccatcc agaatgatta tgatgaagac | 1620 |
| gattactcat actattaccg gccgcgtaga ccaattccac aaggtaaaga tctttattac | 1680 |
| aaaaattacc gttattacgc attaaaatcc ggagggcggc tgaatgcacc tatgccggaa | 1740 |
| aatggcgtgg ccgaaaacaa tgactggatt tttatgggtt atactcaaga gaggctcgc | 1800 |
| aaaaatgcaa tgaaccataa aaataaccga aggatcggtg atttcggcgg attttcgat | 1860 |
| gaggaaaatg gtaaaggtca caatggtgcg ctgaatctaa attttaacgg caaaagtgcc | 1920 |
| cagaaacgtt tccttctgac tggtggcgct aatctgaatg gtaaaatcag tgtgacgcag | 1980 |
| ggtaacgtgc tgctttctgg ccggccaact ccgcatgcac gtgattttgt aaataaatcg | 2040 |
| agcgctcgta aagatgcgca ttttctaaa aataacgagg tcgtgtttga agatgactgg | 2100 |
| ataaatcgca cctttaaagc ggcagaaatc gcggttaatc agagtgcgag cttttcatcg | 2160 |
| ggtaggaatg tatctgatat tacagcaaac attacagcca ctgataatgc gaaggtcaac | 2220 |
| ctgggttata aaacggtga tgaagtttgt gttcgatcgg attacacggg ctatgttacc | 2280 |
| tgcaacactg gcaatctgtc tgataaagcg cttaactctt ttgacgccac gcgcattaac | 2340 |
| gggaatgtga acctgaacca aaacgctgcc ttggtacttg gtaaggccgc gttgtggggt | 2400 |
| aaaattcagg gccagggcaa ctcccgtgtg tctctgaacc agcactcgaa gtggcacctg | 2460 |
| acggggggact cgcaggtgca caacttgtcc ctggccgata gccatattca ccttaacaat | 2520 |
| gcgtccgatg cccagtcagc taataaatat catacgatca aaatcaatca cctctctggc | 2580 |
| aacggtcact ttcactactt aacggatta gcaaaaaact taggggataa agtcctggta | 2640 |
| aaagaatcag cgagcggaca ttatcagtta catgtacaga acaaaacagg cgagccaaat | 2700 |
| caggaaggcc ttgacttatt tgatgcttca tcggtacaag atcgttccag actgttcgtt | 2760 |
| tcactcgcga atcactacgt tgatctgggt gcgctgcgct atactataaa gacggaaaat | 2820 |
| ggcataacac gcctctataa tccctatgcc ggtaacggcc gtccggtgaa acctgctccc | 2880 |
| tgcgtcgac | 2889 |

<210> SEQ ID NO 75
<211> LENGTH: 4296
<212> TYPE: DNA
<213> ORGANISM: Artificial Sequence
<220> FEATURE:
<223> OTHER INFORMATION: chemically synthesized polynucleotide encoding
      a fusion protein

<400> SEQUENCE: 75

| | |
|---|---|
| ggatccttgg tacgagatga cgttgactat caaattttcc gcgactttgc ggaaaataaa | 60 |
| ggtaagttttt tcgtcggcgc cacagacctg tccgtcaaaa ataagagagg ccagaacatc | 120 |
| ggtaacgcac tgagcaacgt ccctatgatt gattttagtg tagcggacgt taataaacgg | 180 |
| attgcaaccg tcgttgatcc gcagtatgct gtcagcgtca acatgctaa agcggaagtt | 240 |
| catacgttct attacgggca atataacggc cataacgatg tggctgataa agaaaatgaa | 300 |
| tatcgcgtgg tcgagcagaa caattacgaa ccgcacaaag cgtggggcgc gagtaattta | 360 |
| ggccgcctgg aggactataa catggcccgt ttcaataaat tcgtgaccga ggtagcaccg | 420 |
| atcgcccca cagatgctgg tggggcctg atacctaca aagataaaaa ccgcttctct | 480 |
| agcttcgtgc gcattggcgc cggtcgtcag ctcgtgtacg agaagggtgt ctatcaccag | 540 |
| gaaggtaatg aaaaggggta cgacctccgt gatttgtccc aggcgtatcg ctacgctatt | 600 |
| gccggaaccc cgtataaaga tattaatatc gatcaaacca tgaataccga aggcctaatt | 660 |

-continued

```
ggtttcggga atcataataa gcaatatagc gcagaagagc taaagcaggc cctcagccaa      720
gatgcgttaa ccaattacgg agtgttaggc gatagcggca gtccgctgtt tgccttcgat      780
aaacagaaaa atcaatgggt gtttctgggc acttatgatt attgggccgg atatggtaaa      840
aagagctggc aggaatggaa tatttataaa aaggaattcg cagacaaaat caagcagcat      900
gacaacgcag gtacggtgaa ggggaacggc gaacatcact ggaagacgac cggcacgaat      960
agtcatatcg gatcgacggc cgttcgcctg gcgaacaatg agggcgatgc aaacaatggg     1020
caaaacgtga cctttgagga caacggtacc ctggtcctta accagaacat aaatcagggc     1080
gcgggaggct tgttctttaa aggcgactat actgttaagg gagcaaacaa tgacatcacc     1140
tggttagggg ccggtattga cgttgcggat ggaaaaaagg tggtttggca ggttaaaaac     1200
cctaacgggg accggctggc aaaaatcggc aaagggacat ggaaattaa tggtaccggt     1260 gtgaatcagg gtcagctgaa agtgggagat gggaccgtga ttctgaacca gaaagcagac     1320
gctgacaaaa aggtgcaagc ctttagccaa gtaggaattg ttagtggtcg tggcacactc     1380
gtcttgaact caagcaacca aataaatccg gataacctgt actttggatt cgtggcgga      1440 cgcctggatg ctaacgggaa tgatctgacc tttgaacata tccgtaacgt tgacgagggt     1500
gcgcgcatag ttaatcataa tactgaccat gcatcaacta tcaccttgac cgggaaaagt     1560
ctgattacaa acccaaactc tctgtcagta cattccatcc agaatgatta tgatgaagac     1620
gattactcat actattaccg gccgcgtaga ccaattccac aaggtaaaga tctttattac     1680
aaaaattacc gttattacgc attaaaatcc ggagggcggc tgaatgcacc tatgccggaa     1740
aatggcgtgg ccgaaaacaa tgactggatt tttatgggtt atactcaaga agaggctcgc     1800
aaaaatgcaa tgaaccataa aaataaccga aggatcggtg atttcggcgg atttttcgat     1860
gaggaaaatg gtaaaggtca caatggtgcg ctgaatctaa attttaacgg caaaagtgcc     1920
cagaaacgtt tccttctgac tggtggcgct aatctgaatg gtaaaatcag tgtgacgcag     1980
ggtaacgtgc tgctttctgg ccggccaact ccgcatgcac gtgattttgt aaataaatcg     2040
agcgctcgta aagatgcgca ttttctaaa aataacgagg tcgtgtttga agatgactgg     2100
ataaatcgca cctttaaagc ggcagaaatc gcggttaatc agagtgcgag cttttcatcg     2160
ggtaggaatg tatctgatat tacagcaaac attacagcca ctgataatgc gaaggtcaac     2220
ctgggttata aaaacggtga tgaagtttgt gttcgatcgg attacacggg ctatgttacc     2280
tgcaacactg gcaatctgtc tgataaagcg cttaactctt ttgacgccac gcgcattaac     2340
gggaatgtga acctgaacca aaacgctgcc ttggtacttg gtaaggccgc gttgtggggt     2400
aaaattcagg gccagggcaa ctcccgtgtg tctctgaacc agcactcgaa gtggcacctg     2460
acgggggact cgcaggtgca caacttgtcc ctggccgata gccatattca ccttaacaat     2520
gcgtccgatg cccagtcagc taataaatat catacgatca aaatcaatca cctctctggc     2580
aacggtcact ttcactactt aacggattta gcaaaaaact taggggataa agtcctggta     2640
aaagaatcag cgagcggaca ttatcagtta catgtacaga acaaaacagg cgagccaaat     2700
caggaaggcc ttgacttatt tgatgcttca tcggtacaag atcgttccag actgttcgtt     2760
tcactcgcga atcactacgt tgatctgggt gcgctgcgct atactataaa gacggaaaat     2820
ggcataacac gcctctataa tccctatgcc ggtaacggcc gtccggtgaa acctgctccc     2880
tgcgtcgacg gcatcattac ctccaaaact aaatctctga tagaaggtag atttggcggt     2940
ttcacgggcg cacgcaaatc agcgcgtaaa cgtaagaacc aggcgctagc gggcggtggc     3000
ggtagcggcg gtggcggtag cggcggtggc ggtagcgcac tagtgctgca gtgtatcaag     3060
```

```
gttaacaact gggatttatt cttcagcccg agtgaagaca acttcaccaa cgacctgaac    3120
aaaggtgaag aaatcacctc agatactaac atcgaagcag ccgaagaaaa catctcgctg    3180
gacctgatcc agcagtacta cctgacccttt aatttcgaca acgagccgga aaacatttct    3240
atcgaaaacc tgagctctga tatcatcggc cagctggaac tgatgccgaa catcgaacgt    3300
ttcccaaacg gtaaaaagta cgagctggac aaatatacca tgttccacta cctgcgcgcg    3360
caggaatttg aacacggcaa atcccgtatc gcactgacta actccgttaa cgaagctctg    3420
ctcaacccgt cccgtgtata caccttcttc tctagcgact acgtgaaaaa ggtcaacaaa    3480
gcgactgaag ctgcaatgtt cttgggttgg gttgaacagc ttgtttatga ttttaccgac    3540
gagacgtccg aagtatctac taccgacaaa attgcggata tcactatcat catcccgtac    3600
atcggtccgg ctctgaacat tggcaacatg ctgtacaaag acgacttcgt tggcgcactg    3660
atcttctccg gtgcggtgat cctgctggag ttcatcccgg aaatcgccat cccggtactg    3720
ggcacctttg ctctggtttc ttacattgca aacaaggttc tgactgtaca aaccatcgac    3780
aacgcgctga gcaaacgtaa cgaaaaatgg gatgaagttt acaaatatat cgtgaccaac    3840
tggctggcta aggttaatac tcagatcgac ctcatccgca aaaaaatgaa agaagcactg    3900
gaaaaccagg cggaagctac caaggcaatc attaactacc agtacaacca gtacaccgag    3960
gaagaaaaaa acaacatcaa cttcaacatc gacgatctgt cctctaaact gaacgaatcc    4020
atcaacaaag ctatgatcaa catcaacaag ttcctgaacc agtgctctgt aagctatctg    4080
atgaactcca tgatcccgta cggtgttaaa cgtctggagg acttcgatgc gtctctgaaa    4140
gacgccctgc tgaaatacat ttacgacaac cgtggcactc tgatcggtca ggttgatcgt    4200
ctgaaggaca aagtgaacaa taccttatcg accgacatcc cttttcagct cagtaaatat    4260
gtcgataacc aacgcctttt gtccactcta gactag                              4296
```

<210> SEQ ID NO 76
<211> LENGTH: 1431
<212> TYPE: PRT
<213> ORGANISM: Artificial Sequence
<220> FEATURE:
<223> OTHER INFORMATION: chemically synthesized fusion protein

<400> SEQUENCE: 76

```
Gly Ser Leu Val Arg Asp Asp Val Asp Tyr Gln Ile Phe Arg Asp Phe
1               5                   10                  15

Ala Glu Asn Lys Gly Lys Phe Phe Val Gly Ala Thr Asp Leu Ser Val
            20                  25                  30

Lys Asn Lys Arg Gly Gln Asn Ile Gly Asn Ala Leu Ser Asn Val Pro
        35                  40                  45

Met Ile Asp Phe Ser Val Ala Asp Val Asn Lys Arg Ile Ala Thr Val
    50                  55                  60

Val Asp Pro Gln Tyr Ala Val Ser Val Lys His Ala Lys Ala Glu Val
65                  70                  75                  80

His Thr Phe Tyr Tyr Gly Gln Tyr Asn Gly His Asn Asp Val Ala Asp
                85                  90                  95

Lys Glu Asn Glu Tyr Arg Val Val Glu Gln Asn Asn Tyr Glu Pro His
            100                 105                 110

Lys Ala Trp Gly Ala Ser Asn Leu Gly Arg Leu Glu Asp Tyr Asn Met
        115                 120                 125

Ala Arg Phe Asn Lys Phe Val Thr Glu Val Ala Pro Ile Ala Pro Thr
    130                 135                 140
```

-continued

Asp Ala Gly Gly Gly Leu Asp Thr Tyr Lys Asp Lys Asn Arg Phe Ser
145                 150                 155                 160

Ser Phe Val Arg Ile Gly Ala Gly Arg Gln Leu Val Tyr Glu Lys Gly
            165                 170                 175

Val Tyr His Gln Glu Gly Asn Glu Lys Gly Tyr Asp Leu Arg Asp Leu
        180                 185                 190

Ser Gln Ala Tyr Arg Tyr Ala Ile Ala Gly Thr Pro Tyr Lys Asp Ile
    195                 200                 205

Asn Ile Asp Gln Thr Met Asn Thr Glu Gly Leu Ile Gly Phe Gly Asn
210                 215                 220

His Asn Lys Gln Tyr Ser Ala Glu Glu Leu Lys Gln Ala Leu Ser Gln
225                 230                 235                 240

Asp Ala Leu Thr Asn Tyr Gly Val Leu Gly Asp Ser Gly Ser Pro Leu
                245                 250                 255

Phe Ala Phe Asp Lys Gln Lys Asn Gln Trp Val Phe Leu Gly Thr Tyr
            260                 265                 270

Asp Tyr Trp Ala Gly Tyr Gly Lys Ser Trp Gln Glu Trp Asn Ile
        275                 280                 285

Tyr Lys Lys Glu Phe Ala Asp Lys Ile Lys Gln His Asp Asn Ala Gly
290                 295                 300

Thr Val Lys Gly Asn Gly Glu His His Trp Lys Thr Thr Gly Thr Asn
305                 310                 315                 320

Ser His Ile Gly Ser Thr Ala Val Arg Leu Ala Asn Asn Glu Gly Asp
            325                 330                 335

Ala Asn Asn Gly Gln Asn Val Thr Phe Glu Asp Asn Gly Thr Leu Val
            340                 345                 350

Leu Asn Gln Asn Ile Asn Gln Gly Ala Gly Gly Leu Phe Phe Lys Gly
            355                 360                 365

Asp Tyr Thr Val Lys Gly Ala Asn Asn Asp Ile Thr Trp Leu Gly Ala
    370                 375                 380

Gly Ile Asp Val Ala Asp Gly Lys Lys Val Val Trp Gln Val Lys Asn
385                 390                 395                 400

Pro Asn Gly Asp Arg Leu Ala Lys Ile Gly Lys Gly Thr Leu Glu Ile
                405                 410                 415

Asn Gly Thr Gly Val Asn Gln Gly Gln Leu Lys Val Gly Asp Gly Thr
            420                 425                 430

Val Ile Leu Asn Gln Lys Ala Asp Ala Asp Lys Lys Val Gln Ala Phe
    435                 440                 445

Ser Gln Val Gly Ile Val Ser Gly Arg Gly Thr Leu Val Leu Asn Ser
    450                 455                 460

Ser Asn Gln Ile Asn Pro Asp Asn Leu Tyr Phe Gly Phe Arg Gly Gly
465                 470                 475                 480

Arg Leu Asp Ala Asn Gly Asn Asp Leu Thr Phe Glu His Ile Arg Asn
            485                 490                 495

Val Asp Glu Gly Ala Arg Ile Val Asn His Asn Thr Asp His Ala Ser
                500                 505                 510

Thr Ile Thr Leu Thr Gly Lys Ser Leu Ile Thr Asn Pro Asn Ser Leu
    515                 520                 525

Ser Val His Ser Ile Gln Asn Asp Tyr Asp Glu Asp Tyr Ser Tyr
    530                 535                 540

Tyr Tyr Arg Pro Arg Arg Pro Ile Pro Gln Gly Lys Asp Leu Tyr Tyr
545                 550                 555                 560

Lys Asn Tyr Arg Tyr Tyr Ala Leu Lys Ser Gly Gly Arg Leu Asn Ala
                565                 570                 575

```
Pro Met Pro Glu Asn Gly Val Ala Glu Asn Asn Asp Trp Ile Phe Met
            580                 585                 590
Gly Tyr Thr Gln Glu Glu Ala Arg Lys Asn Ala Met Asn His Lys Asn
            595                 600                 605
Asn Arg Arg Ile Gly Asp Phe Gly Gly Phe Asp Glu Glu Asn Gly
610             615                 620
Lys Gly His Asn Gly Ala Leu Asn Leu Asn Phe Asn Gly Lys Ser Ala
625             630                 635                 640
Gln Lys Arg Phe Leu Leu Thr Gly Gly Ala Asn Leu Asn Gly Lys Ile
                645                 650                 655
Ser Val Thr Gln Gly Asn Val Leu Leu Ser Gly Arg Pro Thr Pro His
            660                 665                 670
Ala Arg Asp Phe Val Asn Lys Ser Ser Ala Arg Lys Asp Ala His Phe
            675                 680                 685
Ser Lys Asn Asn Glu Val Val Phe Glu Asp Asp Trp Ile Asn Arg Thr
690             695                 700
Phe Lys Ala Ala Glu Ile Ala Val Asn Gln Ser Ala Ser Phe Ser Ser
705             710                 715                 720
Gly Arg Asn Val Ser Asp Ile Thr Ala Asn Ile Thr Ala Thr Asp Asn
                725                 730                 735
Ala Lys Val Asn Leu Gly Tyr Lys Asn Gly Asp Glu Val Cys Val Arg
            740                 745                 750
Ser Asp Tyr Thr Gly Tyr Val Thr Cys Asn Thr Gly Asn Leu Ser Asp
            755                 760                 765
Lys Ala Leu Asn Ser Phe Asp Ala Thr Arg Ile Asn Gly Asn Val Asn
770             775                 780
Leu Asn Gln Asn Ala Ala Leu Val Leu Gly Lys Ala Ala Leu Trp Gly
785             790                 795                 800
Lys Ile Gln Gly Gln Gly Asn Ser Arg Val Ser Leu Asn Gln His Ser
            805                 810                 815
Lys Trp His Leu Thr Gly Asp Ser Gln Val His Asn Leu Ser Leu Ala
            820                 825                 830
Asp Ser His Ile His Leu Asn Asn Ala Ser Asp Ala Gln Ser Ala Asn
            835                 840                 845
Lys Tyr His Thr Ile Lys Ile Asn His Leu Ser Gly Asn Gly His Phe
850             855                 860
His Tyr Leu Thr Asp Leu Ala Lys Asn Leu Gly Asp Lys Val Leu Val
865             870                 875                 880
Lys Glu Ser Ala Ser Gly His Tyr Gln Leu His Val Gln Asn Lys Thr
            885                 890                 895
Gly Glu Pro Asn Gln Glu Gly Leu Asp Leu Phe Asp Ala Ser Ser Val
            900                 905                 910
Gln Asp Arg Ser Arg Leu Phe Val Ser Leu Ala Asn His Tyr Val Asp
            915                 920                 925
Leu Gly Ala Leu Arg Tyr Thr Ile Lys Thr Glu Asn Gly Ile Thr Arg
930             935                 940
Leu Tyr Asn Pro Tyr Ala Gly Asn Gly Arg Pro Val Lys Pro Ala Pro
945             950                 955                 960
Cys Val Asp Gly Ile Ile Thr Ser Lys Thr Lys Ser Leu Ile Glu Gly
                965                 970                 975
Arg Phe Gly Gly Phe Thr Gly Ala Arg Lys Ser Ala Arg Lys Arg Lys
            980                 985                 990
Asn Gln Ala Leu Ala Gly Gly Gly  Gly Ser Gly Gly Gly  Gly Ser Gly
```

-continued

```
              995                 1000                1005
Gly  Gly  Gly  Ser  Ala  Leu  Val  Leu  Gln  Cys  Ile  Lys  Val  Asn  Asn
         1010                 1015                1020

Trp  Asp  Leu  Phe  Phe  Ser  Pro  Ser  Glu  Asp  Asn  Phe  Thr  Asn  Asp
         1025                 1030                1035

Leu  Asn  Lys  Gly  Glu  Glu  Ile  Thr  Ser  Asp  Thr  Asn  Ile  Glu  Ala
         1040                 1045                1050

Ala  Glu  Glu  Asn  Ile  Ser  Leu  Asp  Leu  Ile  Gln  Gln  Tyr  Tyr  Leu
         1055                 1060                1065

Thr  Phe  Asn  Phe  Asp  Asn  Glu  Pro  Glu  Asn  Ile  Ser  Ile  Glu  Asn
         1070                 1075                1080

Leu  Ser  Ser  Asp  Ile  Ile  Gly  Gln  Leu  Glu  Leu  Met  Pro  Asn  Ile
         1085                 1090                1095

Glu  Arg  Phe  Pro  Asn  Gly  Lys  Lys  Tyr  Glu  Leu  Asp  Lys  Tyr  Thr
         1100                 1105                1110

Met  Phe  His  Tyr  Leu  Arg  Ala  Gln  Glu  Phe  Glu  His  Gly  Lys  Ser
         1115                 1120                1125

Arg  Ile  Ala  Leu  Thr  Asn  Ser  Val  Asn  Glu  Ala  Leu  Leu  Asn  Pro
         1130                 1135                1140

Ser  Arg  Val  Tyr  Thr  Phe  Phe  Ser  Ser  Asp  Tyr  Val  Lys  Lys  Val
         1145                 1150                1155

Asn  Lys  Ala  Thr  Glu  Ala  Ala  Met  Phe  Leu  Gly  Trp  Val  Glu  Gln
         1160                 1165                1170

Leu  Val  Tyr  Asp  Phe  Thr  Asp  Glu  Thr  Ser  Glu  Val  Ser  Thr  Thr
         1175                 1180                1185

Asp  Lys  Ile  Ala  Asp  Ile  Thr  Ile  Ile  Pro  Tyr  Ile  Gly  Pro
         1190                 1195                1200

Ala  Leu  Asn  Ile  Gly  Asn  Met  Leu  Tyr  Lys  Asp  Asp  Phe  Val  Gly
         1205                 1210                1215

Ala  Leu  Ile  Phe  Ser  Gly  Ala  Val  Ile  Leu  Leu  Glu  Phe  Ile  Pro
         1220                 1225                1230

Glu  Ile  Ala  Ile  Pro  Val  Leu  Gly  Thr  Phe  Ala  Leu  Val  Ser  Tyr
         1235                 1240                1245

Ile  Ala  Asn  Lys  Val  Leu  Thr  Val  Gln  Thr  Ile  Asp  Asn  Ala  Leu
         1250                 1255                1260

Ser  Lys  Arg  Asn  Glu  Lys  Trp  Asp  Glu  Val  Tyr  Lys  Tyr  Ile  Val
         1265                 1270                1275

Thr  Asn  Trp  Leu  Ala  Lys  Val  Asn  Thr  Gln  Ile  Asp  Leu  Ile  Arg
         1280                 1285                1290

Lys  Lys  Met  Lys  Glu  Ala  Leu  Glu  Asn  Gln  Ala  Glu  Ala  Thr  Lys
         1295                 1300                1305

Ala  Ile  Ile  Asn  Tyr  Gln  Tyr  Asn  Gln  Tyr  Thr  Glu  Glu  Glu  Lys
         1310                 1315                1320

Asn  Asn  Ile  Asn  Phe  Asn  Ile  Asp  Asp  Leu  Ser  Ser  Lys  Leu  Asn
         1325                 1330                1335

Glu  Ser  Ile  Asn  Lys  Ala  Met  Ile  Asn  Ile  Asn  Lys  Phe  Leu  Asn
         1340                 1345                1350

Gln  Cys  Ser  Val  Ser  Tyr  Leu  Met  Asn  Ser  Met  Ile  Pro  Tyr  Gly
         1355                 1360                1365

Val  Lys  Arg  Leu  Glu  Asp  Phe  Asp  Ala  Ser  Leu  Lys  Asp  Ala  Leu
         1370                 1375                1380

Leu  Lys  Tyr  Ile  Tyr  Asp  Asn  Arg  Gly  Thr  Leu  Ile  Gly  Gln  Val
         1385                 1390                1395
```

| Asp | Arg | Leu | Lys | Asp | Lys | Val | Asn | Asn | Thr | Leu | Ser | Thr | Asp | Ile |
|-----|-----|-----|-----|-----|-----|-----|-----|-----|-----|-----|-----|-----|-----|-----|
| 1400 |   |   |   | 1405 |   |   |   |   | 1410 |   |   |   |   |   |

| Pro | Phe | Gln | Leu | Ser | Lys | Tyr | Val | Asp | Asn | Gln | Arg | Leu | Leu | Ser |
|-----|-----|-----|-----|-----|-----|-----|-----|-----|-----|-----|-----|-----|-----|-----|
| 1415 |   |   |   |   | 1420 |   |   |   |   | 1425 |   |   |   |   |

| Thr | Leu | Asp |
|-----|-----|-----|
| 1430 |   |   |

<210> SEQ ID NO 77
<211> LENGTH: 1357
<212> TYPE: DNA
<213> ORGANISM: Artificial Sequence
<220> FEATURE:
<223> OTHER INFORMATION: chemically synthesized polynucleotide encoding histidine tag

<400> SEQUENCE: 77

```
gctagcgggc ggtggcggta gcggcggtgg cggtagcggc ggtggcggta gcgcactagt      60
gctgcagtgt atcaaggtta caactgggga tttattcttc agcccgagtg aagacaactt     120
caccaacgac ctgaacaaag gtgaagaaat cacctcagat actaacatcg aagcagccga     180
agaaaacatc tcgctggacc tgatccagca gtactacctg accttaatt tcgacaacga     240
gccggaaaac atttctatcg aaaacctgag ctctgatatc atcggccagc tggaactgat     300
gccgaacatc gaacgtttcc caaacggtaa aaagtacgag ctggacaaat ataccatgtt     360
ccactacctg cgcgcgcagg aatttgaaca cggcaaatcc cgtatcgcac tgactaactc     420
cgttaacgaa gctctgctca acccgtcccg tgtatacacc ttcttctcta gcgactacgt     480
gaaaaaggtc aacaaagcga ctgaagctgc aatgttcttg ggttgggttg aacagcttgt     540
ttatgatttt accgacgaga cgtccgaagt atctactacc gacaaaattg cggatatcac     600
tatcatcatc ccgtacatcg gtccggctct gaacattggc aacatgctgt acaaagacga     660
cttcgttggc gcactgatct ctctccggtgc ggtgatcctg ctggagttca tcccggaaat     720
cgccatcccg gtactgggca cctttgctct ggtttcttac attgcaaaca aggttctgac     780
tgtacaaacc atcgacaacg cgctgagcaa acgtaacgaa aaatgggatg aagtttacaa     840
atatatcgtg accaactggc tggctaaggt taatactcag atcgacctca tccgcaaaaa     900
aatgaaagaa gcactggaaa accaggcgga agctaccaag gcaatcatta actaccagta     960
caaccagtac accgaggaag aaaaaaacaa catcaacttc aacatcgacg atctgtcctc    1020
taaactgaac gaatccatca acaaagctat gatcaacatc aacaagttcc tgaaccagtg    1080
ctctgtaagc tatctgatga ctccatgat cccgtacggt gttaaacgtc tggaggactt    1140
cgatgcgtct ctgaaagacg ccctgctgaa atacatttac gacaaccgtg gcactctgat    1200
cggtcaggtt gatcgtctga aggacaaagt gaacaatacc ttatcgaccg acatccctttt    1260
tcagctcagt aaatatgtcg ataaccaacg ccttttgtcc actctagaaa tagaaggtag    1320
aagtgggcac catcaccatc accattaatg aaagctt                              1357
```

<210> SEQ ID NO 78
<211> LENGTH: 2745
<212> TYPE: DNA
<213> ORGANISM: Artificial Sequence
<220> FEATURE:
<223> OTHER INFORMATION: chemically synthesized polynucleotide encoding a fusion protein

<400> SEQUENCE: 78

```
ggatccatgg agttcgttaa caaacagttc aactataaag acccagttaa cggtgttgac      60
attgcttaca tcaaaatccc gaacgctggc cagatgcagc cggtaaaggc attcaaaatc     120
```

```
cacaacaaaa tctgggttat cccggaacgt gatacccttta ctaacccgga agaaggtgac    180
ctgaacccgc caccggaagc gaaacaggtg ccggtatctt actatgactc cacctacctg    240
tctaccgata acgaaaagga caactacctg aaaggtgtta ctaaactgtt cgagcgtatt    300
tactccaccg acctgggccg tatgctgctg actagcatcg ttcgcggtat cccgttctgg    360
ggcggttcta ccatcgatac cgaactgaaa gtaatcgaca ctaactgcat caacgttatt    420
cagccggacg gttcctatcg ttccgaagaa ctgaacctgg tgatcatcgg cccgtctgct    480
gatatcatcc agttcgagtg taagagcttt ggtcacgaag ttctgaacct cacccgtaac    540
ggctacggtt ccactcagta catccgtttc tctccggact tcaccttcgg ttttgaagaa    600
tccctggaag tagacacgaa cccactgctg ggcgctggta aattcgcaac tgatcctgcg    660
gttaccctgg ctcacgaact gattcatgca ggccaccgcc tgtacggtat cgccatcaat    720
ccgaaccgtg tcttcaaagt taacaccaac gcgtattacg agatgtccgg tctggaagtt    780
agcttcgaag aactgcgtac ttttggcggt cacgacgcta aattcatcga ctctctgcaa    840
gaaaacgagt tccgtctgta ctactataac aagttcaaag atatcgcatc caccctgaac    900
aaagcgaaat ccatcgtggg taccactgct tctctccagt acatgaagaa cgttttaaa    960 gaaaaatacc tgctcagcga agacacctcc ggcaaattct ctgtagacaa gttgaaattc   1020
gataaacttt acaaaatgct gactgaaatt tacaccgaag acaacttcgt taagttcttt   1080
aaagttctga accgcaaaac ctatctgaac ttcgacaagg cagtattcaa aatcaacatc   1140
gtgccgaaag ttaactacac tatctacgat ggtttcaacc tgcgtaacac caacctggct   1200
gctaatttta acggccagaa cacggaaatc aacaacatga acttcacaaa actgaaaaac   1260
ttcactggtc tgttcgagtt ttacaagctg ctgtgcgtcg acggcatcat tacctccaaa   1320
actaaatctc tgatagaagg tagatttggc ggtttcacgg gcgcacgcaa atcagcgcgt   1380
aaacgtaaga accaggcgct agcgggcggt ggcggtagcg gcgtggcgg tagcggcggt   1440 ggcggtagcg cactagtgct gcagtgtatc aaggttaaca actgggattt attcttcagc   1500
ccgagtgaag acaacttcac caacgacctg aacaaaggtg aagaaatcac ctcagatact   1560
aacatcgaag cagccgaaga aaacatctcg ctggacctga tccagcagta ctacctgacc   1620
tttaatttcg acaacgagcc ggaaaacatt tctatcgaaa acctgagctc tgatatcatc   1680
ggccagctgg aactgatgcc gaacatcgaa cgtttcccaa acgtaaaaa gtacgagctg   1740 gacaaatata ccatgttcca ctacctgcgc gcgcaggaat ttgaacacgg caaatcccgt   1800
atcgcactga ctaactccgt taacgaagct ctgctcaacc cgtcccgtgt atacacctc    1860 ttctctagcg actacgtgaa aaaggtcaac aaagcgactg aagctgcaat gttcttgggt   1920
tgggttgaac agcttgttta tgattttacc gacgagacgt ccgaagtatc tactaccgac   1980
aaaattgcgg atatcactat catcatcccg tacatcggtc cggctctgaa cattggcaac   2040
atgctgtaca agacgactt cgttggcgca ctgatcttct ccggtgcggt gatcctgctg   2100
gagttcatcc cggaaatcgc catcccggta ctgggcacct ttgctctggt tcttacatt   2160 gcaaacaagg ttctgactgt acaaaccatc gacaacgcgc tgagcaaacg taacgaaaaa   2220
tgggatgaag tttacaaata tatcgtgacc aactggctgg ctaaggttaa tactcagatc   2280
gacctcatcc gcaaaaaat gaagaagca ctggaaaacc aggcggaagc taccaaggca   2340
atcattaact accagtacaa ccagtacacc gaggaagaaa aaacaacat caacttcaac   2400 atcgacgatc tgtcctctaa actgaacgaa tccatcaaca agctatgat caacatcaac   2460 aagttcctga accagtgctc tgtaagctat ctgatgaact ccatgatccc gtacggtgtt   2520
```

```
aaacgtctgg aggacttcga tgcgtctctg aaagacgccc tgctgaaata catttacgac   2580
aaccgtggca ctctgatcgg tcaggttgat cgtctgaagg acaaagtgaa caataccta    2640 tcgaccgaca tcccttttca gctcagtaaa tatgtcgata accaacgcct tttgtccact   2700
ctagaaatag aaggtagaag tgggcaccat caccatcacc attaa                  2745

<210> SEQ ID NO 79
<211> LENGTH: 914
<212> TYPE: PRT
<213> ORGANISM: Artificial Sequence
<220> FEATURE:
<223> OTHER INFORMATION: chemically synthesized fusion protein

<400> SEQUENCE: 79

Gly Ser Met Glu Phe Val Asn Lys Gln Phe Asn Tyr Lys Asp Pro Val
1               5                   10                  15

Asn Gly Val Asp Ile Ala Tyr Ile Lys Ile Pro Asn Ala Gly Gln Met
            20                  25                  30

Gln Pro Val Lys Ala Phe Lys Ile His Asn Lys Ile Trp Val Ile Pro
        35                  40                  45

Glu Arg Asp Thr Phe Thr Asn Pro Glu Glu Gly Asp Leu Asn Pro Pro
    50                  55                  60

Pro Glu Ala Lys Gln Val Pro Val Ser Tyr Tyr Asp Ser Thr Tyr Leu
65                  70                  75                  80

Ser Thr Asp Asn Glu Lys Asp Asn Tyr Leu Lys Gly Val Thr Lys Leu
                85                  90                  95

Phe Glu Arg Ile Tyr Ser Thr Asp Leu Gly Arg Met Leu Leu Thr Ser
            100                 105                 110

Ile Val Arg Gly Ile Pro Phe Trp Gly Gly Ser Thr Ile Asp Thr Glu
        115                 120                 125

Leu Lys Val Ile Asp Thr Asn Cys Ile Asn Val Ile Gln Pro Asp Gly
    130                 135                 140

Ser Tyr Arg Ser Glu Glu Leu Asn Leu Val Ile Ile Gly Pro Ser Ala
145                 150                 155                 160

Asp Ile Ile Gln Phe Glu Cys Lys Ser Phe Gly His Glu Val Leu Asn
                165                 170                 175

Leu Thr Arg Asn Gly Tyr Gly Ser Thr Gln Tyr Ile Arg Phe Ser Pro
            180                 185                 190

Asp Phe Thr Phe Gly Phe Glu Glu Ser Leu Glu Val Asp Thr Asn Pro
        195                 200                 205

Leu Leu Gly Ala Gly Lys Phe Ala Thr Asp Pro Ala Val Thr Leu Ala
    210                 215                 220

His Glu Leu Ile His Ala Gly His Arg Leu Tyr Gly Ile Ala Ile Asn
225                 230                 235                 240

Pro Asn Arg Val Phe Lys Val Asn Thr Asn Ala Tyr Tyr Glu Met Ser
                245                 250                 255

Gly Leu Glu Val Ser Phe Glu Glu Leu Arg Thr Phe Gly Gly His Asp
            260                 265                 270

Ala Lys Phe Ile Asp Ser Leu Gln Glu Asn Glu Phe Arg Leu Tyr Tyr
        275                 280                 285

Tyr Asn Lys Phe Lys Asp Ile Ala Ser Thr Leu Asn Lys Ala Lys Ser
    290                 295                 300

Ile Val Gly Thr Thr Ala Ser Leu Gln Tyr Met Lys Asn Val Phe Lys
305                 310                 315                 320

Glu Lys Tyr Leu Leu Ser Glu Asp Thr Ser Gly Lys Phe Ser Val Asp
```

```
                    325                 330                 335
Lys Leu Lys Phe Asp Lys Leu Tyr Lys Met Leu Thr Glu Ile Tyr Thr
                340                 345                 350
Glu Asp Asn Phe Val Lys Phe Phe Lys Val Leu Asn Arg Lys Thr Tyr
                355                 360                 365
Leu Asn Phe Asp Lys Ala Val Phe Lys Ile Asn Ile Val Pro Lys Val
            370                 375                 380
Asn Tyr Thr Ile Tyr Asp Gly Phe Asn Leu Arg Asn Thr Asn Leu Ala
385                 390                 395                 400
Ala Asn Phe Asn Gly Gln Asn Thr Glu Ile Asn Asn Met Asn Phe Thr
                405                 410                 415
Lys Leu Lys Asn Phe Thr Gly Leu Phe Glu Phe Tyr Lys Leu Leu Cys
                420                 425                 430
Val Asp Gly Ile Ile Thr Ser Lys Thr Lys Ser Leu Ile Glu Gly Arg
            435                 440                 445
Phe Gly Gly Phe Thr Gly Ala Arg Lys Ser Ala Arg Lys Arg Lys Asn
        450                 455                 460
Gln Ala Leu Ala Gly Gly Gly Ser Gly Gly Gly Ser Gly Gly
465                 470                 475                 480
Gly Gly Ser Ala Leu Val Leu Gln Cys Ile Lys Val Asn Asn Trp Asp
                485                 490                 495
Leu Phe Phe Ser Pro Ser Glu Asp Asn Phe Thr Asn Asp Leu Asn Lys
                500                 505                 510
Gly Glu Glu Ile Thr Ser Asp Thr Asn Ile Glu Ala Ala Glu Glu Asn
            515                 520                 525
Ile Ser Leu Asp Leu Ile Gln Gln Tyr Tyr Leu Thr Phe Asn Phe Asp
530                 535                 540
Asn Glu Pro Glu Asn Ile Ser Ile Glu Asn Leu Ser Ser Asp Ile Ile
545                 550                 555                 560
Gly Gln Leu Glu Leu Met Pro Asn Ile Glu Arg Phe Pro Asn Gly Lys
                565                 570                 575
Lys Tyr Glu Leu Asp Lys Tyr Thr Met Phe His Tyr Leu Arg Ala Gln
                580                 585                 590
Glu Phe Glu His Gly Lys Ser Arg Ile Ala Leu Thr Asn Ser Val Asn
            595                 600                 605
Glu Ala Leu Leu Asn Pro Ser Arg Val Tyr Thr Phe Phe Ser Ser Asp
            610                 615                 620
Tyr Val Lys Lys Val Asn Lys Ala Thr Glu Ala Ala Met Phe Leu Gly
625                 630                 635                 640
Trp Val Glu Gln Leu Val Tyr Asp Phe Thr Asp Glu Thr Ser Glu Val
                645                 650                 655
Ser Thr Thr Asp Lys Ile Ala Asp Ile Thr Ile Ile Pro Tyr Ile
            660                 665                 670
Gly Pro Ala Leu Asn Ile Gly Asn Met Leu Tyr Lys Asp Asp Phe Val
        675                 680                 685
Gly Ala Leu Ile Phe Ser Gly Ala Val Ile Leu Leu Glu Phe Ile Pro
    690                 695                 700
Glu Ile Ala Ile Pro Val Leu Gly Thr Phe Ala Leu Val Ser Tyr Ile
705                 710                 715                 720
Ala Asn Lys Val Leu Thr Val Gln Thr Ile Asp Asn Ala Leu Ser Lys
                725                 730                 735
Arg Asn Glu Lys Trp Asp Glu Val Tyr Lys Tyr Ile Val Thr Asn Trp
            740                 745                 750
```

```
Leu Ala Lys Val Asn Thr Gln Ile Asp Leu Ile Arg Lys Lys Met Lys
        755                 760                 765

Glu Ala Leu Glu Asn Gln Ala Glu Ala Thr Lys Ala Ile Ile Asn Tyr
    770                 775                 780

Gln Tyr Asn Gln Tyr Thr Glu Glu Lys Asn Asn Ile Asn Phe Asn
785                 790                 795                 800

Ile Asp Asp Leu Ser Ser Lys Leu Asn Glu Ser Ile Asn Lys Ala Met
                805                 810                 815

Ile Asn Ile Asn Lys Phe Leu Asn Gln Cys Ser Val Ser Tyr Leu Met
            820                 825                 830

Asn Ser Met Ile Pro Tyr Gly Val Lys Arg Leu Glu Asp Phe Asp Ala
        835                 840                 845

Ser Leu Lys Asp Ala Leu Leu Lys Tyr Ile Tyr Asp Asn Arg Gly Thr
    850                 855                 860

Leu Ile Gly Gln Val Asp Arg Leu Lys Asp Lys Val Asn Asn Thr Leu
865                 870                 875                 880

Ser Thr Asp Ile Pro Phe Gln Leu Ser Lys Tyr Val Asp Asn Gln Arg
                885                 890                 895

Leu Leu Ser Thr Leu Glu Ile Glu Gly Arg Ser Gly His His His His
            900                 905                 910

His His
```

<210> SEQ ID NO 80
<211> LENGTH: 619
<212> TYPE: DNA
<213> ORGANISM: Artificial Sequence
<220> FEATURE:
<223> OTHER INFORMATION: chemically synthesized polynucleotide encoding translocation domain

<400> SEQUENCE: 80

```
gctagcgggc ggtggcggta gcggcggtgg cggtagcggc ggtggcggta gcgcactagt      60
gctgcagtgt atcaatctgg attgggacgt aatccgtgat aagaccaaaa caaaaatcga     120
gtctttgaaa gaacacggcc cgatcaaaaa taagatgtct gaatcaccca ataaaactgt     180
ttcggaggaa aaagcgaaac agtatttgga agagtttcat caaaccgcgc ttgaacatcc     240
ggagctcagt gaactgaaaa cagtgacggg aacgaatcct gttttttgcag gcgcaaacta     300
tgcggcttgg gccgtgaatg ttgcccaagt aattgatagt gagaccgcag acaacctgga     360
aaagacgacc gcagcgttaa gcattttacc ggggattggt tccgtgatgg gtatagcgga     420
tggagcggtc caccataaca ctgaggaaat tgtcgcccag tcaatcgctc tgagttccct     480
gatggttgca caggctatcc cactcgtggg ggaactggtt gacataggtt tcgccgccta     540
caacttcgta gaaagcatta ttaatctttt tcaggtggtg cataacagct acaaccgccc     600
tctagaatga taaaagctt                                                  619
```

<210> SEQ ID NO 81
<211> LENGTH: 1971
<212> TYPE: DNA
<213> ORGANISM: Artificial Sequence
<220> FEATURE:
<223> OTHER INFORMATION: chemically synthesized polynucleotide encoding a fusion protein

<400> SEQUENCE: 81

```
ggatccatgg agttcgttaa caaacagttc aactataaag acccagttaa cggtgttgac      60
attgcttaca tcaaaatccc gaacgctggc cagatgcagc cggtaaaggc attcaaaatc     120
```

| | |
|---|---|
| cacaacaaaa tctgggttat cccggaacgt gataccttta ctaaccccgga agaaggtgac | 180 |
| ctgaacccgc caccggaagc gaaacaggtg ccggtatctt actatgactc cacctacctg | 240 |
| tctaccgata acgaaaagga caactacctg aaaggtgtta ctaaactgtt cgagcgtatt | 300 |
| tactccaccg acctgggccg tatgctgctg actagcatcg ttcgcggtat cccgttctgg | 360 |
| ggcggttcta ccatcgatac cgaactgaaa gtaatcgaca ctaactgcat caacgttatt | 420 |
| cagccggacg gttcctatcg ttccgaagaa ctgaacctgg tgatcatcgg cccgtctgct | 480 |
| gatatcatcc agttcgagtg taagagcttt ggtcacgaag ttctgaacct cacccgtaac | 540 |
| ggctacggtt ccactcagta catccgtttc tctccggact tcaccttcgg ttttgaagaa | 600 |
| tccctggaag tagacacgaa cccactgctg ggcgctggta aattcgcaac tgatcctgcg | 660 |
| gttaccctgg ctcacgaact gattcatgca ggccaccgcc tgtacggtat cgccatcaat | 720 |
| ccgaaccgtg tcttcaaagt taacaccaac gcgtattacg agatgtccgg tctggaagtt | 780 |
| agcttcgaag aactgcgtac ttttggcggt cacgacgcta aattcatcga ctctctgcaa | 840 |
| gaaaacgagt ccgtctgta ctactataac aagttcaaag atatcgcatc caccctgaac | 900 |
| aaagcgaaat ccatcgtggg taccactgct ctctccagt acatgaagaa cgttttaaa | 960 |
| gaaaaatacc tgctcagcga agacacctcc ggcaaattct ctgtagacaa gttgaaattc | 1020 |
| gataaacttt acaaaatgct gactgaaatt tacaccgaag acaacttcgt taagttctt | 1080 |
| aaagttctga accgcaaaac ctatctgaac ttcgacaagg cagtattcaa aatcaacatc | 1140 |
| gtgccgaaag ttaactacac tatctacgat ggtttcaacc tgcgtaacac caacctggct | 1200 |
| gctaatttta acggccagaa cacggaaatc aacaacatga acttcacaaa actgaaaaac | 1260 |
| ttcactggtc tgttcgagtt ttacaagctg ctgtgcgtcg acggcatcat acctccaaaa | 1320 |
| actaaatctc tgatagaagg tagatacggt ggtttcctgg cgctagcggg cggtggcggt | 1380 |
| agcggcggtg gcggtagcgg cggtggcggt agcgcactag tgctgcagtg tatcaatctg | 1440 |
| gattgggacg taatccgtga taagaccaaa acaaaaatcg agtctttgaa agaacacggc | 1500 |
| ccgatcaaaa ataagatgtc tgaatcaccc aataaaactg tttcggagga aaaagcgaaa | 1560 |
| cagtatttgg aagagtttca tcaaaccgcg cttgaacatc cggagctcag tgaactgaaa | 1620 |
| acagtgacgg gaacgaatcc tgttttttgca ggcgcaaact atgcggcttg ggccgtgaat | 1680 |
| gttgcccaag taattgatag tgagaccgca gacaacctgg aaaagacgac cgcagcgtta | 1740 |
| agcattttac cggggattgg ttccgtgatg ggtatagcgg atggagcggt ccaccataac | 1800 |
| actgaggaaa ttgtcgccca gtcaatcgct ctgagttccc tgatggttgc acaggctatc | 1860 |
| ccactcgtgg gggaactggt tgacataggt ttcgccgcct acaacttcgt agaaagcatt | 1920 |
| attaatcttt ttcaggtggt gcataacagc tacaaccgcc tctagaatg a | 1971 |

<210> SEQ ID NO 82
<211> LENGTH: 656
<212> TYPE: PRT
<213> ORGANISM: Artificial Sequence
<220> FEATURE:
<223> OTHER INFORMATION: chemically synthesized fusion protein

<400> SEQUENCE: 82

```
Gly Ser Met Glu Phe Val Asn Lys Gln Phe Asn Tyr Lys Asp Pro Val
1               5                   10                  15

Asn Gly Val Asp Ile Ala Tyr Ile Lys Ile Pro Asn Ala Gly Gln Met
            20                  25                  30

Gln Pro Val Lys Ala Phe Lys Ile His Asn Lys Ile Trp Val Ile Pro
        35                  40                  45
```

```
Glu Arg Asp Thr Phe Thr Asn Pro Glu Glu Gly Asp Leu Asn Pro Pro
    50                  55                  60

Pro Glu Ala Lys Gln Val Pro Val Ser Tyr Tyr Asp Ser Thr Tyr Leu
65                  70                  75                  80

Ser Thr Asp Asn Glu Lys Asp Asn Tyr Leu Lys Gly Val Thr Lys Leu
                85                  90                  95

Phe Glu Arg Ile Tyr Ser Thr Asp Leu Gly Arg Met Leu Leu Thr Ser
               100                 105                 110

Ile Val Arg Gly Ile Pro Phe Trp Gly Gly Ser Thr Ile Asp Thr Glu
               115                 120                 125

Leu Lys Val Ile Asp Thr Asn Cys Ile Asn Val Ile Gln Pro Asp Gly
               130                 135                 140

Ser Tyr Arg Ser Glu Glu Leu Asn Leu Val Ile Ile Gly Pro Ser Ala
145                 150                 155                 160

Asp Ile Ile Gln Phe Glu Cys Lys Ser Phe Gly His Glu Val Leu Asn
               165                 170                 175

Leu Thr Arg Asn Gly Tyr Gly Ser Thr Gln Tyr Ile Arg Phe Ser Pro
               180                 185                 190

Asp Phe Thr Phe Gly Phe Glu Glu Ser Leu Glu Val Asp Thr Asn Pro
               195                 200                 205

Leu Leu Gly Ala Gly Lys Phe Ala Thr Asp Pro Ala Val Thr Leu Ala
               210                 215                 220

His Glu Leu Ile His Ala Gly His Arg Leu Tyr Gly Ile Ala Ile Asn
225                 230                 235                 240

Pro Asn Arg Val Phe Lys Val Asn Thr Asn Ala Tyr Tyr Glu Met Ser
               245                 250                 255

Gly Leu Glu Val Ser Phe Glu Glu Leu Arg Thr Phe Gly Gly His Asp
               260                 265                 270

Ala Lys Phe Ile Asp Ser Leu Gln Glu Asn Glu Phe Arg Leu Tyr Tyr
               275                 280                 285

Tyr Asn Lys Phe Lys Asp Ile Ala Ser Thr Leu Asn Lys Ala Lys Ser
               290                 295                 300

Ile Val Gly Thr Thr Ala Ser Leu Gln Tyr Met Lys Asn Val Phe Lys
305                 310                 315                 320

Glu Lys Tyr Leu Leu Ser Glu Asp Thr Ser Gly Lys Phe Ser Val Asp
               325                 330                 335

Lys Leu Lys Phe Asp Lys Leu Tyr Lys Met Leu Thr Glu Ile Tyr Thr
               340                 345                 350

Glu Asp Asn Phe Val Lys Phe Phe Lys Val Leu Asn Arg Lys Thr Tyr
               355                 360                 365

Leu Asn Phe Asp Lys Ala Val Phe Lys Ile Asn Ile Val Pro Lys Val
               370                 375                 380

Asn Tyr Thr Ile Tyr Asp Gly Phe Asn Leu Arg Asn Thr Asn Leu Ala
385                 390                 395                 400

Ala Asn Phe Asn Gly Gln Asn Thr Glu Ile Asn Asn Met Asn Phe Thr
               405                 410                 415

Lys Leu Lys Asn Phe Thr Gly Leu Phe Glu Phe Tyr Lys Leu Leu Cys
               420                 425                 430

Val Asp Gly Ile Ile Thr Ser Lys Thr Lys Ser Leu Ile Glu Gly Arg
               435                 440                 445

Tyr Gly Gly Phe Leu Ala Leu Ala Gly Gly Gly Ser Gly Gly Gly
450                 455                 460

Gly Ser Gly Gly Gly Gly Ser Ala Leu Val Leu Gln Cys Ile Asn Leu
```

```
                465                 470                 475                 480
Asp Trp Asp Val Ile Arg Asp Lys Thr Lys Thr Lys Ile Glu Ser Leu
                    485                 490                 495
Lys Glu His Gly Pro Ile Lys Asn Lys Met Ser Glu Ser Pro Asn Lys
                500                 505                 510
Thr Val Ser Glu Glu Lys Ala Lys Gln Tyr Leu Glu Glu Phe His Gln
        515                 520                 525
Thr Ala Leu Glu His Pro Glu Leu Ser Glu Leu Lys Thr Val Thr Gly
        530                 535                 540
Thr Asn Pro Val Phe Ala Gly Ala Asn Tyr Ala Ala Trp Ala Val Asn
545                 550                 555                 560
Val Ala Gln Val Ile Asp Ser Glu Thr Ala Asp Asn Leu Glu Lys Thr
                565                 570                 575
Thr Ala Ala Leu Ser Ile Leu Pro Gly Ile Gly Ser Val Met Gly Ile
                580                 585                 590
Ala Asp Gly Ala Val His His Asn Thr Glu Glu Ile Val Ala Gln Ser
            595                 600                 605
Ile Ala Leu Ser Ser Leu Met Val Ala Gln Ala Ile Pro Leu Val Gly
        610                 615                 620
Glu Leu Val Asp Ile Gly Phe Ala Ala Tyr Asn Phe Val Glu Ser Ile
625                 630                 635                 640
Ile Asn Leu Phe Gln Val Val His Ser Tyr Asn Arg Pro Leu Glu
                645                 650                 655

<210> SEQ ID NO 83
<211> LENGTH: 1329
<212> TYPE: DNA
<213> ORGANISM: Artificial Sequence
<220> FEATURE:
<223> OTHER INFORMATION: chemically synthesized polynucleotide encoding
      tetanus toxin light chain

<400> SEQUENCE: 83
ggatccatgc ctattactat taacaatttt cgttatagcg atcccgtcaa caatgacacc      60
attatcatga tggaaccgcc atattgcaaa ggactggaca tttactataa agccttcaag     120
attactgacc gcatttggat tgttccagag cgttacgagt tcgggacgaa accagaagat     180
tttaaccccgc cttcatcgct gatcgaagga gcatcagagt tattacgatcc gaactatctg     240
cgtacggaca gcgataaaga ccgcttctta cagaccatgg tcaaactttt taaccgtatt     300
aagaacaatg tggccggaga agcactcttg ataagatta tcaacgcgat tccatacctg     360
ggcaattctt acagcctgct ggataaattt gacacaaata gtaattcagt cagctttaac     420
ctgttagaac aagatccgag tggcgcaacc acgaagtctg ccatgctgac aaatctgatc     480
atttttggtc aggtcctgt actgaataaa aatgaagtac gcggcatcgt tctccgcgtg     540
gacaataaga actacttccc atgccgtgac ggcttcggtt cgatcatgca gatggctttc     600
tgtccggagt acgttccgac gtttgataat gttattgaga atatcacgag tttaacaatc     660
ggtaagtcaa atattttca agatccggcc cttctcctta tgcatgaact gattcacgtg     720
ctgcacggct tatatggtat gcaagtgtcc tcgcatgaaa tcattccgtc caaacaggaa     780
atttatatgc agcataccta cccgattca gctgaagagt tgtttacgtt tggtggccag     840
gacgcgaatt tgatctccat cgacatcaaa aacgatctgt atgagaaaac attaaatgac     900
tataaagcga ttgcgaacaa actgtctcag gtgactagct gcaacgatcc taacattgat     960
attgattcct acaaacaaat ttatcaacag aaataccagt tcgataaaga cagcaatggt    1020
```

-continued

| | | |
|---|---|---|
| cagtatatcg taaacgaaga taaatttcag atcctgtata acagcattat gtatggcttt | 1080 |
| accgaaattg agttggggaa gaaatttaac attaaaaccc gtctgtctta ttttagtatg | 1140 |
| aaccatgatc cggtgaaaat ccccaatctg cttgatgata ccatttataa tgataccgaa | 1200 |
| gggttcaaca ttgaatctaa ggatctgaaa tccgaataca aaggccaaaa tatgcgtgtt | 1260 |
| aatactaacg ctttccgtaa tgttgatggt agtggactcg tctcgaaact gattgggttg | 1320 |
| tgtgtcgac | 1329 |

<210> SEQ ID NO 84
<211> LENGTH: 2736
<212> TYPE: DNA
<213> ORGANISM: Artificial Sequence
<220> FEATURE:
<223> OTHER INFORMATION: chemically synthesized polynucleotide encoding a fusion protein

<400> SEQUENCE: 84

| | | |
|---|---|---|
| ggatccatgc ctattactat taacaatttt cgttatagcg atcccgtcaa caatgacacc | 60 |
| attatcatga tggaaccgcc atattgcaaa ggactggaca tttactataa agccttcaag | 120 |
| attactgacc gcatttggat tgttccagag cgttacgagt tcgggacgaa accagaagat | 180 |
| tttaacccgc cttcatcgct gatcgaagga gcatcagagt attacgatcc gaactatctg | 240 |
| cgtacggaca gcgataaaga ccgcttctta cagaccatgg tcaaactttt taaccgtatt | 300 |
| aagaacaatg tggccggaga agcactcttg ataagatta tcaacgcgat tccatacctg | 360 |
| ggcaattctt acagcctgct ggataaattt gacacaaata gtaattcagt cagctttaac | 420 |
| ctgttagaac aagatccgag tggcgcaacc acgaagtctg ccatgctgac aaatctgatc | 480 |
| attttggtc caggtcctgt actgaataaa atgaagtac gcggcatcgt tctccgcgtg | 540 |
| gacaataaga actacttccc atgccgtgac ggcttcggtt cgatcatgca gatggctttc | 600 |
| tgtccggagt acgttccgac gtttgataat gttattgaga atatcacgag tttaacaatc | 660 |
| ggtaagtcaa atattttca agatccggcc cttctcctta tgcatgaact gattcacgtg | 720 |
| ctgcacggct tatatggtat gcaagtgtcc tcgcatgaaa tcattccgtc aaacaggaa | 780 |
| atttatatgc agcatacca cccgatttca gctgaagagt tgtttacgtt tggtggccag | 840 |
| gacgcgaatt tgatctccat cgacatcaaa acgatctgt atgagaaaac attaaatgac | 900 |
| tataaagcga ttgcgaacaa actgtctcag gtgactagct gcaacgatcc taacattgat | 960 |
| attgattcct acaaacaaat ttatcaacag aaataccagt tcgataaaga cagcaatggt | 1020 |
| cagtatatcg taaacgaaga taaatttcag atcctgtata acagcattat gtatggcttt | 1080 |
| accgaaattg agttggggaa gaaatttaac attaaaaccc gtctgtctta ttttagtatg | 1140 |
| aaccatgatc cggtgaaaat ccccaatctg cttgatgata ccatttataa tgataccgaa | 1200 |
| gggttcaaca ttgaatctaa ggatctgaaa tccgaataca aaggccaaaa tatgcgtgtt | 1260 |
| aatactaacg ctttccgtaa tgttgatggt agtggactcg tctcgaaact gattgggttg | 1320 |
| tgtgtcgacg gcatcattac ctccaaaact aaatctctga tagaaggtag atttggcggt | 1380 |
| ttcacgggcg cacgcaaatc agcgcgtaaa cgtaagaacc aggcgctagc gggcggtggc | 1440 |
| ggtagcggcg gtggcggtag cggcggtggc ggtagcgcac tagtgctgca gtgtatcaag | 1500 |
| gttaacaact gggatttatt cttcagcccg agtgaagaca acttcaccaa cgacctgaac | 1560 |
| aaaggtgaag aaatcacctc agatactaac atcgaagcag ccgaagaaaa catctcgctg | 1620 |
| gacctgatcc agcagtacta cctgaccttt aatttcgaca acgagccgga aaacattct | 1680 |
| atcgaaaacc tgagctctga tatcatcggc cagctggaac tgatgccgaa catcgaacgt | 1740 |

```
ttcccaaacg gtaaaaagta cgagctggac aaatatacca tgttccacta cctgcgcgcg    1800
caggaatttg aacacggcaa atcccgtatc gcactgacta actccgttaa cgaagctctg    1860
ctcaacccgt cccgtgtata caccttcttc tctagcgact acgtgaaaaa ggtcaacaaa    1920
gcgactgaag ctgcaatgtt cttgggttgg gttgaacagc ttgtttatga ttttaccgac    1980
gagacgtccg aagtatctac taccgacaaa attgcggata tcactatcat catcccgtac    2040
atcggtccgg ctctgaacat tggcaacatg ctgtacaaag acgacttcgt tggcgcactg    2100
atcttctccg gtgcggtgat cctgctggag ttcatcccgg aaatcgccat cccggtactg    2160
ggcacctttg ctctggtttc ttacattgca aacaaggttc tgactgtaca aaccatcgac    2220
aacgcgctga gcaaacgtaa cgaaaaatgg gatgaagttt acaaatatat cgtgaccaac    2280
tggctggcta aggttaatac tcagatcgac ctcatccgca aaaaaatgaa agaagcactg    2340
gaaaaccagg cggaagctac caaggcaatc attaactacc agtacaacca gtacaccgag    2400
gaagaaaaaa acaacatcaa cttcaacatc gacgatctgt cctctaaact gaacgaatcc    2460
atcaacaaag ctatgatcaa catcaacaag ttcctgaacc agtgctctgt aagctatctg    2520
atgaactcca tgatcccgta cggtgttaaa cgtctggagg acttcgatgc gtctctgaaa    2580
gacgccctgc tgaaatacat ttacgacaac cgtggcactc tgatcggtca ggttgatcgt    2640
ctgaaggaca aagtgaacaa taccttatcg accgacatcc cttttcagct cagtaaatat    2700
gtcgataacc aacgcctttt gtccactcta gactag                              2736
```

<210> SEQ ID NO 85
<211> LENGTH: 911
<212> TYPE: PRT
<213> ORGANISM: Artificial Sequence
<220> FEATURE:
<223> OTHER INFORMATION: chemically synthesized fusion protein

<400> SEQUENCE: 85

```
Gly Ser Met Pro Ile Thr Ile Asn Asn Phe Arg Tyr Ser Asp Pro Val
1               5                   10                  15

Asn Asn Asp Thr Ile Ile Met Met Glu Pro Pro Tyr Cys Lys Gly Leu
            20                  25                  30

Asp Ile Tyr Tyr Lys Ala Phe Lys Ile Thr Asp Arg Ile Trp Ile Val
        35                  40                  45

Pro Glu Arg Tyr Glu Phe Gly Thr Lys Pro Glu Asp Phe Asn Pro Pro
    50                  55                  60

Ser Ser Leu Ile Glu Gly Ala Ser Glu Tyr Tyr Asp Pro Asn Tyr Leu
65                  70                  75                  80

Arg Thr Asp Ser Asp Lys Asp Arg Phe Leu Gln Thr Met Val Lys Leu
                85                  90                  95

Phe Asn Arg Ile Lys Asn Asn Val Ala Gly Glu Ala Leu Leu Asp Lys
            100                 105                 110

Ile Ile Asn Ala Ile Pro Tyr Leu Gly Asn Ser Tyr Ser Leu Leu Asp
        115                 120                 125

Lys Phe Asp Thr Asn Ser Asn Ser Val Ser Phe Asn Leu Leu Glu Gln
    130                 135                 140

Asp Pro Ser Gly Ala Thr Thr Lys Ser Ala Met Leu Thr Asn Leu Ile
145                 150                 155                 160

Ile Phe Gly Pro Gly Pro Val Leu Asn Lys Asn Glu Val Arg Gly Ile
                165                 170                 175

Val Leu Arg Val Asp Asn Lys Asn Tyr Phe Pro Cys Arg Asp Gly Phe
            180                 185                 190
```

```
Gly Ser Ile Met Gln Met Ala Phe Cys Pro Glu Tyr Val Pro Thr Phe
            195                 200                 205

Asp Asn Val Ile Glu Asn Ile Thr Ser Leu Thr Ile Gly Lys Ser Lys
            210                 215                 220

Tyr Phe Gln Asp Pro Ala Leu Leu Leu Met His Glu Leu Ile His Val
225                 230                 235                 240

Leu His Gly Leu Tyr Gly Met Gln Val Ser Ser His Glu Ile Ile Pro
                245                 250                 255

Ser Lys Gln Glu Ile Tyr Met Gln His Thr Tyr Pro Ile Ser Ala Glu
            260                 265                 270

Glu Leu Phe Thr Phe Gly Gly Gln Asp Ala Asn Leu Ile Ser Ile Asp
            275                 280                 285

Ile Lys Asn Asp Leu Tyr Glu Lys Thr Leu Asn Asp Tyr Lys Ala Ile
            290                 295                 300

Ala Asn Lys Leu Ser Gln Val Thr Ser Cys Asn Asp Pro Asn Ile Asp
305                 310                 315                 320

Ile Asp Ser Tyr Lys Gln Ile Tyr Gln Gln Lys Tyr Gln Phe Asp Lys
                325                 330                 335

Asp Ser Asn Gly Gln Tyr Ile Val Asn Glu Asp Lys Phe Gln Ile Leu
            340                 345                 350

Tyr Asn Ser Ile Met Tyr Gly Phe Thr Glu Ile Glu Leu Gly Lys Lys
            355                 360                 365

Phe Asn Ile Lys Thr Arg Leu Ser Tyr Phe Ser Met Asn His Asp Pro
370                 375                 380

Val Lys Ile Pro Asn Leu Leu Asp Asp Thr Ile Tyr Asn Asp Thr Glu
385                 390                 395                 400

Gly Phe Asn Ile Glu Ser Lys Asp Leu Lys Ser Glu Tyr Lys Gly Gln
                405                 410                 415

Asn Met Arg Val Asn Thr Asn Ala Phe Arg Asn Val Asp Gly Ser Gly
            420                 425                 430

Leu Val Ser Lys Leu Ile Gly Leu Cys Val Asp Gly Ile Ile Thr Ser
            435                 440                 445

Lys Thr Lys Ser Leu Ile Glu Gly Arg Phe Gly Gly Phe Thr Gly Ala
            450                 455                 460

Arg Lys Ser Ala Arg Lys Arg Lys Asn Gln Ala Leu Ala Gly Gly Gly
465                 470                 475                 480

Gly Ser Gly Gly Gly Gly Ser Gly Gly Gly Gly Ser Ala Leu Val Leu
                485                 490                 495

Gln Cys Ile Lys Val Asn Asn Trp Asp Leu Phe Phe Ser Pro Ser Glu
            500                 505                 510

Asp Asn Phe Thr Asn Asp Leu Asn Lys Gly Glu Glu Ile Thr Ser Asp
            515                 520                 525

Thr Asn Ile Glu Ala Ala Glu Glu Asn Ile Ser Leu Asp Leu Ile Gln
            530                 535                 540

Gln Tyr Tyr Leu Thr Phe Asn Phe Asp Asn Glu Pro Glu Asn Ile Ser
545                 550                 555                 560

Ile Glu Asn Leu Ser Ser Asp Ile Ile Gly Gln Leu Glu Leu Met Pro
                565                 570                 575

Asn Ile Glu Arg Phe Pro Asn Gly Lys Lys Tyr Glu Leu Asp Lys Tyr
            580                 585                 590

Thr Met Phe His Tyr Leu Arg Ala Gln Glu Phe Glu His Gly Lys Ser
            595                 600                 605

Arg Ile Ala Leu Thr Asn Ser Val Asn Glu Ala Leu Leu Asn Pro Ser
```

```
                610               615                620
Arg Val Tyr Thr Phe Phe Ser Ser Asp Tyr Val Lys Val Asn Lys
625                 630                 635                 640

Ala Thr Glu Ala Ala Met Phe Leu Gly Trp Val Gln Leu Val Tyr
                645                 650                 655

Asp Phe Thr Asp Glu Thr Ser Glu Val Ser Thr Thr Asp Lys Ile Ala
            660                 665                 670

Asp Ile Thr Ile Ile Ile Pro Tyr Ile Gly Pro Ala Leu Asn Ile Gly
            675                 680                 685

Asn Met Leu Tyr Lys Asp Asp Phe Val Gly Ala Leu Ile Phe Ser Gly
        690                 695                 700

Ala Val Ile Leu Leu Glu Phe Ile Pro Glu Ile Ala Ile Pro Val Leu
705                 710                 715                 720

Gly Thr Phe Ala Leu Val Ser Tyr Ile Ala Asn Lys Val Leu Thr Val
                725                 730                 735

Gln Thr Ile Asp Asn Ala Leu Ser Lys Arg Asn Glu Lys Trp Asp Glu
            740                 745                 750

Val Tyr Lys Tyr Ile Val Thr Asn Trp Leu Ala Lys Val Asn Thr Gln
        755                 760                 765

Ile Asp Leu Ile Arg Lys Lys Met Lys Glu Ala Leu Glu Asn Gln Ala
770                 775                 780

Glu Ala Thr Lys Ala Ile Ile Asn Tyr Gln Tyr Asn Gln Tyr Thr Glu
785                 790                 795                 800

Glu Glu Lys Asn Asn Ile Asn Phe Asn Ile Asp Asp Leu Ser Ser Lys
                805                 810                 815

Leu Asn Glu Ser Ile Asn Lys Ala Met Ile Asn Ile Asn Lys Phe Leu
            820                 825                 830

Asn Gln Cys Ser Val Ser Tyr Leu Met Asn Ser Met Ile Pro Tyr Gly
        835                 840                 845

Val Lys Arg Leu Glu Asp Phe Asp Ala Ser Leu Lys Asp Ala Leu Leu
        850                 855                 860

Lys Tyr Ile Tyr Asp Asn Arg Gly Thr Leu Ile Gly Gln Val Asp Arg
865                 870                 875                 880

Leu Lys Asp Lys Val Asn Asn Thr Leu Ser Thr Asp Ile Pro Phe Gln
                885                 890                 895

Leu Ser Lys Tyr Val Asp Asn Gln Arg Leu Leu Ser Thr Leu Asp
            900                 905                 910

<210> SEQ ID NO 86
<211> LENGTH: 180
<212> TYPE: DNA
<213> ORGANISM: Artificial Sequence
<220> FEATURE:
<223> OTHER INFORMATION: chemically synthesized polynucleotide encoding
      a linker

<400> SEQUENCE: 86
ggatccacgc acgtcgacgc gattgatggt cgttttggcg gtttcacggg cgcacgcaaa      60
tcagcgcgta acgtaagaa ccaggcgcta gcgggcggtg gcggtagcgg cggtggcggt     120
agcggcggtg gcggtagcgc actagtgctg cagacgcacg gtctagaatg ataaaagctt    180

<210> SEQ ID NO 87
<211> LENGTH: 2715
<212> TYPE: DNA
<213> ORGANISM: Artificial Sequence
<220> FEATURE:
<223> OTHER INFORMATION: chemically synthesized polynucleotide encoding
``` a fusion protein

<400> SEQUENCE: 87

```
ggatccgaat tcatgccgat caccatcaac aacttcaact acagcgatcc ggtggataac      60
aaaaacatcc tgtacctgga tacccatctg aatccctgg cgaacgaacc ggaaaaagcg     120
tttcgtatca ccggcaacat tgggttatt ccggatcgtt ttagccgtaa cagcaacccg     180
aatctgaata accgccgcg tgttaccagc ccgaaaagcg gttattacga tccgaactat     240
ctgagcaccg atagcgataa agataccttc ctgaaagaaa tcatcaaact gttcaaacgc     300
atcaacagcc gtgaaattgg cgaagaactg atctatcgcc tgagcaccga tattccgttt     360
ccgggcaaca caacaccccc gatcaacacc tttgatttcg atgtggattt caacagcgtt     420
gatgttaaaa cccgccaggg taacaattgg gtgaaaaccg gcagcattaa cccgagcgtg     480
attattaccg gtccgcgcga aacattatt gatccggaaa ccagcacctt taaactgacc     540
aacaacacct tgcggcgca ggaaggtttt ggcgcgctga gcattattag cattagcccg     600
cgctttatgc tgacctatag caacgcgacc aacgatgttg gtgaaggccg tttcagcaaa     660
agcgaatttt gcatggaccc gatcctgatc ctgatgcatg aactgaacca tgcgatgcat     720
aacctgtatg gcatcgcgat tccgaacgat cagaccatta gcagcgtgac cagcaacatc     780
ttttacagcc agtacaacgt gaaactggaa tatgcgaaaa tctatgcgtt tggcggtccg     840
accattgatc tgattccgaa aagcgcgcgc aaatacttcg aagaaaaagc gctggattac     900
tatcgcagca ttgcgaaacg tctgaacagc attaccaccg cgaatccgag cagcttcaac     960
aaatatatcg gcgaatataa acagaaactg atccgcaaat atcgctttgt ggtggaaagc    1020
agcggcgaag ttaccgttaa ccgcaataaa ttcgtggaac tgtacaacga actgacccag    1080
atcttcaccg aatttaacta tgcgaaaatc tataacgtgc agaaccgtaa aatctacctg    1140
agcaacgtgt ataccccggt gaccgcgaat attctggatg ataacgtgta cgatatccag    1200
aacggctta acatcccgaa aagcaacctg aacgttctgt ttatgggcca gaacctgagc    1260
cgtaatccgg cgctgcgtaa agtgaacccg aaaacatgc tgtacctgtt caccaaattt    1320
tgcgtcgacg cgattgatgg tcgttttggc ggtttcacgg gcgcacgcaa atcagcgcgt    1380
aaacgtaaga accaggcgct agcgggcggt ggcggtagcg gcggtggcgg tagcggcggt    1440
ggcggtagcg cactagtgct gcagtgtcgt gaactgctgg tgaaaaacac cgatctgccg    1500
tttattggcg atatcagcga tgtgaaaacc gatatcttcc tgcgcaaaga tatcaacgaa    1560
gaaaccgaag tgatctacta cccggataac gtgagcgttg atcaggtgat cctgagcaaa    1620
aacaccagcg aacatggtca gctggatctg ctgtatccga gcattgatag cgaaagcgaa    1680
attctgccgg gcgaaaacca ggtgtttttac gataaccgta cccagaacgt ggattacctg    1740
aacagctatt actacctgga aagccagaaa ctgagcgata cgtggaaga ttttaccttt    1800
acccgcagca ttgaagaagc gctggataac agcgcgaaag tttacaccta ttttccgacc    1860
ctggcgaaca agttaatgc gggtgttcag ggcggtctgt ttctgatgtg ggcgaacgat    1920
gtggtggaag atttcaccac caacatcctg cgtaaagata ccctggataa aatcagcgat    1980
gttagcgcga ttattccgta tattggtccg cgcctgaaca ttagcaatag cgtgcgtcgt    2040
ggcaatttta ccgaagcgtt tgcggttacc ggtgtgacca ttctgctgga agcgttccg    2100
gaatttacca ttccggcgct gggtgcgttt gtgatctata gcaaagtgca ggaacgcaac    2160
gaaatcatca aaaccatcga taactgcctg aacagcgta ttaaacgctg aaagatagc    2220
tatgaatgga tgatgggcac ctggctgagc cgtattatca cccagttcaa caacatcagc    2280
```

-continued

```
taccagatgt acgatagcct gaactatcag gcgggtgcga ttaaagcgaa aatcgatctg    2340
gaatacaaaa aatacagcgg cagcgataaa gaaaacatca aaagccaggt tgaaaacctg    2400
aaaaacagcc tggatgtgaa aattagcgaa gcgatgaata acatcaacaa attcatccgc    2460
gaatgcagcg tgacctacct gttcaaaaac atgctgccga agtgatcga tgaactgaac     2520 gaatttgatc gcaacaccaa agcgaaactg atcaacctga tcgatagcca caacattatt    2580
ctggtgggcg aagtggataa actgaaagcg aaagttaaca acagcttcca gaacaccatc    2640
ccgtttaaca tcttcagcta taccaacaac agcctgctga agatatcat caacgaatac    2700 ttcaatctag actag                                                     2715
```

<210> SEQ ID NO 88
<211> LENGTH: 904
<212> TYPE: PRT
<213> ORGANISM: Artificial Sequence
<220> FEATURE:
<223> OTHER INFORMATION: chemically synthesized fusion protein

<400> SEQUENCE: 88

```
Gly Ser Glu Phe Met Pro Ile Thr Ile Asn Asn Phe Asn Tyr Ser Asp
1               5                   10                  15

Pro Val Asp Asn Lys Asn Ile Leu Tyr Leu Asp Thr His Leu Asn Thr
            20                  25                  30

Leu Ala Asn Glu Pro Glu Lys Ala Phe Arg Ile Thr Gly Asn Ile Trp
        35                  40                  45

Val Ile Pro Asp Arg Phe Ser Arg Asn Ser Asn Pro Asn Leu Asn Lys
    50                  55                  60

Pro Pro Arg Val Thr Ser Pro Lys Ser Gly Tyr Tyr Asp Pro Asn Tyr
65                  70                  75                  80

Leu Ser Thr Asp Ser Asp Lys Asp Thr Phe Leu Lys Glu Ile Ile Lys
                85                  90                  95

Leu Phe Lys Arg Ile Asn Ser Arg Glu Ile Gly Glu Glu Leu Ile Tyr
            100                 105                 110

Arg Leu Ser Thr Asp Ile Pro Phe Pro Gly Asn Asn Asn Thr Pro Ile
        115                 120                 125

Asn Thr Phe Asp Phe Asp Val Asp Phe Asn Ser Val Asp Val Lys Thr
    130                 135                 140

Arg Gln Gly Asn Asn Trp Val Lys Thr Gly Ser Ile Asn Pro Ser Val
145                 150                 155                 160

Ile Ile Thr Gly Pro Arg Glu Asn Ile Ile Asp Pro Glu Thr Ser Thr
                165                 170                 175

Phe Lys Leu Thr Asn Asn Thr Phe Ala Ala Gln Glu Gly Phe Gly Ala
            180                 185                 190

Leu Ser Ile Ile Ser Ile Ser Pro Arg Phe Met Leu Thr Tyr Ser Asn
        195                 200                 205

Ala Thr Asn Asp Val Gly Glu Gly Arg Phe Ser Lys Ser Glu Phe Cys
    210                 215                 220

Met Asp Pro Ile Leu Ile Leu Met His Glu Leu Asn His Ala Met His
225                 230                 235                 240

Asn Leu Tyr Gly Ile Ala Ile Pro Asn Asp Gln Thr Ile Ser Ser Val
                245                 250                 255

Thr Ser Asn Ile Phe Tyr Ser Gln Tyr Asn Val Lys Leu Glu Tyr Ala
            260                 265                 270

Glu Ile Tyr Ala Phe Gly Gly Pro Thr Ile Asp Leu Ile Pro Lys Ser
        275                 280                 285
```

-continued

Ala Arg Lys Tyr Phe Glu Glu Lys Ala Leu Asp Tyr Tyr Arg Ser Ile
290                 295                 300

Ala Lys Arg Leu Asn Ser Ile Thr Thr Ala Asn Pro Ser Ser Phe Asn
305                 310                 315                 320

Lys Tyr Ile Gly Glu Tyr Lys Gln Lys Leu Ile Arg Lys Tyr Arg Phe
                325                 330                 335

Val Val Glu Ser Ser Gly Glu Val Thr Val Asn Arg Asn Lys Phe Val
                340                 345                 350

Glu Leu Tyr Asn Glu Leu Thr Gln Ile Phe Thr Glu Phe Asn Tyr Ala
                355                 360                 365

Lys Ile Tyr Asn Val Gln Asn Arg Lys Ile Tyr Leu Ser Asn Val Tyr
370                 375                 380

Thr Pro Val Thr Ala Asn Ile Leu Asp Asp Asn Val Tyr Asp Ile Gln
385                 390                 395                 400

Asn Gly Phe Asn Ile Pro Lys Ser Asn Leu Asn Val Leu Phe Met Gly
                405                 410                 415

Gln Asn Leu Ser Arg Asn Pro Ala Leu Arg Lys Val Asn Pro Glu Asn
                420                 425                 430

Met Leu Tyr Leu Phe Thr Lys Phe Cys Val Asp Ala Ile Asp Gly Arg
                435                 440                 445

Phe Gly Gly Phe Thr Gly Ala Arg Lys Ser Ala Arg Lys Arg Lys Asn
450                 455                 460

Gln Ala Leu Ala Gly Gly Gly Ser Gly Gly Gly Ser Gly Gly
465                 470                 475                 480

Gly Gly Ser Ala Leu Val Leu Gln Cys Arg Glu Leu Leu Val Lys Asn
                485                 490                 495

Thr Asp Leu Pro Phe Ile Gly Asp Ile Ser Asp Val Lys Thr Asp Ile
                500                 505                 510

Phe Leu Arg Lys Asp Ile Asn Glu Glu Thr Glu Val Ile Tyr Tyr Pro
                515                 520                 525

Asp Asn Val Ser Val Asp Gln Val Ile Leu Ser Lys Asn Thr Ser Glu
530                 535                 540

His Gly Gln Leu Asp Leu Leu Tyr Pro Ser Ile Asp Ser Glu Ser Glu
545                 550                 555                 560

Ile Leu Pro Gly Glu Asn Gln Val Phe Tyr Asp Asn Arg Thr Gln Asn
                565                 570                 575

Val Asp Tyr Leu Asn Ser Tyr Tyr Leu Glu Ser Gln Lys Leu Ser
                580                 585                 590

Asp Asn Val Glu Asp Phe Thr Phe Thr Arg Ser Ile Glu Glu Ala Leu
                595                 600                 605

Asp Asn Ser Ala Lys Val Tyr Thr Tyr Phe Pro Thr Leu Ala Asn Lys
610                 615                 620

Val Asn Ala Gly Val Gln Gly Gly Leu Phe Leu Met Trp Ala Asn Asp
625                 630                 635                 640

Val Val Glu Asp Phe Thr Thr Asn Ile Leu Arg Lys Asp Thr Leu Asp
                645                 650                 655

Lys Ile Ser Asp Val Ser Ala Ile Ile Pro Tyr Ile Gly Pro Ala Leu
                660                 665                 670

Asn Ile Ser Asn Ser Val Arg Arg Gly Asn Phe Thr Glu Ala Phe Ala
                675                 680                 685

Val Thr Gly Val Thr Ile Leu Leu Glu Ala Phe Pro Glu Phe Thr Ile
                690                 695                 700

Pro Ala Leu Gly Ala Phe Val Ile Tyr Ser Lys Val Gln Glu Arg Asn
705                 710                 715                 720

Glu Ile Ile Lys Thr Ile Asp Asn Cys Leu Glu Gln Arg Ile Lys Arg
                725                 730                 735

Trp Lys Asp Ser Tyr Glu Trp Met Met Gly Thr Trp Leu Ser Arg Ile
            740                 745                 750

Ile Thr Gln Phe Asn Asn Ile Ser Tyr Gln Met Tyr Asp Ser Leu Asn
        755                 760                 765

Tyr Gln Ala Gly Ala Ile Lys Ala Lys Ile Asp Leu Glu Tyr Lys Lys
    770                 775                 780

Tyr Ser Gly Ser Asp Lys Glu Asn Ile Lys Ser Gln Val Glu Asn Leu
785                 790                 795                 800

Lys Asn Ser Leu Asp Val Lys Ile Ser Glu Ala Met Asn Asn Ile Asn
                805                 810                 815

Lys Phe Ile Arg Glu Cys Ser Val Thr Tyr Leu Phe Lys Asn Met Leu
            820                 825                 830

Pro Lys Val Ile Asp Glu Leu Asn Glu Phe Asp Arg Asn Thr Lys Ala
        835                 840                 845

Lys Leu Ile Asn Leu Ile Asp Ser His Asn Ile Ile Leu Val Gly Glu
    850                 855                 860

Val Asp Lys Leu Lys Ala Lys Val Asn Asn Ser Phe Gln Asn Thr Ile
865                 870                 875                 880

Pro Phe Asn Ile Phe Ser Tyr Thr Asn Asn Ser Leu Leu Lys Asp Ile
                885                 890                 895

Ile Asn Glu Tyr Phe Asn Leu Asp
            900

<210> SEQ ID NO 89
<211> LENGTH: 5
<212> TYPE: PRT
<213> ORGANISM: Artificial Sequence
<220> FEATURE:
<223> OTHER INFORMATION: chemically synthesized enterokinase protease
      cleavage site

<400> SEQUENCE: 89

Asp Asp Asp Asp Lys
1               5

<210> SEQ ID NO 90
<211> LENGTH: 8
<212> TYPE: PRT
<213> ORGANISM: Artificial Sequence
<220> FEATURE:
<223> OTHER INFORMATION: chemically synthesized factor Xa protease
      cleavage site

<400> SEQUENCE: 90

Ile Glu Gly Arg Ile Asp Gly Arg
1               5

<210> SEQ ID NO 91
<211> LENGTH: 7
<212> TYPE: PRT
<213> ORGANISM: Artificial Sequence
<220> FEATURE:
<223> OTHER INFORMATION: chemically synthesized Tobacco Etch Virus
      protease cleavage site

<400> SEQUENCE: 91

Glu Asn Leu Tyr Phe Gln Gly
1               5

```
<210> SEQ ID NO 92
<211> LENGTH: 6
<212> TYPE: PRT
<213> ORGANISM: Artificial Sequence
<220> FEATURE:
<223> OTHER INFORMATION: chemically synthesized Thrombin protease
      cleavage site

<400> SEQUENCE: 92

Leu Val Pro Arg Gly Ser
1               5

<210> SEQ ID NO 93
<211> LENGTH: 8
<212> TYPE: PRT
<213> ORGANISM: Artificial Sequence
<220> FEATURE:
<223> OTHER INFORMATION: chemically synthesized PreScission protease
      cleavage site

<400> SEQUENCE: 93

Leu Glu Val Leu Phe Gln Gly Pro
1               5

<210> SEQ ID NO 94
<211> LENGTH: 25
<212> TYPE: PRT
<213> ORGANISM: Clostridium botulimun

<400> SEQUENCE: 94

Cys Val Arg Gly Ile Ile Thr Ser Lys Thr Lys Ser Leu Asp Lys Gly
1               5                   10                  15

Tyr Asn Lys Ala Leu Asn Asp Leu Cys
            20                  25

<210> SEQ ID NO 95
<211> LENGTH: 25
<212> TYPE: PRT
<213> ORGANISM: Clostridium botulimun

<400> SEQUENCE: 95

Cys Val Arg Gly Ile Ile Pro Phe Lys Thr Lys Ser Leu Asp Glu Gly
1               5                   10                  15

Tyr Asn Lys Ala Leu Asn Asp Leu Cys
            20                  25

<210> SEQ ID NO 96
<211> LENGTH: 10
<212> TYPE: PRT
<213> ORGANISM: Clostridium botulimun

<400> SEQUENCE: 96

Cys Lys Ser Val Lys Ala Pro Gly Ile Cys
1               5                   10

<210> SEQ ID NO 97
<211> LENGTH: 17
<212> TYPE: PRT
<213> ORGANISM: Clostridium botulimun

<400> SEQUENCE: 97

Cys His Lys Ala Ile Asp Gly Arg Ser Leu Tyr Asn Lys Thr Leu Asp
1               5                   10                  15

Cys
```

```
<210> SEQ ID NO 98
<211> LENGTH: 14
<212> TYPE: PRT
<213> ORGANISM: Clostridium botulimun

<400> SEQUENCE: 98

Cys Leu Arg Leu Thr Lys Asn Ser Arg Asp Asp Ser Thr Cys
1               5                   10

<210> SEQ ID NO 99
<211> LENGTH: 15
<212> TYPE: PRT
<213> ORGANISM: Clostridium botulimun

<400> SEQUENCE: 99

Cys Lys Asn Ile Val Ser Val Lys Gly Ile Arg Lys Ser Ile Cys
1               5                   10                  15

<210> SEQ ID NO 100
<211> LENGTH: 17
<212> TYPE: PRT
<213> ORGANISM: Clostridium botulimun

<400> SEQUENCE: 100

Cys Lys Ser Val Ile Pro Arg Lys Gly Thr Lys Ala Pro Pro Arg
1               5                   10                  15

Leu Cys

<210> SEQ ID NO 101
<211> LENGTH: 15
<212> TYPE: PRT
<213> ORGANISM: Clostridium botulimun

<400> SEQUENCE: 101

Cys Lys Pro Val Met Tyr Lys Asn Thr Gly Lys Ser Glu Gln Cys
1               5                   10                  15

<210> SEQ ID NO 102
<211> LENGTH: 29
<212> TYPE: PRT
<213> ORGANISM: Clostridium botulimun

<400> SEQUENCE: 102

Cys Lys Lys Ile Ile Pro Pro Thr Asn Ile Arg Glu Asn Leu Tyr Asn
1               5                   10                  15

Arg Thr Ala Ser Leu Thr Asp Leu Gly Gly Glu Leu Cys
            20                  25

<210> SEQ ID NO 103
<211> LENGTH: 23
<212> TYPE: PRT
<213> ORGANISM: Influenza virus

<400> SEQUENCE: 103

Gly Leu Phe Gly Ala Ile Ala Gly Phe Ile Glu Asn Gly Trp Glu Gly
1               5                   10                  15

Met Ile Asp Gly Trp Tyr Gly
            20

<210> SEQ ID NO 104
<211> LENGTH: 23
<212> TYPE: PRT
<213> ORGANISM: Artificial Sequence
<220> FEATURE:
<223> OTHER INFORMATION: chemically synthesized linker
```

<400> SEQUENCE: 104

Val Arg Gly Ile Ile Thr Ser Lys Thr Lys Ser Leu Asp Lys Gly Tyr
1               5                   10                  15

Asn Lys Ala Leu Asn Asp Leu
            20

<210> SEQ ID NO 105
<211> LENGTH: 5
<212> TYPE: PRT
<213> ORGANISM: Artificial Sequence
<220> FEATURE:
<223> OTHER INFORMATION: chemically synthesized met-enkephalin ligand

<400> SEQUENCE: 105

Tyr Gly Gly Phe Met
1               5

<210> SEQ ID NO 106
<211> LENGTH: 13
<212> TYPE: PRT
<213> ORGANISM: Artificial Sequence
<220> FEATURE:
<223> OTHER INFORMATION: chemically synthesized linker

<400> SEQUENCE: 106

Ala Leu Ala Gly Gly Gly Gly Ser Ala Leu Val Leu Gln
1               5                   10

<210> SEQ ID NO 107
<211> LENGTH: 18
<212> TYPE: PRT
<213> ORGANISM: Artificial Sequence
<220> FEATURE:
<223> OTHER INFORMATION: chemically synthesized linker

<400> SEQUENCE: 107

Ala Leu Ala Gly Gly Gly Gly Ser Gly Gly Gly Gly Ser Ala Leu Val
1               5                   10                  15

Leu Gln

<210> SEQ ID NO 108
<211> LENGTH: 28
<212> TYPE: PRT
<213> ORGANISM: Artificial Sequence
<220> FEATURE:
<223> OTHER INFORMATION: chemically synthesized linker

<400> SEQUENCE: 108

Ala Leu Ala Gly Gly Gly Gly Ser Gly Gly Gly Gly Ser Gly Gly Gly
1               5                   10                  15

Gly Ser Gly Gly Gly Gly Ser Ala Leu Val Leu Gln
            20                  25

<210> SEQ ID NO 109
<211> LENGTH: 33
<212> TYPE: PRT
<213> ORGANISM: Artificial Sequence
<220> FEATURE:
<223> OTHER INFORMATION: chemically synthesized linker

<400> SEQUENCE: 109

Ala Leu Ala Gly Gly Gly Gly Ser Gly Gly Gly Gly Ser Gly Gly Gly
1               5                   10                  15

Gly Ser Gly Gly Gly Gly Ser Gly Gly Gly Gly Ser Ala Leu Val Leu

```
                    20              25              30
Gln

<210> SEQ ID NO 110
<211> LENGTH: 30
<212> TYPE: PRT
<213> ORGANISM: Artificial Sequence
<220> FEATURE:
<223> OTHER INFORMATION: chemically synthesized linker

<400> SEQUENCE: 110

Ala Leu Ala Ala Glu Ala Ala Ala Lys Glu Ala Ala Lys Glu Ala
1               5                   10                  15

Ala Ala Lys Ala Gly Gly Gly Gly Ser Ala Leu Val Leu Gln
            20                  25                  30
```